(12) United States Patent
Hartwell

(10) Patent No.: US 10,220,125 B2
(45) Date of Patent: Mar. 5, 2019

(54) APPARATUSES AND METHODS FOR WOUND THERAPY

(71) Applicant: Smith & Nephew PLC, London (GB)

(72) Inventor: Edward Yerbury Hartwell, Hull (GB)

(73) Assignee: Smith & Nephew PLC, London (GB)

( * ) Notice: Subject to any disclaimer, the term of this patent is extended or adjusted under 35 U.S.C. 154(b) by 273 days.

(21) Appl. No.: 14/905,266

(22) PCT Filed: Jul. 15, 2014

(86) PCT No.: PCT/GB2014/052155
§ 371 (c)(1),
(2) Date: Jan. 14, 2016

(87) PCT Pub. No.: WO2015/008054
PCT Pub. Date: Jan. 22, 2015

(65) Prior Publication Data
US 2016/0166744 A1 Jun. 16, 2016

Related U.S. Application Data

(60) Provisional application No. 61/929,871, filed on Jan. 21, 2014, provisional application No. 61/847,019, filed on Jul. 16, 2013.

(51) Int. Cl.
*A61M 1/00* (2006.01)
*A61F 13/00* (2006.01)

(52) U.S. Cl.
CPC ..... *A61M 1/0088* (2013.01); *A61F 13/00021* (2013.01); *A61F 13/00068* (2013.01); *A61F 2013/00357* (2013.01)

(58) Field of Classification Search
CPC ............ A61M 1/0088; A61F 13/00068; A61F 13/00021; A61F 2013/00357; A61F 2013/00842
See application file for complete search history.

(56) References Cited

U.S. PATENT DOCUMENTS 3,194,239 A 7/1965 Sullivan
3,789,851 A 2/1974 LeVeen
(Continued)

FOREIGN PATENT DOCUMENTS

AU 2012261793 B2 11/2014
CN 1438904 8/2003
(Continued)

OTHER PUBLICATIONS

International Search Report and Written Opinion for International Application No. PCT/GB2014/052155 dated Nov. 20, 2014 in 12 pages.
(Continued)

*Primary Examiner* — Adam Marcetich
(74) *Attorney, Agent, or Firm* — Knobbe, Martens, Olson & Bear, LLP

(57) ABSTRACT

Some embodiments of the present disclosure relate to a wound packing material, suitable for use in negative pressure wound therapy, comprising a body of a porous material, the body comprising frangible regions defining a plurality of portions, the frangible regions allowing the portions to be selectively removed from the body. The wound packing material can be shaped to partially or fully surround a secondary wound packing member, such as a stabilizing structure. Some embodiments further relate to methods of manufacturing the wound packing material, and to methods of its use.

20 Claims, 100 Drawing Sheets

(56) References Cited

U.S. PATENT DOCUMENTS

| | | | |
|---|---|---|---|
| 4,467,805 A | 8/1984 | Fukuda | |
| 4,608,041 A | 8/1986 | Nielsen | |
| 4,699,134 A | 10/1987 | Samuelsen | |
| 4,815,468 A | 3/1989 | Annand | |
| 5,176,663 A | 1/1993 | Svedman et al. | |
| 5,264,218 A * | 11/1993 | Rogozinski | A61F 13/023 424/443 |
| 5,376,067 A | 12/1994 | Daneshvar | |
| 5,409,472 A | 4/1995 | Rawlings et al. | |
| 5,415,715 A | 5/1995 | Delage et al. | |
| 5,423,857 A | 6/1995 | Rosenman et al. | |
| 5,512,041 A | 4/1996 | Bogart | |
| 5,562,107 A | 10/1996 | Lavender et al. | |
| 5,584,859 A | 12/1996 | Brotz | |
| 5,636,643 A | 6/1997 | Argenta et al. | |
| 5,695,777 A | 12/1997 | Donovan et al. | |
| 6,176,868 B1 | 1/2001 | Detour | |
| 6,503,208 B1 | 1/2003 | Skovlund | |
| 6,548,727 B1 | 4/2003 | Swenson | |
| 6,566,575 B1 | 5/2003 | Stickels et al. | |
| 6,685,681 B2 | 2/2004 | Lockwood et al. | |
| 6,770,794 B2 | 8/2004 | Fleischmann | |
| 6,787,682 B2 | 9/2004 | Gilman | |
| 6,977,323 B1 | 12/2005 | Swenson | |
| 7,004,915 B2 | 2/2006 | Boynton et al. | |
| 7,144,390 B1 | 12/2006 | Hannigan et al. | |
| 7,315,183 B2 | 1/2008 | Hinterscher | |
| 7,351,250 B2 | 4/2008 | Zamierowski | |
| 7,361,184 B2 | 4/2008 | Joshi | |
| 7,438,705 B2 | 10/2008 | Karpowicz et al. | |
| 7,615,036 B2 | 11/2009 | Joshi et al. | |
| 7,622,629 B2 | 11/2009 | Aali | |
| 7,625,362 B2 | 12/2009 | Boehringer et al. | |
| 7,683,667 B2 | 3/2010 | Kim | |
| 7,700,819 B2 | 4/2010 | Ambrosio et al. | |
| 7,754,937 B2 | 7/2010 | Boehringer et al. | |
| 7,779,625 B2 | 8/2010 | Joshi et al. | |
| 7,815,616 B2 | 10/2010 | Boehringer et al. | |
| 7,857,806 B2 | 12/2010 | Karpowicz et al. | |
| 7,863,495 B2 | 1/2011 | Aali | |
| 7,892,181 B2 | 2/2011 | Christensen et al. | |
| 7,896,856 B2 | 3/2011 | Petrosenko et al. | |
| 7,909,805 B2 | 3/2011 | Weston | |
| 7,931,774 B2 | 4/2011 | Hall et al. | |
| 7,942,866 B2 | 5/2011 | Radl et al. | |
| 7,951,124 B2 | 5/2011 | Boehringer et al. | |
| 7,964,766 B2 | 6/2011 | Blott et al. | |
| 7,976,519 B2 | 7/2011 | Bubb et al. | |
| 7,976,524 B2 | 7/2011 | Kudo et al. | |
| 7,981,098 B2 | 7/2011 | Boehringer et al. | |
| 8,030,534 B2 | 10/2011 | Radl et al. | |
| 8,057,447 B2 | 11/2011 | Olson et al. | |
| 8,062,331 B2 | 11/2011 | Zamierowski | |
| 8,067,662 B2 | 11/2011 | Aali et al. | |
| 8,070,773 B2 | 12/2011 | Zamierowski | |
| 8,114,126 B2 | 2/2012 | Heaton et al. | |
| 8,123,781 B2 | 2/2012 | Zamierowski | |
| 8,142,419 B2 | 3/2012 | Heaton et al. | |
| 8,172,816 B2 | 5/2012 | Kazala, Jr. et al. | |
| 8,187,237 B2 | 5/2012 | Seegert | |
| 8,188,331 B2 | 5/2012 | Barta et al. | |
| 8,197,467 B2 | 6/2012 | Heaton et al. | |
| 8,207,392 B2 | 6/2012 | Haggstrom et al. | |
| 8,235,955 B2 | 8/2012 | Blott et al. | |
| 8,246,590 B2 | 8/2012 | Hu et al. | |
| 8,257,328 B2 | 9/2012 | Augustine et al. | |
| 8,273,105 B2 | 9/2012 | Cohen et al. | |
| 8,328,776 B2 | 12/2012 | Kelch et al. | |
| 8,337,411 B2 | 12/2012 | Nishtala et al. | |
| 8,353,931 B2 | 1/2013 | Stopek et al. | |
| 8,357,131 B2 | 1/2013 | Olson | |
| 8,362,315 B2 | 1/2013 | Aali | |
| 8,376,972 B2 | 2/2013 | Fleischmann | |
| 8,430,867 B2 | 4/2013 | Robinson et al. | |
| 8,447,375 B2 | 5/2013 | Shuler | |
| 8,454,990 B2 | 6/2013 | Canada et al. | |
| 8,460,255 B2 | 6/2013 | Joshi et al. | |
| 8,460,257 B2 | 6/2013 | Locke et al. | |
| 8,481,804 B2 | 7/2013 | Timothy | |
| 8,486,032 B2 | 7/2013 | Seegert et al. | |
| 8,500,704 B2 | 8/2013 | Boehringer et al. | |
| 8,500,776 B2 | 8/2013 | Ebner | |
| 8,523,832 B2 | 9/2013 | Seegert | |
| 8,535,296 B2 | 9/2013 | Blott et al. | |
| 8,608,776 B2 | 12/2013 | Coward et al. | |
| 8,628,505 B2 | 1/2014 | Weston | |
| 8,632,523 B2 | 1/2014 | Eriksson et al. | |
| 8,673,992 B2 | 3/2014 | Eckstein et al. | |
| 8,679,080 B2 | 3/2014 | Kazala, Jr. et al. | |
| 8,679,153 B2 | 3/2014 | Dennis | |
| 8,680,360 B2 | 3/2014 | Greener et al. | |
| 8,708,984 B2 | 4/2014 | Robinson et al. | |
| 8,721,629 B2 | 5/2014 | Hardman et al. | |
| 8,746,662 B2 | 6/2014 | Poppe | |
| 8,764,732 B2 | 7/2014 | Hartwell | |
| 8,791,316 B2 | 7/2014 | Greener | |
| 8,802,916 B2 | 8/2014 | Griffey et al. | |
| 8,814,842 B2 | 8/2014 | Coulthard et al. | |
| 8,821,535 B2 | 9/2014 | Greener | |
| 8,843,327 B2 | 9/2014 | Vernon-Harcourt et al. | |
| 8,945,030 B2 | 2/2015 | Weston | |
| 9,044,579 B2 | 6/2015 | Blott et al. | |
| 9,061,095 B2 | 6/2015 | Adie et al. | |
| 9,084,845 B2 | 7/2015 | Adie et al. | |
| 9,180,231 B2 | 11/2015 | Greener | |
| 9,220,822 B2 | 12/2015 | Hartwell et al. | |
| 9,408,755 B2 | 8/2016 | Larsson et al. | |
| 9,421,132 B2 | 8/2016 | Dunn | |
| 9,655,807 B2 | 5/2017 | Locke et al. | |
| 9,849,023 B2 | 12/2017 | Hall et al. | |
| 9,895,270 B2 | 2/2018 | Coward et al. | |
| 2001/0029956 A1 | 10/2001 | Argenta | |
| 2001/0034499 A1 | 10/2001 | Sessions et al. | |
| 2002/0077661 A1 | 6/2002 | Saadat | |
| 2002/0161346 A1 | 10/2002 | Lockwood et al. | |
| 2003/0108587 A1* | 6/2003 | Orgill | A61L 15/42 424/423 |
| 2004/0064132 A1 | 4/2004 | Boehringer et al. | |
| 2004/0162512 A1 | 8/2004 | Liedtke et al. | |
| 2004/0267312 A1 | 12/2004 | Kanner et al. | |
| 2005/0142331 A1* | 6/2005 | Anderson | B31F 1/07 428/152 |
| 2005/0182445 A1 | 8/2005 | Zamierowski | |
| 2005/0209574 A1* | 9/2005 | Boehringer | A61F 13/36 604/289 |
| 2005/0267424 A1 | 12/2005 | Eriksson et al. | |
| 2006/0020269 A1 | 1/2006 | Cheng | |
| 2006/0058842 A1 | 3/2006 | Wilke et al. | |
| 2006/0069357 A1 | 3/2006 | Marasco | |
| 2006/0213527 A1 | 9/2006 | Argenta et al. | |
| 2006/0217795 A1 | 9/2006 | Besselink et al. | |
| 2006/0271018 A1 | 11/2006 | Korf | |
| 2007/0032763 A1 | 2/2007 | Vogel | |
| 2007/0052144 A1 | 3/2007 | Knirck et al. | |
| 2007/0104941 A1* | 5/2007 | Kameda | B01D 61/14 428/314.2 |
| 2007/0118096 A1 | 5/2007 | Smith et al. | |
| 2007/0123973 A1 | 5/2007 | Roth et al. | |
| 2007/0129660 A1 | 6/2007 | McLeod et al. | |
| 2007/0149910 A1 | 6/2007 | Zocher | |
| 2007/0185463 A1 | 8/2007 | Mulligan | |
| 2007/0213597 A1 | 9/2007 | Wooster | |
| 2007/0282309 A1 | 12/2007 | Bengtson et al. | |
| 2008/0041401 A1 | 2/2008 | Casola et al. | |
| 2008/0108977 A1 | 5/2008 | Heaton et al. | |
| 2008/0275409 A1 | 11/2008 | Kane et al. | |
| 2009/0005716 A1 | 1/2009 | Abuzaina et al. | |
| 2009/0005744 A1 | 1/2009 | Karpowicz et al. | |
| 2009/0099519 A1 | 4/2009 | Kaplan | |
| 2009/0105670 A1 | 4/2009 | Bentley et al. | |
| 2009/0137973 A1 | 5/2009 | Karpowicz et al. | |
| 2009/0204423 A1 | 8/2009 | DeGheest et al. | |
| 2009/0299303 A1* | 12/2009 | Seegert | A61M 1/0088 604/290 |

(56) References Cited

U.S. PATENT DOCUMENTS

| | | |
|---|---|---|
| 2010/0022990 A1 | 1/2010 | Karpowicz et al. |
| 2010/0047324 A1 | 2/2010 | Fritz et al. |
| 2010/0069858 A1* | 3/2010 | Olson ............... A61F 13/00987 604/319 |
| 2010/0081983 A1 | 4/2010 | Zocher et al. |
| 2010/0106184 A1 | 4/2010 | Coward et al. |
| 2010/0121287 A1 | 5/2010 | Smith et al. |
| 2010/0125233 A1* | 5/2010 | Edward S ........... A61M 1/0088 602/42 |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0160876 A1* | 6/2010 | Robinson ............ A61F 13/0203 604/319 |
| 2010/0179515 A1 | 7/2010 | Swain et al. |
| 2010/0198128 A1 | 8/2010 | Turnlund et al. |
| 2010/0262106 A1* | 10/2010 | Hartwell ................ A61F 13/36 604/367 |
| 2010/0280468 A1 | 11/2010 | Haggstrom et al. |
| 2010/0305490 A1 | 12/2010 | Coulthard et al. |
| 2010/0312159 A1* | 12/2010 | Aali ................ A61F 13/00068 602/44 |
| 2011/0021965 A1 | 1/2011 | Karp et al. |
| 2011/0022082 A1 | 1/2011 | Burke et al. |
| 2011/0054283 A1 | 3/2011 | Shuler |
| 2011/0059291 A1* | 3/2011 | Boyce ......................... C08J 5/00 428/136 |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0213287 A1 | 9/2011 | Lattimore et al. |
| 2011/0224631 A1 | 9/2011 | Simmons |
| 2011/0224632 A1 | 9/2011 | Zimitsky et al. |
| 2011/0224634 A1 | 9/2011 | Locke et al. |
| 2011/0238026 A1 | 9/2011 | Zhang et al. |
| 2011/0245682 A1 | 10/2011 | Robinson et al. |
| 2011/0245788 A1 | 10/2011 | Marquez Canada |
| 2011/0264138 A1 | 10/2011 | Avelar et al. |
| 2011/0282310 A1 | 11/2011 | Boehringer et al. |
| 2011/0305736 A1* | 12/2011 | Wieland ............ A61F 13/00021 424/401 |
| 2011/0313374 A1 | 12/2011 | Lockwood et al. |
| 2011/0319804 A1* | 12/2011 | Greener ............ A61F 13/00987 602/46 |
| 2012/0004631 A9 | 1/2012 | Hartwell |
| 2012/0016321 A1 | 1/2012 | Wu et al. |
| 2012/0016322 A1 | 1/2012 | Goulthard |
| 2012/0029455 A1 | 2/2012 | Perez-Foullerat et al. |
| 2012/0041402 A1 | 2/2012 | Greener |
| 2012/0059412 A1 | 3/2012 | Fleischmann |
| 2012/0065664 A1 | 3/2012 | Avitable et al. |
| 2012/0095426 A1 | 4/2012 | Visscher et al. |
| 2012/0123358 A1 | 5/2012 | Hall et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0150133 A1 | 6/2012 | Heaton et al. |
| 2012/0172778 A1 | 7/2012 | Rastegar et al. |
| 2012/0172926 A1 | 7/2012 | Hotter |
| 2012/0191132 A1 | 7/2012 | Sargeant |
| 2012/0203189 A1 | 8/2012 | Barta et al. |
| 2012/0209226 A1 | 8/2012 | Simmons et al. |
| 2012/0209227 A1* | 8/2012 | Dunn ...................... A61B 17/08 604/319 |
| 2012/0220968 A1 | 8/2012 | Confalone et al. |
| 2012/0222687 A1 | 9/2012 | Czajka, Jr. et al. |
| 2012/0253302 A1 | 10/2012 | Corley |
| 2012/0302440 A1 | 11/2012 | Theliander et al. |
| 2013/0131564 A1 | 5/2013 | Locke et al. |
| 2013/0138054 A1 | 5/2013 | Fleischmann |
| 2013/0197457 A1 | 8/2013 | Kazala et al. |
| 2013/0204213 A1* | 8/2013 | Heagle .................... A61F 13/02 604/304 |
| 2013/0245527 A1 | 9/2013 | Croizat et al. |
| 2013/0253401 A1 | 9/2013 | Locke et al. |
| 2013/0310781 A1 | 11/2013 | Phillips et al. |
| 2013/0325142 A1* | 12/2013 | Hunter ..................... C22C 1/08 623/23.51 |
| 2013/0331757 A1 | 12/2013 | Belson |
| 2014/0068914 A1 | 3/2014 | Coward et al. |
| 2014/0094730 A1 | 4/2014 | Greener |
| 2014/0163415 A1 | 6/2014 | Zaiken et al. |
| 2014/0249495 A1 | 9/2014 | Mumby |
| 2015/0025484 A1 | 1/2015 | Simmons et al. |
| 2015/0065968 A1 | 3/2015 | Sealy et al. |
| 2015/0119837 A1 | 4/2015 | Thompson, Jr. et al. |
| 2015/0157758 A1 | 6/2015 | Blucher et al. |
| 2015/0159066 A1 | 6/2015 | Hartwell et al. |
| 2015/0174304 A1 | 6/2015 | Askem et al. |
| 2015/0320602 A1 | 11/2015 | Locke et al. |
| 2015/0374561 A1 | 12/2015 | Hubbard, Jr. et al. |

FOREIGN PATENT DOCUMENTS

| | | |
|---|---|---|
| CN | 101112326 A | 1/2008 |
| CN | 101123930 | 2/2008 |
| CN | 101588836 | 11/2009 |
| CN | 102046117 | 5/2011 |
| CN | 102196830 | 9/2011 |
| CN | 102256637 | 11/2011 |
| CN | 102781380 | 11/2012 |
| CN | 203408163 | 1/2014 |
| DE | 2 949 920 | 3/1981 |
| DE | 10 2005 007016 | 8/2006 |
| EP | 1 320 342 | 6/2003 |
| EP | 2 279 016 | 2/2011 |
| EP | 2 366 721 | 9/2011 |
| EP | 2 341 955 | 12/2012 |
| EP | 2 567 717 | 3/2013 |
| EP | 2567682 A1 | 3/2013 |
| EP | 2 594 299 | 5/2013 |
| EP | 2 601 984 A2 | 6/2013 |
| EP | 2 623 137 | 8/2013 |
| EP | 2 367 517 | 9/2013 |
| EP | 3 225 261 | 10/2017 |
| GB | 2389794 | 12/2003 |
| GB | 2423019 A | 8/2006 |
| GB | 2489947 | 10/2012 |
| GB | 2496310 | 5/2013 |
| JP | H09-503923 | 4/1997 |
| JP | 2007-505678 | 3/2007 |
| JP | 2008-529618 | 8/2008 |
| JP | 2009-536851 | 10/2009 |
| JP | 2011-500170 | 1/2011 |
| JP | 2011-523575 | 8/2011 |
| JP | 2012-105840 | 6/2012 |
| RU | 62504 | 4/2007 |
| SU | 1818103 | 5/1993 |
| WO | WO 2001/085248 | 11/2001 |
| WO | WO 2001/89392 | 11/2001 |
| WO | WO 2002/05737 | 1/2002 |
| WO | WO 2003/003948 | 1/2003 |
| WO | WO 2004/018020 | 3/2004 |
| WO | WO 2004/037334 | 5/2004 |
| WO | WO 2005/046761 | 5/2005 |
| WO | WO 2005/105174 | 11/2005 |
| WO | WO 2006/046060 | 5/2006 |
| WO | WO 2007/030601 | 3/2007 |
| WO | WO 2007/133618 | 11/2007 |
| WO | WO 2008/027449 | 3/2008 |
| WO | WO 2008/039223 | 4/2008 |
| WO | WO 2008/064502 | 6/2008 |
| WO | WO 2008/091521 | 7/2008 |
| WO | WO 2008/104609 | 9/2008 |
| WO | WO 2009/112062 | 9/2009 |
| WO | WO 2009/112848 | 9/2009 |
| WO | WO 2009/114624 | 9/2009 |
| WO | WO 2009/158132 | 12/2009 |

(56) References Cited

FOREIGN PATENT DOCUMENTS

| WO | WO 2010/033725 | 3/2010 |
|---|---|---|
| WO | WO 2010/051073 | 5/2010 |
| WO | WO 2010/059612 | 5/2010 |
| WO | WO 2010/075180 | 7/2010 |
| WO | WO 2010/079359 | 7/2010 |
| WO | WO 2010/092334 | 8/2010 |
| WO | WO 2010/097570 | 9/2010 |
| WO | WO 2011/023384 | 3/2011 |
| WO | WO 2011/106722 | 9/2011 |
| WO | WO 2011/135284 | 11/2011 |
| WO | WO 2011/137230 | 11/2011 |
| WO | WO 2011/144888 | 11/2011 |
| WO | WO 2012/021553 | 2/2012 |
| WO | WO 2012/082716 | 6/2012 |
| WO | WO 2012/082876 | 6/2012 |
| WO | WO 2012/112204 | 8/2012 |
| WO | WO 2012/136707 | 10/2012 |
| WO | WO 2012/142473 | 10/2012 |
| WO | WO 2013/007973 | 1/2013 |
| WO | WO 2013/012381 | 1/2013 |
| WO | WO 2013/043258 | 3/2013 |
| WO | WO 2013/071243 | 5/2013 |
| WO | WO 2013/079947 | 6/2013 |
| WO | WO 2013/175309 | 11/2013 |
| WO | WO 2013/175310 | 11/2013 |
| WO | WO 2014/013348 | 1/2014 |
| WO | WO 2014/014842 | 1/2014 |
| WO | WO 2014/014871 | 1/2014 |
| WO | WO 2014/014922 | 1/2014 |
| WO | WO 2014/024048 | 2/2014 |
| WO | WO 2014/140578 | 9/2014 |
| WO | WO 2014/158526 | 10/2014 |
| WO | WO 2014/165275 | 10/2014 |
| WO | WO 2014/194786 | 12/2014 |
| WO | WO 2015/008054 | 1/2015 |
| WO | WO 2015/061352 | 4/2015 |
| WO | WO 2015/109359 | 7/2015 |
| WO | WO 2015/110409 | 7/2015 |
| WO | WO 2015/110410 | 7/2015 |
| WO | WO 2015/169637 | 11/2015 |
| WO | WO 2015/172108 | 11/2015 |
| WO | WO 2016/176513 | 11/2016 |

OTHER PUBLICATIONS

Hougaard, et al., "The open abdomen: temporary closure with a modified negative pressure therapy technique", International Wound Journal, (2014), ISSN 1742-4801, pp. 13-16.
Kapischke, et al., "Self-fixating mesh for the Lichtenstein procedure-a prestudy", Langenbecks Arch Surg (2010), 395 pp. 317-322.
U.S. Appl. No. 61/913,210, filed Dec. 6, 2013, Dunn et al.
Definition of "Adhere", The Free Dictionary, accessed Mar. 23, 2017, in 6 pages. URL: http://www.thefreedictionary.com/adhere.
U.S. Appl. No. 61/930,423, filed Jan. 22, 2014, Phillips.
U.S. Appl. No. 61/930,426, filed Jan. 22, 2014, Dunn et al.
U.S. Appl. No. 61/930,427, filed Jan. 22, 2014, Dunn et al.
U.S. Appl. No. 61/930,436, filed Jan. 22, 2014, Saxby.
U.S. Appl. No. 61/930,913, filed Jan. 23, 2014, Phillips.
International Preliminary Report on Patentability, re PCT Application No. PCT/GB2014/052155, dated Jan. 28, 2016.
Notice of Opposition to European Patent No. EP 3 021 806 dated Oct. 31, 2018 in 132 pages, including a Statement of Facts and Evidence and prior art references D1—WO 2010/092334 A1, D2—JP 2012-105840 A, D2a—English translation of D2, D3—US 2011/0213287 A1, and D4—US 2012/0209227 A1 attached with the Notice.

* cited by examiner

The blade length (end to end of each cross) is 18mm

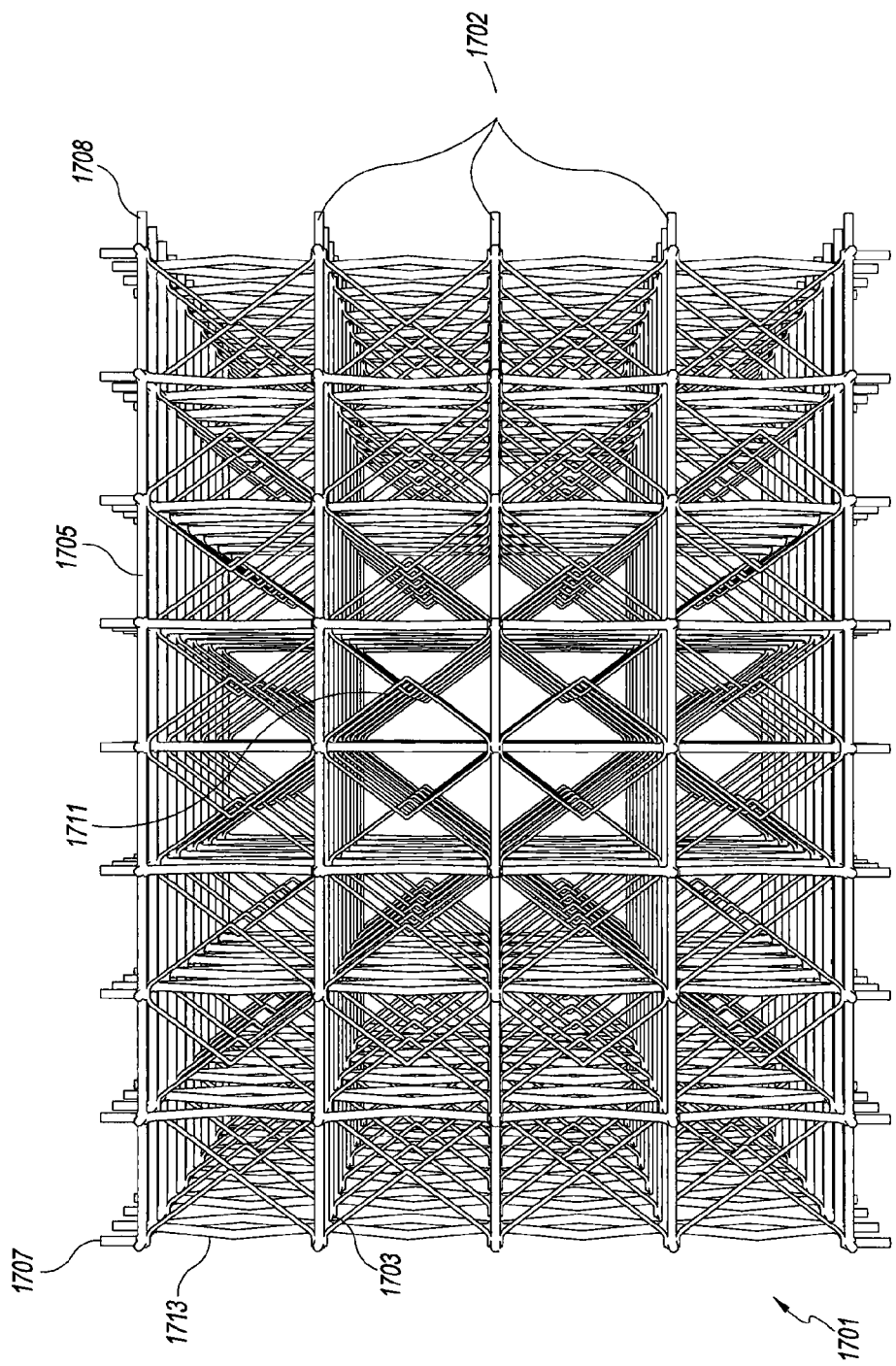
FIG. IIC

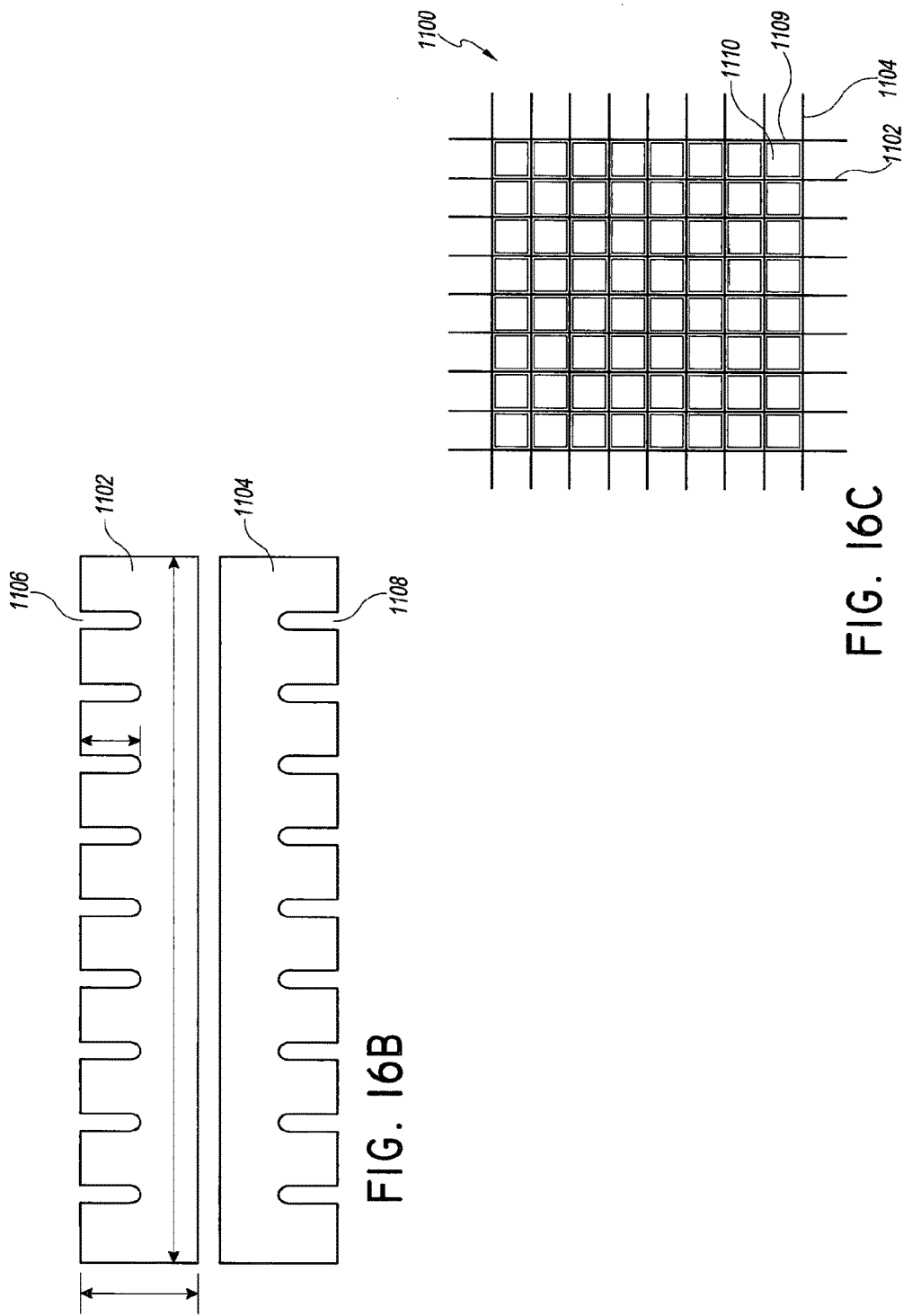

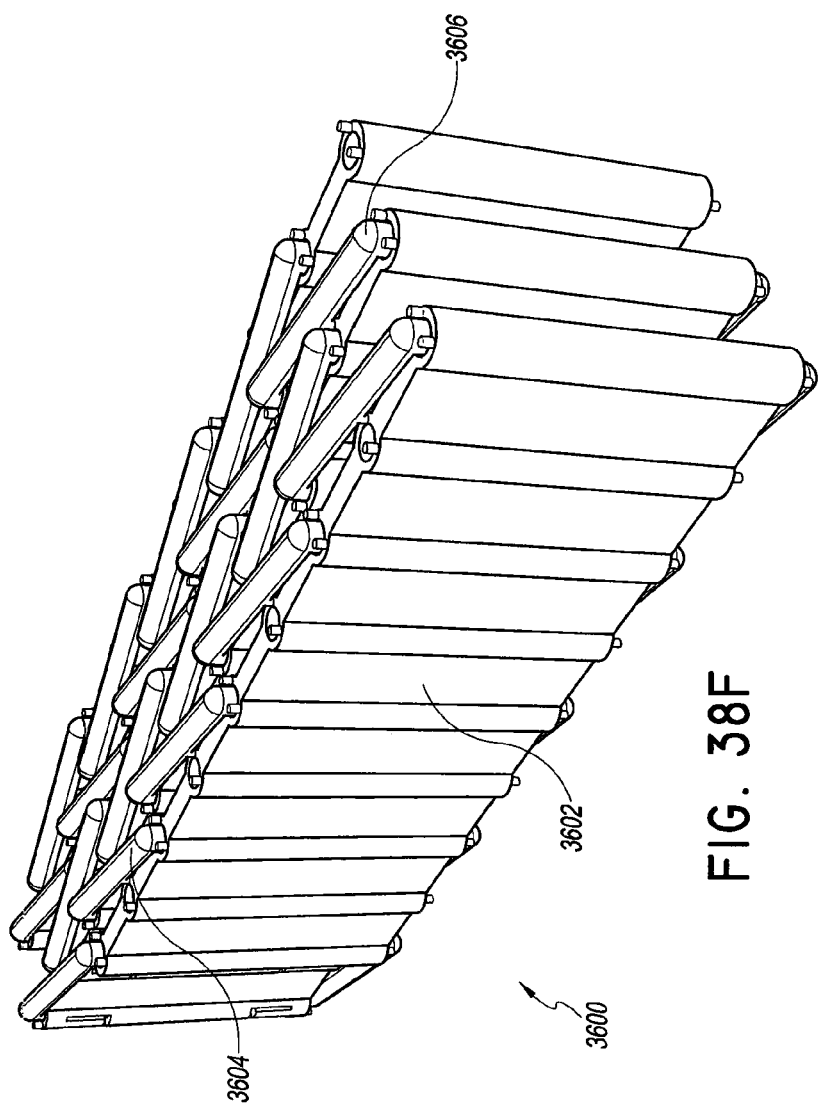

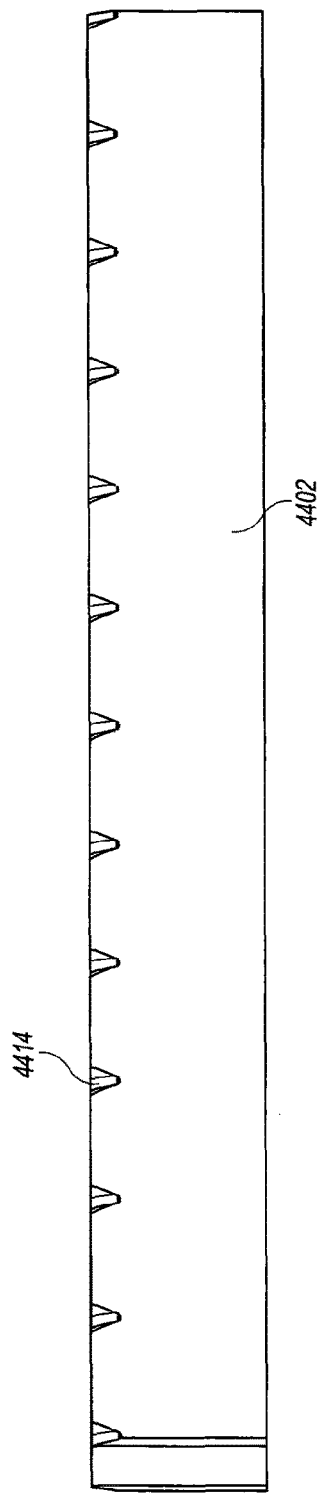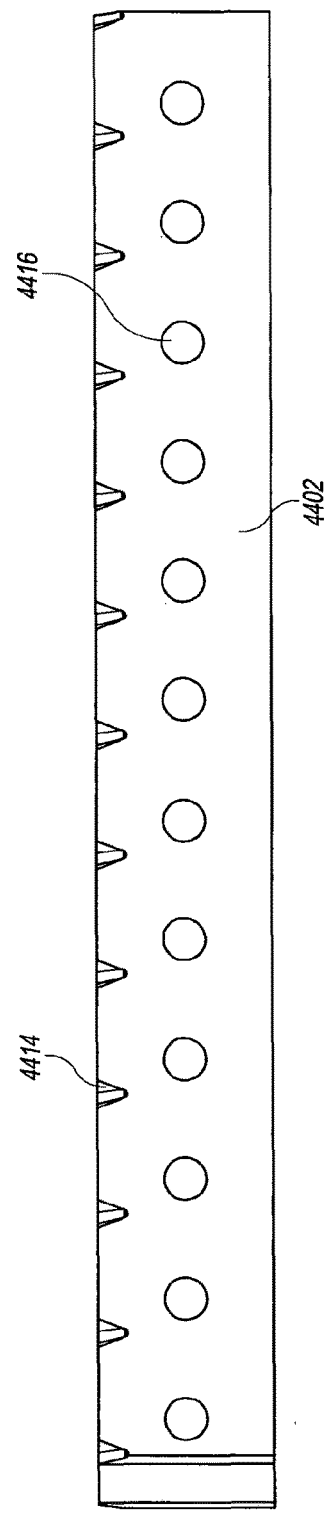
FIG. 46B
FIG. 46C

APPARATUSES AND METHODS FOR WOUND THERAPY

CROSS-REFERENCE TO RELATED APPLICATIONS

This application claims the benefit of U.S. Provisional Application No. 61/847,019, filed Jul. 16, 2013, entitled APPARATUSES AND METHODS FOR WOUND THERAPY and U.S. Provisional Application 61/929,871 filed Jan. 21, 2014, entitled APPARATUSES AND METHODS FOR WOUND THERAPY. The contents of the aforementioned applications are hereby incorporated by reference in their entireties as if fully set forth herein. The benefit of priority to the foregoing applications is claimed under the appropriate legal basis, including, without limitation, under 35 U.S.C. § 119(e). This application also incorporates by reference the entirety of U.S. application Ser. No. 13/365,615, filed Feb. 3, 2012, entitled NEGATIVE PRESSURE WOUND CLOSURE DEVICE, and published as US 2012/0209227. This application further incorporates by reference PCT Application No. PCT/US2013/050698, filed Jul. 16, 2013, entitled NEGATIVE PRESSURE WOUND CLOSURE DEVICE. The contents of the aforementioned applications are hereby incorporated by reference in their entireties as if fully set forth herein.

BACKGROUND OF THE DISCLOSURE

Field of the Invention

This application describes embodiments of apparatuses, methods, and systems for the treatment of wounds, specifically to aid in the closure of large wounds, in conjunction with the administration of negative pressure.

Some embodiments of the present disclosure relate to methods of manufacture and use of porous wound packing materials and wound closure devices that may be utilized with the wound packing materials. In particular embodiments, a wound packing material may be easily shaped and configured to the shape of a wound closure device to be received within the wound packing material. Such wound packing materials and wound closure devices are particularly suitable for negative pressure wound therapy (NPWT).

Description of the Related Art

Typically in NPWT the wound cavity or surface is filled or covered with a material that allows the transmission of a partial vacuum (i.e. does not completely collapse) to the wound bed when a negative pressure is applied to the wound area, and also allows fluids to pass from the wound bed towards the source of negative pressure. There are two primary approaches to NPWT, i.e. gauze or foam types. The gauze type (also referred to as the Chariker-Jeter technique) involves the use of a drain wrapped in gauze topped by a sealed dressing. The foam type involves the use of foam placed over or in the wound. Some embodiments of the present disclosure are directed primarily towards the foam type of NPWT.

In foam based NPWT the wound cavity is filled or covered with a porous foam packing material and covered over and sealed with flexible sheet (a drape) that is fairly impermeable to fluids. A tube is inserted under or through the drape into the wound site and its distal end is connected to a vacuum source (commonly a pump). The wound cavity, enclosed by the drape and tissue, contracts under the force of atmospheric pressure and compresses the packing material visibly. Gross tissue movement ceases after a few tens of seconds and fluid flow from the wound (withdrawn from the tissue) ensues. The fluid is transmitted through the packing material and up the vacuum tube to a collection receptacle positioned between the distal end of the tube and the vacuum source. The wound packing material mechanically supports the tissue to which it is applied, and also allows the free flow of fluids away from the site when a vacuum is applied, even when compressed. A good material for this application is hydrophobic, reticulated polyurethane foam of very high free internal volume.

The packing material for use in NPWT must be shaped to fit the wound to be packed. This is typically achieved by the medical practitioner (typically physician or nurse) cutting a preformed block of foam (usually a cuboid) to approximately fit the wound using a scalpel, knife or scissors. This operation can be complex, time consuming and messy for the medical practitioner, and indeed can be dangerous with the possibility of particulate foam material contaminating the wound site or of an accident during the cutting process. Accordingly, the process of shaping the wound dressing is currently an unaddressed problem in the field of NPWT which is a barrier to its effective and widespread use.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created on the patient. Closure of this wound, while minimizing the risk of secondary infections and other complications, and after the underlying edema has subsided, then becomes a priority.

Other large or incisional wounds, either as a result of surgery, trauma, or other conditions, may also require closure. For example, wounds resulting from sterniotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds that is also capable of being shaped to a wound.

SUMMARY OF SOME EMBODIMENTS OF THE DISCLOSURE

Embodiments of the present invention relate to negative pressure wound closure devices, methods, and systems that facilitate closure of a wound. The devices, methods, and systems may be customizable to fit to the shape of a wound. The devices, methods, and systems may operate to reduce the need for repetitive replacement of wound filler material currently employed and can advance the rate of healing. The devices, methods, and systems may be simultaneously used with negative pressure to remove wound fluids.

In one embodiment there is provided a wound packing material comprising a body of a porous material, the body comprising frangible regions defining a plurality of portions, the frangible regions allowing the portions to be selectively removed from the body.

The term frangible is intended to mean that the material has been weakened in some manner which allows the portion to be removed relatively easily (e.g. manually) from the body without substantially damaging the remainder of the body, but where the overall structure of the body is sufficiently strong that the body remains intact during normal use, i.e. in the absence of manipulation to remove a portion. It is preferred that the portions can be removed manually, without the use of additional tools such as scissors, knives, scalpels etc. This allows a medical practitioner to remove portions to achieve a desired shape of the body quickly and simply without the need to use additional tools.

Preferably the frangible regions are defined by partial pre-cuts formed in the body.

Use of the term partial pre-cuts is intended to mean a region of the body where the material of the body has been removed or severed to at least partially separate a portion of the body from the rest of the body, but where sufficient material of the body has been left such that the body retains its general structural integrity, i.e. sufficient integrity for general storage, handling and use as a wound packing material. However, the remaining material is sufficiently weak (i.e. frangible) that it is relatively easily severable with manually applied force, e.g. by a medical practitioner tearing the portion from the body.

It should be noted that the term partial pre-cuts is intended to cover both a situation where material is removed by cutting or otherwise removing or severing regions of a preformed body of porous material, and also where the pre-cuts are formed during initial production of the body, e.g. formed during a moulding process.

The wound packing material may be a wound packing foam suitable for use in negative pressure wound therapy (NPWT). Particularly suitable foams for NPWT include polyurethane foam, typically reticulated polyurethane foam of very high free internal volume, e.g. 80% or higher, preferably 90% or higher free internal volume. Typical foams used in NPWT have porosities in the range 30-60 ppi (pores per inch) and pore diameters in the range 300-800 μm. However, other suitable foams are known in the art and may be equally suitable. In certain embodiments, any foam disclosed herein this section or elsewhere in the specification may be used. In general, suitable foams have an open porous structure, to allow transmission of the negative pressure to the wound bed, and sufficient mechanical strength to prevent the negative pressure (typically approximately 80-125 mm Hg below ambient atmospheric pressure) from substantially collapsing the structure of the foam.

It is preferred that the wound packing material is sterile. This can be achieved using conventional sterilisation techniques which are known for sterilising surgical foams and dressings.

It will be clear to the person skilled in the art that the size and shape of the selectively removable portions will be determined by the number of frangible regions provided per unit volume of the body, and the number of different orientations and configurations that the frangible regions are provided in.

As mentioned above, the frangible regions are preferably defined by partial pre-cuts within the body. The following description will focus on embodiments whereby the frangible regions are formed in this way, but it will be understood that frangible regions could be formed in other manners (e.g. selectively weakening the foam structure at selected regions using chemically agents or heat) and that such variants are within the scope of the present disclosure.

In some embodiments the partial pre-cuts are generally planar. For example, flat planar partial pre-cuts may be preferred as they provide for regularly shaped portions. However, it is perfectly possible that the planes could be curved where a curved profile on an exposed region of the body following removal of the portions is preferred.

In one embodiment the body comprises a first set of substantially parallel planar partial pre-cuts in a first orientation. The set may comprise a plurality of planar pre-cuts, each planar pre-cut comprising a series of individual pre-cuts, each individual pre-cut being spaced from the adjacent pre-cut by a gap. The individual pre-cuts are aligned with the plane defined by the planar parallel partial pre-cut. Preferably the parallel planar partial pre-cuts of the set are regularly spaced. Where one set of parallel planar partial pre-cuts is provided in a single orientation it will be apparent that the removable portions defined by the set of planar partial pre-cuts will be slices of the body; each slice is removable from the next slice as a result of the planar parallel partial pre-cut between them.

In one embodiment, the spacing between each of the parallel planar pre-cuts in the set is 30 mm or less, preferably 25 mm or less, especially 20 mm or less, and optionally 15 mm or less. The sizes of the portions are defined by the spacing between the parallel planar pre-cuts in the set—in this case the slices would have a thickness corresponding to the spacing between each plane.

The partial pre-cuts sever a substantial amount of the material in the plane being cut, leaving one or more relatively narrow pieces of material attaching the portion to the body (i.e. a gap), the relatively narrow piece of material thus forming the frangible region. It is desirable that the partial pre-cuts define a repeating pattern of severed regions with intervening frangible regions, i.e. perforation. The severed regions may have a width of from 10 mm to 30 mm, preferably from 15 mm to 25 mm, and optionally from 16 to 22 mm, especially around 18 mm, and that the remaining frangible regions have a width of from 1 mm to 5 mm, preferably 1 to 3 mm, especially around 2 mm.

In another way of considering the spacing and size of the individual partial pre-cuts, typically the ratio of length of severed material to remaining material will be around 3 to 1 or higher (e.g. 15 mm severed and 5 mm remaining, or a ratio equivalent thereof), preferably 6 to 1 or higher (e.g. 18 mm severed and 3 mm remaining, or a ratio equivalent thereof), especially 9 to 1 or higher (e.g. 18 mm severed and 2 mm remaining, or a ratio equivalent thereof).

In a particularly preferred embodiment the pre-cut severs from 15 to 19 mm and leaves a frangible region of from 1 to 5 mm, preferably 17 to 19 mm and leaves a frangible region of from 1 to 3 mm, and especially approximately 18 mm leaving a frangible region of approximately 2 mm width.

Conveniently such a cut can be made using a die cutting apparatus comprising an array of a set of parallel planar blades, the set comprising a plurality of series of blades arranged in a plane, each blade having a width corresponding to the width of the region to be severed, and a spacing between the adjacent blades within a series corresponding to the width of the frangible region. The spacing between each planar series of blades defines the thickness of the frangible portion.

In certain embodiments, the cuts may be made using a laser to ablate materials in the area of a cut. In some embodiments, a high pressure water jet may be used to ablate materials in the areas of a cut. Laser and/or high pressure water jet ablation allow for high cutting accuracy in 3 dimension when controlled via computer numerical control (CNC) drivers.

Thus, in any embodiments of the present disclosure, the wound packing material can comprise partial pre-cuts formed by die-cutting. Alternative methods of forming the partial pre-cuts such as laser cutting or high pressure fluid cutting might be used as alternatives to die-cutting.

In some embodiments, it is preferred that the body comprises a second set of parallel planar partial pre-cuts in a second orientation. Again, it is preferred that the partial pre-cuts are regularly spaced, and the dimensions set out above in relation to the first set of partial parallel planar pre-cuts are equally applicable to the second set.

The second set of partial pre-cuts may also be made by die cutting.

The second set may suitably be provided at a second orientation which is substantially perpendicular to the first orientation, i.e. where the first second sets of pre-cuts intersect, it will be substantially at a right angle. The pre-cuts of the first and second sets could thus be said to lie on nominal X and Y planes respectively.

It will be apparent that where two sets of pre-cuts are provided, the selectively removable portions will typically be smaller than where one set of partial pre-cuts is provided, i.e. the second set will sub-divide the portions formed by the first set. Thus it could be said that the body has a higher volumetric resolution in that it is split into finer units.

Generally the shape of portion provided when a first and second set of partial pre-cuts is used will be substantially a cuboid, the width and breadth of which is defined by the spacing of the planes in each of the partial pre-cuts, the length being defined by the relative dimension of the body in a nominal Z plane. This applies for flat planar pre-cuts; where non-flat planar cuts are provided, such regular shapes will not be provided.

In some embodiments, it is preferred that the body comprises a third set of parallel planar partial pre-cuts in a third orientation. Again, it is preferred that the pre-cuts are regularly spaced, and the dimensions set out above in relation to the first and second sets of partial pre-cuts are equally applicable to the third set.

The third set may suitably be provided at a third orientation which is substantially perpendicular to both the first and second set of pre-cuts. Thus it could be said that the third set of pre-cuts lies on the Z plane, relative to the X and Y planes of the first and second sets respectively. Where three such sets are provided, the resultant selectively removable portions will be generally cuboids. Where the spacing between the planar partial pre-cuts are the same in each of the three sets, the resultant selectively removable portions will be substantially cubic.

It is of course possible to provide more than three sets of partial pre-cuts, and vary the angles between the pre-cuts to increase resolution and provide for a greater control over the shape and size of the selectively removable portions. However, where more than three sets are provided, the engineering difficulties in terms of physically forming the pre-cuts and also in retaining the general structural integrity of the body become considerable. In fact, even providing three sets of cuts in the X, Y and Z planes (i.e. a 3D pre-cut body) is somewhat difficult to achieve, and, in some embodiments, it is a significant aspect that this has made possible. For example, if the pre-cuts are not performed correctly, the pre-cut body will simply fall apart and be unsuitable for treating a wound.

As mentioned above, the spacing of the parallel planar partial pre-cuts, in particular the spacing between each pre-cut plane, dictates the size and shape of the selectively removable portions. A spacing of 20 mm, for example, in all 3 sets of a 3D pre-cut body provides for portions which are cubes of approximately 20 mm in each dimension. This allows a medical practitioner to remove cube shaped portions of foam to shape the body to the desired shape for wound packing, and to achieve a fit to the shape of the wound to within 20 mm. Alternatively, blocks of 20×20×10 mm may be a suitable shape allowing increased resolution in dimension, but retaining a relatively manageable number of portions. It is, of course, generally desirable to allow the medical practitioner to shape the body of wound packing material as closely as possible to the desired shape for wound packing, but this must be balanced against the need for ease of manufacture and simplicity of handling. It has been found that such a balance can be achieved using dimensions of from 10 to 20 mm for the removable portions.

It should be pointed out that in certain instances it may be sufficient to have the ability to remove portions to achieve a far less precise shape of body of wound packing material. In such situations a body comprising three sets of pre-cuts may not be required, and a body comprising one or two sets of parallel planar partial pre-cuts may provide sufficient scope for customisation of shape.

Some embodiments are configured to provide a wound packing material which is highly customisable, and that a body comprising three or more sets of parallel planar partial pre-cuts is generally preferred.

Accordingly, some embodiments provide a wound packing material comprising a body of a porous material, the body comprising frangible regions defining a plurality of selectively removable cuboidal portions, the frangible regions being defined by partial pre-cuts provided in the body of the body.

Preferably the body is entirely comprised of selectively removable cuboidal portions interconnected by frangible regions, each of the edges of the cuboids being 5 to 30 mm, preferably from 10 to 24 mm, especially from 10 to 20 mm.

More preferably the cuboidal portions are cubic and have an edge length of from 5 to 30 mm, preferably from 10 to 24 mm, especially from 10 to 20 mm.

In some embodiments, the body is generally cuboidal in shape, prior to the removal of any selectively removable portions. The body may suitably be a cube, or it may be a rectangular cuboid or square cuboid. Various shapes of body may be useful for different wound shapes and sizes. Typically NPWT foam is provided as a rectangular cuboid of approximate dimensions 200×100×30 mm, and this is a suitable shape for the body of the present disclosure. For such a shape and size, portions of approximately 20×20×10 mm are very suitable to allow customisation of shape.

A further aspect the present disclosure provides a method of manufacture of a wound packing material, the method comprising the steps of:

providing a body of a porous wound packing material;

forming at least one partial pre-cut in a first orientation in said body, said at least one partial pre-cut severing regions of the body to leave frangible regions of the body, the frangible regions allowing the portions to be selectively removed from the body.

Preferably the at least one partial pre-cut is a parallel planar partial pre-cut.

Preferably the at least one partial pre-cut is formed by die cutting.

The die cutting may involve providing at least one blade and pushing said blade through the body to cut a region of the body and leave at least one frangible region. In some embodiments, the cutting may be performed via laser and/or waterjet cutting to cut a region of the body and leave behind at least one frangible region.

It is preferred that the die cutting involves providing a plurality of blades in a suitable arrangement to provide desired partial pre-cuts and frangible regions. Dimensions and other details of the partial pre-cuts are set out above.

The blades may have a length great enough to pass completely through the body. It should be noted that the body may be compressed as it is cut, and therefore the blades need only be long enough to pass completely through the body as it is compressed in the cutting process. Alternatively the blades may be shorter where it is not desirable to cut all the way through the body, or where cuts from two sides will be made to cut completely through the body; in the latter case the blades will generally have a length of approximately half of the relevant dimension of the compressed body to be cut.

The blades may suitably be arranged as an array of a set of parallel planar flat blades, the set comprising a plurality of series of individual flat blades arranged in a plane, each individual flat blade having a width corresponding to the width of the region to be severed, and a gap between the individual flat blades corresponding to the width of the frangible region. Suitable details of the blades are set out above.

The method may involve the step of forming a second partial pre-cut in a second orientation, especially a second set of partial pre-cuts as discussed above. Preferably the second orientation is perpendicular to the first orientation. Preferably the second partial pre-cut is a parallel planar partial pre-cut.

The method may involve the step of forming a third partial pre-cut in a third orientation, especially a third set of partial pre-cuts as discussed above. Preferably the third orientation is perpendicular to the first and second orientations. Preferably the third partial pre-cut is a parallel partial planar pre-cut.

Thus the method may involve providing three partial pre-cuts in nominal X, Y and Z planes. Suitably the X, Y and Z planes are congruent with the faces of the body, where the body is a cuboid.

The method may involve forming partial pre-cuts to define a plurality of regularly shaped and sized cuboidal portions interconnected by frangible regions. Suitably the entire body is formed of selectively removable cuboidal portions. Suitably the cuboidal portions are cubes.

In certain embodiments two or more sets of pre-cuts can be made simultaneously. This can be suitably carried out using a single array of blades comprising two sets of blades in two orientations, e.g. an array of cruciform blades.

Where there is a risk of excessive distortion to the body during the cutting process it is useful to support the foam structure during the cutting process.

A further aspect of the present disclosure relates to a method of preparing a wound packing material comprising the steps of:
providing a wound packing material as set out above; and
removing portions of the body of said would packing material such that the body is a desirable shape, wherein the desirable shape can partially or fully surround a second wound filler or packing member which can be more rigid in a vertical direction than a lateral direction, the vertical direction being approximately perpendicular to the wound surface.

Preferably the body is shaped to approximately fit the shape of a wound to be packed.

Preferably the portions are removed manually, i.e. without the use of tools.

A further aspect the present disclosure provides a method of treating a wound comprising the steps of;
providing a wound packing material as set out above;
removing portions of the body of said would packing material such that the body is a desirable shape to fit within said wound; and
packing the wound with said wound packing material.

Preferably the method provides the step of applying a negative pressure to the wound through the wound packing material, i.e. the method is NPWT. In general this can be achieved by providing a substantially fluid impermeable sheet over the wound and wound dressing, thus defining a sealed volume, and applying a negative pressure inside said sealed volume. The seal need not be completely hermetic, but should be sufficient to allow a suitable negative pressure to be sustained. The source of negative pressure, e.g. a pipe form a vacuum pump, is provided at a position such that it draws fluids from the wound bed through the wound packing material.

The negative pressure may be in the range of from 80 to 125 mm Hg below ambient atmospheric pressure.

A further aspect the present disclosure provides the use of a wound packing material as set out above in wound treatment, especially NPWT.

In some embodiments, a wound treatment apparatus comprises:
a body of a porous material, the body comprising frangible regions defining a plurality of portions, the frangible regions allowing the portions to be selectively removed from the body so as to form a recess in the body, the recess being bound by a bottom surface and a wall portion; and a secondary wound filler for positioning within the recess in the body.

In certain embodiments, the portions may be removed manually. In some embodiments, the frangible regions may be defined by pre-cuts formed in the body. The pre-cuts may be parallel and/or may be defined by a first set of parallel pre-cuts formed in the body. The frangible regions can further be defined by a second set of parallel pre-cuts formed in the body. The frangible regions may further be defined by a third set of parallel pre-cuts formed in the body.

In embodiments, the pre-cuts are formed via laser ablation and/or via waterjet ablation. In particular embodiments, the pre-cuts may be formed via die-cutting.

The body of porous material may be formed from a wound packing foam. The body can comprise a bottom portion, the bottom portion comprising a non-frangible section of porous material. The bottom portion may be 5-20 mm thick.

A wound cover may be positioned over the body and over the wound closure device and sealed to skin surrounding a wound. In some embodiments, a source of negative pressure may be connected.

In certain embodiments, the body of porous material may comprise a bowl shaped recess. In some embodiments, the body of porous material may have a cubic shape.

In some embodiments, a method of treating a wound, comprises:

providing a body of porous material, wherein the body comprises frangible regions;

removing portions of the porous body such that the body is a desirable shape to fit within a wound;

removing portions of the body to create a recess configured to receive a secondary wound filler; and placing the secondary wound filler within the recess.

In certain embodiments, the method may further comprise positioning the body and the wound closure device within a wound, and covering the body and the secondary wound filler with a wound cover. The method may further comprise applying negative pressure to the wound through the wound cover, the secondary wound filler and the body.

Other embodiments of wound closure devices, stabilizing structures and associated apparatuses are described below.

BRIEF DESCRIPTION OF THE DRAWINGS

Embodiments of the present disclosure will now be described, by way of example only, with reference to the accompanying drawings, in which:

FIGS. 11A-D illustrate different views of embodiments of a wound closure device comprising a stabilizing structure.

FIGS. 16A-E illustrate additional embodiments of a wound closure device comprising a stabilizing structure.

FIGS. 38A-G illustrate multiple views of an embodiment of a stabilizing structure.

FIGS. 46A-C illustrate multiple embodiments of a stabilizing structure.

DETAILED DESCRIPTION OF THE PREFERRED EMBODIMENTS

Figure 1:
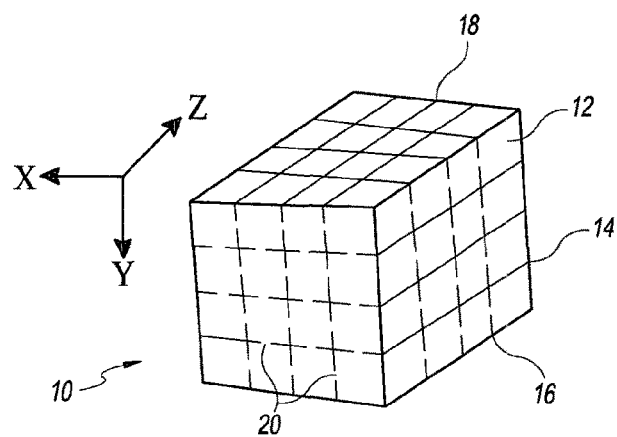
FIG. 1 illustrates an embodiment of a body of porous wound packing material after being pre-cut in the x, y and z dimensions.

Some of the embodiments disclosed herein relate to apparatuses and methods of treating a wound with reduced pressure, including pump and wound dressing components and apparatuses. Generally, the embodiments including the wound fillers described herein may be used in combination with a negative pressure system comprising a drape or wound cover placed over the filler. A vacuum source, such as a pump, may be connected to the cover, for example, through one or more tubes connected to an aperture or port made in or under the cover. The apparatuses and components comprising the wound overlay and packing materials, if any, are sometimes collectively referred to herein as dressings. Further details of methods and apparatuses, such as dressing components and inflatable bladders, as well as any of the wound packing or support members disclosed therein that are, for example, more rigid in a vertical or perpendicular direction relative to the wound than in a lateral direction of the wound, so as to support a drape above the wound without substantially inhibiting the closing forces applied to the wound, are found in the following application, which is hereby incorporated by reference in its entirety: U.S. patent application Ser. No. 13/365,615, titled "Negative Pressure Wound Closure Device," filed Feb. 3, 2012, published as US 2012/0209227.

It will be appreciated that throughout this specification reference is made to a wound or wounds. It is to be understood that the term wound is to be broadly construed and encompasses open and closed wounds in which skin is torn, cut or punctured, or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. Further examples include abdominal wounds or other large or incisional wounds, either as a result of surgery, trauma, sterniotomies, fasciotomies, or other conditions. In some embodiments, the components of the negative pressure treatment system described herein can be particularly suited for incisional wounds that exude a small amount of wound exudate. Thus, while some embodiments and methods disclosed herein are described in the context of treating abdominal wounds, the apparatuses and methods disclosed herein are applicable to any wound in a body.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). Unless stated otherwise, the term approximately is meant to represent a range of +/−10% of the stated value.

The negative pressure range for some embodiments of the present disclosure can be approximately −80 mmHg, or between about −10 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas. In some embodiments of wound closure devices described in this specification, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "Wound treatment apparatus and method," filed Oct. 26, 2007, published as US 2009/0306609; and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227. Further, any of the embodiments disclosed herein may be used without the application of reduced or negative pressure.

It should be noted that throughout this specification reference is often made to: a cut, cuts, cutting, and pre-cuts. It will be understood by one of ordinary skill in the art that the cuts may be generated by a variety of means. For example, the cuts may be made via a blade, via chemical treatment, via a laser, via a cutting waterjet, or via other suitable means. Thus, when reference is made to a "cut" and/or "cutting" the means by which the cut is made can include all of the aforementioned methods. Consequently, one of ordinary skill in the art will understand that even when mention is made to cutting via blades in one embodiment, the cut may also be made by any other means described herein this section or elsewhere in the specification.

Frangible Wound Fillers of FIGS. 1-7

As shown in FIG. 1, a body 10 of porous material, such as foam, is generally a cube in shape having three dimensions, x, y and z. The porous material is suitable for wound packing and may be constructed from any of the materials described herein this section or elsewhere in the specification. For example, the material may be reticulated polyurethane foam with very high free internal volume. The body 10 could be a different shape, e.g. a comparatively flat cuboid, which is a conventional shape for foams for NPWT.

Figure 2:
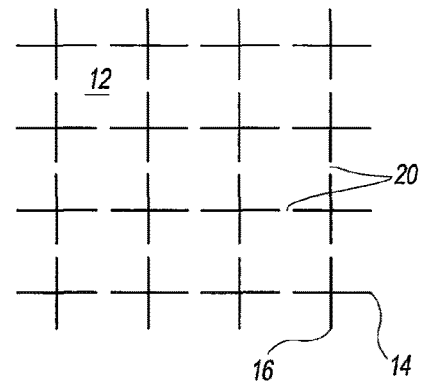
FIG. 2 schematically illustrates an embodiment of a set of pre-cuts in the x and y dimension.
Figure 3:
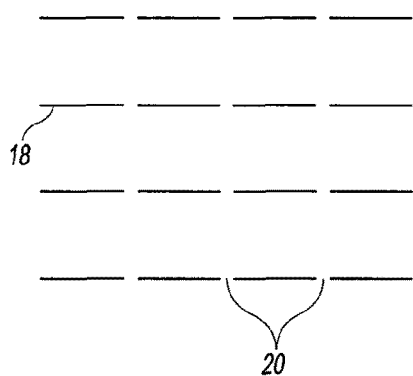
FIG. 3 schematically illustrates embodiments of sets of pre-cuts in the z dimension.

As shown in FIG. 2, the body 10 is partially pre-cut by a suitable cutting technique, such as die cutting (though other techniques may be useable), to define a first and second set of parallel planar partial pre-cuts 14, 16. The body 10 may also be partially pre-cut in another dimension to define a third set of parallel planar partial pre-cuts 18. The three sets of partial pre-cuts 14, 16, 18 define individual cubic portions 12 of approximately equal volume. For example, as depicted in FIG. 2, the first cut 14 may be in the xz plane, while a second cut 16 may be in the xy plane, with a third possible cut 18 in the yz plane.

The three sets of partial pre-cuts 14, 16, 18 are intermittent, the gaps in the pre-cuts defining frangible regions 20 on each internal face of each portion 12 (in other words they are perforated for easy removal of the portions). The frangible regions 20 connect adjacent portions 12 together thereby to ensure the portions 12 remain connected together when the body 10 is stored, compressed or extended, i.e. when being used as a wound packing in NPWT.

The frangible regions 20 extend between face sides of each portion 12 and are elongate. The thickness of each frangible region 20 is suitable to provide adequate strength to ensure adjacent portions 12 remain connected when the body 10 is being compressed or extended during normal use, whilst allowing one or more portions 12 to be easily pulled from the body 10 by compromising the integrity of the frangible regions 20 attaching the portion 12 to the body. For typical NPWT foams, a frangible region of approximately 2 mm of thickness provides a good compromise of strength versus tearability.

One or more portions 12 can be selectively removed by hand from the body 10 to shape the body 10 for a particular wound packing application. Advantageously, cutting tools such as knives, scalpels and scissors are not required to shape the body 10 of porous material.

Figure 4:
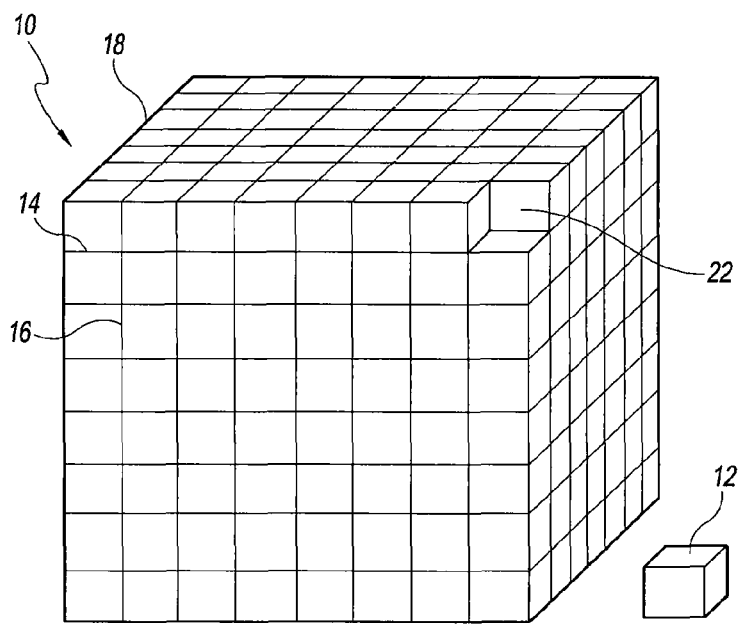
FIG. 4 illustrates an embodiment of a body with a single portion removed.
Figure 5:
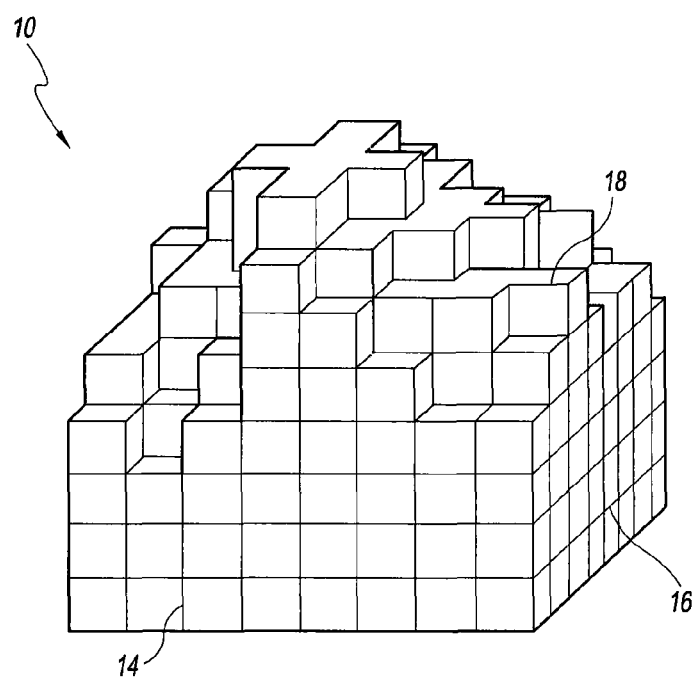
FIG. 5 illustrates an embodiment of FIG. 4 with a plurality of portions removed.
Figure 6:
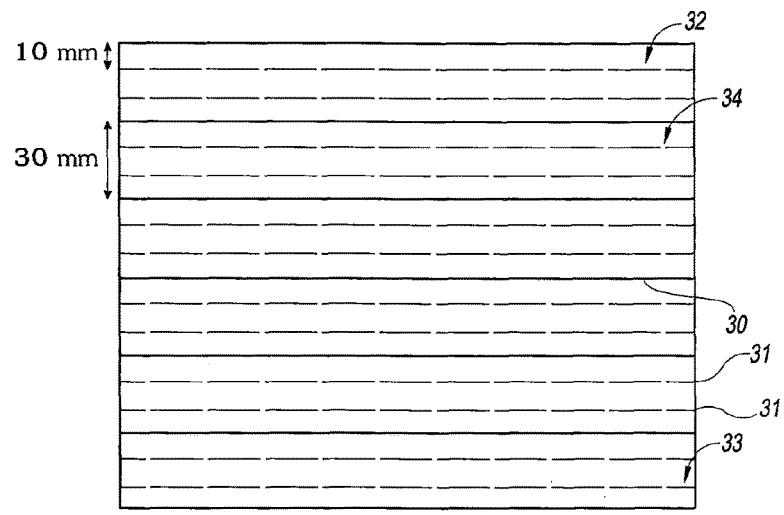
FIG. 6 illustrates an embodiment of a first array of a set of blades suitable for forming a partial pre-cut in a first orientation in a body of wound packing material.

As shown in FIGS. 4 and 5, in one embodiment, the body 10 is a cube of volume 448000 mm$^3$, which is pre-cut in the x, y and z dimensions to define 448 (i.e. 7×8×8) equally sized 1000 mm$^3$ portions 12 (i.e. 10×10×10 mm). Adjacent portions 12 are connected by a frangible portion 20 of 2 mm thick porous material (not shown).

The frangible regions 20 ensure the body 10 retains its structural integrity for storage and handling purposes whilst allowing one or more portions 12 to be selectively removed therefrom. FIG. 4 shows a single portion 12 removed from the body 10 to leave a hole 22, whilst FIG. 5 shows a plurality of portions 12 removed from the body 10 to selectively shape the body 10 for a particular application of wound packing. The body 10 may be shaped to complement the external contours of a patient or to fit in a cavity.

Of course, the dimensions of the body 10 and the portions 12 may be different than those described above for a particular application and the number and orientation of partial pre-cuts lines 14, 16, 18 may be varied and may be planar or curved to define regular or irregular portions 12 accordingly.

To form a wound packing material similar to the above the following general process may be used. The present process describes a process for converting a single cuboid block of foam into 6 cuboidal wound packing material bodies. The block is initially approximately 200 mm by 100 mm by 180 mm and is cut into 6 blocks of 200 mm by 100 mm by 30 mm. It will be apparent that variations of this method could be used to manufacture wound packing materials of a great variety of different shapes and sizes, and having varying portion size and shapes.

A body of porous material is provided which has the dimensions set out above.

A first set of parallel planar partial pre-cuts is made in the body using an array of blades 30. The pre-cuts are made perpendicular to, and into, a first face of the body The array (FIG. 6) comprises a number of planes 31 made up of a series of 18 mm wide flat blades 32, and a 9 mm blade 33 at each end of the plane; a gap of 2 mm is provided between each blade in the series. A gap of 10 mm is left between each plane of blades. The array also comprises 5 continuous 100 mm long planar blades 36 which acts to cut the initial block completely into 6 smaller blocks.

The first set of partial pre-cuts is achieved by placing the block of foam against the array of blades 30 and urging the blades into and through the block. The pressure required may be generated by a hydraulic press (also known as a clicker press). This is a conventional form of die cutting and the necessary apparatus and techniques are well known to one skilled in the art.

Figure 7:
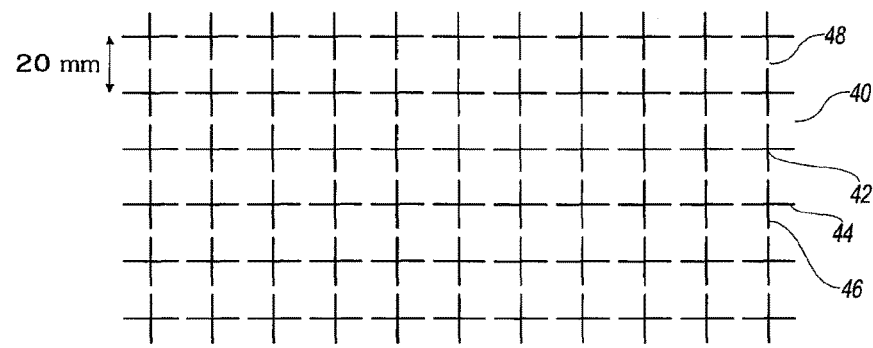
FIG. 7 illustrates an embodiment of a second array of sets of blades suitable for making second and third sets of partial pre-cuts in a body of wound packing material in second and third orientations.

Second and third sets of partial pre-cuts are made using a second array 40 of blades (see FIG. 7). In the second array a plurality of cruciform blades 42 are provided. Due to the shape and arrangement of the blades 42, the array is suitable to make two sets of parallel planar partial pre-cuts in two orientations, which are perpendicular to each other. Thus, in one cutting action, two sets of parallel planar partial pre-cuts are made. Each cruciform blade 42 comprises two 18 mm long linear blade elements 44,46 intercepting at each of their midpoints at a right angle to define the cruciform blade.

The cruciform blades are arranged in the array to form a square matrix with gaps of 2 mm provided between each cruciform blade. As with the first cut, the second cut is made by applying pressure to drive the blades 42 through the body. The length of the blades in the first and second array are sufficient to pass completely through the body and emerge at the other side.

This process forms 6 cuboids of foam measuring 200 mm×100 mm×30 mm, which are each formed of cuboids measuring approximately 20 mm×20 mm×10 mm, each of the cuboid portions being interconnected with adjacent portions by frangible regions of approximately 2 mm thickness.

It should be noted that where a generally cubic body of foam is being prepared the order of the cuts is not particularly significant as the cube is equally structurally stable in all 3 dimensions. However, when preparing a body with a relatively thin minor dimension, as set out in the method above, it is important that the first cut made is the one perpendicular to the plane of the thin dimension (i.e. the smallest face of the cuboid), or that the shape of the block is supported as the cut is made. If the order is reversed, or the block shape is not supported, there is generally an unacceptable amount of crushing and/or corrugation of the body resulting in a significant distortion to the desired cut geometry.

The result of this process is a wound packing material which can be custom shaped by manually removing cuboid portions by tearing the frangible regions interconnecting the portions making up the body. This allows a medical practitioner to shape the body of wound packing material to fit the wound to be packed or dressed. Once the wound packing material has been shaped appropriately, the wound can be dressed for NPWT.

Wound Fillers and Treatment Apparatuses of FIGS. 8A-10.

Any of the foregoing embodiments, or any other embodiments disclosed herein (including those incorporated by reference) can be configured such that a user or medical practitioner can remove portions of the porous body to create a recess within the porous body that can be used to partially or fully surround a perimeter of any additional wound filler, wound packing member, wound support member, stabilizing structure, and/or wound closure device. All of the aforementioned structures that may be positioned within the recess of the porous body are generally referred to herein as "secondary wound fillers." In some embodiments, wound closure devices positioned in the recess of the porous body comprise stabilizing structures that are configured to collapse more significantly in one direction compared to another direction when subjected to negative pressure. Further details regarding the stabilizing structures and wound closure devices to be used in combination with the embodiments of FIGS. 1-10 are described below in relation to FIGS. 11A-49F. Examples of stabilizing structures and wound closure devices that can be used with any of the wound fillers or foam bodies of any of the embodiments disclosed herein may be found in U.S. application Ser. No. 13/365,615 and PCT Application No. PCT/US2013/050698, both incorporated by reference above.

Additionally, in any embodiment, any stabilizing structure or secondary wound filler can be positioned within any of the recesses or pockets/pouches formed in the frangible wound filler to help contain or encapsulate the stabilizing structure or secondary wound filler. This can be useful for secondary wound fillers, such as 3-D knitted fabrics, super absorbers, gauze, or other materials that tend to stray or shed, that make have compromised structural integrity or which may shed fibers or otherwise into the wound. By partially or fully surrounding at least a perimeter of such secondary wound fillers, any such fibers or shed material can be prevented from contaminating the wound.

Advantageously, if the secondary wound filler, for example the stabilizing structures and wound closure devices described herein this section and elsewhere in the specification, comprises sharp or undesirable edges, the surrounding wound packing material will prevent damage to the surrounding tissue. Consequently, materials that would otherwise be discarded due to concerns regarding damage to the surrounding tissue may instead be used in combination with the surrounding wound filler.

In any embodiments, an outside perimeter of the frangible wound filler can be modified by removing the removable filler elements from an outside portion of the frangible wound filler. Additionally or alternatively, in any embodiments disclosed herein, an inside contour of the frangible wound filler can be modified by removing the removable filler elements from an inside portion of the frangible wound filler. In some embodiments, a portion or a layer of non-frangible material can be positioned between any number of removable elements to provide structural robustness and/or integrity to the frangible wound filler. For example, a bottom layer or a top layer that is not slit or frangible can be integrally formed with portions that are frangible or removable. The depth of the slits in any embodiments can be controlled by limiting the depth of any cutting tools, such as cutting knives, used to form the foam body.

In some embodiments, a bottom portion of the frangible wound filler may remain uncut and non-frangible by limiting the depth of cutting. For example, at most around 5 mm of wound filler may remain uncut, at most 10 mm, at most 15 mm, at most 20 mm, at most 25 mm, or more than 25 mm. The bottom uncut portion of the frangible wound filler may be of the same material as the remainder of the frangible wound filler.

In any of these and other arrangements, therefore, the medical practitioner can create any desired shape of a wound filler on an inside and/or an outside portion of the wound filler. Therefore, oblong shapes such as oval-shaped, circular shapes, triangular shapes, extended oval-shaped wherein the length is significantly greater than a with, or any other irregular shape can be formed by removing portions of the wound filler or foam body.

Additionally, any of the foam bodies or wound fillers (collectively referred to herein as wound fillers) disclosed herein can be configured such that a user or medical practitioner can remove portions of the foam or porous material so as to create a pouch or pocket that can nearly or completely surround a wound support member. Additionally, any of the embodiments disclosed herein can have a combination of non-frangible portions or layers and frangible portions or layers. In any of the embodiments disclosed herein, a secondary wound filler or stabilizing structure can be positioned within the recess or the pouch formed in the wound filler or foam body.

Figure 8A:
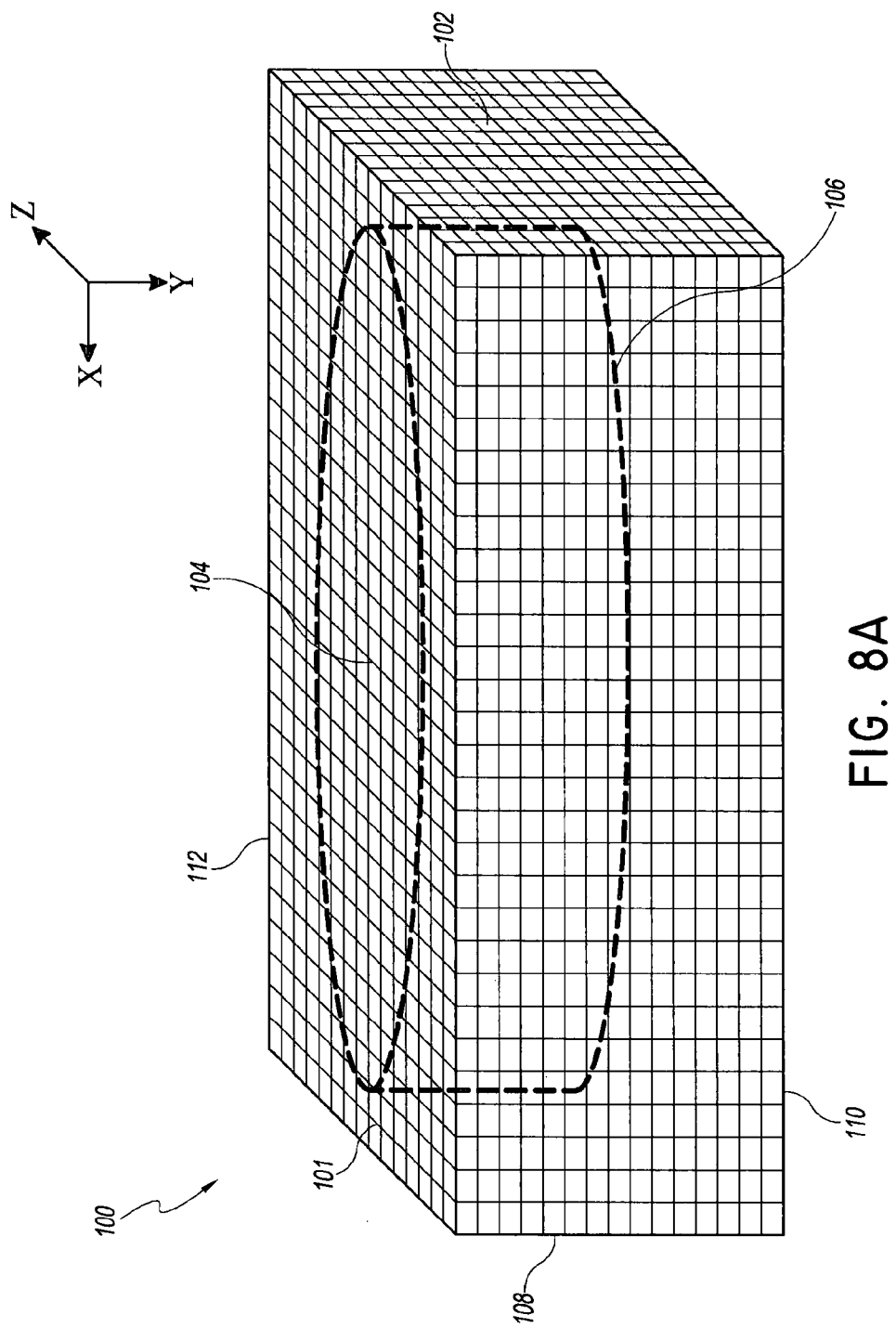
FIGS. 8A-C illustrate embodiments of a porous wound packing material with cuts for a bowl.
Figure 8B:
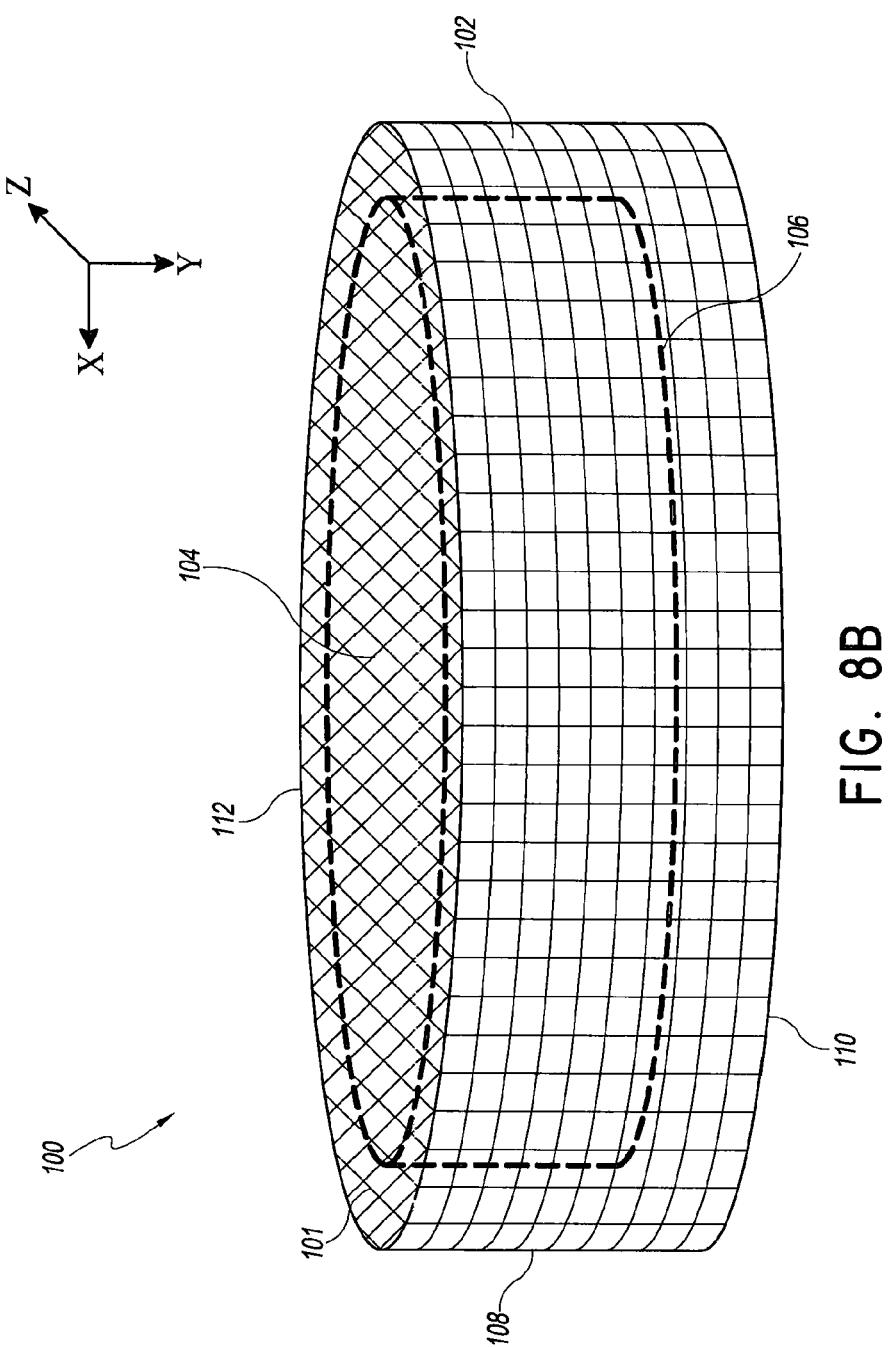
Figure 8C:
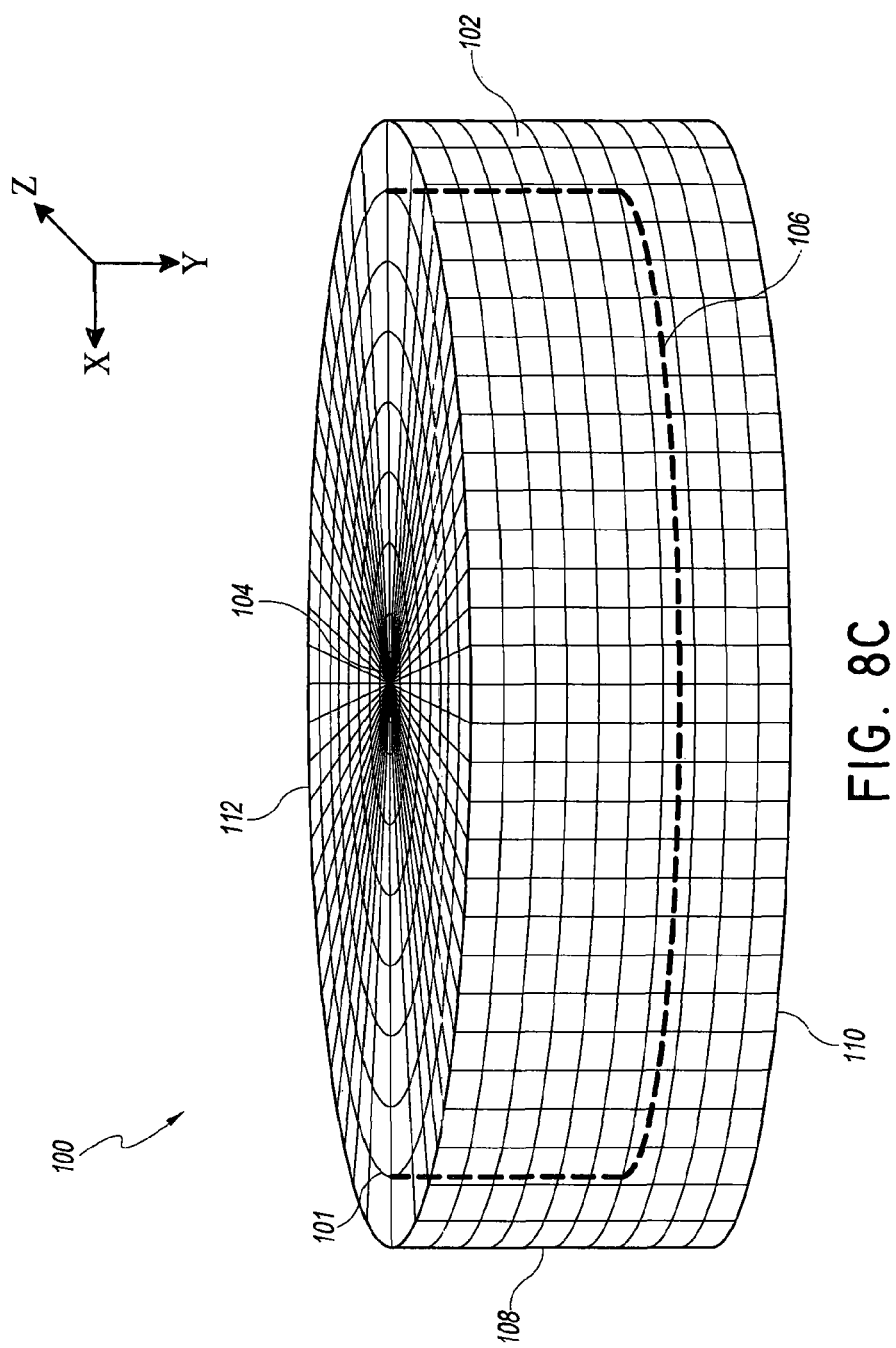

For example, as shown in FIGS. 8A-C, a body 100 of porous material, which can be formed from any of the materials such as the foam materials disclosed herein, can have any desired shape having three dimensions, x, y and z. As depicted in FIG. 8A, in certain embodiments, the body 100 may have a cuboidal shape with straight cuts 101. FIG. 8B depicts an oval-shaped body having an approximately rounded perimeter and something of a planar bottom surface and a planar top surface. The embodiment of FIG. 8B may have straight cuts 101 much like those depicted in FIG. 8A. As shown in FIG. 8C, in embodiments, the shape may have elliptical and/or concentric cuts 101. As described elsewhere, the porous material is suitable for wound packing. Again, the body 100 can be formed from any suitable material, such as reticulated polyurethane foam of very high free internal volume. Some embodiments may call for the use of polyvinyl alcohol (PVA) foam as this type of foam may have a low internal free volume and be advantageous for use in wounds with exposed bone and tendon. Preferably, the density of PVA foam may be between 40-70 kg/m$^3$. One of skill in the art will recognize that standard foams used in NPWT are typically in the range of 23 kg/m$^3$.

As depicted in FIGS. 8A-C, the body 100 can have a plurality of frangible or removable elements 102 defined by the cuts 101 to form a recess portion 104 by the user. The dotted lines of FIGS. 8A-C are an approximate representation of a possible embodiment of the shape of a recess, although in practice the recess may be slightly more cuboid-shaped. The user can form the recess 104, or the recess can be preformed in the body 100. The recess 104 can have a bottom surface 106 configured to support a secondary wound filler element. The body can define a wall portion or perimeter portion 108, a bottom layer or portion 110, and a top layer or portion 112. In any embodiments disclosed herein, including without limitation embodiment 100, a portion of the wall portion 108, the bottom portion 110, and/or the top portion 112 can have a combination of frangible and nonfrangible elements or layers to provide additional support to the body.

It will be understood by one of skill in the art that the number of frangible portions depicted in FIGS. 8A-C is non-limiting. In some embodiments, additional frangible portions may surround the recess, allowing for many possible shapes and sizes for the recess and for the outer shape of the body 100.

Figure 9A:
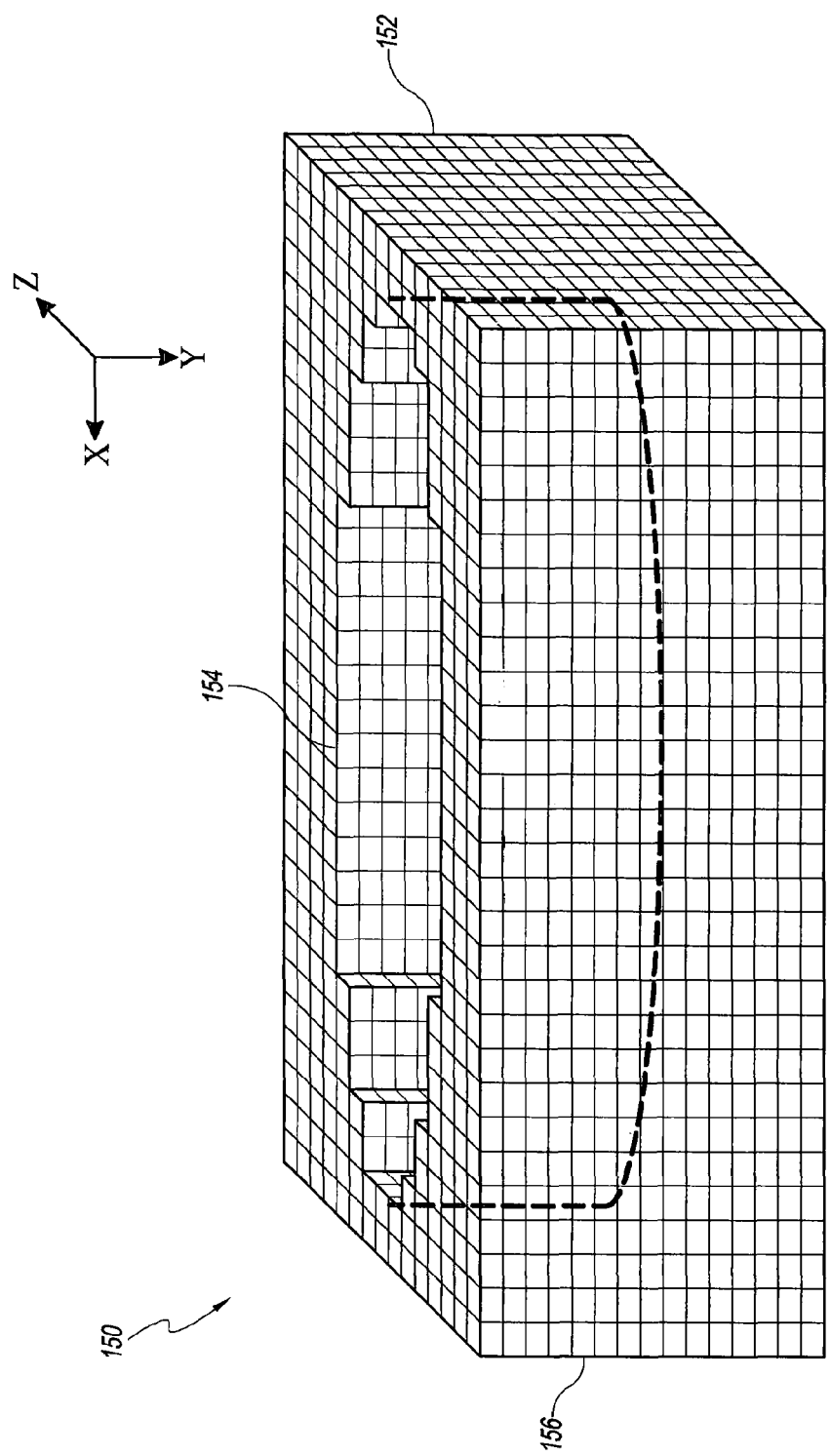
FIGS. 9A-C illustrate embodiments of a porous wound packing material with an open bowl central portion.
Figure 9B:
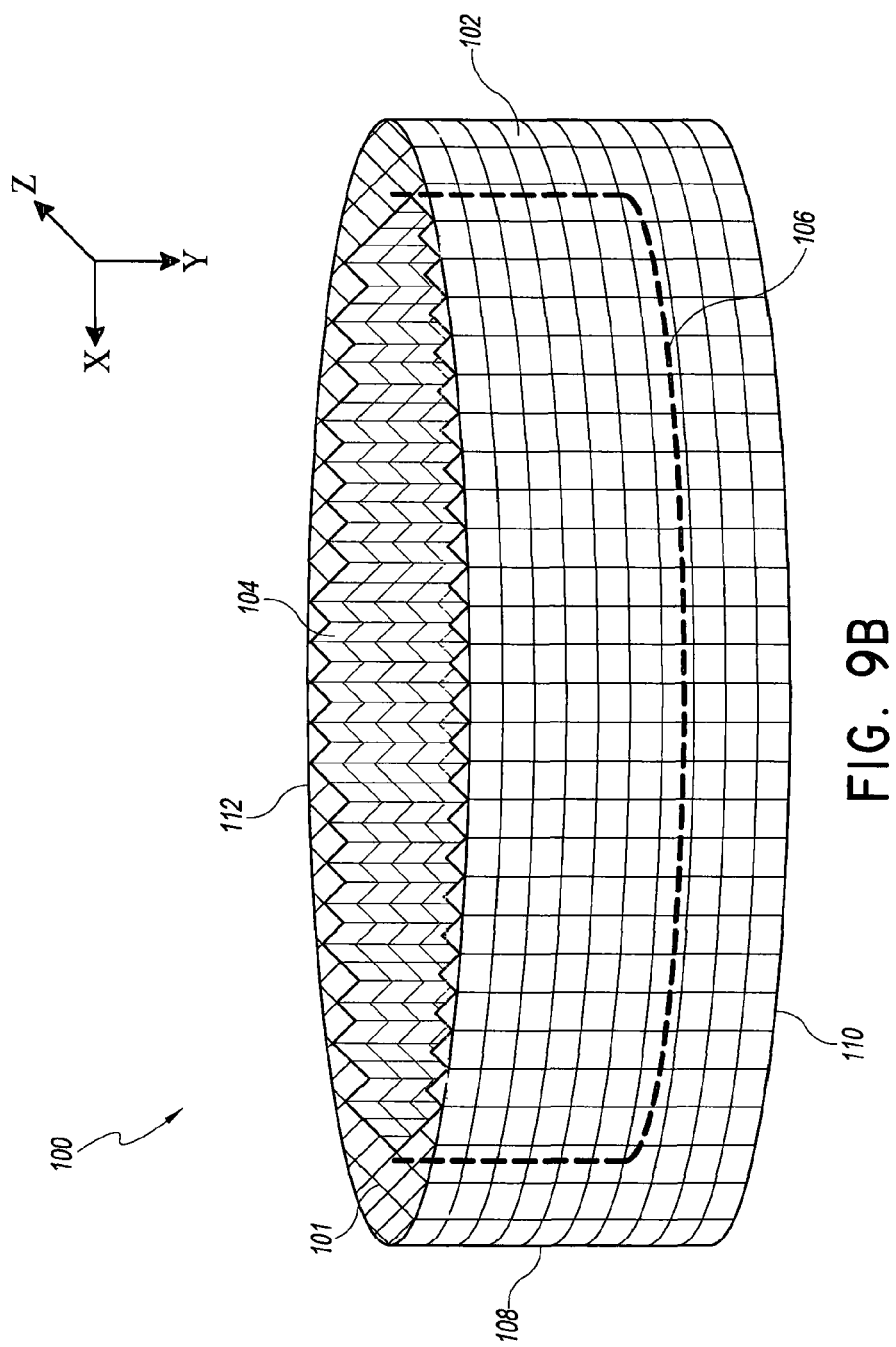
Figure 9C:
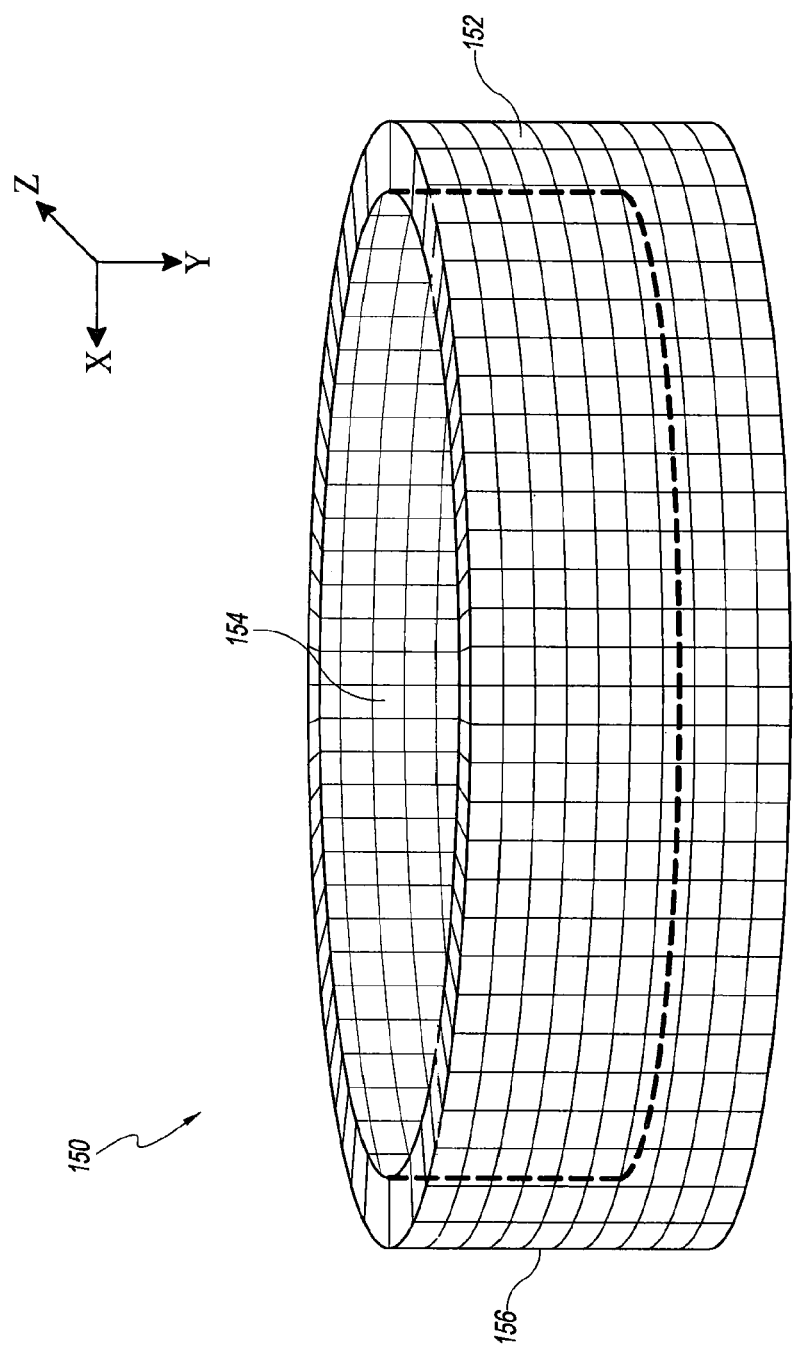

Additionally, with reference to FIGS. 9A-C, any embodiments disclosed herein can be configured such that the recess can be formed in an internal portion of the body. FIGS. 9A-C are similar to FIGS. 8A-C and illustrate a wound filler body 150 comprising a plurality of removable or frangible elements 152 and an opening 154 that can be preformed in the body 150 or formed by removing removable portions 152. The dotted lines of FIGS. 9A-C depict a possible embodiment of the shape of an opening or recess, although much like FIGS. 8A-C, these dotted lines are an approximate representation of a possible embodiment of the shape of a recess, which may be slightly more cuboid-shaped in practice. The opening or recess 154 can have an internal surface 156 therein configured to support a secondary wound filler such as a stabilizing structure or wound closure device such as those disclosed herein this section or elsewhere in the specification, particularly as depicted in FIGS. 11A-49F. As with any other embodiments disclosed herein, any portions of the inside surface of the body and/or the outside surface of the body can have removable elements so as to permit a user to shape or contour such portions, and/or non-removable portions configured to provide support to the body.

Figure 10:
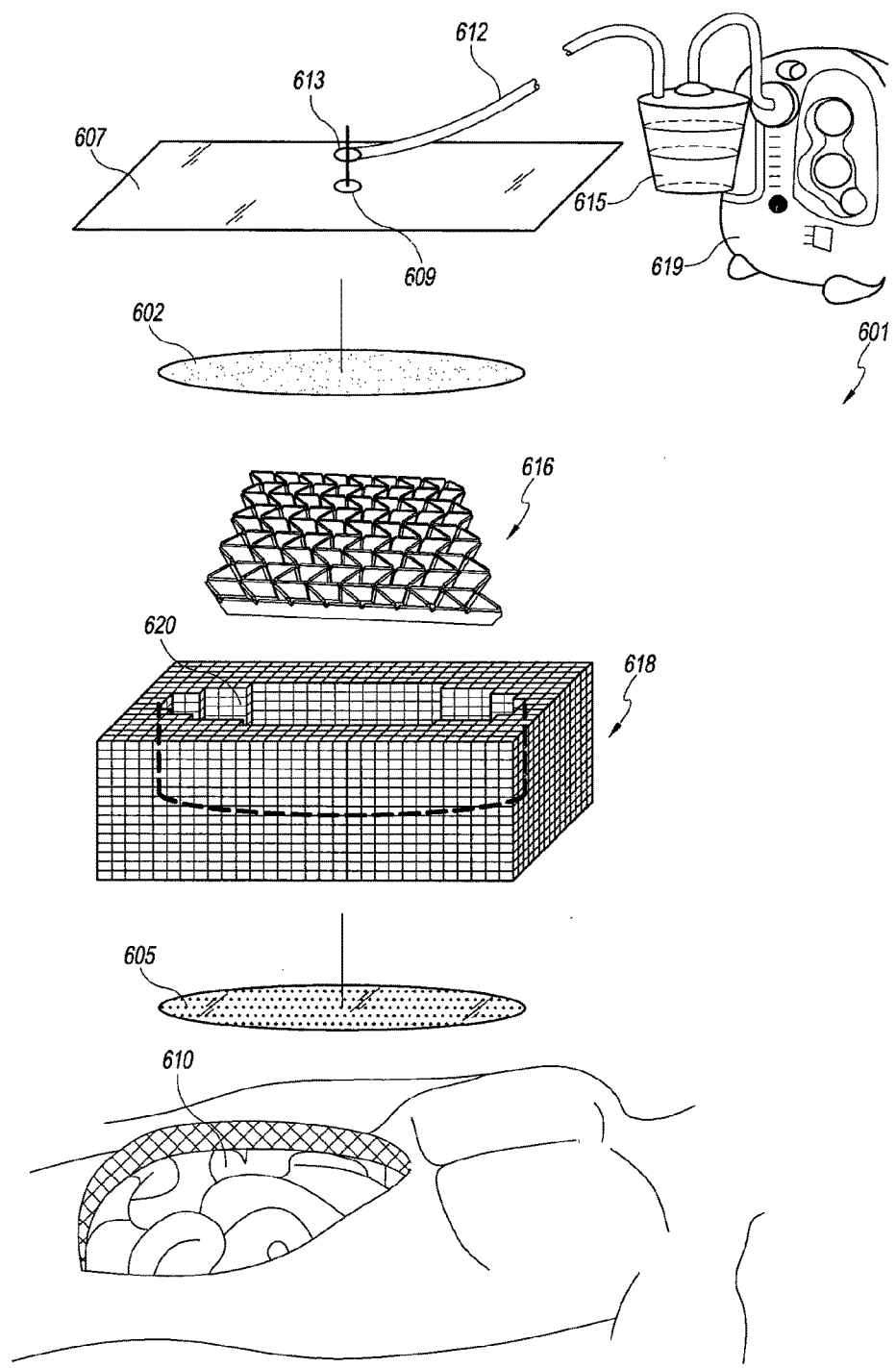
FIG. 10 illustrates an embodiment of a negative pressure treatment system with a porous wound packing material.

With reference to FIG. 10 (not drawn to scale), treatment of a wound with negative pressure in certain embodiments uses a negative pressure treatment system 601 as illustrated schematically here. The frangible fillers disclosed herein this section or elsewhere in the specification can be used in any wound. However, in the embodiment illustrated in FIG. 10, the wound filler body 618 is illustrated as being used to treat an abdominal wound. In this embodiment, a wound site 610, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 610 can be beneficial to a patient.

Accordingly, certain embodiments provide for an organ protection layer 605 which may be cut to size to be placed over the wound site 610. Preferably, the organ protection layer 605 can be a material which will not adhere to the wound site or the exposed viscera in close proximity. In one embodiment, the organ protection layer is permeable. For example, the organ protection layer 605 can be provided with openings, such as holes, slits, or channels, to allow the removal of fluids from the wound site 610 or the transmittal of negative pressure to the wound site 610. Additional embodiments of the organ protection layer 605 are described in further detail below.

Certain embodiments of the negative pressure treatment system 601 may also use one or more wound filler bodies 618 similar to the wound filler bodies depicted in relation to FIGS. 8A-9C configured to partially or completely surround a secondary wound filler, stabilizing structure and/or wound closure device 616, similar to those depicted in FIGS. 11A-49F. In certain embodiments, the stabilizing structure or wound closure device 616 may be of any of the embodiments disclosed herein this section or elsewhere in the specification.

The wound filler body 618, as discussed above, can be shaped and sized by removing any desired number of removable portions to fit within the wound and to surround the stabilizing structure or wound closure device 616. The wound filler body may be shaped to create a recess 620, as described above in relation to FIGS. 8A-9C. The recess may serve as a receptacle for the secondary wound filler 616. The secondary wound filler 616 may be placed into the wound filler body 618 before both are placed simultaneously into the wound. Alternatively, the body 618 may be placed in the wound first, followed by positioning of the secondary wound filler 616 in the recess 620 of the body 618.

Though not illustrated in FIG. 10, in certain embodiments, a foam layer can be disposed over the organ protection layer 605. Though not required, an additional foam layer 602 can be positioned over the frangible wound filler body 618 and the stabilizing structure and/or wound closure device. In other embodiments, one or both of the foam layers positioned above or below the frangible foam body 618 are optional, and may not be used at all. Additionally, the wound filler body 618 can have a frangible or non-frangible upper layer that is configured to cover an upper surface of the secondary wound filler 616.

The foam layer(s) above and/or below the wound filler body 618 can protect the wound cover and assist in fluid flow. In some embodiments, any of the foam layers or bodies can have a thickness of the range of, or wall portions having a thickness of the range of, approximately 10 mm, or approximately 1 mm to approximately 20 mm, for example between approximately 5 mm and approximately 15 mm.

A wound cover 607 is used to seal the wound site 610. The wound cover 607 can be at least partially liquid impermeable, such that at least a partial negative pressure may be maintained at the wound site. Suitable materials for the wound cover 607 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the wound cover may be hydrophobic or hydrophilic. Examples of suitable materials include Transeal® available from DeRoyal and Op Site® available from Smith & Nephew. In order to aid patient comfort and avoid skin maceration, the wound cover in certain embodiments are at least partly breathable, such that water vapor is able to pass through without remaining trapped under the dressing. An adhesive layer may be provided on at least a portion the underside of the wound cover 607 to secure the wound cover to the skin of the patient, although certain embodiments may instead use a separate adhesive or adhesive strip. Optionally, a release layer may be disposed over the adhesive layer to protect it prior to use and to facilitate handling the wound cover 607; in some embodiments, the release layer may be composed of multiple sections.

The negative pressure system 601 can be connected to a source of negative pressure, for example a pump 614. One example of a suitable pump is the Renasys EZ pump available from Smith & Nephew. The wound cover 607 may be connected to the source of negative pressure 614 via a conduit 612. The conduit 612 may be connected to a port 613 situated over an aperture 609 in the wound cover 607, or else the conduit 612 may be connected directly through the aperture 609 without the use of a port. In a further alternative, the conduit may pass underneath the wound cover and extend from a side of the wound cover. U.S. Pat. No. 7,524,315 discloses other similar aspects of negative pressure systems and is hereby incorporated by reference in its entirety and should be considered a part of this specification.

In many applications, a container or other storage unit 615 may be interposed between the source of negative pressure 614 and the conduit 612 so as to permit wound exudate and other fluids removed from the wound site to be stored without entering the source of negative pressure. Certain types of negative pressure sources—for example, peristaltic pumps—may also permit a container 615 to be placed after the pump 614. Some embodiments may also use a filter to prevent fluids, aerosols, and other microbial contaminants from leaving the container 615 and/or entering the source of negative pressure 614. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

In some embodiments, the secondary wound filler (illustrated by reference number 616 in FIG. 10) may include a material or materials that are more compressible in a horizontal plane than in a vertical dimension, as described in more detail in relation to FIGS. 11A-49F. Such materials may compress horizontally as negative pressure is applied to cause the wound edges to draw closer together, while maintaining relatively rigid to prevent vertical collapse of the wound cover 607 described below. In some embodiments, any of the secondary wound fillers disclosed herein this section or elsewhere in the specification can be used in the negative pressure wound therapy system illustrated in FIG. 10.

Any of the embodiments of the wound fillers disclosed herein can be made from any suitable type of material, including open celled foam, hydrophilic foam, hydrophobic foam, polyvinyl phones such as white polyvinyl alcohol foam, reticulated foam, or any combination of the foregoing. For example, the foam embodiments can comprise multiple layers of foam, wherein each layer can be made from any of the foregoing materials. Further examples of suitable materials and structures may be found herein this section or elsewhere in the specification.

Stabilizing Structures and Wound Closure Devices of FIGS. 11A-12E

As with the other stabilizing structures and wound closure devices described elsewhere in the specification, the stabilizing structures and wound closure devices of FIGS. 11A-12E may be incorporated into the wound packing and wound treatment apparatus embodiments described elsewhere in the specification, such as in relation to FIGS. 8A-10.

Embodiments of various stabilizing structures and wound closure devices will now be described. Any of these embodiments may be incorporated into the wound treatment system depicted in FIG. 10. Further embodiments of stabilizing structures and wound closure devices, as well as related methods of manufacture and use, are described throughout the specification and in the claims of International Application No. PCT/US2013/050619, filed Jul. 16, 2013, and International Application No. PCT/US2013/050698, filed Jul. 16, 2013, the entireties of both of which are hereby incorporated by reference.

FIGS. 11A-D illustrate different views of an embodiment of a wound closure device comprising a stabilizing structure 1701. Here, the stabilizing structure 1701 comprises a first set of beams 1703 that are rigidly or semi-rigidly attached or bonded to a second set of intersecting beams 1705. These beams 1703, 1705 form a planar support structure 1702 that is preferably substantially rigid within a plane. The beams 1703, 1705 may meet at right angles to each other (although other configurations, e.g., honeycombs are possible). Two or more planar support structures 1702 may be joined together to form the stabilizing structure 1701, and each planar support structure 1702 is preferably separated from the other by spring elements 1711 and 1713, described in further detail below. The number of planar support structures 1702 used in the stabilizing structure may be tailored in relation to the size of the wound. For example, there may be 2, 3, 4, 5 or more planar support structures 1702 arranged parallel or substantially parallel to one another. The spring elements 1711, 1713 are preferably arranged so as to allow for compression of the stabilizing structure 1701 in one direction so as to bring the planar support structures 1702 closer together. In a preferred embodiment, the stabilizing structure 1701 may collapse to 40% or less of its original size, preferably 30% or less of its original size; more preferably, 20% or less of its original size; even more preferably, 10% or less of its original size. In some embodiments, the stabilizing structure 1701 may collapse to 5% or less of its original size.

The spring elements 1711, 1713 are preferably resiliently flexible and biased to be resiliently collapsible along a direction perpendicular to the plane defined by the planar support structure 1702. In some embodiments, the elements 1711, 1713 may be inelastic, and retain their shape when collapsed. In such embodiments, the spring elements or the stabilizing structure may be constructed with a ratchet mechanism that maintains the spring elements 1711, 1713 in their collapsed configuration.

Figure 11A:
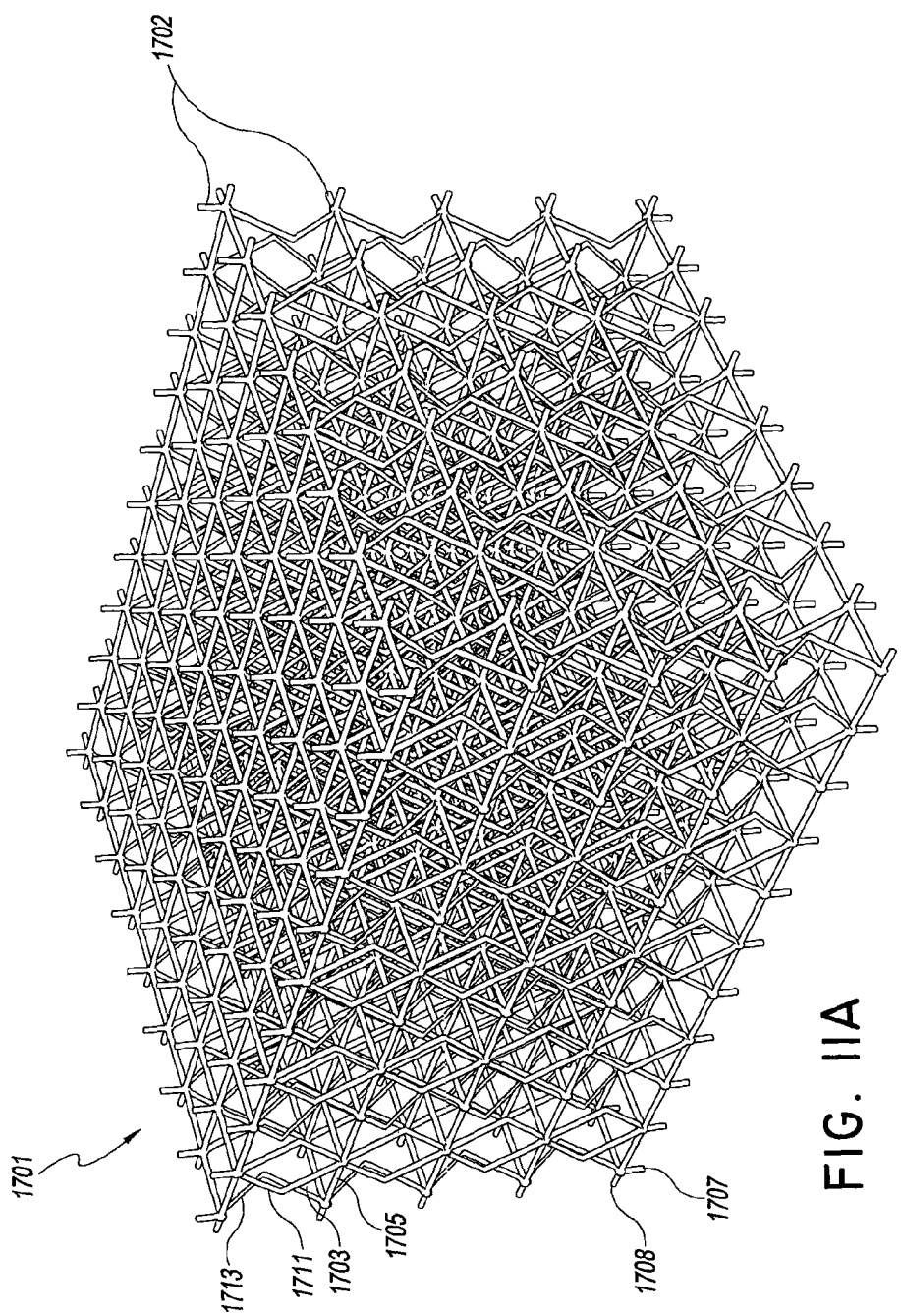
Figure 11B:
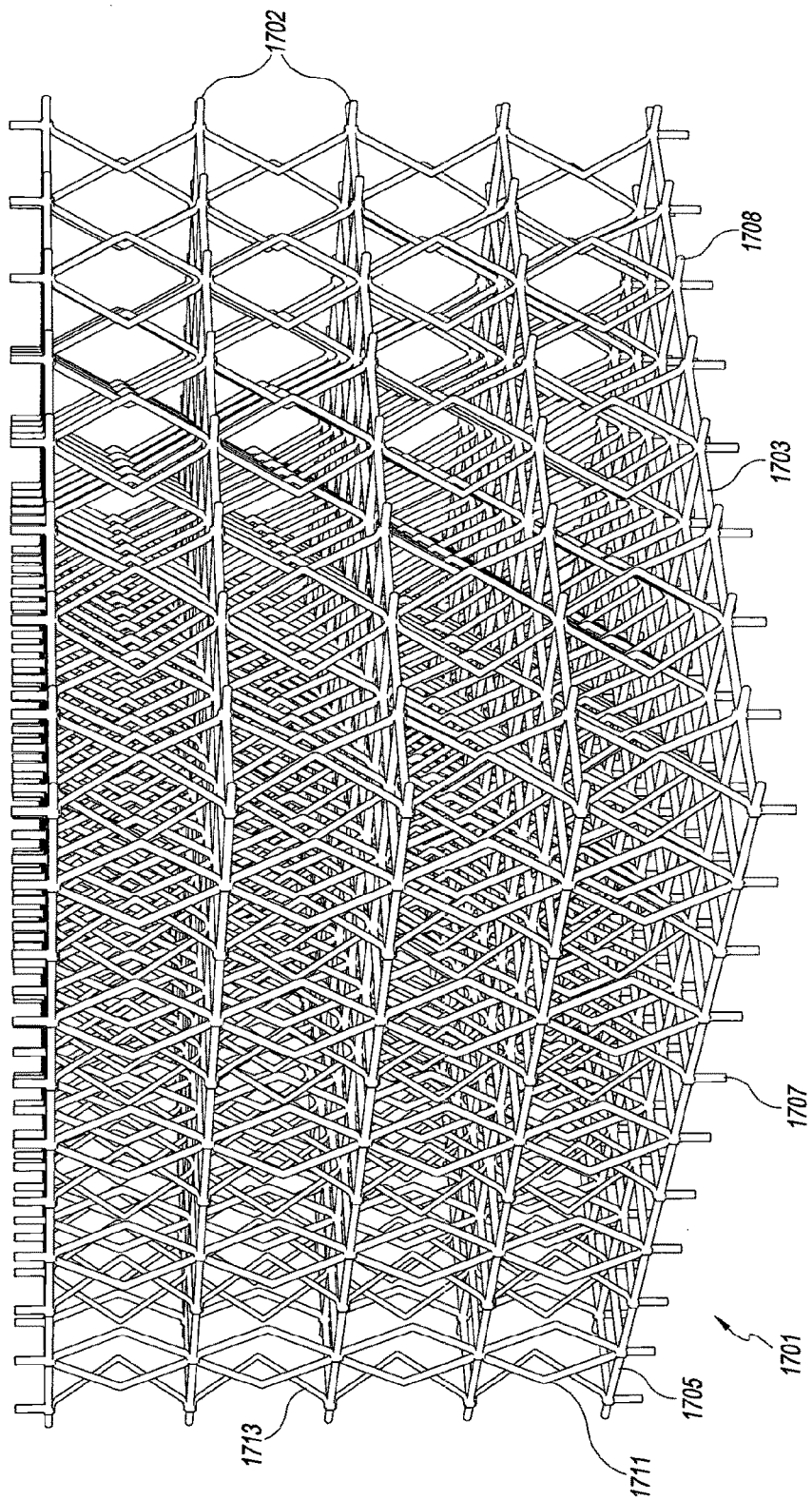
Figure 11D:
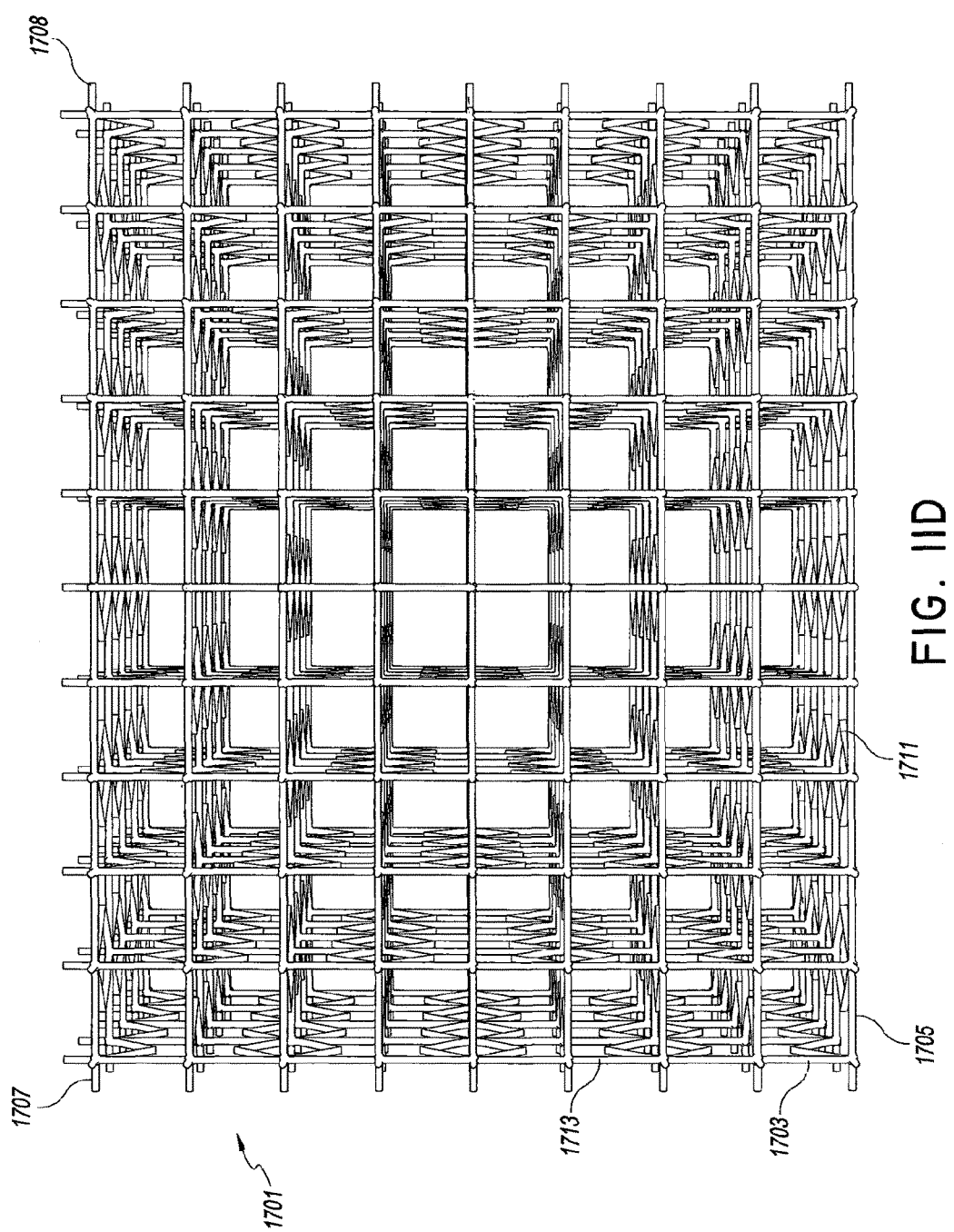
Figure 12A:
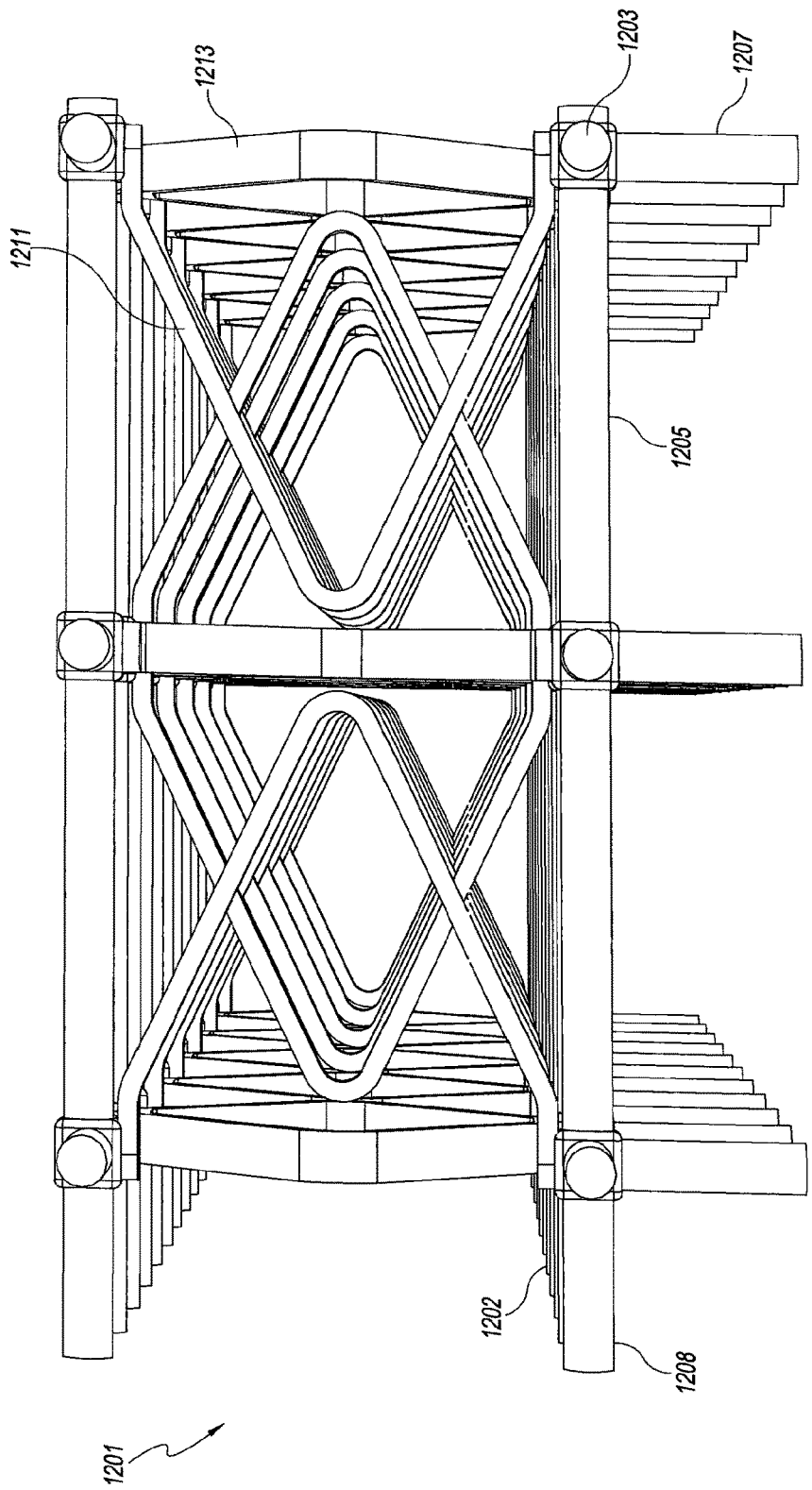
FIGS. 12A-E illustrate different views and photographs of embodiments of a wound closure device comprising a stabilizing structure.
Figure 12B:
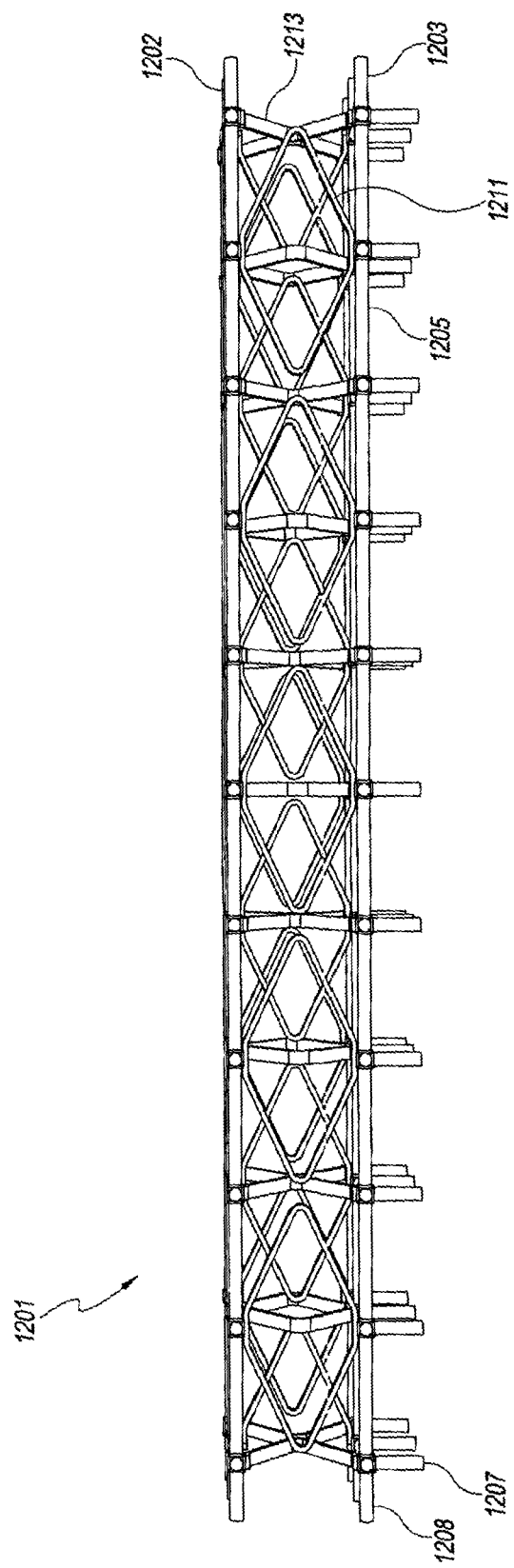
Figure 12C:
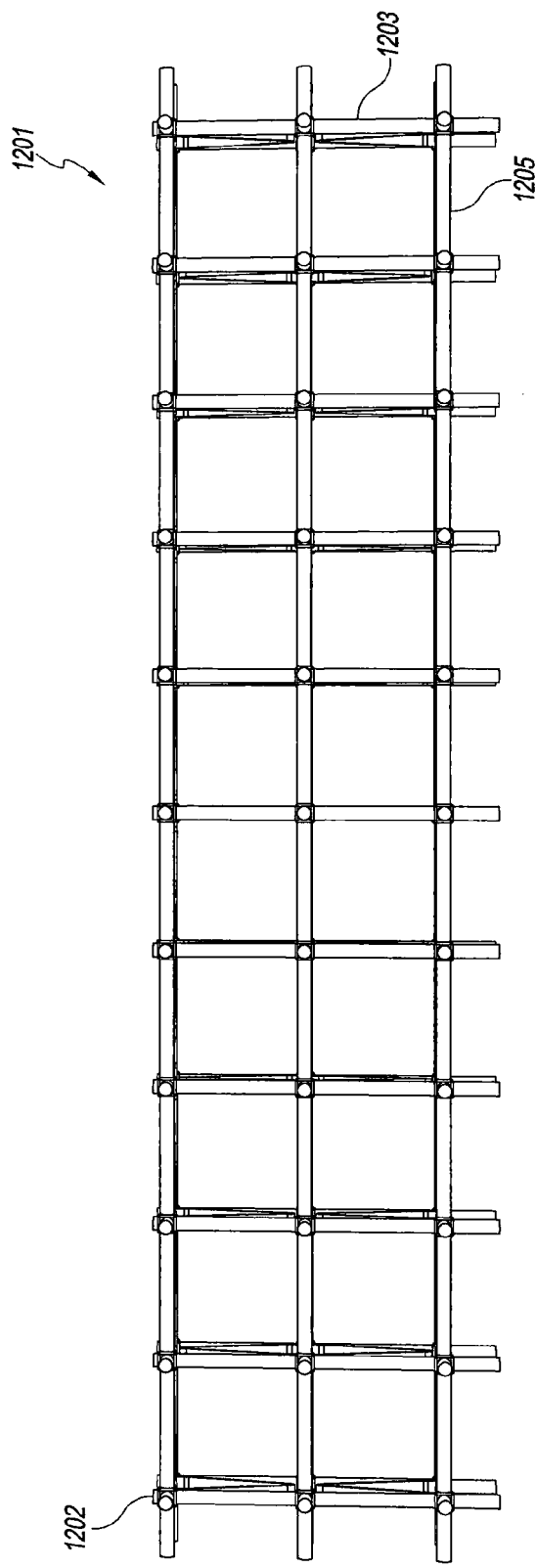
Figure 12D:
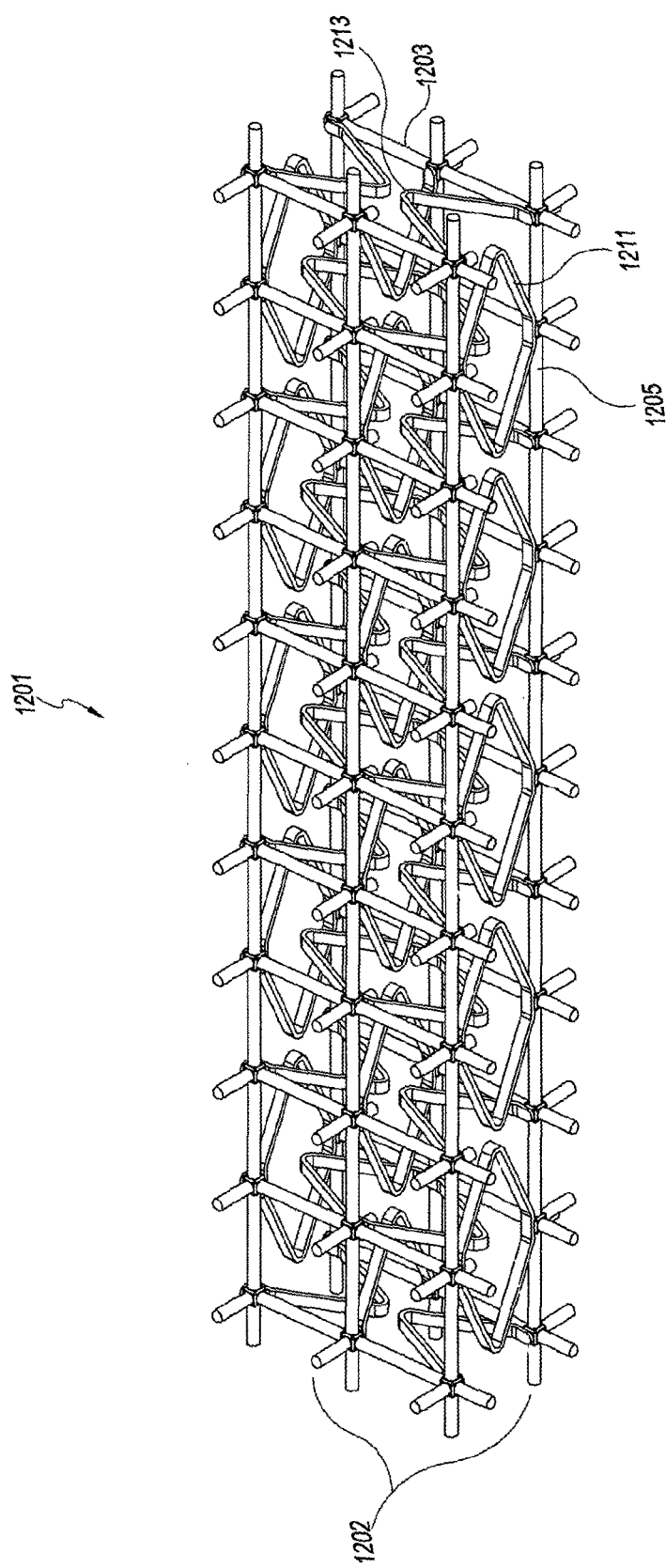
Figure 12E:
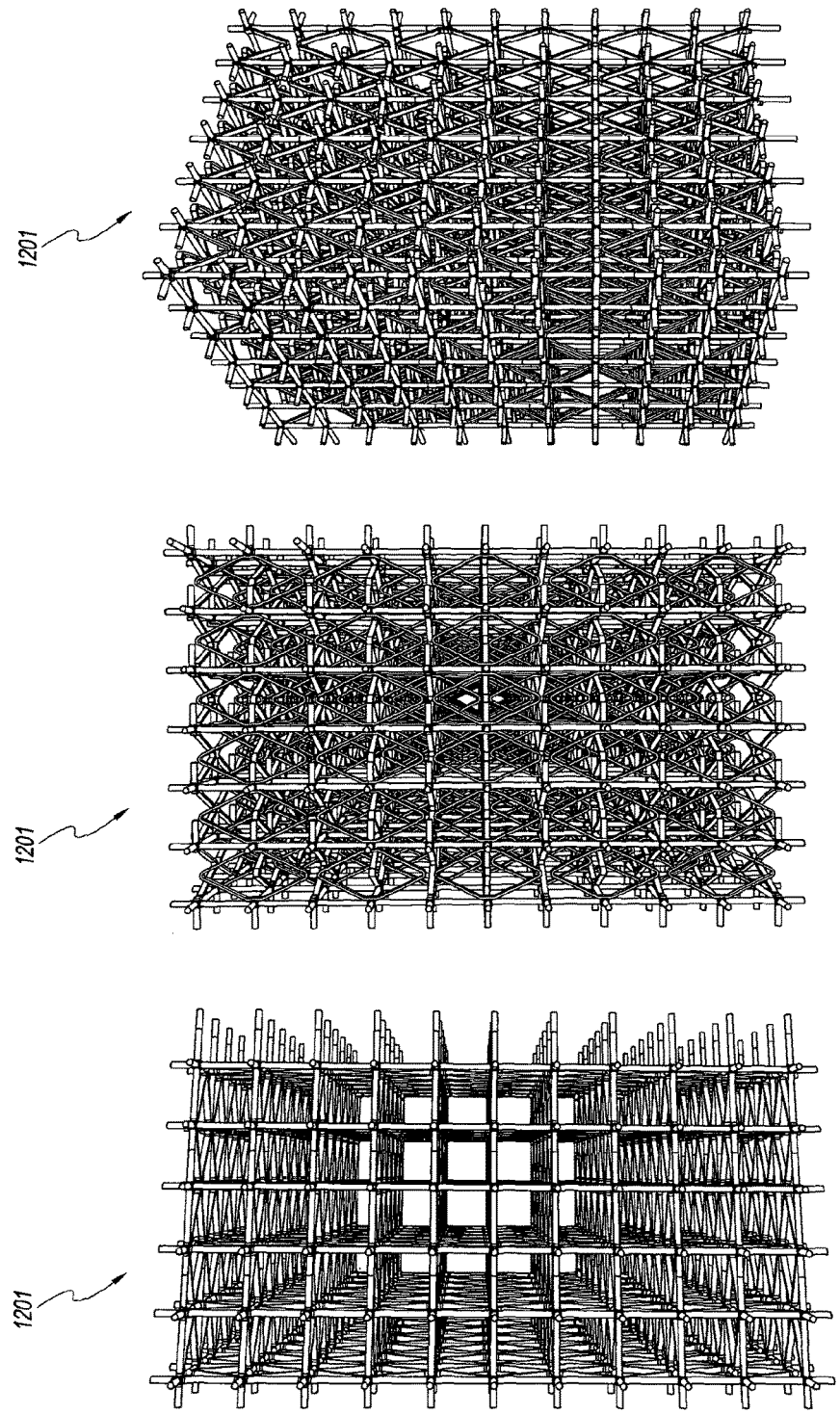

In a preferred embodiment, these spring elements 1711, 1713 may be V- or U-shaped. Each spring element may comprise two elongated portions that are bent relative to each other and form an obtuse angle (as shown in FIGS. 11A-C), or an acute angle (as shown in FIG. 12A). Spring elements 1711 preferably run in a plane parallel to beam 1705, and may be attached to either the beam 1703 or 1705. Similarly, spring elements 1713 preferably run in a plane parallel to beam 1703, and may be attached to either the beam 1703 or 1705. For both spring elements 1711, 1713, a preferred attachment point is at the junction between beams 1703 and 1705. Preferably, the spring elements 1711 are arranged in a first plurality of parallel planes, which run parallel to the direction of the beam 1705, and the spring elements 1713 are arranged in a second plurality of parallel planes which run parallel to the direction of the beam 1703. The spring elements 1711 located between two adjacent planar support structures 1702 may be arranged in a repeating pattern within the first plurality of parallel planes. The spring elements 1713 located between two adjacent planar support structures 1702 may be arranged in a repeating pattern within the second plurality of parallel planes. In one embodiment as illustrated in FIGS. 11A and 11C, adjacent spring elements 1711 and 1713 form a diamond shape. However, different patterns, arrangements and numbers of spring elements may be employed. In some embodiments, the spring elements 1711, 1713 may have a spring constant ranging between 10 and 30 N/m, more preferably between 15 and 25 N/m, and even more preferably 23 N/m. In some preferred embodiments, the force required to compress seven spring elements by 15 mm equals 250 g. In some embodiments, the force required to compress the same seven springs by the same distance ranges between 180 and 230 g. In some embodiments, there are a total of four spring elements 1711, 1713 per 10 cm3. Of course, one will recognize that factors such as the spring constants and/or number of springs may be tailored to the particular tissue type and wound closure desired, and that higher or lower spring constants or numbers of springs may be used.

Standoffs 1707 and 1708 may be provided at the edges or along the outer faces of the structure 1701, and which may be configured to contact the wound. In some embodiments, the standoffs 1707, 1708 may be extensions of the beams 1703, 1705, or may be provided separately. In some embodiments, the standoffs 1707, 1708 may be provided with hook or anchor elements configured to anchor tissue placed into contact with them. Additionally or alternatively, hook or anchor elements attached to the structure 1701 may be provided separately from or instead of the standoffs 1707, 1708. Such hook or anchor elements may be useful to enhance fascial tissue closure by ensuring that different tissue layers (e.g., muscle tissue, fat tissue) are closed at approximately the same rate. Preferably, the hook or anchor elements are configured so as to be have a release force (once engaged into tissue) that causes no or minimal pain to the patient while permitting sufficient pulling force to be applied thereto so as to allow for wound closure. In some embodiments, different anchor elements may be used to engage different types of tissue. For example, the release force to release an anchor element from subcutaneous fatty tissue may be lower than the force needed to release another anchor element from muscle tissue.

Further, the anchor elements, by virtue of their attachment to the surrounding tissue, may be useful in helping prevent a drape or other materials placed over the wound from going into the edges between the skin and the structure 1701. In some embodiments, the anchor elements may be broken off, which may aid in sizing the device as described below so as to fit into a wound. Additionally, all or part of the structure 1701 may be covered or embedded within a porous wound filler material. In such configurations, the standoffs 1707, 1708 may be used to provide additional securement to any such wound filler material.

In use, the stabilizing structure 1701 may be cut to size as appropriate to fit the wound. Optionally, a porous material such as foam may be placed around the perimeter of the structure 1701, and may be secured using one or more of the standoffs 1707, 1708. The porous material may also surround or envelop the entire device, for example by using a foam enclosure. Foam may also be added into the entire structure 1701, including its interior portions, and if this is done during manufacturing, the structure 1701 is preferably capable of withstanding a reticulation process. Such a device comprising foam will have composite tensile structures that are to be considered when inserting the device into the wound. When inserting the device into the wound, the stabilizing structure 1701 is preferably oriented such that the planar support structures 1702 are aligned such that they are perpendicular or substantially perpendicular to the general direction of wound closure, or perpendicular or substantially perpendicular to the patient's skin. Optionally, an organ protection layer, which may comprise a polymer sheet or other flexible material, optionally provided with apertures, may be placed into contact with at least the bottom portion of the wound. A drape may be sealed over the skin surrounding the wound, and a source of negative pressure may be placed into fluid communication with the wound so as to effectuate wound closure. Further details regarding the drape, the application of negative pressure, and other apparatuses and methods that may be used with these stabilizing structures, are described below with respect to other embodiments.

FIGS. 12A-E illustrate different views and photographs of embodiments of a wound closure device comprising a stabilizing structure 1201. This embodiment is similar in some respects and in function to the embodiment described above in relation to FIGS. 11A-D, and share similar elements. The device comprises beams 1203 and 1205 that form a planar support structure 1202 separated by spring elements 1211 and 1213. Standoffs 1207 and 1208 may also be provided. Here, however, the spring elements 1211 and 1213 are thicker and have portions that are bent relative to each other at acute angles. Additionally, compared to FIGS. 11A-D, the structure 1201 has a greater volume and greater number of spring elements 1211, 1213. As illustrated best in FIG. 12D, the spring elements 1211 form a repeating diamond pattern within a first plurality of parallel planes, with the diamond location being staggered between adjacent parallel planes. A corresponding pattern is employed for spring elements 1213 with a second plurality of parallel planes. A similar configuration may be seen in FIGS. 11A-D.

Example 2

Figure 13A:
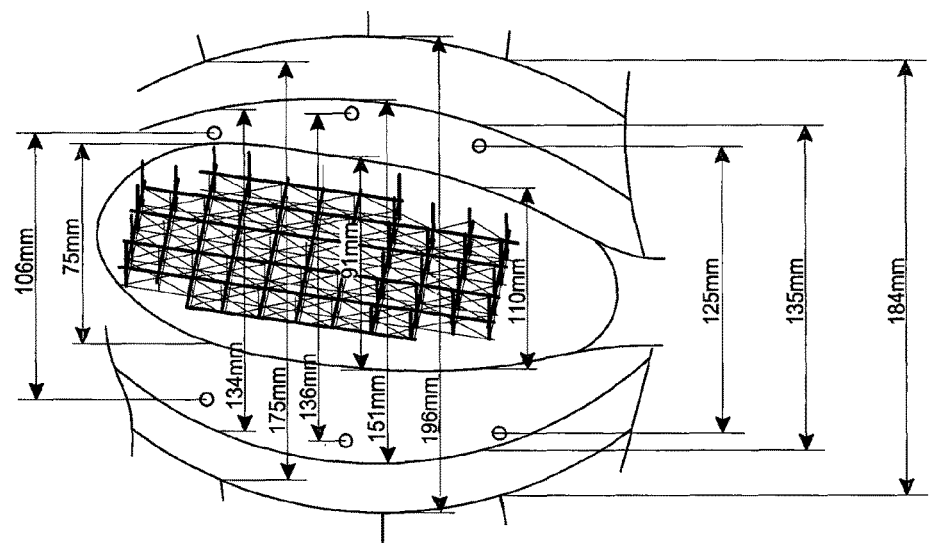
FIGS. 13A-B, 14A-B, and 15A-B are before and after photographs of experiments performed to determine the efficacy of certain embodiments of wound closure devices.
Figure 13B:
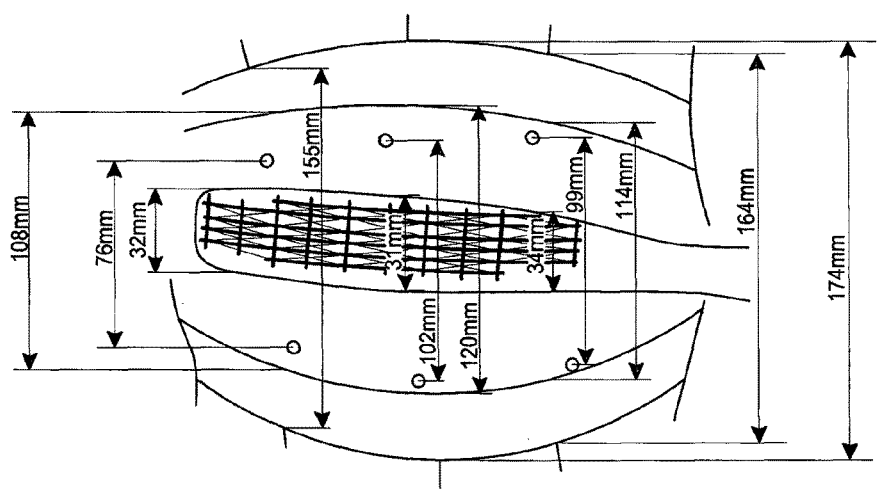

By means of a non-limiting example, an experiment was conducted to determine the effectiveness of an embodiment of the wound closure devices described above, with testing being performed on a cadaveric model. FIGS. 13A-B illustrate the results where a structure with foam, similar to the embodiments of FIGS. 12A-E, was placed into a wound. The perimeter of the structure was wrapped in a layer of foam.

Wound area measurements before and after application of negative pressure indicated that the wound area decreased by 64%, from 152 mm2 to 55 mm2.

Example 3

Figure 14A:
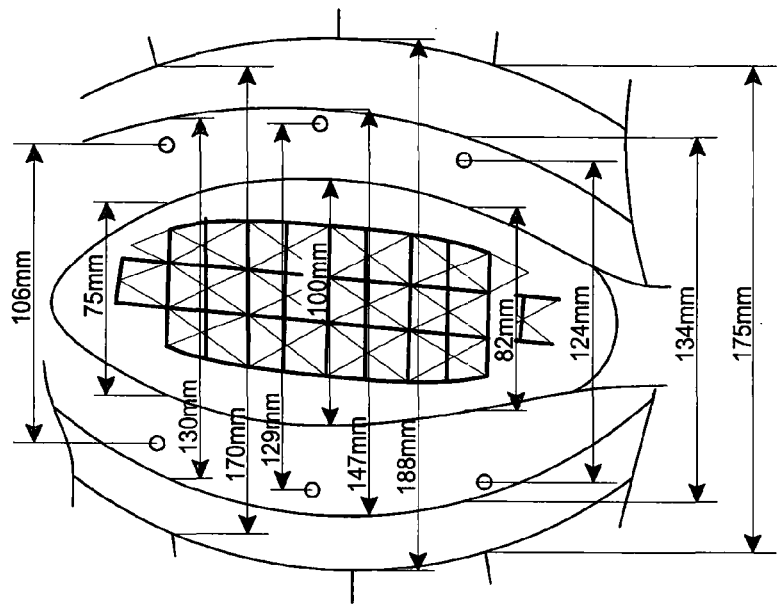
Figure 14B:
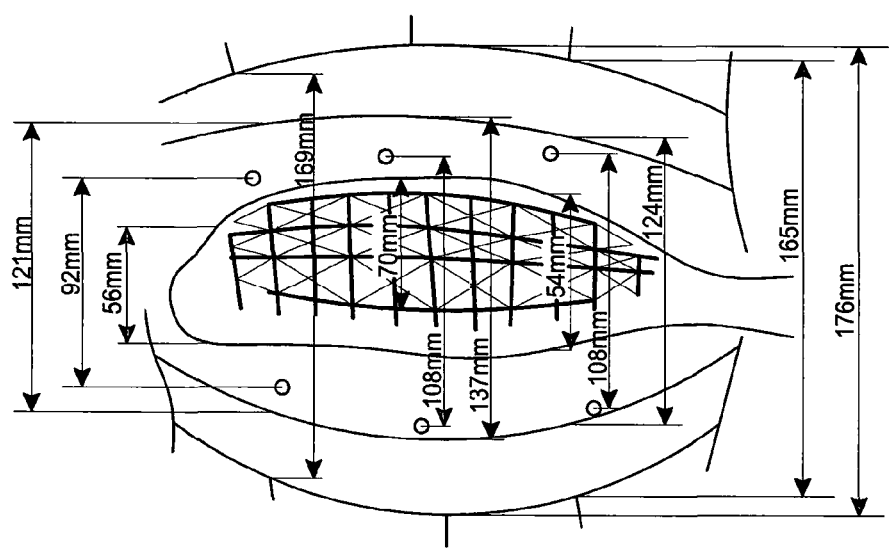

This non-limiting experiment tested a structure wrapped in foam and prestretched along its width and held in place by bendable plastic strips, but otherwise similar to the embodiments of FIGS. 12A-E. FIGS. 14A-B illustrate the wound size before and after application of negative pressure. Here, the wound area measured 154 mm2 before the application of negative pressure, and 101 mm2 afterwards, for a 34% reduction in wound area.

Example 4

Figure 15A:
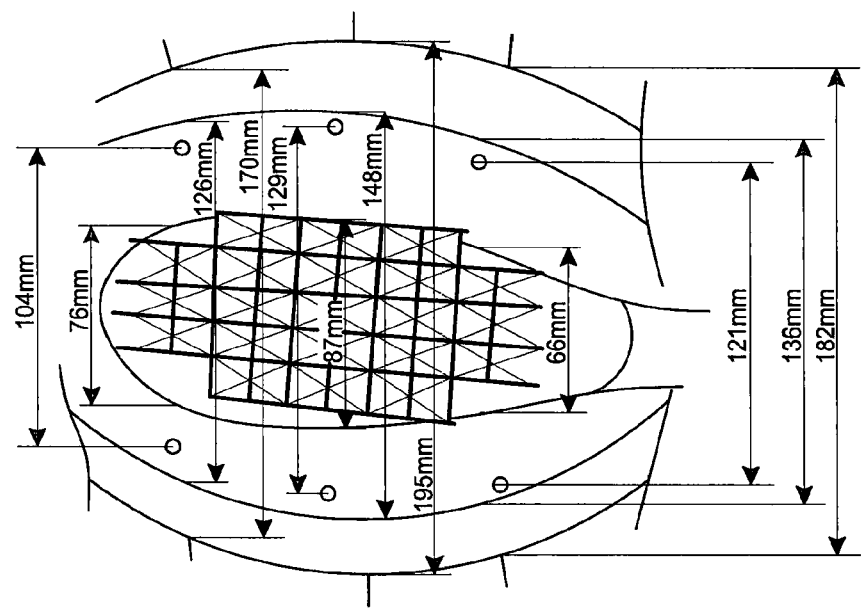
Figure 15B:
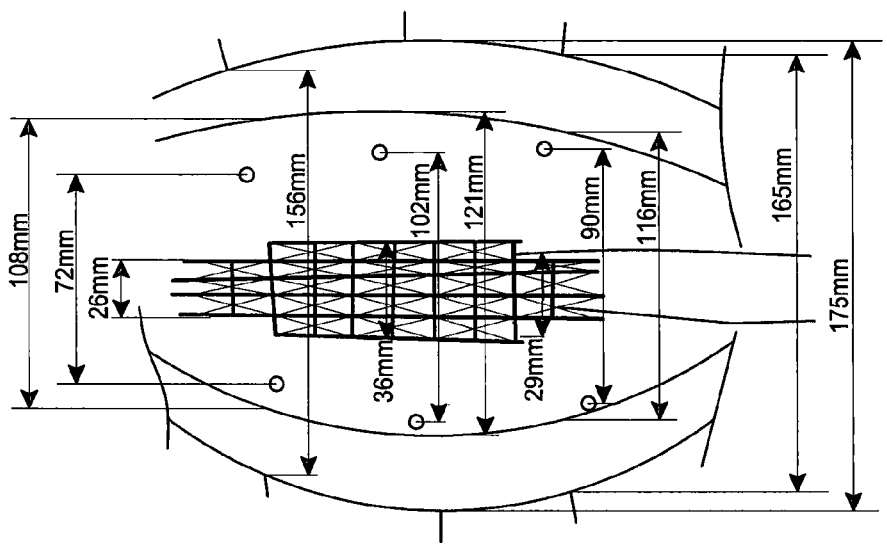

FIGS. 15A-B illustrate the non-limiting results of an experiment where a structure similar to the embodiment of FIGS. 12A-E was placed into a wound without any foam wrapping. The experiment was performed similarly to the other examples described in this section or elsewhere in this specification, and here, the wound area measured 126 mm2 before application of negative pressure, and 53 mm2 afterwards, for a 58% reduction in wound area.

Stabilizing Structures and Wound Closure Devices of FIGS. 16A-24B 27-28B and 40

As with the other stabilizing structures and wound closure devices described elsewhere in the specification, the stabilizing structures and wound closure devices of FIGS. 16A-24B, 27-28B, and 40 may be incorporated into the wound packing and wound treatment apparatus embodiments described elsewhere in the specification, such as in relation to FIGS. 8A-10.

Figure 16A:
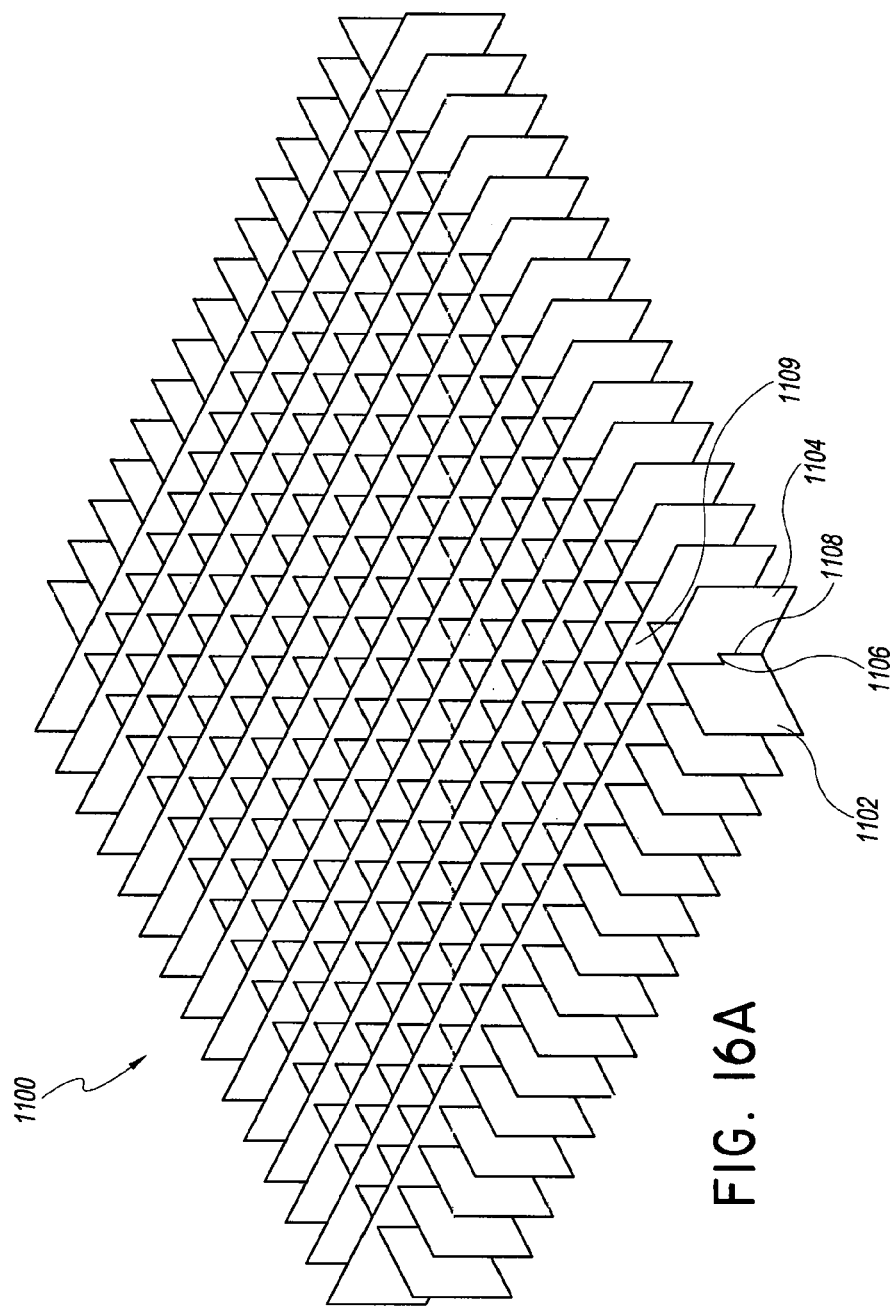

FIGS. 16A-E illustrate additional embodiments of a wound closure device comprising a stabilizing structure 1100. FIG. 16A shows a perspective view of an embodiment of a stabilizing structure 1100. Here, the stabilizing structure 1100 is preferably comprised of two or more interlocking strips (described below in more detail with relation to FIG. 16B) that extend in directions approximately perpendicular to each other when in a substantially uncollapsed configuration. The stabilizing structure is preferably configured to collapse in one direction or along a first plane while remaining relatively rigid and collapse-resistant in a direction perpendicular to the first direction or plane.

FIG. 16B illustrates side views of a bottom strip 1102 and a top strip 1104 that may be used to make a stabilizing structure 1100 such as the embodiment illustrated in FIG. 16A. Each of the top and bottom strips 1102, 1104 are preferably configured to movably interlock with each other, for example via matching notches 1106 and 1108. One or more notches 1106 may be provided on a top side of bottom strip 1102, and similarly, one or more notches 1108 may be provided on a bottom side of top strip 1104. When assembled together, the one or more top and bottom strips 1102, 1104 may be positioned so that the notches 1106, 1108 line up. Preferably, the top and bottom strips 1102, 1104 are positioned at substantially perpendicular angles to each other, thereby permitting the notches 1106, 1108 to slot together so as to create a movably interlocking structure. Typically, the number of notches 1106 on the bottom strip 1102 will equal the number of top strips 1108 that will form the stabilizing structure 1100, and vice versa. The notches 1106, 1108 are preferably shaped with a width that permits the strips 1102, 1104 to move from approximately perpendicular angles to angles far from perpendicular (i.e., close to parallel) to each other, thus permitting the stabilizing structure 1100 to articulate and collapse along one direction or plane.

In a preferred embodiment, the strips 1102, 1104 are constructed from a rigid or semi-rigid material, such as a polymer. Examples of suitable polymers include polyethylene, polypropylene, polyurethane, polyvinyl chloride, polystyrene, polyacrylate, polymethyl methacrylate, PEEK, silicone, polyurethane, polycarbonate, composites and laminates, or combinations thereof. In some embodiments, the material may include compressed or "felted" reticulated foam. Of course, other materials, such as cardboard or metal may be used. Preferably, the materials may be at least partially porous so as to permit fluid to flow through the material. Further, such properties may aid in distributing negative pressure through the device and to the wound, and may aid in removing fluid from the wound dressing. Such materials may include, for example, low density polypropylene, foamed material, or sintered material. The material used does not necessarily need to be strong along the length of the strips 1102, 1104, but should preferably be able to withstand pressure applied to a top or bottom edge. Preferably, the material is capable of withstanding the pressure from atmospheric pressure exerted on a drape when up to 200 mmHg negative pressure is applied to the wound. In some embodiments, the material can withstand a force of 5 psi applied to a top or bottom edge.

In a preferred embodiment, each strip 1102, 1104 measures 180 mm long by 30 mm high. The thickness of the strips 1102, 1104 may range, for example, between 1.50 to 2.40 mm, although the thickness will be selected at least partly based on the ability of the material to withstand pressure being applied along its edge. The thickness is preferably balanced between keeping the material thin enough to minimize the compressed thickness of the stabilizing structure 1000, while keeping the material thick enough to avoid causing excessive localized pressure upon the wound bed. The notches 1106, 1108 may measure approximately 15 mm in height, and may be spaced apart from other notches by 18 mm. Although the notches 1106, 1108 are shown with rounded bottoms, these may also be cut with squared-off or triangular bottoms. In some embodiments, the rounded edges reduce stresses onto the strips 1102, 1104 so as to prevent fracture and crack propagation, and may also increase the springiness of the stabilizing structure 1100.

It will be understood that the interlocking strips 1102, 1104 may not necessarily need to be joined together via notches. Hinges or other devices could be used to provide the articulation or movable interlocking ability illustrated above. In some embodiments, hinges may be constructed from thinner areas of the same material used to construct the strips 1102, 1104, and are configured to flex or bend to a predetermined position. The stabilizing structure 1100 could also be molded as a single piece such that the interlocking strips 1102, 1104 form a single unit.

Returning to FIG. 16A, the perspective view illustrates an example of a stabilizing structure 1100 configuration with multiple interlocking top and bottom strips 1102, 1104 movably interlocked via multiple notches 1106, 1108. The intersections of two top strips 1102 and two bottom strips 1104 form a quadrilateral-shaped boundary space 1109. When the top and bottom strips 1102, 1104 are at perpendicular angles to each other, the space 1109 will be square or rectangular. However, as the stabilizing structure 1100 collapses along a direction or plane, the space 1109 will become more diamond- or parallelogram-shaped. The stabilizing structure 1100 will preferably comprise multiple spaces 1109, which form cells defined by the walls of the top and bottom strips and with openings on top and bottom ends.

FIG. 16C illustrates a top view of an embodiment of the stabilizing structure 1100 where a porous wound filler material 1110 has been placed into the quadrilateral-shaped boundary space 1109. Here, the porous wound filler material 1110 used is preferably soft and conformable so as to be able to adapt to the any change in the configuration of the stabilizing structure 1100 if it collapses. Preferably, the porous wound filler material is a foam, such as a polyurethane foam. This porous wound filler material may be cast around the stabilizing structure 1100 so as to completely encapsulate it. When used, the resulting stabilizing structure 1100 may be cut to size so as to fit into a wound. Such porous wound filler material 1110 may be used to aid in the fluid transmission or wicking of fluid from within a wound, and may also, when in contact with the wound (e.g., when used in negative pressure wound therapy), aid in the healing of the wound.

Figure 16D:
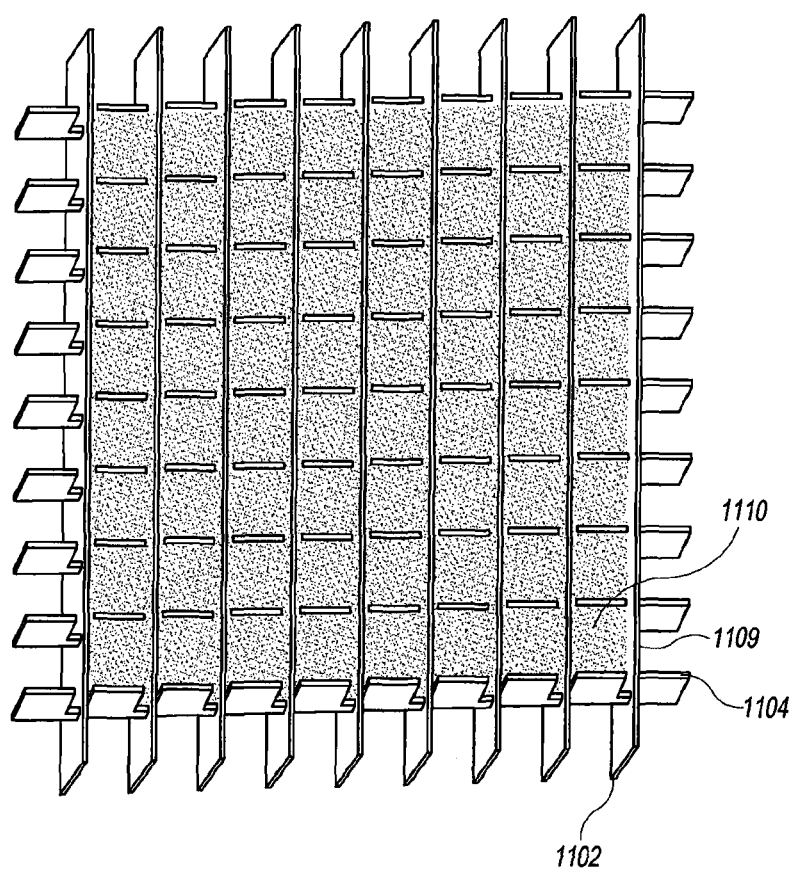

FIG. 16D illustrates a perspective photograph of an embodiment of the stabilizing structure 1100 with a porous wound filler material 1110 inserted into the spaces 1109. In some embodiments, additional porous wound filler material may also be used to encapsulate or surround the structure 1100. For example, a sock or wrap may be fitted around the structure 1100, and may for example be constructed from foam or gauze. When inserted into a wound, the stabilizing structure 1100 may be preferably oriented so as to collapse in a direction generally parallel with the orientation of collagen and other fibrous tissue fibers in the body. This orientation is sometimes referred to as Langer's lines or Kraissl's lines, and closing a wound in a direction coinciding with (and preferably parallel to) these lines may heal faster and more easily than attempting to close a wound in a direction perpendicular or opposed to these lines. It will be appreciated that the other embodiments of stabilizing structures described in this specification may also be oriented in the same manner with respect to Langer's lines or Kraissl's lines, or other landmarks.

Advantageously for some types of wounds, the stabilizing structure of FIG. 16A may elongate in a direction perpendicular to the primary direction of closure, but still within the horizontal plane. Such elongation can be beneficial to wound healing as the physiology of the wound may dictate that it should lengthen as it closes.

In use, the stabilizing structure 1100 may be placed into a wound such that the upward facing portion of the structure 1100 is substantially rigid and resists collapse in the vertical direction once negative pressure is applied to the wound (e.g., once covered by a drape as described previously). A porous material such as foam may be placed around, into, and/or so as to surround or encapsulate the stabilizing structure 1100. In some embodiments, an organ protection layer as described previously may be placed into contact with at least the bottom portion of the wound. As negative pressure is applied, the structure 1100 will then preferably collapse in the plane perpendicular to the vertical direction, aiding in wound closure. Due to the relative incompressibility of the vertical dimension of the device, the pressure on the drape transmitted from the greater atmospheric pressure onto the wound will reduce the pressure applied to the stabilizing structure 1100 onto the wound margins in comparison to existing prior art devices. Optionally, in this and other embodiments described in this section or elsewhere in this specification, negative pressure may be applied so as to increase transmission of negative pressure to the sides of the wound rather than the bottom portions thereof. This may be accomplished, for example, by providing an organ protection layer that at least partially shields the bottom of the wound from negative pressure. In a preferred embodiment, the sides of the wound would be provided with negative pressure of at least 100 mmHg, preferably 120 mmHg, 140 mmHg, 180 mmHg, or 200 mmHg, while the bottom of the wound would be provided with at most 120 mmHg, more preferably 80 mmHg, 40 mmHg, 20 mmHg, or 10 mmHg.

Figure 16E:
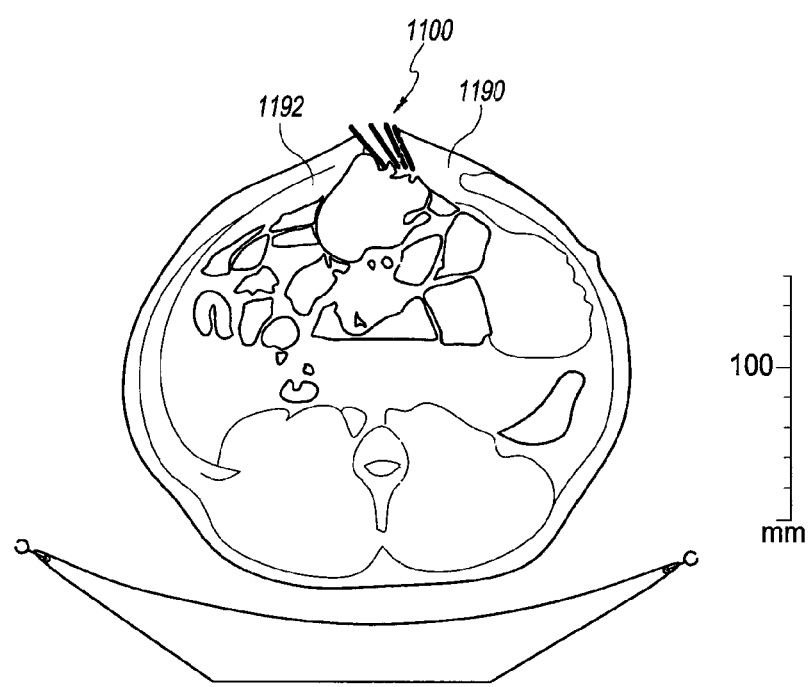

FIG. 16E illustrates a CT image of an embodiment of a stabilizing structure 1100 described in FIGS. 16A-D inserted into an abdominal wound. The tissue fascia layers are also visible, with a subcutaneous fat layer 1190 above a layer of muscle tissue 1192. With the application of negative pressure (as illustrated), improved fascial reapproximation and wound closure may be observed. In particular, the muscle tissue layers 1192 on opposite sides of the wound have been moved much closer together, while remaining attached to the other fascial layers. In measurements, the width of the wound along the view illustrated reduced from approximately 82 mm to 28 mm, a reduction of 65%.

Figure 17A:
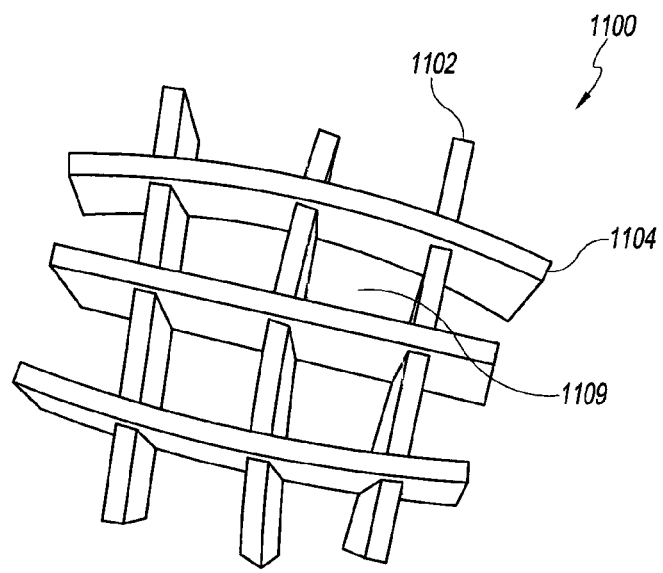
FIGS. 17A-C illustrate an embodiment of a stabilizing structure manufactured from felted foam.
Figure 17B:
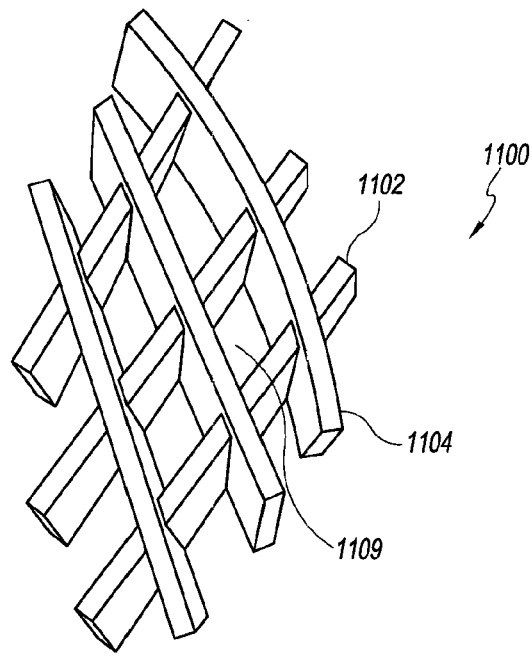
Figure 17C:
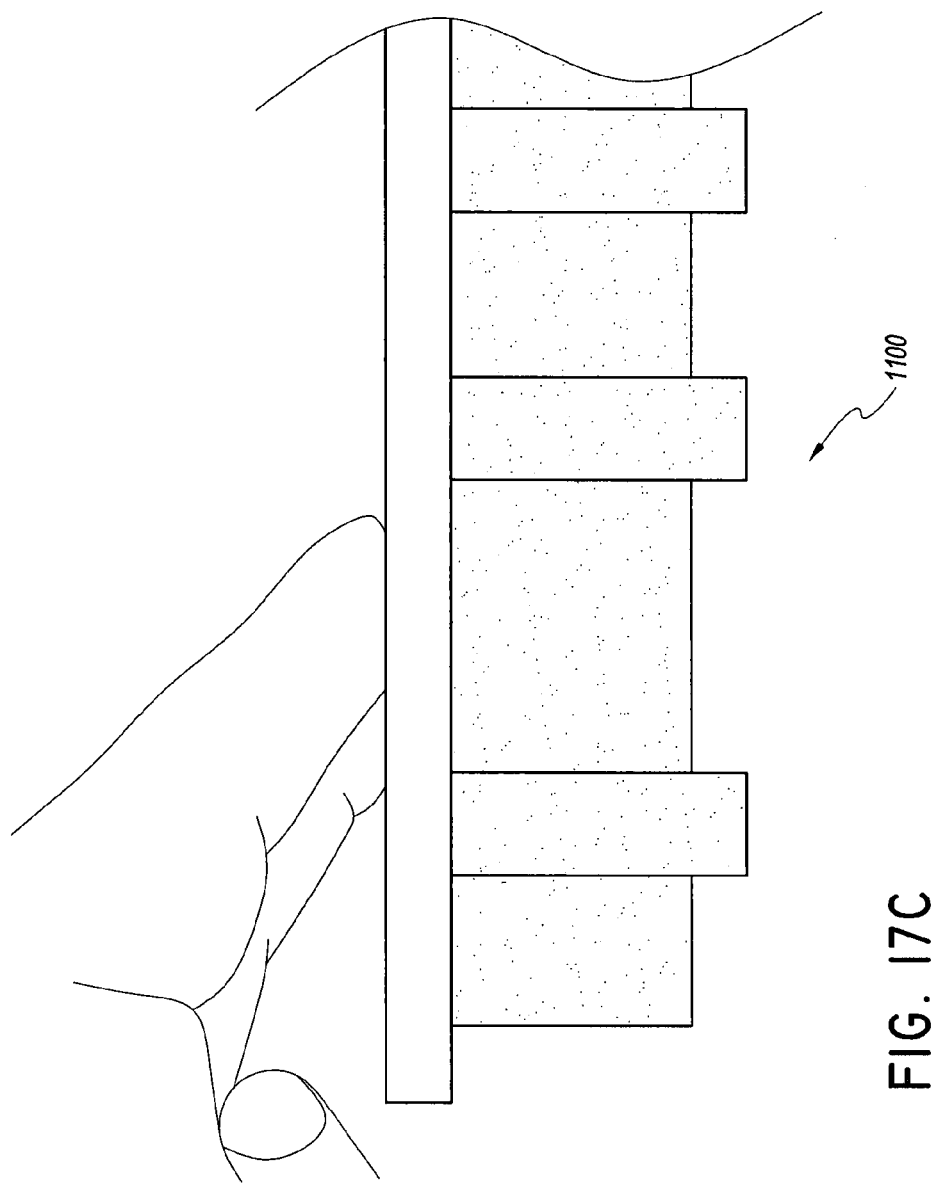

FIGS. 17A-C illustrate an embodiment of a wound closure device comprising a stabilizing structure 1100 similar to that described above in relation to FIGS. 16A-E. Here, the stabilizing structure 1100 is constructed from interlocking strips constructed from felted foam. The physical relationship between and the mechanism for the interlocking top and bottom strips 1102 and 1104 are substantially similar to what was discussed previously above, and will not be repeated here. Felted foam, however, is foam (e.g., polyurethane foam) that has been heated and compressed. After this procedure, the foam will be stiffer and less compressible, while still remaining porous. Such a material may be advantageously used in a stabilizing structure 1100 used for a wound closure device, as the material may be compressible in a plane defined by the top and bottom strips 1102, 1104, as shown in FIG. 17B. However, the material is substantially rigid in the vertical direction, as illustrated in FIG. 17C, where a weight has been placed over the foam without substantial buckling. Here, the foam can support approximately 6 kg of weight, and embodiments of the device have been measured to support at least 3 psi of applied pressure without collapse. Further, while such material is substantially rigid, the porous nature of the material permits negative pressure to be transmitted to the wound and for wound exudate to be removed.

Figure 18A:
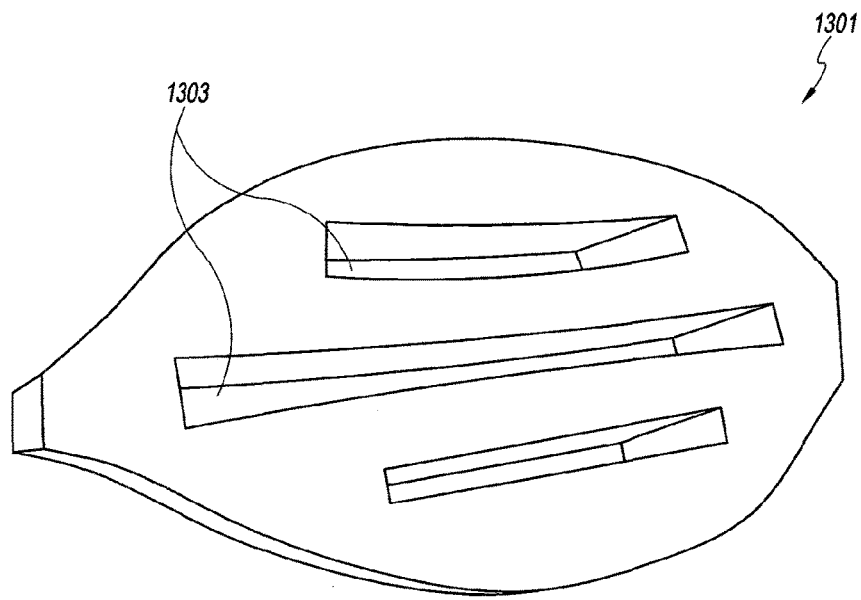
FIGS. 18A-B are photographs of further embodiments of wound closure devices comprising a porous wound filler material.
Figure 18B:
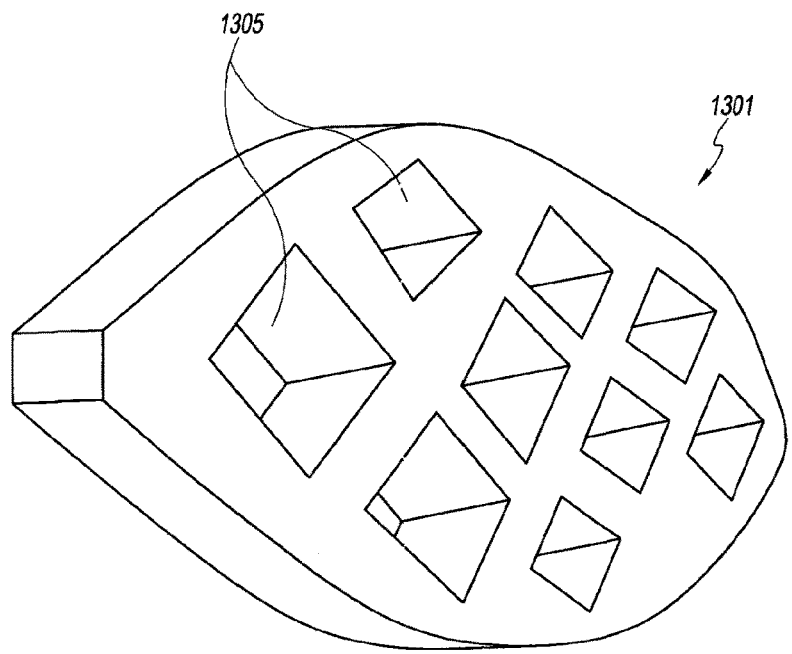

FIGS. 18A-B are photographs of further embodiments of wound closure devices. FIG. 18A illustrates an embodiment of a wound closure device 1301 that preferentially collapses along one direction. Here, the wound closure device 1301 comprises a porous wound filler material (e.g., foam) into which one or more slots 1303 have been cut. These slots 1303 preferably extend longitudinally through the thickness of the wound closure device 1301. Accordingly, the empty space will permit the wound closure device to preferentially collapse in a direction when a force is applied in a direction perpendicular to the slots 1303. Because the empty space is easier to compress than the remainder of the foam, the width and thickness of the foam will preferably not (or minimally) compress compared to the resulting compression perpendicular to the length of the wound closure device 1301.

Figure 19A:
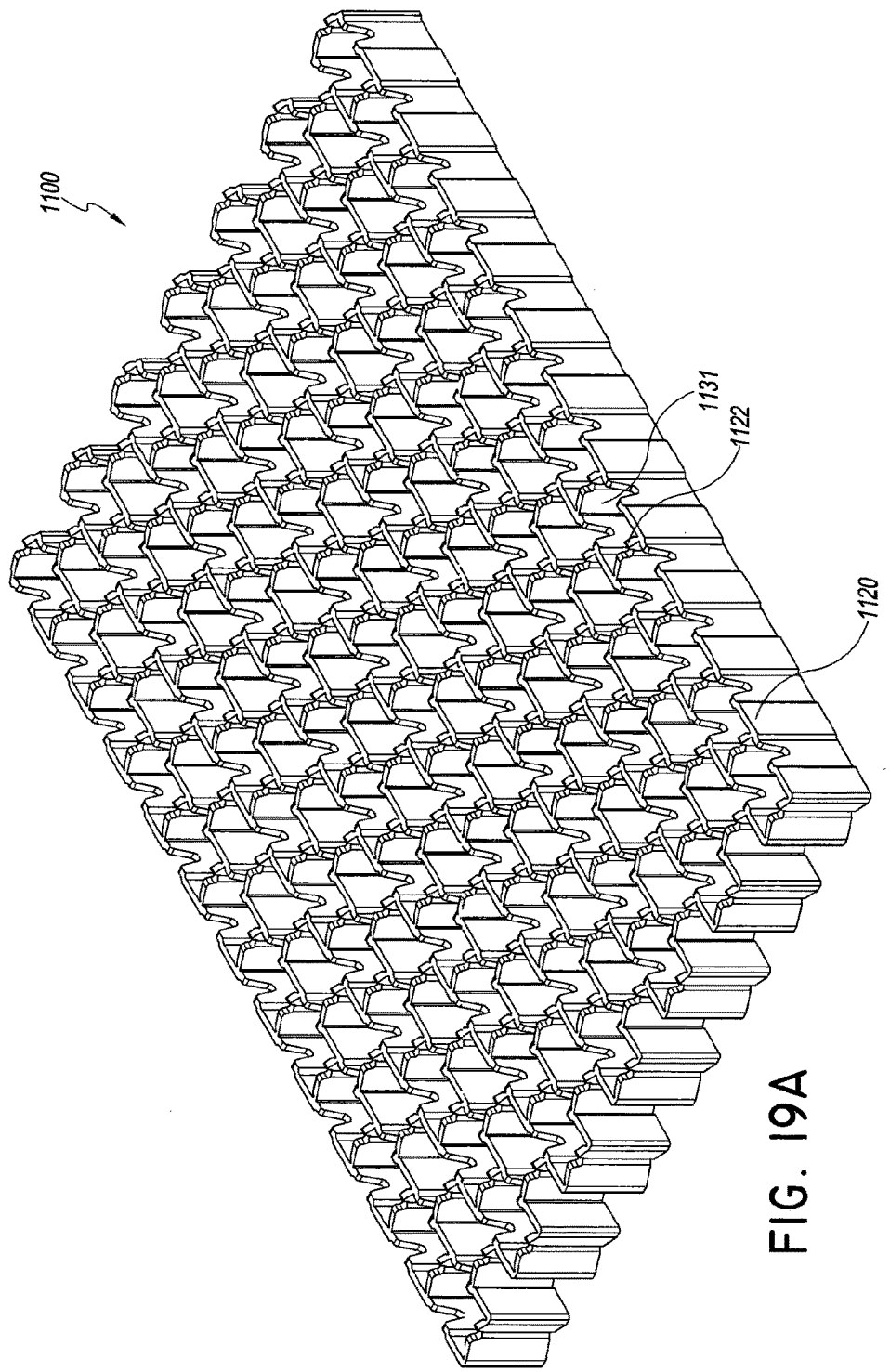
FIGS. 19A-B, 20, 21, 22, 23, and 24A-B illustrate additional embodiments of wound closure devices comprising a stabilizing structure.
Figure 19B:
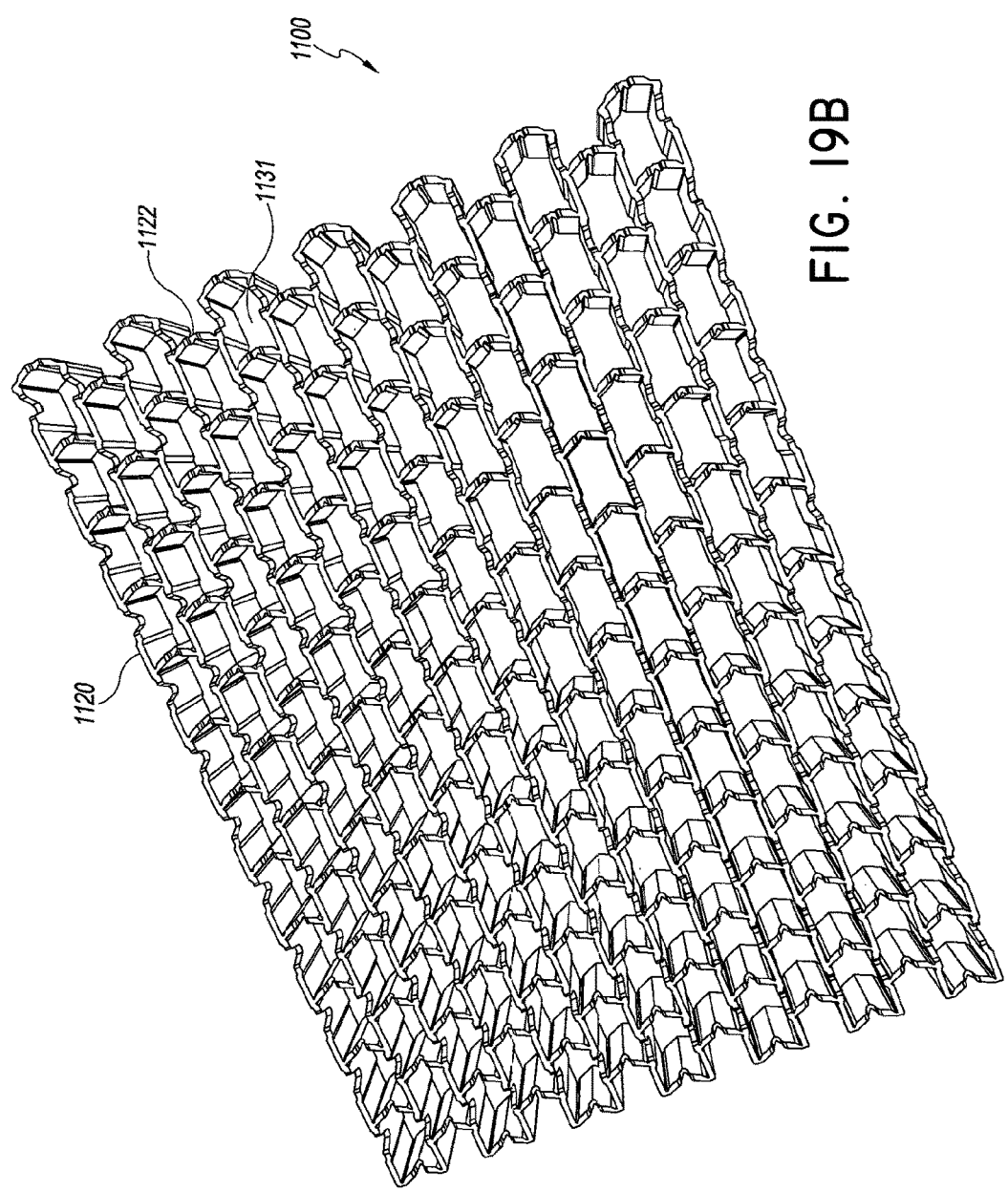

As illustrated in FIG. 19B, the wound closure device 1301 may also be provided with holes or cells 1305 in other configurations, such as diamond-shaped holes forming a lattice. This configuration permits compression along the length and width of the wound closure device due to the compressible holes 1305, while the comparatively more rigid thickness of the foam resists compression to a greater extent.

In some embodiments, stabilizing structures similar to those illustrated above in FIGS. 16A-E may be constructed as a single unit, for example by molding, rather than from multiple parts. As with the previously-described embodiments, the stabilizing structures are configured to form an array of one or more cells defined by one or more walls and forming a plane, with each cell having a top and bottom end with an opening extending through the top and bottom ends in a direction perpendicular to the plane. In some embodiments, the stabilizing structures may have cells that are square, diamond, oblong, oval, lozenge, and/or parallelepiped, and non-limiting examples of the same are illustrated in FIGS. 19-28. While some embodiments may have cells that are all the same shape, the cells may also be tailored to be larger, smaller, or differently-shaped than other cells in the structure. The shape and size of the cells may be tailored to the desired characteristics (e.g., resilience and ease of collapse) for optimal wound closure and healing.

Construction of a single unit stabilizing structure may be advantageous in terms of ease of use and cost. For example, single unit stabilizing structures may be trimmed as necessary to fit into a wound site. The material used is preferably biocompatible, and even more preferably nonadherent to the wound site. Suitable materials are preferably chosen to be soft while remaining sufficiently strong to resist collapse in a vertical direction, and may include polymers, such as polyethylene, polypropylene, polyurethane, silicone (including siloxanes), ethyl vinyl acetate, and copolymers and blends thereof. The hardness of the material may affect the thickness of the resulting stabilizing structure, and may be selected based upon the desired thickness of the stabilizing structure components (including hinges and other joints thereof) and the ability of the stabilizing structure to resist collapse, e.g., due to the atmospheric pressure acting upon a drape placed over the stabilizing structure. Suitable durometer hardnesses of materials used range from about 30 shore to 120 shore (as measured on the Shore durometer type A scale), preferably from about 40 shore to 60 shore, and even more preferably about 42 shore. Generally, the material chosen is preferably softer (while still satisfactorily meeting other material requirements), as harder materials may provide reduced levels of closure as the hardness increases.

Figure 27:
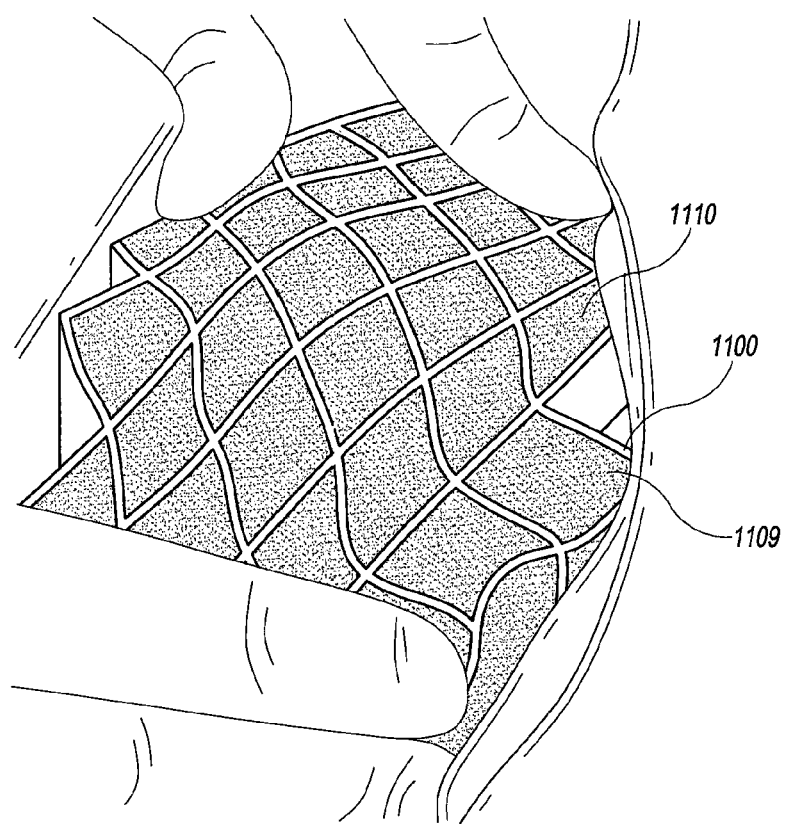
FIG. 27 is a photograph of an experiment performed to determine the efficacy of certain embodiments of wound closure devices.

FIG. 27 is a photograph of an embodiment of such device 1100 constructed as a single unit. The apertures 1109 are filled with a porous material 1110, which in some embodiments may comprise foam. Here, the device 1100 is inserted into a wound.

FIGS. 19A-B illustrate an embodiment of a stabilizing structure 1100 configured to preferentially collapse in only one horizontal direction while remaining substantially rigid or uncollapsed when force is applied in a vertical direction. Preferably, the stabilizing structure 1100 is constructed as a single unit as illustrated so as to form one or more cells 1131. Here, two or more longitudinal strips 1120 (which form the walls of the cells) may have relatively straight configurations, and are connected together via one or more collapsible cross strips 1122. It will be appreciated that in a single unit embodiment, the strips are merely portions of the same material that may have been formed together to form the entire single unit structure. The collapsible cross strips 1122 may be angled or indented so as to make them more likely to collapse in a direction generally parallel to their length. In this embodiment illustrated in this section or elsewhere in this specification, the collapsible cross strip 1122 is more likely to collapse at the apex of the angled portion and at the junctions to the longitudinal strips 1120 when a force is applied in a direction approximately parallel to the general length of the collapsible cross strip 1122. In some embodiments, the collapsible cross strip is configured to fold into a portion (which may be thinner) of the longitudinal cross strip 1120.

In some configurations, one or both of the longitudinal strips 1120 and/or collapsible cross strips 1122 may comprise one or more notches positioned along a length thereof. These notches promote fluid transfer across the structure, and aid in distributing negative pressure. In some embodiments, notches may be used in conjunction with a porous material so as to enhance fluid transfer. In relation to the longitudinal strips 1120, the collapsible cross strips 1122 may be positioned alternately along the length of the longitudinal strips 1120, as best illustrated in FIG. 19B, to form a configuration somewhat analogous to a "stretcher bond" used in bricklaying. Of course, other configurations are possible. Further, although this embodiment is illustrated as being formed as a single unit, those of skill in the art will recognize that this embodiment (and the others described below) may be constructed from multiple pieces joined or connected together.

Figure 28A:
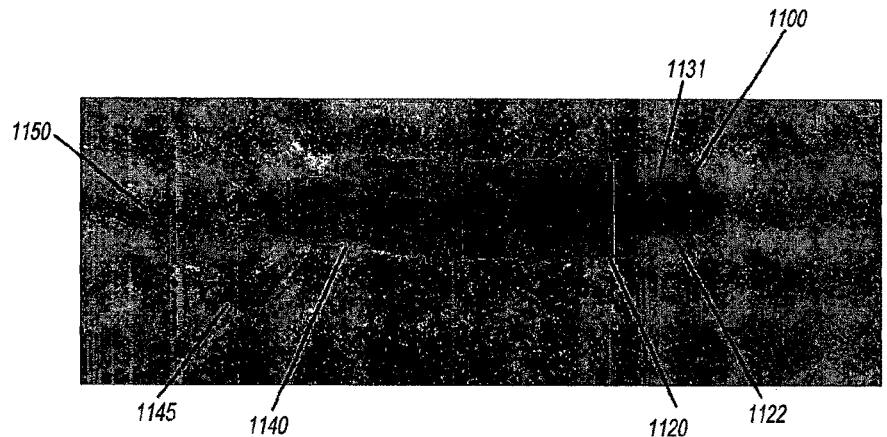
FIGS. 28A-B are photographs of experiments performed to determine the efficacy of certain embodiments of wound closure devices.
Figure 28B:
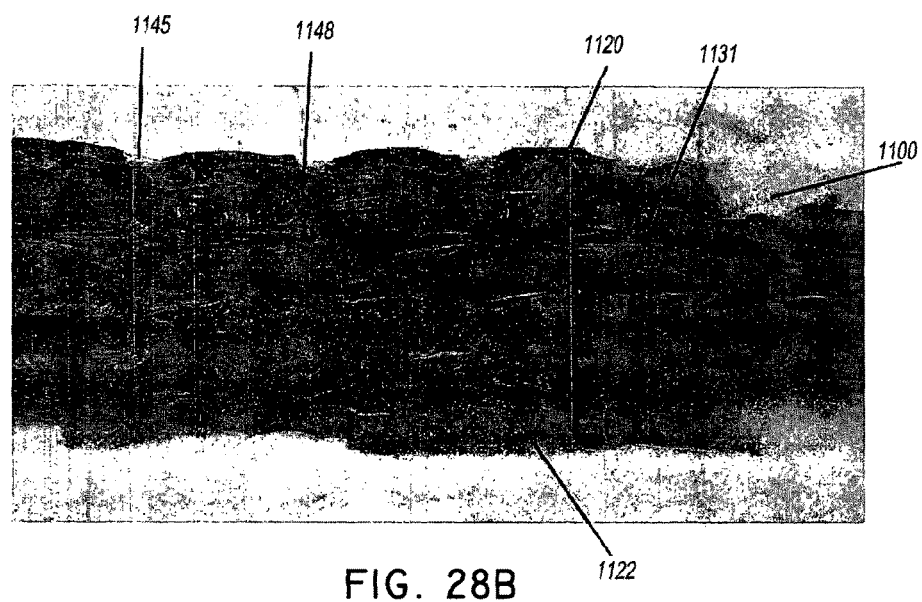

The FIGS. 28A-B are photographs of an embodiment of a stabilizing structure 1100 similar to the one described above in relation to FIGS. 19A-B. Here, the structure 1100 is inserted into a wound 1140 and placed under a drape 1145. A source of negative pressure is connected via a fluidic connector 1150. FIG. 28B is a closeup view of the stabilizing structure 1100 photographed in FIG. 28A, which illustrates how the cells 1131 collapse upon the application of negative pressure while under the drape 1145. An optional porous wound filler 1148 is also illustrated.

Figure 20:
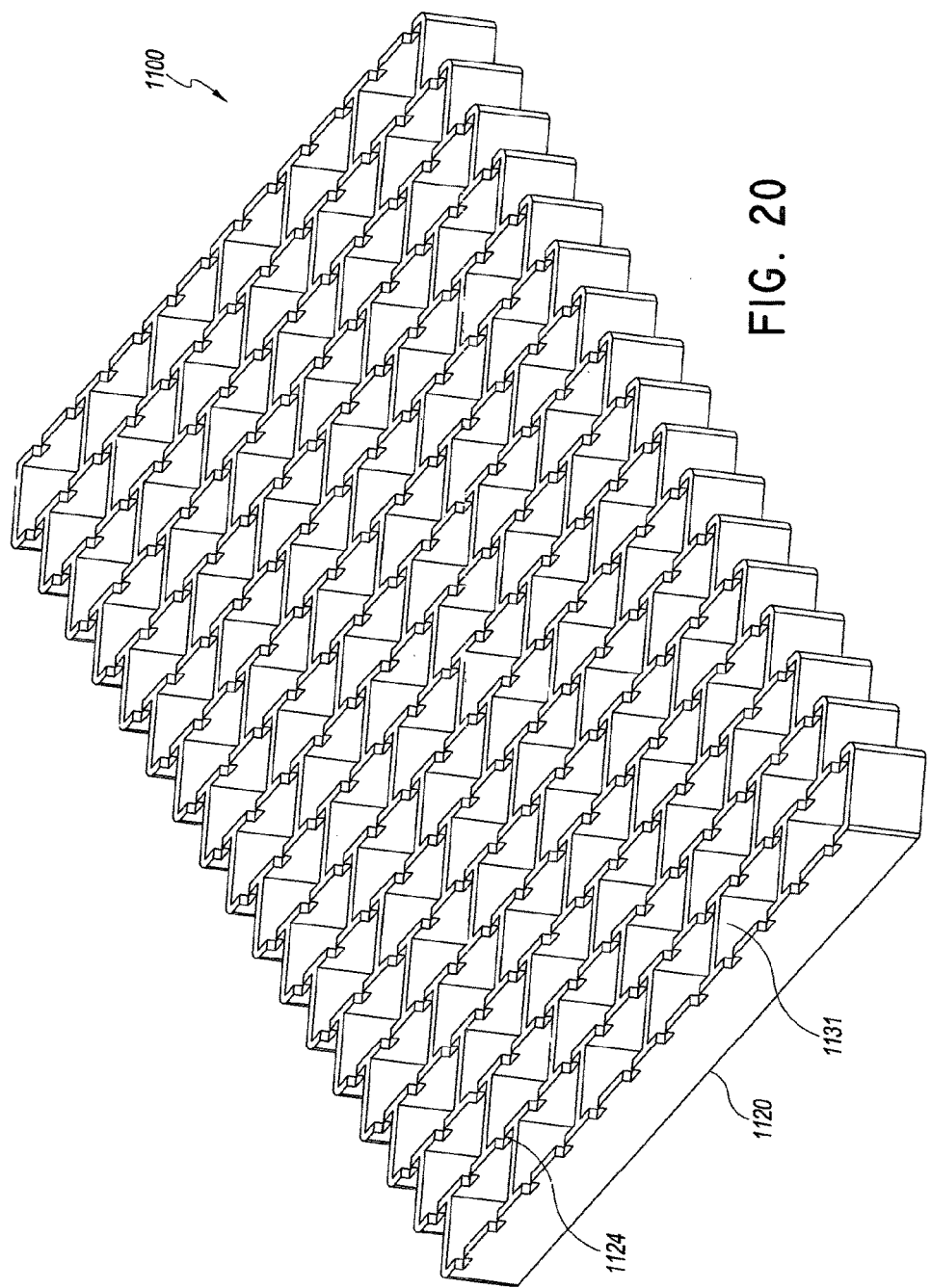

FIG. 20 illustrates another embodiment of a stabilizing structure 1100, here comprising two or more longitudinal strips 1120 attached to each other via one or more angled cross strips 1124 so as to form cells 1131. As with the embodiment illustrated in the preceding figure, the stabilizing structure 1100 is configured to collapse when pushed in a direction perpendicular to the length of the longitudinal strips 1120, while remaining substantially rigid or uncollapsed when force is applied in a vertical direction. The angled cross strips 1124 are preferably attached to the longitudinal strips 1120 so as to form a non-perpendicular angle so as to promote collapse of the stabilizing structure 1100 in the direction perpendicular to the length of the longitudinal strips 1120. As with FIGS. 19A-B, one or more notches may be formed on either or both of the longitudinal strips 1120 and/or angled cross strips 1124.

Figure 21:
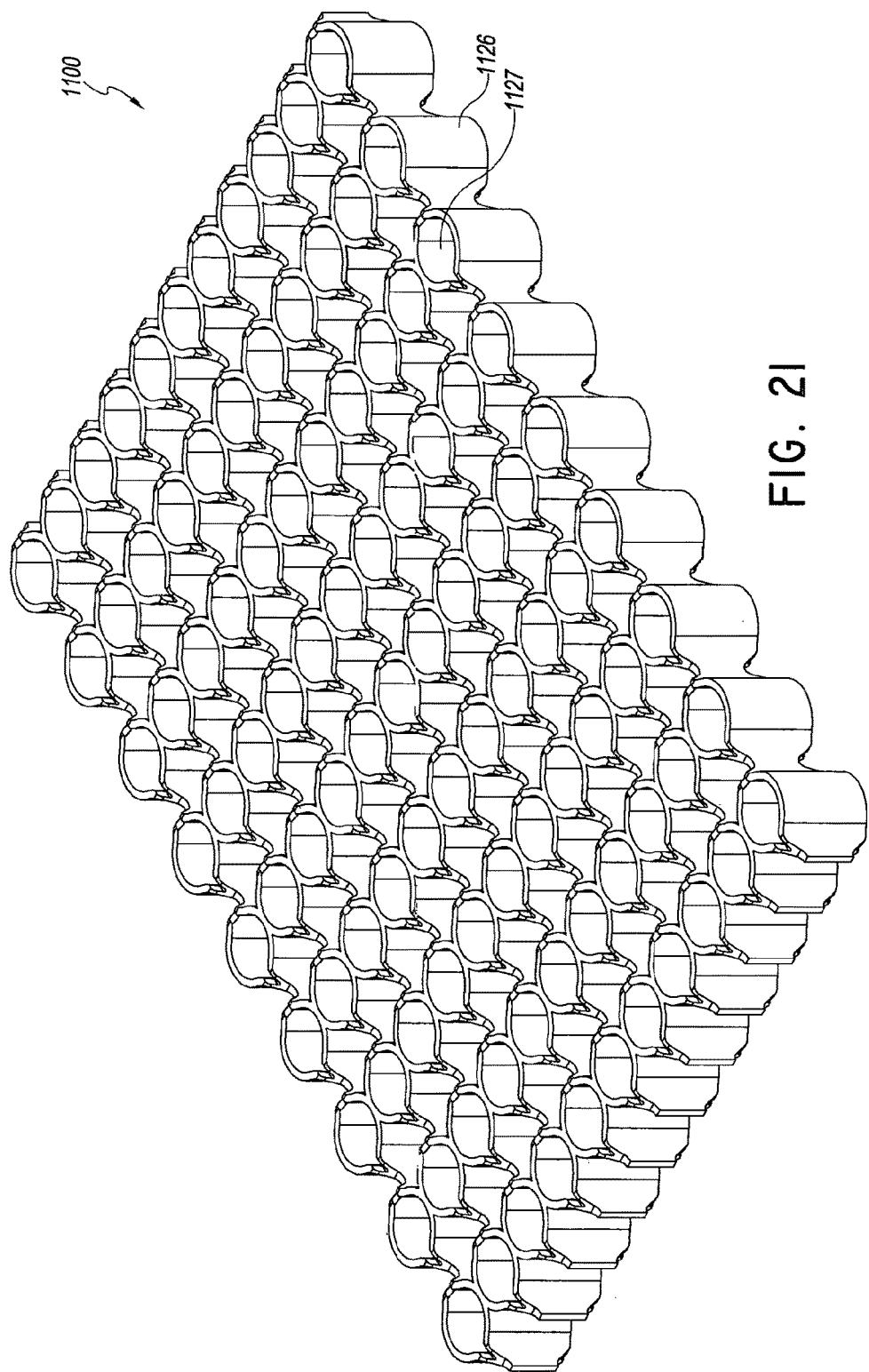

FIG. 21 illustrates a single unit stabilizing structure 1100 comprising one or more pairs of curved longitudinal strips 1126. Each individual longitudinal strip 1126 may be formed as a "wavy" strip (when seen from a vertical orientation) that, when joined face-to-face, form a one or more circular or ovoid cells 1127. As with the other stabilizing structures illustrated in this section or elsewhere in this specification, this structure 1100 is configured to preferably collapse along a horizontal plane or direction while remaining substantially rigid or uncollapsed when force is applied in a vertical direction. Although the structure 1100 is illustrated here as being formed from a single unit, the structure may be constructed from two or more curved longitudinal strips 1126 welded or attached together at the points shown. As with several other embodiments described in this section or elsewhere in this specification, one or more notches may be made onto the walls so as to aid in fluid transfer across and through the structure 1100.

Figure 22:
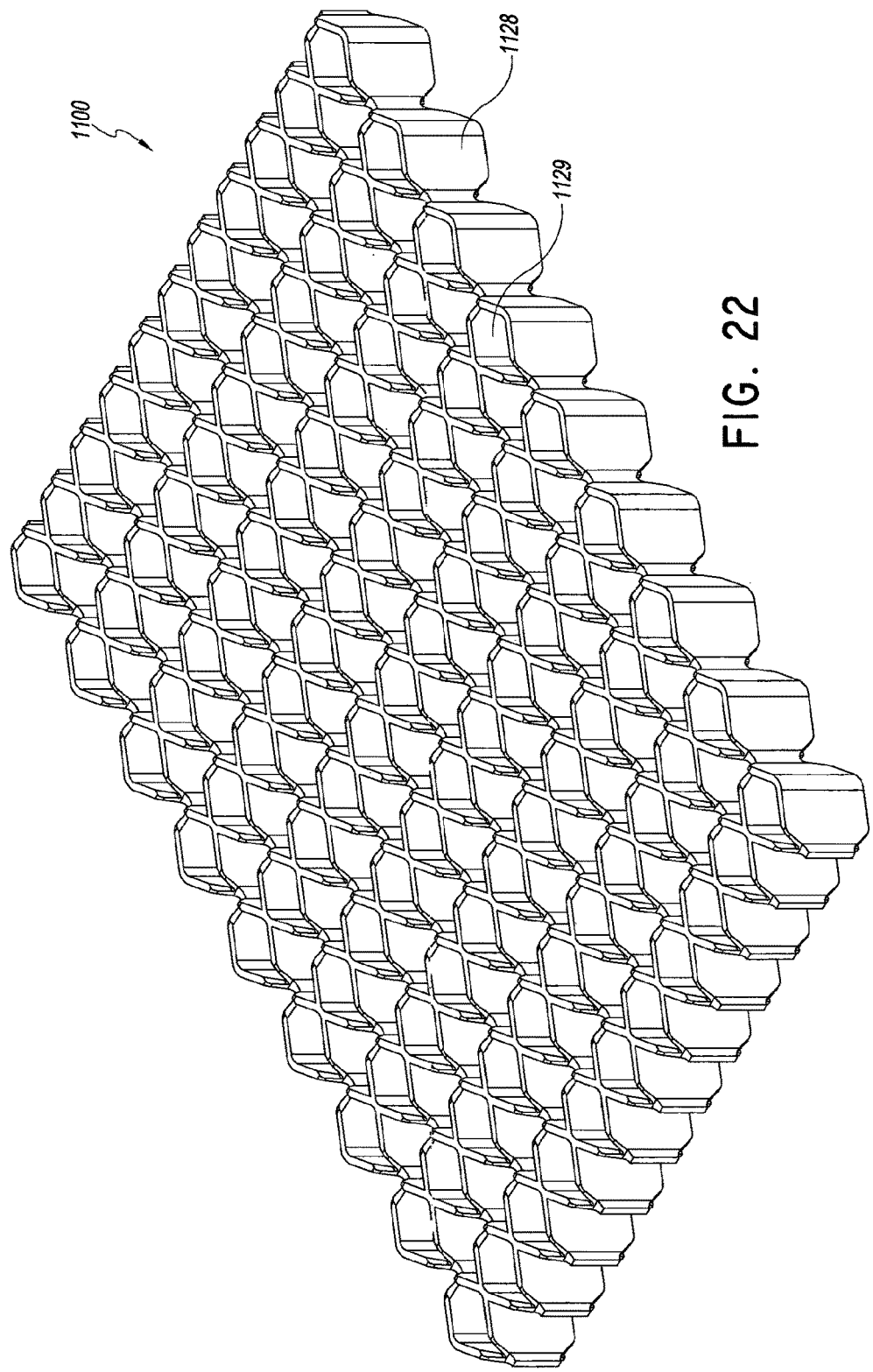

FIG. 22 illustrates a stabilizing structure 1100 similar to the one illustrated in FIG. 21. Here, however, zigzag longitudinal strips 1128 are joined to form diamond-shaped (rather than circular or ovoid) cells 1129. It will be of course appreciated that this embodiment may also be manufactured using substantially straight strips in a style similar to the embodiments illustrated in FIGS. 16A-D.

Figure 23:
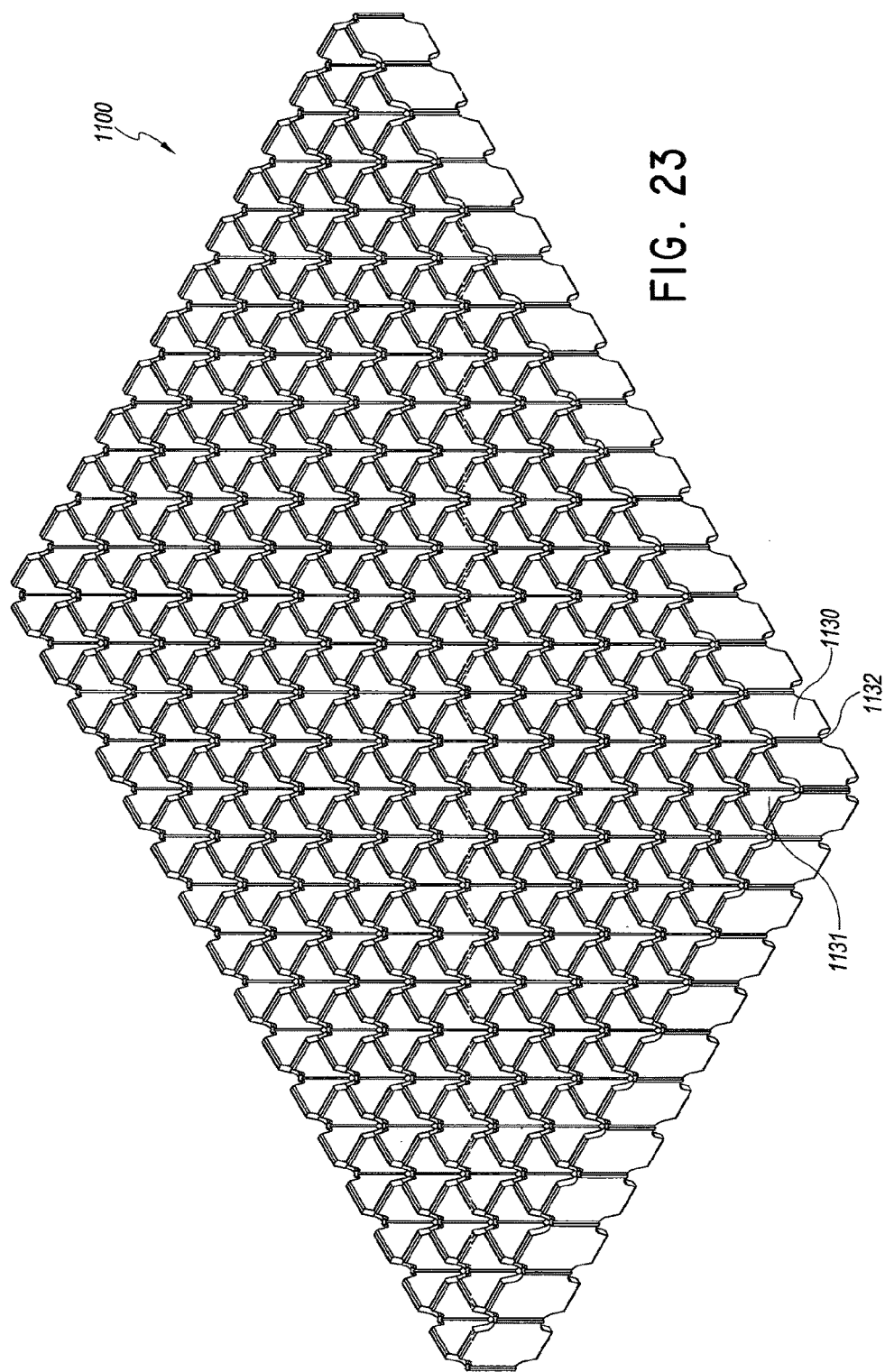

FIG. 23 illustrates a stabilizing structure 1100 comprising vertical segments 1130 joined together at approximately perpendicular angles so as to form quadrilateral or square cells 1131. Preferably, the vertical segments 1130 are of a square or rectangular shape, with tapers 1132 that join the segments together in a movable and flexible configuration. As with the other embodiments described in this section or elsewhere in this specification, this stabilizing structure 1100 may be manufactured as a single unit, and is preferably configured to collapse in a horizontal plane or direction while remaining substantially uncollapsed in a vertical direction.

Figure 24A:
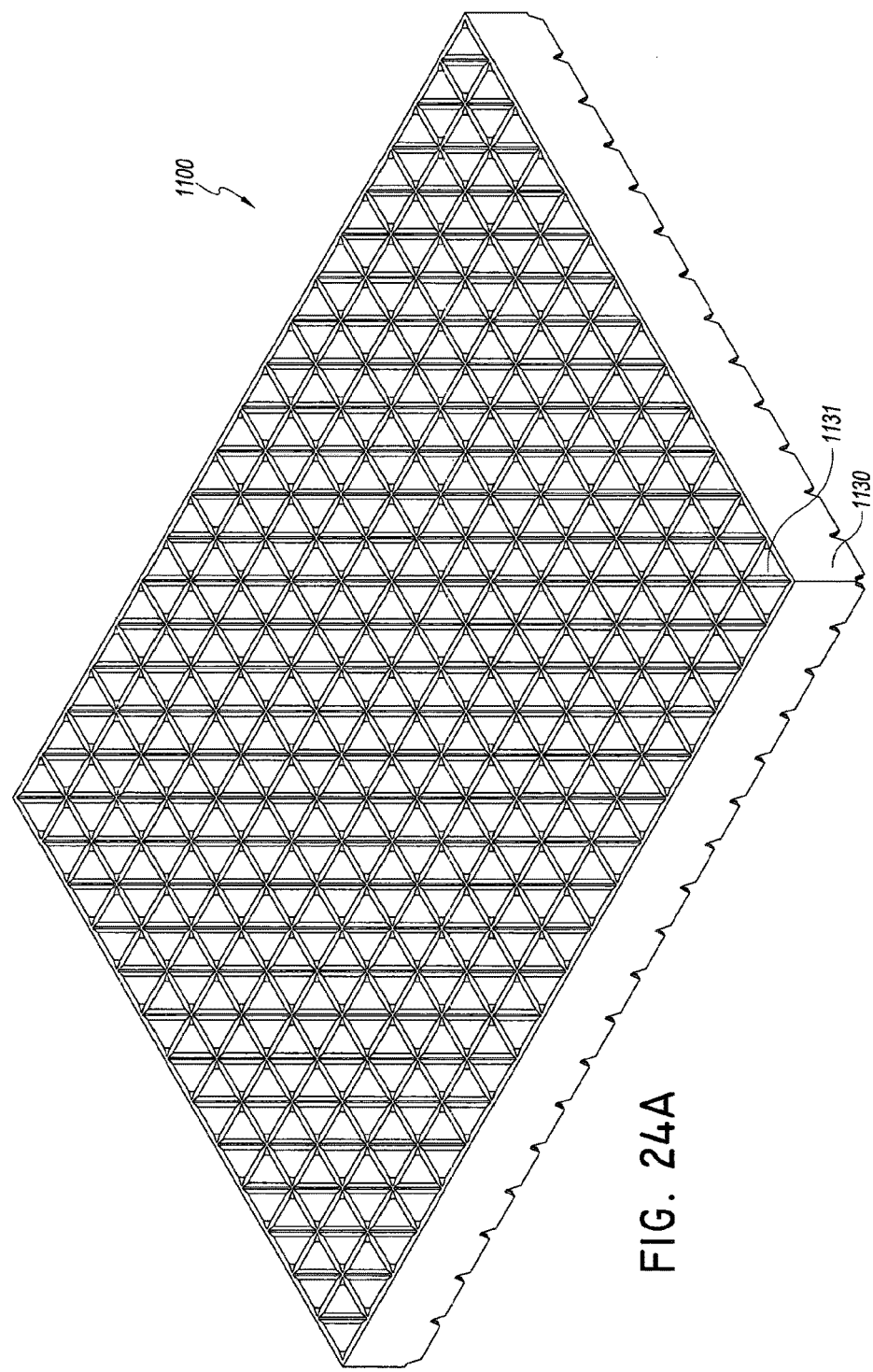
Figure 24B:
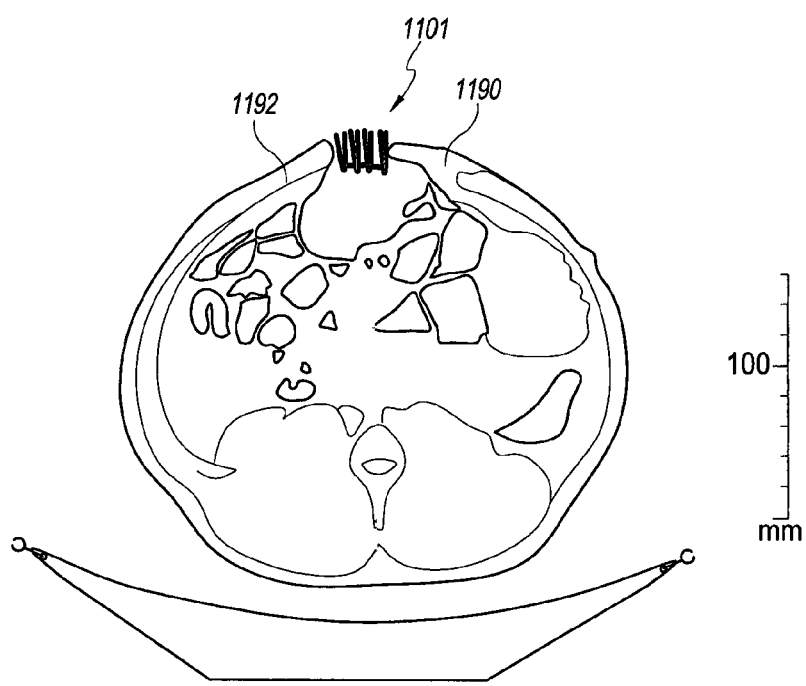

FIG. 24A-B illustrates another stabilizing structure 1100 similar to the embodiment illustrated above in FIG. 23. The vertical segments 1130 are preferably joined together so as to form one or more quadrilateral or square cells 1131. Here, however, the vertical segments 1130 do not comprise a tapered portion 1132. However, one or more notches may be present on the underside (wound-facing side) of the structure 1100, and which function as described in preceding embodiments. Although this embodiment may be manufactured from multiple vertical segments 1130, it is preferably molded as a single unit.

FIG. 24B illustrates a CT image of an embodiment of a stabilizing structure 1100 as described above in relation to FIG. 24A, and which has been inserted into an abdominal wound. Subcutaneous fat layers 1190 are bilateral and present over muscle tissue layer 1192. Upon application of negative pressure (as illustrated), improved fascial re-approximation and wound closure may be observed. Here, the width of the wound along the view illustrated reduced from approximately 82 mm to 52 mm, a reduction of 37%.

In some embodiments, the stabilizing structures described in this section or elsewhere in this specification (such as those described in FIGS. 19A-24B) may be entirely molded from a single type of material, such as a plastic. In other embodiments, the stabilizing structures described in this section or elsewhere in this specification may be constructed via an overmolding process whereby the more rigid portions of the structure are molded first and the hinges or flexible portions are molded second. In further embodiments of the stabilizing structure described in this section or elsewhere in this specification, a soft polymer could be molded over the entire structure to soften the feel of the device, thereby protecting the surrounding organs and/or other tissues. In other embodiments, the soft polymer could be molded only over the bottom portion of the stabilizing device, while in some embodiments the softer polymer can be molded over the top and/or the sides of the device. In some embodiments, the soft polymer could be molded over particular edges of the stabilizing structure, such as those on the bottom, sides, and/or top. In certain embodiments, the soft polymer could be molded over any side or combination of sides of the stabilizing device. The soft polymer may act like a softened rim surrounding the hard edges of the stabilizing structure.

Figure 40:
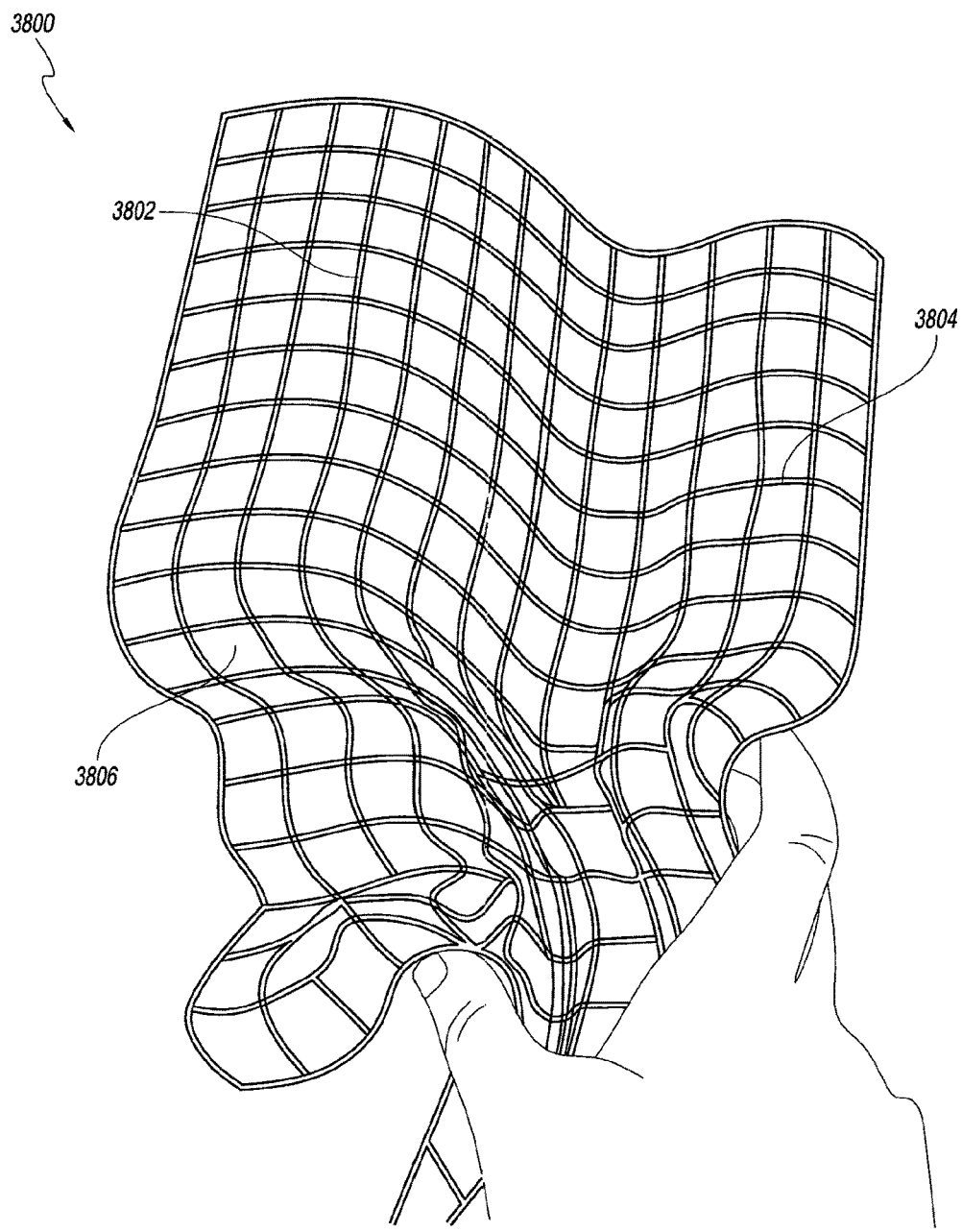
FIG. 40 illustrates an embodiment of a fully flexible stabilizing structure.

FIG. 40 illustrates an embodiment of a stabilizing structure 3800 similar to the structures described in FIGS. 19-24A. In this embodiment, the longitudinal strips 3802 and cross strips 3804 are formed from a single piece of material and form rows of flexible cells 3806 that are configured to collapse in a horizontal plane. Because each of the longitudinal and cross strips are formed from the same flexible material, applying a lateral force to the structure causes the cells to collapse generally independently of each other. In other words, the collapse of one or more cells in a row does not necessarily cause the collapse of other cells in the same row.

Example 5

Figure 25A:
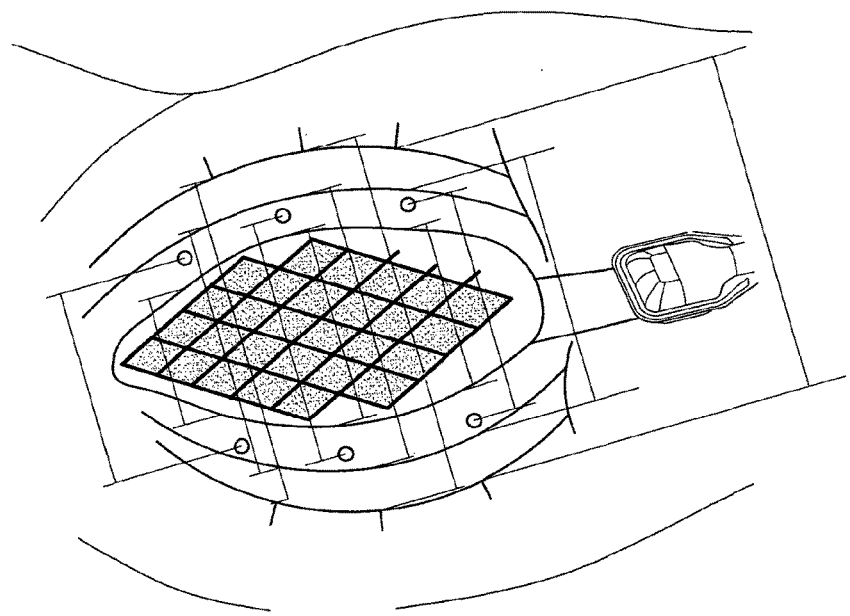
FIGS. 25A-B, 26A-B are before and after photographs of experiments performed to determine the efficacy of certain embodiments of wound closure devices.

In this next non-limiting experiment, the wound described in the preceding examples had an embodiment of the stabilizing structure device described above in relation to FIGS. 16A-E inserted into the abdominal cavity. In this experiment, and as illustrated in FIG. 25A, white foam inserts were placed into the quadrilateral openings of the stabilizing structure, and the outer edges (in contact with the wound) were wrapped in black foam. The wound and stabilizing structure were then sealed with a drape and connected to a source of negative pressure as described previously.

Figure 25B:
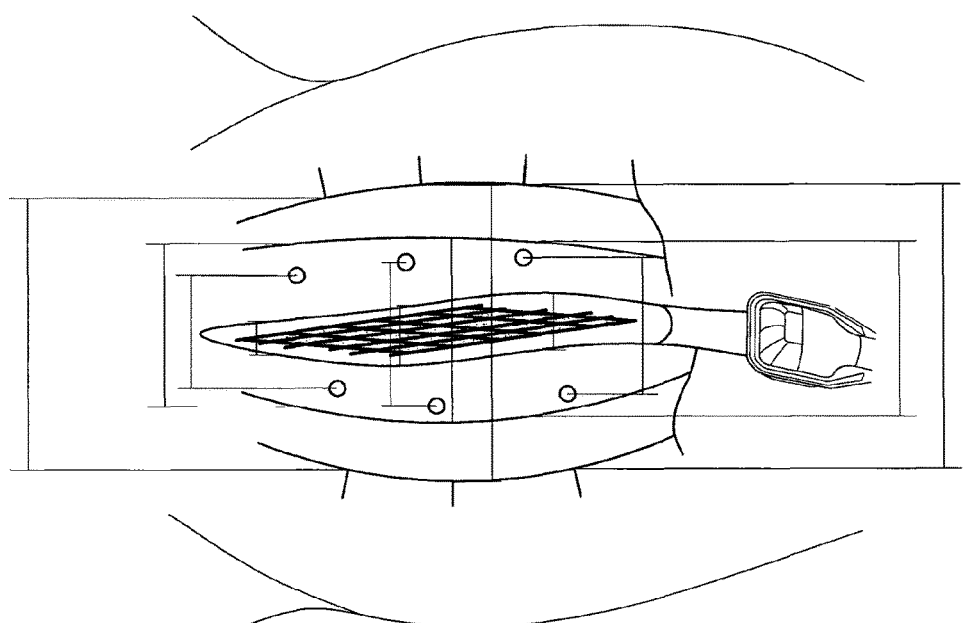

Wound area measurements were taken before and after activation of the negative pressure source. Here, the size of the wound before application of negative pressure was measured as 171 mm2. Upon the application of negative pressure, as illustrated in FIG. 25B, the area of the wound was greatly reduced to 55 mm2, a reduction of 68%. It is noted that here and in the following examples, as the wound area contracts along its width, the length of the wound increases slightly, indicating that the tissue margins are returning to their original anatomical position.

Example 6

Figure 26A:
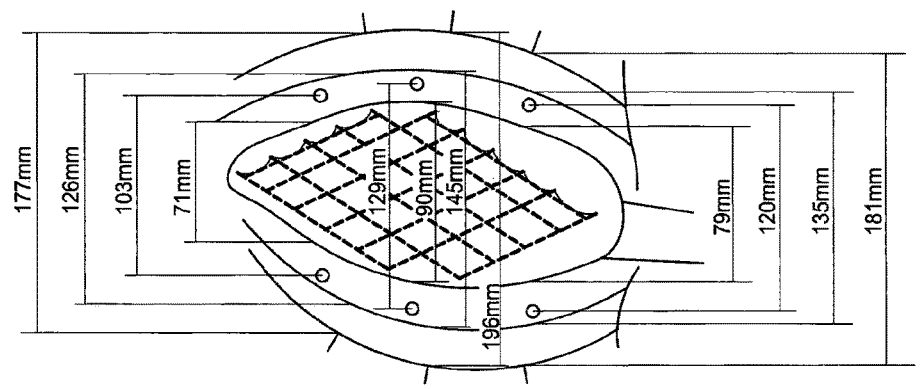
Figure 26B:
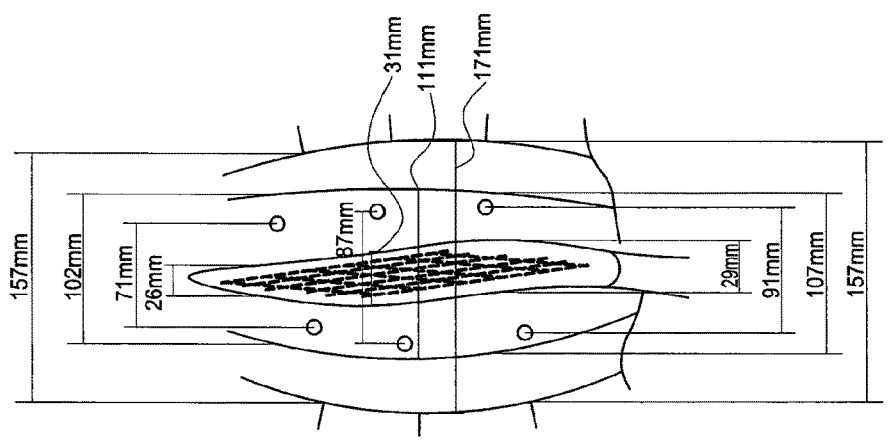

FIGS. 26A-B illustrate the results of a non-limiting experiment similar to those illustrated above, where a stabilizing structure similar to the embodiments of FIGS. 16A-E was inserted into the abdominal cavity. Here, the spaces in the quadrilateral openings of the stabilizing structure were empty, and a layer of foam was wrapped around the outer edges of the structure.

Wound area measurements before and after application of negative pressure indicated that the wound area decreased by 63%, from 155 mm2 to 58 mm2.

Without wishing to be bound by theory, the greater reduction in wound area in the preceding examples, as compared to the black foam control of Example 1, is believed to be due to the fact that the wound devices used therein do not significantly compress in a vertical direction when negative pressure is applied. This is different from traditional foam dressings, where the application of negative pressure causes downward pressure on the foam due to the air pressure pressing onto the drape, [thus causing the foam to collapse towards the wound bed, creating a concave shape to the drape. The atmosphere acts predominantly in a perpendicular direction to the surface of the drape. Thus, on the periphery of the concave shape, closest to the wound edge or where the drape approaches an angle perpendicular to the plane of the wound, the atmosphere now creates a force in a direction that pushes the wound apart.] Similarly, pressure is transmitted along the foam dressing into a horizontal force that pushes the wound margins outward. With the use of a stabilizing structure as used in the various examples illustrated here, the foam and other dressing components are not pushed outward, and thus the wound margins may be approximated more easily so as to achieve faster wound closure. In fact, in some experiments, certain embodiments of the wound devices projected upward over the wound margins, and these vertical surfaces may therefore allow for atmospheric pressure to produce contractile forces onto the devices and/or the wound margins.

Traditional negative pressure wound treatment typically uses foam (or other porous materials) placed into a wound underneath a drape, to which negative pressure is applied to the wound. In such situations, the application of negative pressure may cause downward pressure on the foam due to the air pressure pressing onto the drape, which is then transmitted along the foam dressing into a horizontal force that pushes the wound margins outward. Without wishing to be bound by theory, it is believed that some of the embodiments of stabilizing structures, wound closure devices, and wound treatment devices, methods, and systems described below are able to cause a greater reduction in wound area as compared to traditional negative pressure treatment. One of these factors is believed to be because embodiments of the stabilizing structures and wound closure devices described in this section or elsewhere in this specification do not significantly compress in a vertical direction when negative pressure is applied. With the use of certain embodiments described in this section or elsewhere in this specification, foam and other dressing components are not pushed outward due to negative pressure, and thus the wound margins may be approximated more easily so as to achieve faster wound closure and better wound healing.

Stabilizing Structures and Wound Closure Devices of FIGS. 29A-35B

As with the other stabilizing structures and wound closure devices described elsewhere in the specification, the stabilizing structures and wound closure devices of FIGS. 29A-35B may be incorporated into the wound packing and wound treatment apparatus embodiments described elsewhere in the specification, such as in relation to FIGS. 8A-10.

Figure 29A:
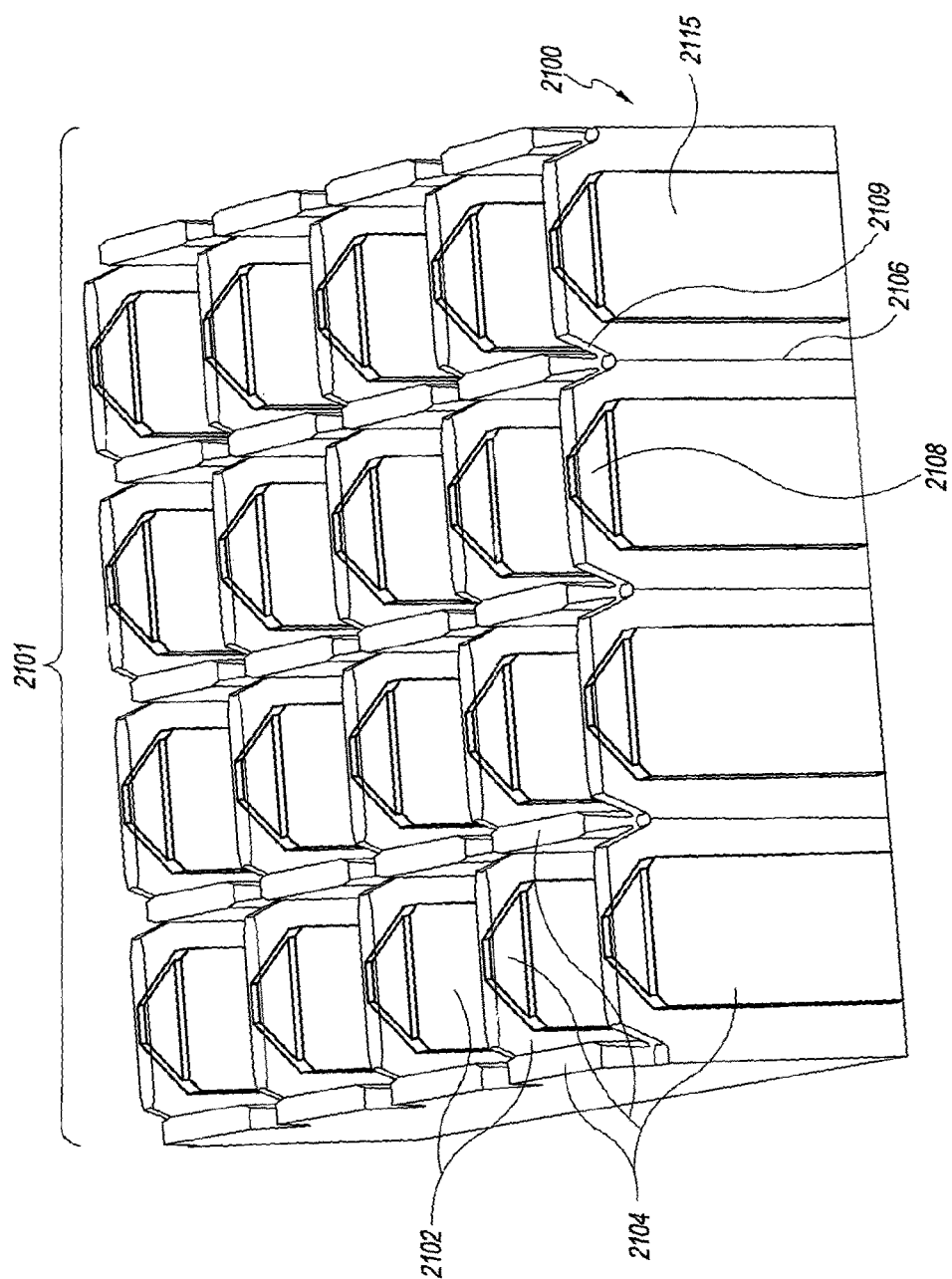
FIGS. 29A-E are photographs of various embodiments of stabilizing structures comprising inserts disposed therein.

FIG. 29A is a photograph of an embodiment of a wound closure device comprising a stabilizing structure 2100 that may be placed or inserted into a wound. Here, the device comprises a plurality of cells 2102 provided side-by-side in a generally planar configuration. Preferably, the stabilizing structure 2100 is configured to collapse in a direction along a plane 2101 defined by the width of the device, without significantly collapsing in a direction perpendicular to the plane 2101. That is, when viewed in the figure, the stabilizing structure 2100 will collapse in the horizontal direction, but will not compress in the vertical direction. In some embodiments, the stabilizing structure collapses in conjunction with the movement of tissue. Here, the cells 2102 are preferably open at both ends in a direction perpendicular to the plane 2101.

Each of the cells 2102 is preferably formed with four walls 2104, each wall 2104 being joined to the next by a flexible joint 2106. The joints 2106 are preferably designed so as to be more flexible than the walls 2104, and promote collapse of the stabilizing structure 2100 in the direction of the plane. Of course, it will be understood that other configurations are possible, and in some embodiments each cell 2102 may be defined by less than or greater than four walls 2104, for example five walls or six walls, thus forming pentagonal or hexagonal cells. The cells 2102 may not necessarily be symmetric, and can form rectangular, diamond, rhomboidal, trapezoidal, parallelepiped, oblong, oval, lozenge and other such shapes in addition to the square-walled embodiment illustrated in this section or elsewhere in this specification.

One or more of the walls 2104 defining the one or more cells 2102 may further comprise an insert 2115 disposed therein, and described in greater detail below in FIGS. 30A-F. Preferably, the insert 2115 will be constructed from a material more rigid than the material used to construct the remainder of the wall 2104. Some suitable materials may include metals such as titanium, stainless steel, and largely inert alloys (such as monel and hastelloy), and/or polymers such as polyurethane, silicone, rubber, isoprene, polyethylene, polypropylene, nylon, polyacrylate, polycarbonate, and PEEK. Some embodiments may also comprise composite materials, including resin-reinforced fiber composites where the resin may be, for example, various types of epoxies. Suitable fibers may include glass, carbon, carbon nanotubes, graphene, and aramids (e.g., Kevlar). Preferably, the material chosen for the insert 2115 is not only sufficiently rigid, but also able to adhere to the material used in the wall 2104. For example, the insert material is preferably able to adhere to softer polymers such as silicones or polyurethanes used in the wall 2104. The more rigid materials used in the insert 2115 may provide for additional collapse resistance in the direction perpendicular to the plane for the stabilizing structure 2100.

In some embodiments, one or more notches 2109 may be provided between multiple walls 2104, and which may further aid in permitting the flexible joints 2106 to move. Without wishing to be bound by theory, the notches 2109 may also aid in distributing negative pressure and transmitting fluid throughout the stabilizing structure 2100 when negative pressure is applied, for example in a clinical care setting. Some embodiments may also comprises holes in the walls 2104 or joints 2106, or be constructed from porous materials.

Preferably, a cavity 2108 is provided within each wall 2104 for the insert 2110 to be disposed therein. The walls 2104 may be molded around each insert 2115. An insert 2115 may also be inserted into the cavity 2108 after the wall 2104 is manufactured. While the embodiment illustrated here and in the subsequent images shows a single insert 2115 in each wall 2104, some embodiments may be provided with one or more inserts 2115 disposed therein.

Figure 29B:
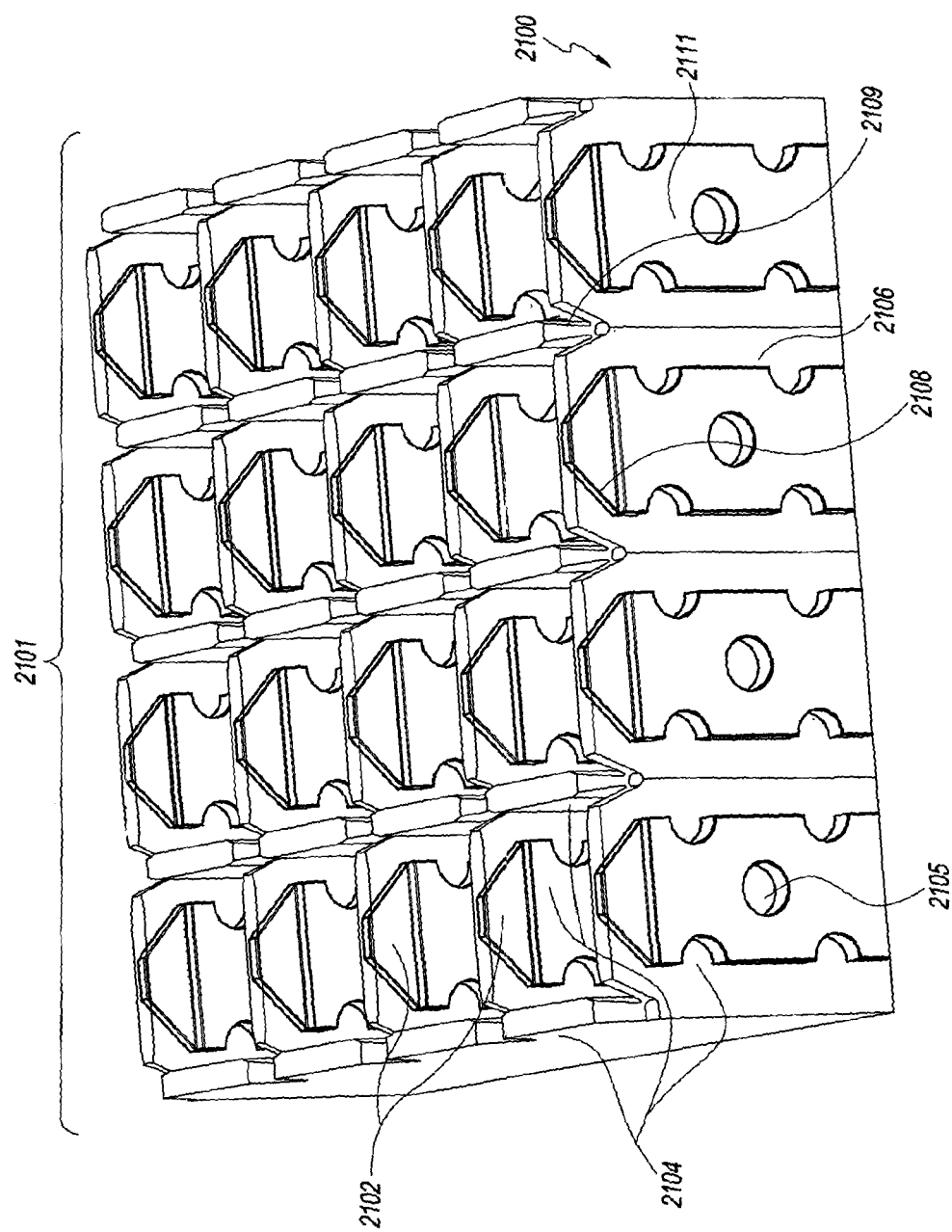

FIG. 29B illustrates an embodiment of a stabilizing structure 2100 with many similar features to FIG. 29A. Here, an insert 2111 comprises structural differences compared to the insert 2110, and is discussed in more detail below in relation to FIG. 30E. When inserted or placed within the cavity 2108, one or more of the walls 2104 may comprise a hole 2105 communicating through at least one aperture in the insert 2111. In addition to any notches 2109, the one or more holes 2105 may permit additional displacement of wound exudate and distribution of negative pressure within the stabilizing structure 2100.

Figure 29C:
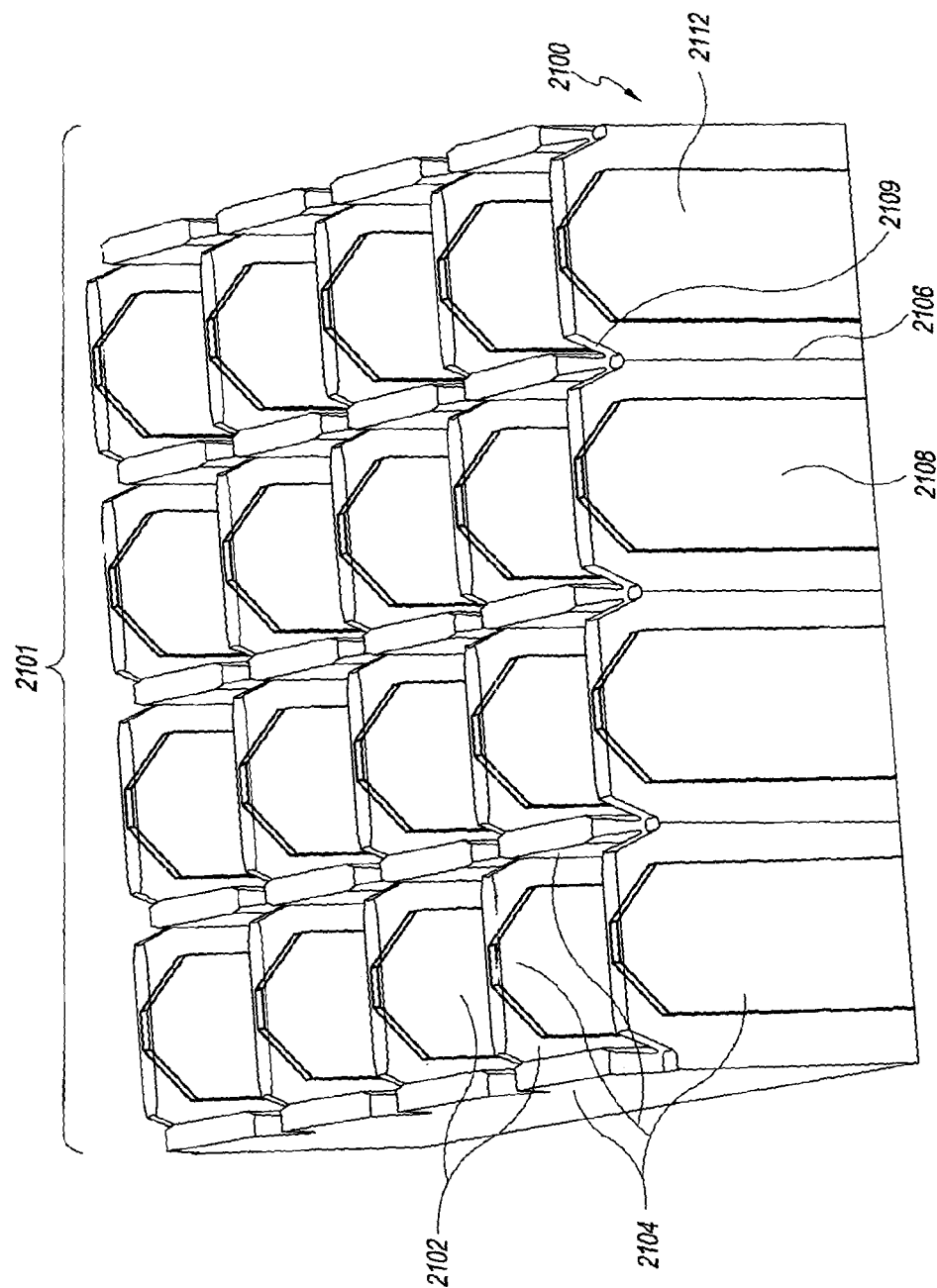

FIG. 29C illustrates an embodiment of a stabilizing structure 2100 with similar features as the other embodiments described previously. In this embodiment, the stabilizing structure 2100 comprises an insert 2112 described in greater detail below in FIG. 22F.

Figure 29D:
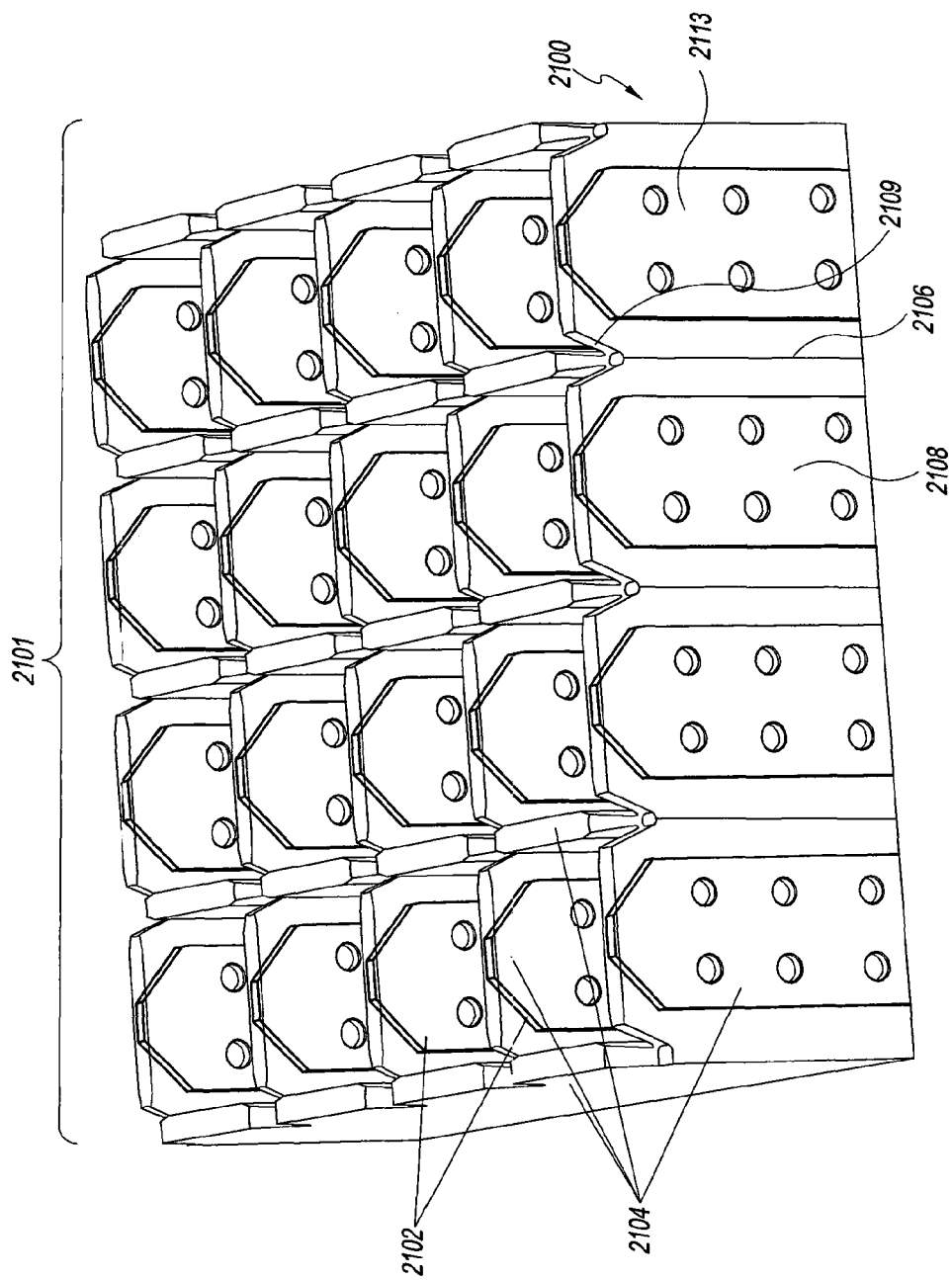
Figure 29E:
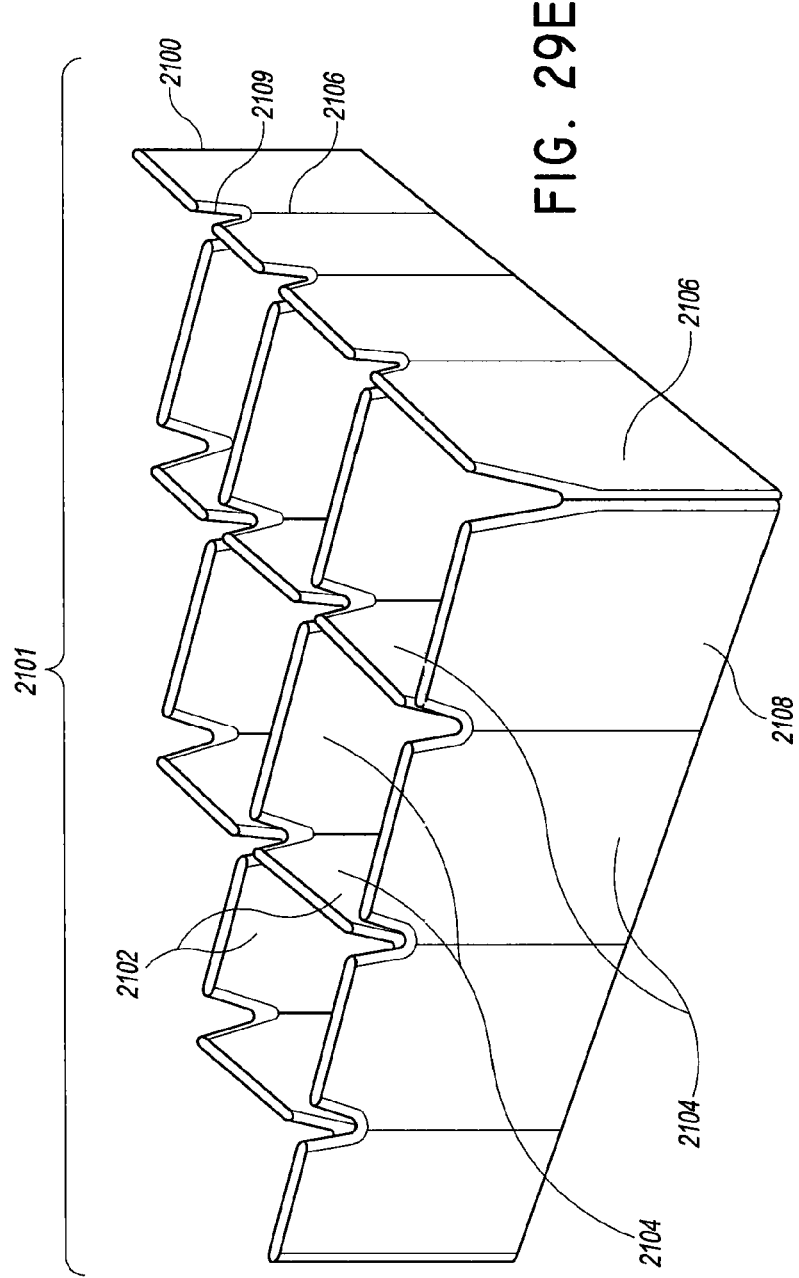

Similarly, FIG. 29D illustrates an embodiment of a stabilizing structure 2100 comprising an insert 2113 described in greater detail below in FIG. 30D. FIG. 24E illustrates an embodiment of a stabilizing structure 2100 comprising an insert 2114 described in greater detail in relation to FIG. 25A.

In the preceding embodiments of stabilizing structures 2100 comprising various inserts 2110, 2111, 2112, 2113, 2114, and 2115, it will of course be understood that embodiments of the stabilizing structure 2100 does not need to contain only one type of insert. Likewise, each cell 2102 or wall 2104 may comprise one or more different types of inserts, or no inserts at all. Varying the different inserts and other properties of the cells 2102 and walls 2104 may thus permit the stabilizing structure 2100 to be tailored to the appropriate wound type so as to effect optimal wound closure and/or treatment.

FIGS. 30A-F illustrate examples of different inserts that may be used as part of a stabilizing structure 2100. Preferably, these inserts may be placed, molded into, or formed as part of a wall 2104 in a stabilizing structure 2100 (e.g., of the types illustrated above in FIG. 29A-E). Various modifications may be made, as described below, that may improve or alter characteristics of the inserts.

Figure 30D:
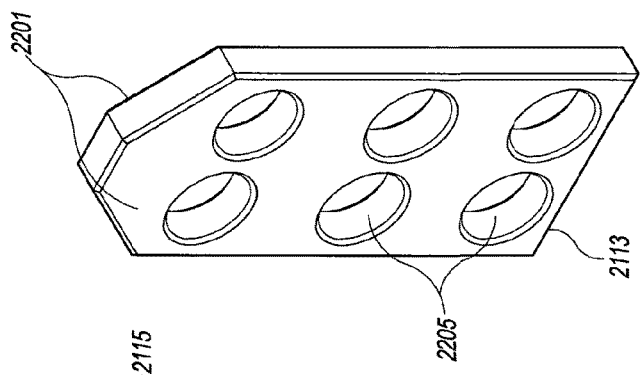
FIGS. 30A-F illustrate various embodiments of inserts that may be used in stabilizing structures.
Figure 30C:
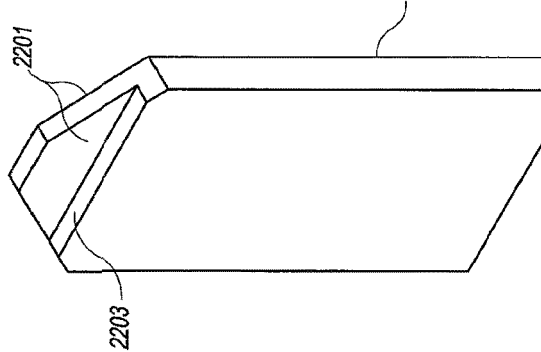
Figure 30B:
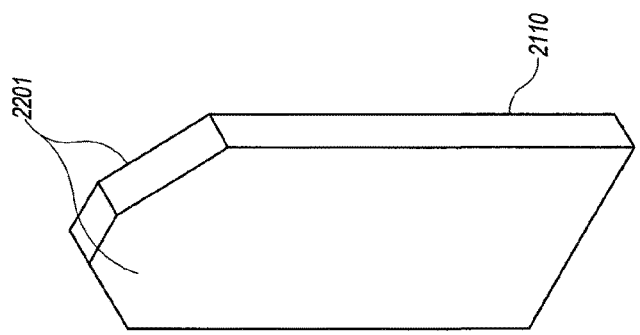
Figure 30A:
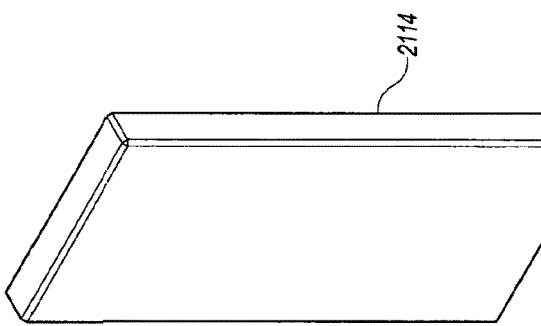

Turning now to FIG. 30A, the embodiment of the insert 2114 illustrated here is approximately rectangular in shape, and is adapted to be inserted or formed into one or more of the walls 2104 of an embodiment of the stabilizing structure 2100. In some embodiments, one or more of the inserts 2114 may have a height greater than the width, and the wall 2104 may have a height of at least about 1 mm, at least about 5 mm, at least about 10 mm, at least about 15 mm, at least about 20 mm, at least about 25 mm, at least about 30 mm, at least about 35 mm, at least about 40 mm, at least about 50 mm, at least about 75 mm, at least about 100 mm, at least about 150 mm, at least about 200 mm, at least about 250 mm, at least about 300 mm, at least about 350 mm, at least about 400 mm, or more than 400 mm, particularly in extremely obese patients. Preferably, in average patients, the heights may range from about 10 mm to 40 mm. These measurements may apply to any stabilizing structure described in this section or elsewhere in this specification.

In some embodiments of any stabilizing structure described in this section or elsewhere in this specification, the width may be between about 1 mm to 30 mm, 2 mm to 25 mm, 4 mm to 20 mm, 6 mm to 18 mm, 8 mm to 16 mm, or 10 mm to 14 mm, preferably about 10.8 mm. These measurements may apply to any stabilizing structure described in this section or elsewhere in this specification.

The insert 2114 is preferably thin but with enough structural strength to resist collapse, and in some embodiments of any stabilizing structure described in this section or elsewhere in this specification, the thickness may be at least about 0.01 mm to 10 mm, 0.2 mm to 8 mm, 0.4 mm to 6 mm, 0.5 mm to 4 mm, 0.75 mm to 3 mm, or 1-2 mm. These measurements may apply to any stabilizing structure described in this section or elsewhere in this specification.

In some embodiments of any stabilizing structure described in this section or elsewhere in this specification, multiple discrete stabilizing structures may be stacked on top of one another to form the wound closure device, to extend the height of the device to any of the dimensions described in this section or elsewhere in this specification (including the dimensions provided for the inserts above). The stacking of multiple stabilizing structures may allow the clinician to have further flexibility in their treatment strategies.

FIG. 30B illustrates an embodiment of the insert 2110 with a generally rectangular configuration, but provided with two notches 2201 cut diagonally across a top end of the insert 2100. The notches 2201 may facilitate clearance of the insert 2100 from any notches 2109 that may be provided in the walls 2104. Further, the notches 2201 may also aid in the insertion of the insert 2100 into the cavity 2108 of the wall 2104. The notches 2201 may also be helpful in conjunction with the notches 2109 in further defining a channel or other opening for fluid to be transmitted or transferred between and through each cell 2102. The notches 2201 may also aid in ensuring that the entire stabilizing structure is able to more easily collapse.

FIG. 30C illustrates an embodiment of an insert 2115 provided with two notches 2201 as well as a horizontal lip 2203. The horizontal lip 2203 may aid in inserting the insert 2115 into the cavity 2108 of the wall 2104, or may aid in fixing the wall 2104 around the insert 2115 when the wall is molded around it. The horizontal lip 2203 may be beneficial in effectively reducing the bulk of the insert at one end of the wall 2104, and in conjunction with a softer material used in the wall 2104, may thereby increase comfort due to the correspondingly greater amount of wall material. In some embodiments, the horizontal lip 2203 and/or notches 2201 may be present on both ends of the insert 2115 or other inserts described in this section or elsewhere in this specification. In some embodiments, the horizontal lip 2203 is approximately half the thickness of the overall insert 2115. For example, the insert 2115 may be between 0.5 mm and 4 mm in thickness, preferably 2 mm. If the insert 2115 measures 2 mm in thickness, the thickness of horizontal lip 2203 may be 1 mm.

FIG. 30D illustrates an embodiment of the insert 2113, and which is similar to the embodiment used in the stabilizing structure 2100 illustrated in FIG. 29D. This insert 2113 may comprise one or more apertures 2205, which in some embodiments may communicate with one or more holes 2105 that may be formed through one or more walls 2104. In some embodiments, the apertures 2205 are arranged in a 2×3 pattern illustrated here, although other arrangements are possible. Notches 2201 may also be present.

Figure 30F:
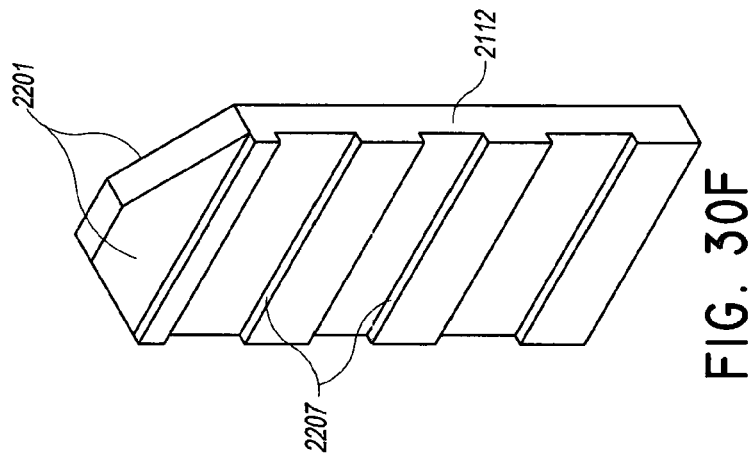
Figure 30E:
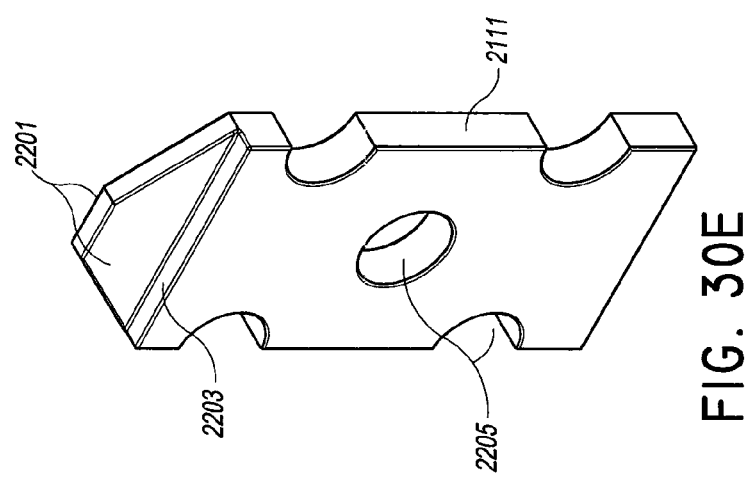

FIG. 30E illustrates an embodiment of the insert 2111, which is similar to the embodiment used in the stabilizing structure 2100 illustrated in FIG. 29B. The insert 2111 preferably comprises two notches 2201. A horizontal lip 2203 may also be provided. Preferably, one or more apertures 2205 may be formed therein. In some embodiments, one or more of the apertures 2205 may extend to the edge of the insert 2111 as illustrated. In some embodiments, the apertures 2205 may be configured to have four apertures arranged around a central aperture, although other configurations are of course possible. In some embodiments, the reduced amount of insert material at the locations of the apertures may be advantageous to provide a greater amount of softer wall material at a hinge point, where this may consequently increase flexibility. In a preferred embodiment, the insert 2111 has a height of 25 mm and a width of 10.8 mm, with a thickness of 2 mm. The first set of apertures may be centered approximately 5 mm from the bottom edge of the insert 2111, the central aperture may then be centered approximately 11 mm from the bottom, and the top set of apertures may be centered 17 mm from the bottom.

FIG. 30F illustrates an embodiment of the insert 2112, which shares some similarities to the embodiment used in the stabilizing structure 2100 illustrated above in FIG. 29C. The insert 2112 preferably may comprise one or more channels 2207 formed therein. Preferably, the one or more channels 2207 are disposed in a horizontal configuration across the width of the insert 2112. While the insert 2112 is preferably configured, like several other embodiments described in this section or elsewhere in this specification, to remain substantially uncompressed in the vertical direction, the inclusion of one or more horizontal channels 2207 may aid in providing additional rigidity in the direction of the plane defined by the cells 2102. In such a case, the rigidity of the one or more walls 2104 may be enhanced, and may thus control the compression of the stabilizing structure 2100 such that any collapse or bending occurs substantially only at the one or more joints 2106.

FIGS. 31A-F illustrate an embodiment of a stabilizing structure 3001 configured to be inserted into a wound. The stabilizing structure 3001 preferably comprises at least one top strip 3002 extending in a first direction (e.g., along an x axis) and at least one bottom strip 3004 extending in a second direction (e.g., along a y axis perpendicular to the x axis), these being preferably arranged into an array comprising multiple strips 3002, 3004. The strips 3002, 3004 are preferably connected together in a movably interlocking configuration, which preferably comprises an interlock mechanism 3006. The strips 3002, 3004 are preferably arranged in an un-collapsed configuration wherein the strips 3002 and 3004 are disposed at angles approximately perpendicular to each other. This arrangement forms a first plane that the stabilizing structure 3001 preferably adopts. Preferably, the stabilizing structure 3001 is more rigid in the direction perpendicular to the plane (i.e., in the vertical direction or along a z axis), and thereby substantially resists compression or deformation in that direction.

Figure 31A:
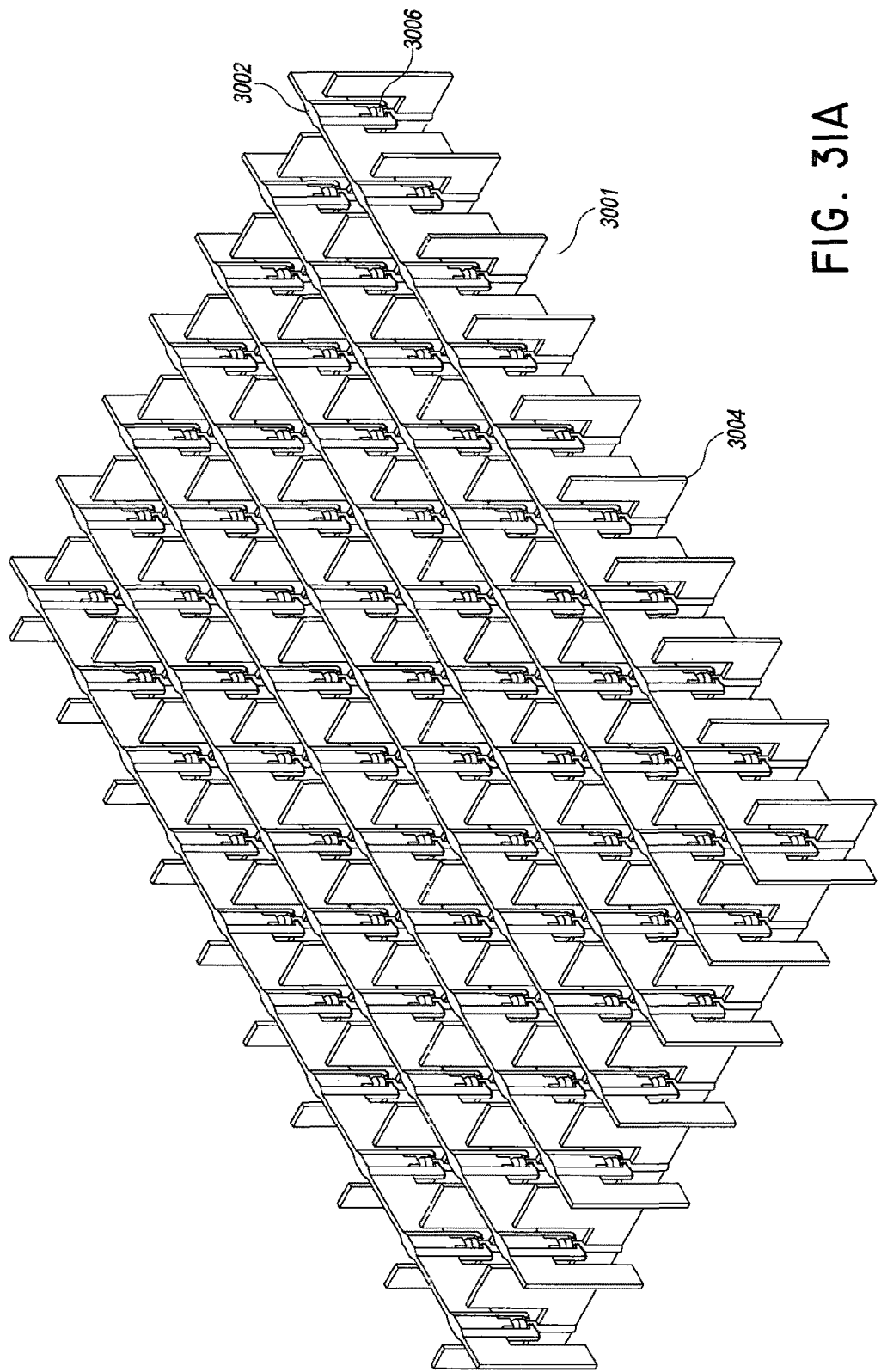
FIGS. 31A-F illustrate multiple views of an embodiment of a stabilizing structure.
Figure 31B:
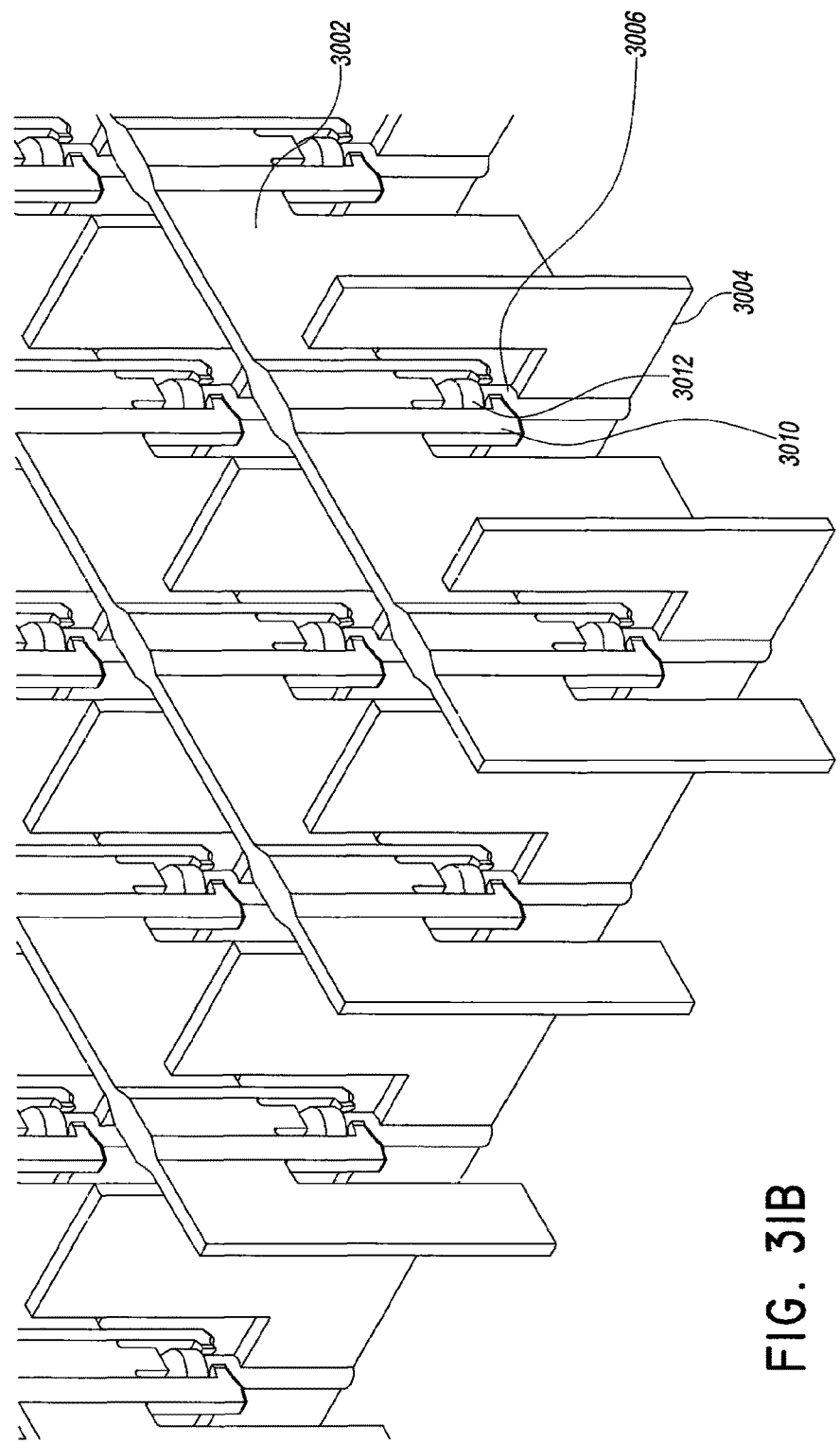
Figure 31C:
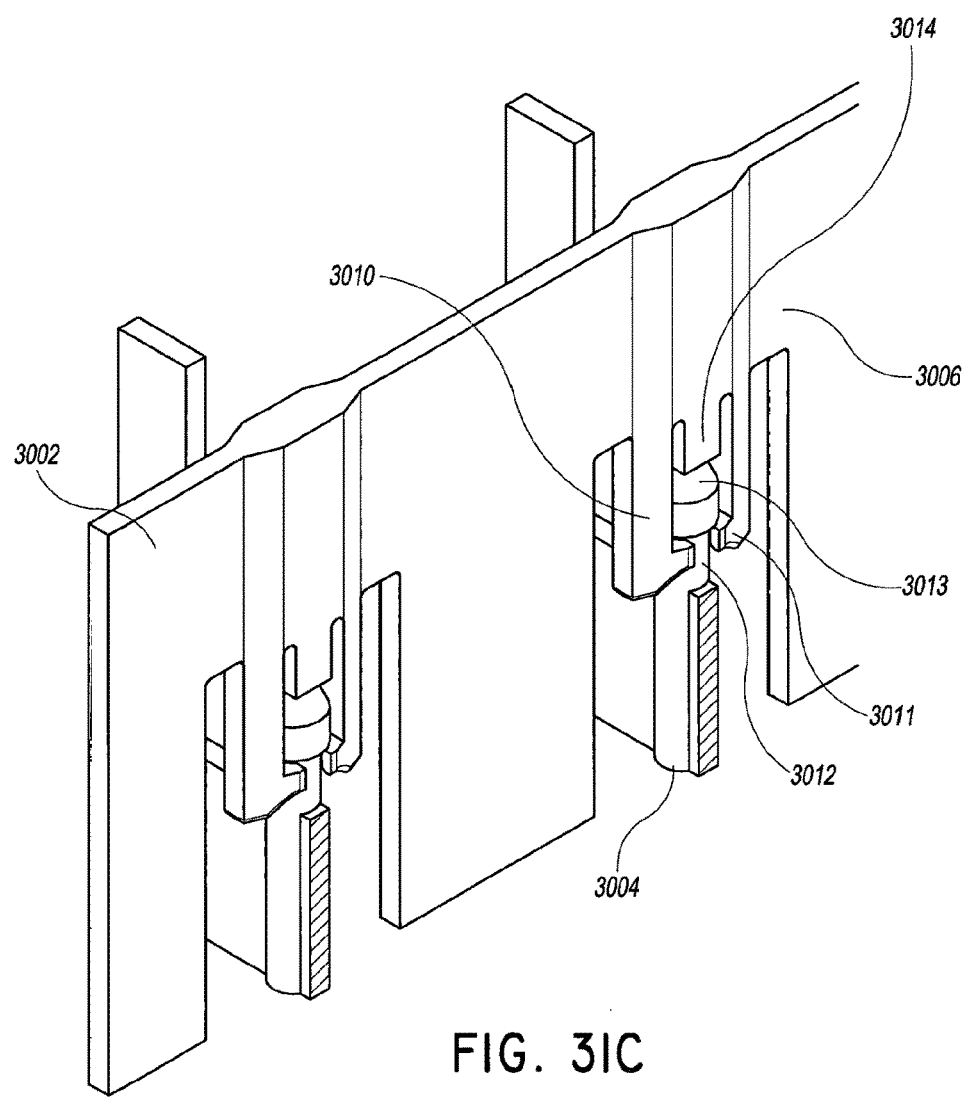
Figure 31D:
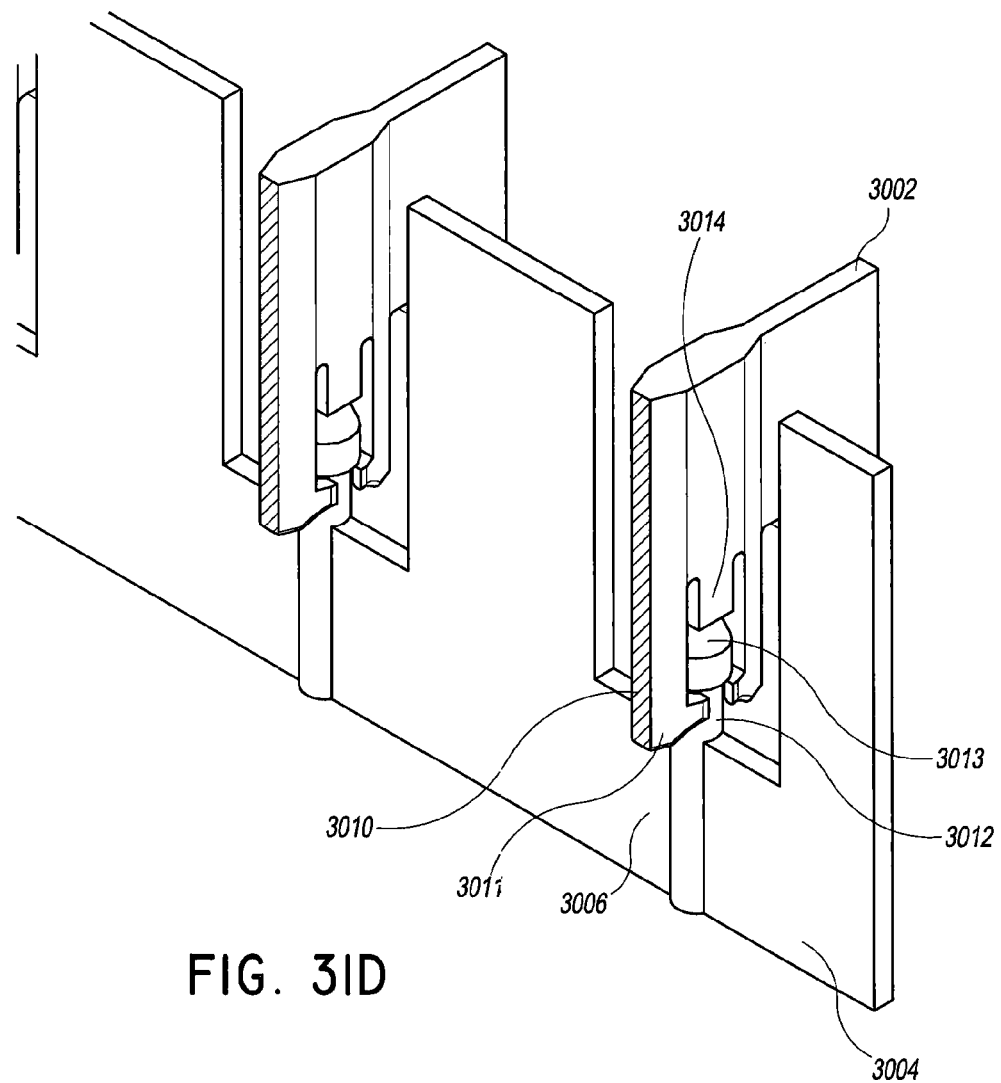
Figure 31E:
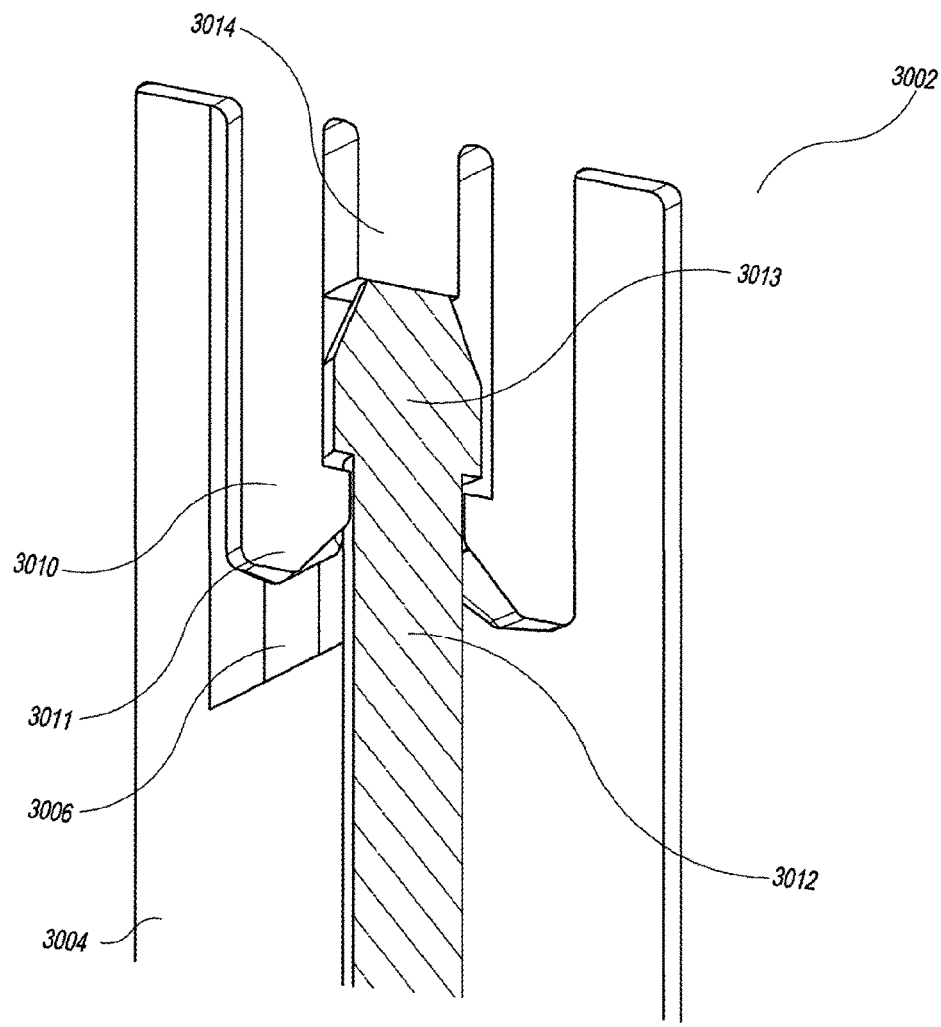
Figure 31F:
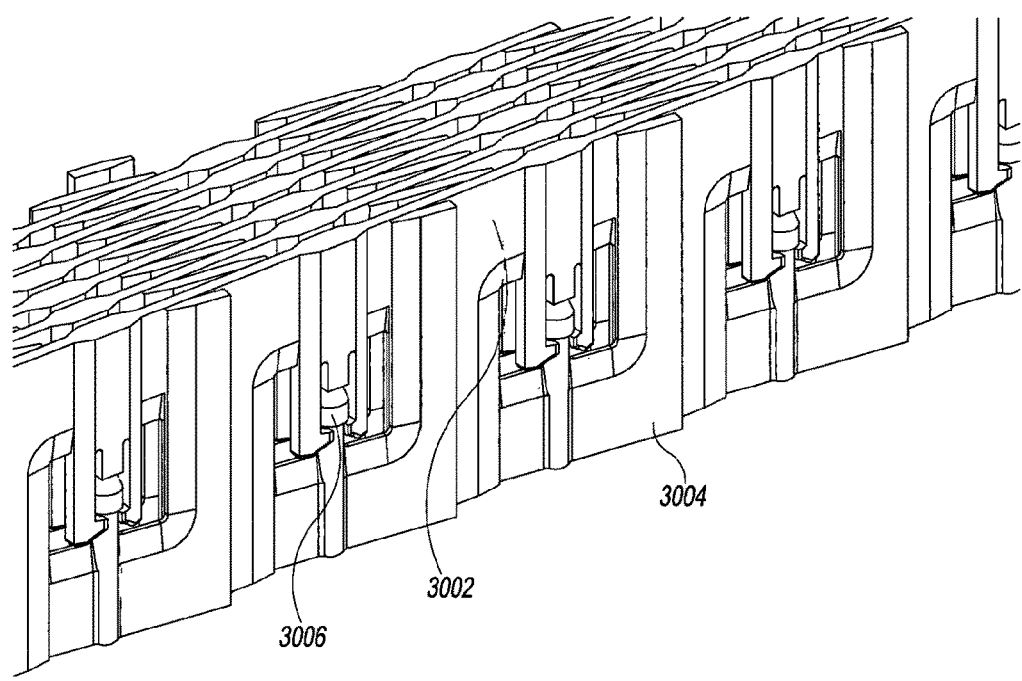

To aid in the closure of a wound, the stabilizing structure 3001 is preferably movable from the substantially un-collapsed configuration to a collapsed configuration, as illustrated in FIG. 31F. This may be beneficial for wound closure and healing, as described previously. In use, negative pressure may apply a closing force across the margins of the wound that the stabilizing structure 3001 is inserted into. As the structure 3001 is preferably configured to be substantially rigid in the vertical direction (i.e., perpendicular to the plane defined by the structure 3001), pressure resulting from atmospheric pressure exerted onto the structure 3001 via the drape is focused substantially downward rather than outward, such that the wound margins are no longer pushed outward as in conventional negative pressure dressings.

Preferably, the structure 3001 adopts a smaller area in the first plane as a result of moving to the compressed configuration. As such, the structure 3001 aids in wound closure by aiding re-approximation of the wound margins. In some embodiments, the stabilizing structures described in this section or elsewhere in this specification are able to reduce their captured volume when in a collapsed configuration (i.e., the volume change between an uncompressed and compressed stabilizing structure) by at least 10%, preferably at least 15%, and even more preferably at least 25%.

FIGS. 31C-E illustrate close-ups of the interlock mechanism 3006. It is to be noted that although reference may be made to various parts of the interlock mechanism 3006 being present on either the top strip 3002 or bottom strip 3004, this description should not be considered as limiting in terms of orientation, and the same interlock mechanism 3006 may be constructed with the top or bottom strips 3002, 3004 reversed.

In a preferred embodiment, the interlock mechanism 3006 preferably comprises two clasps 3010 extending downward from the top strip 3002. Preferably, the clasps 3010 are parallel to each other so as to be on opposite sides of a projection 3012 extending upward from the bottom strip 3004. The clasps 3010 preferably comprise a lip or hook 3011 that may secure themselves under an end 3013 located at the distal end of the projection 3012. In a preferred configuration, the enlarged end 3013 is arranged such that all or a portion of the lip 3011 engages with the enlarged end 3013. The combination of the lip 3011 and enlarged end 3012 may aid in preventing the top strip 3002 from disengaging in a vertical direction away from the bottom strip 3004. In some embodiments, the projection 3012 may abut on the bottom edge of the top strip 3002. In some embodiments, however, and as illustrated here, a stabilizing post 3014 may be present to locate the distal side of the projection 3012 and enlarged end 3013.

FIGS. 32A-D illustrate an embodiment of a stabilizing structure 3201 assembled in a similar manner to the embodiment illustrated above in FIGS. 31A-F. Here, the interlock mechanism 3006 comprises four clasps 3010 surrounding the projection 3012 and the enlarged end 3013 of the projection 3012. Preferably, the clasps 3010 are arranged in a mutually orthogonal configuration, although different orientations are contemplated as well. It will be understood that any number of clasps 3010 may be used to secure the projection 3012, for example three or five clasps 3010.

Figure 32A:
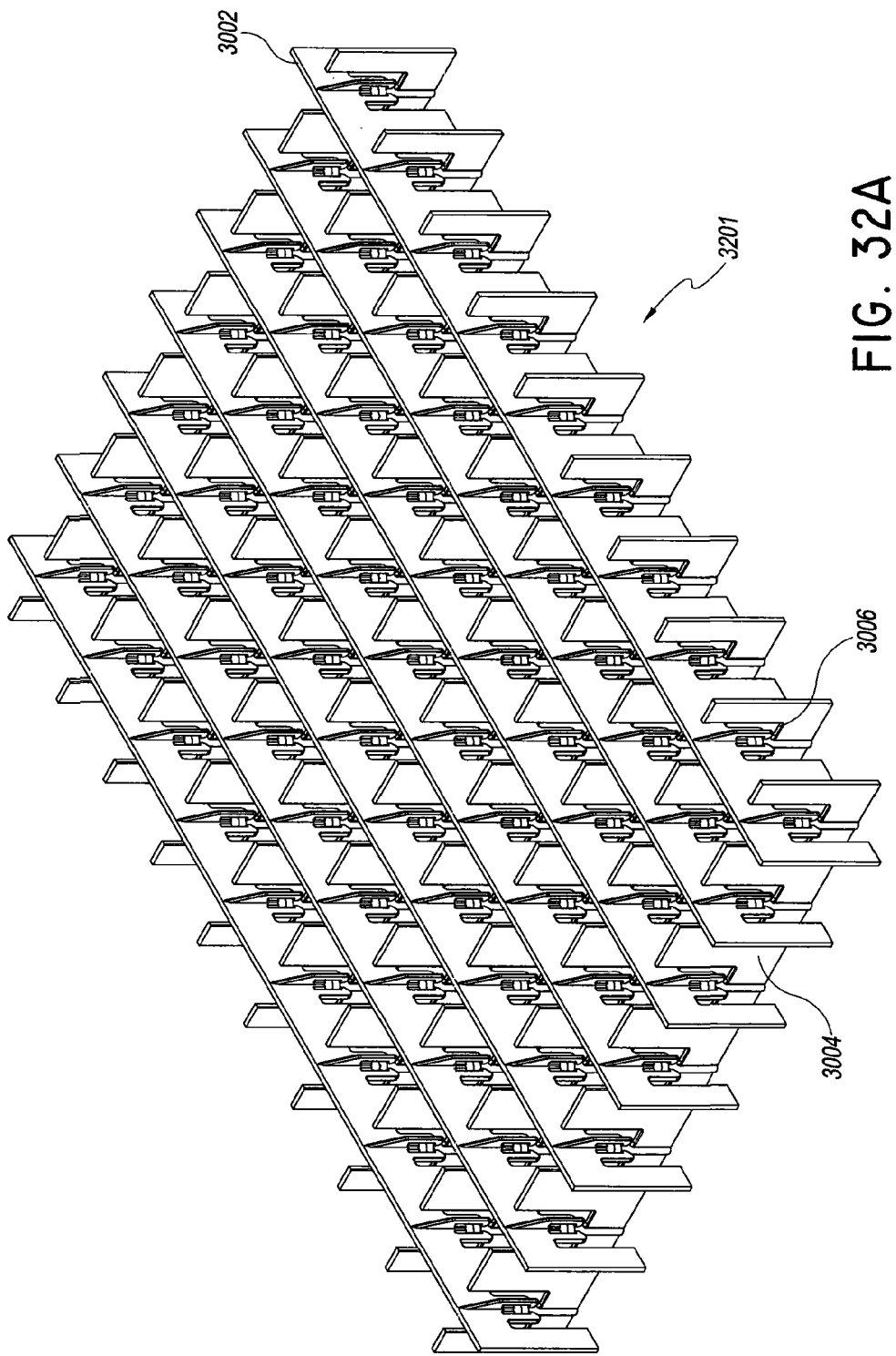
FIGS. 32A-D illustrate multiple views of an embodiment of a stabilizing structure.
Figure 32B:
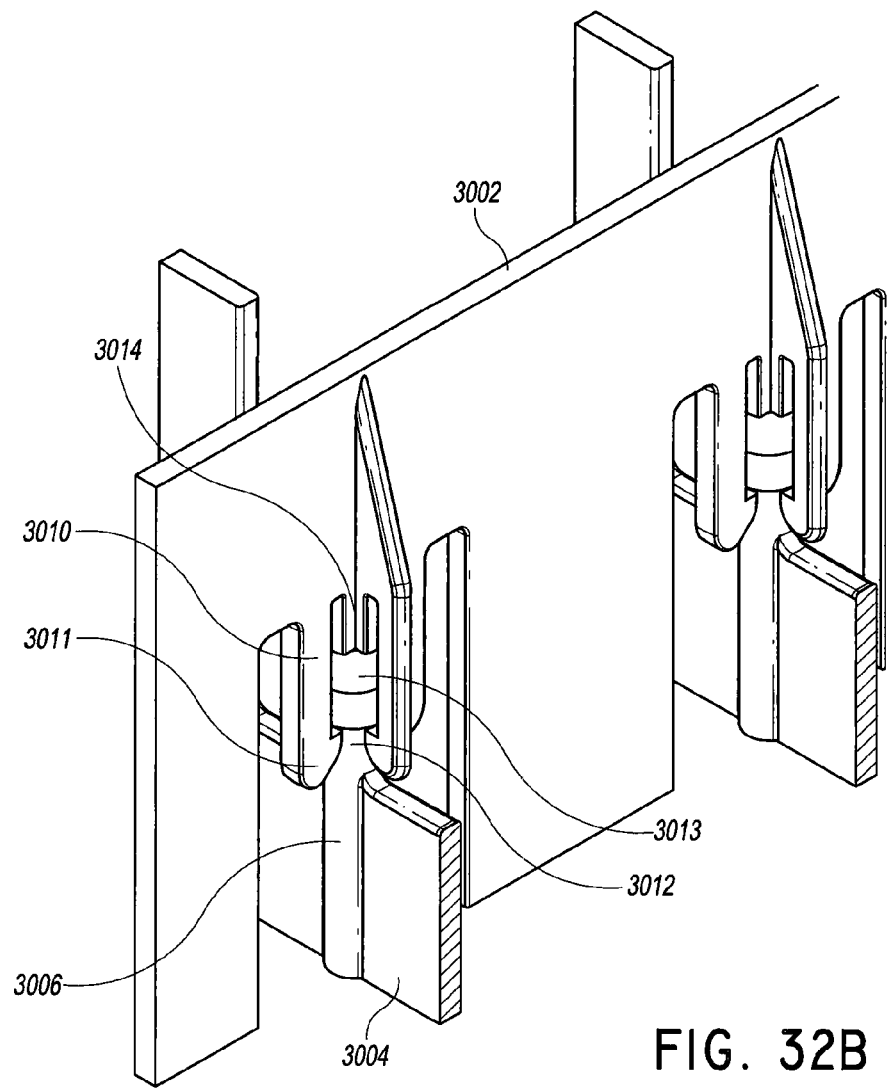
Figure 32C:
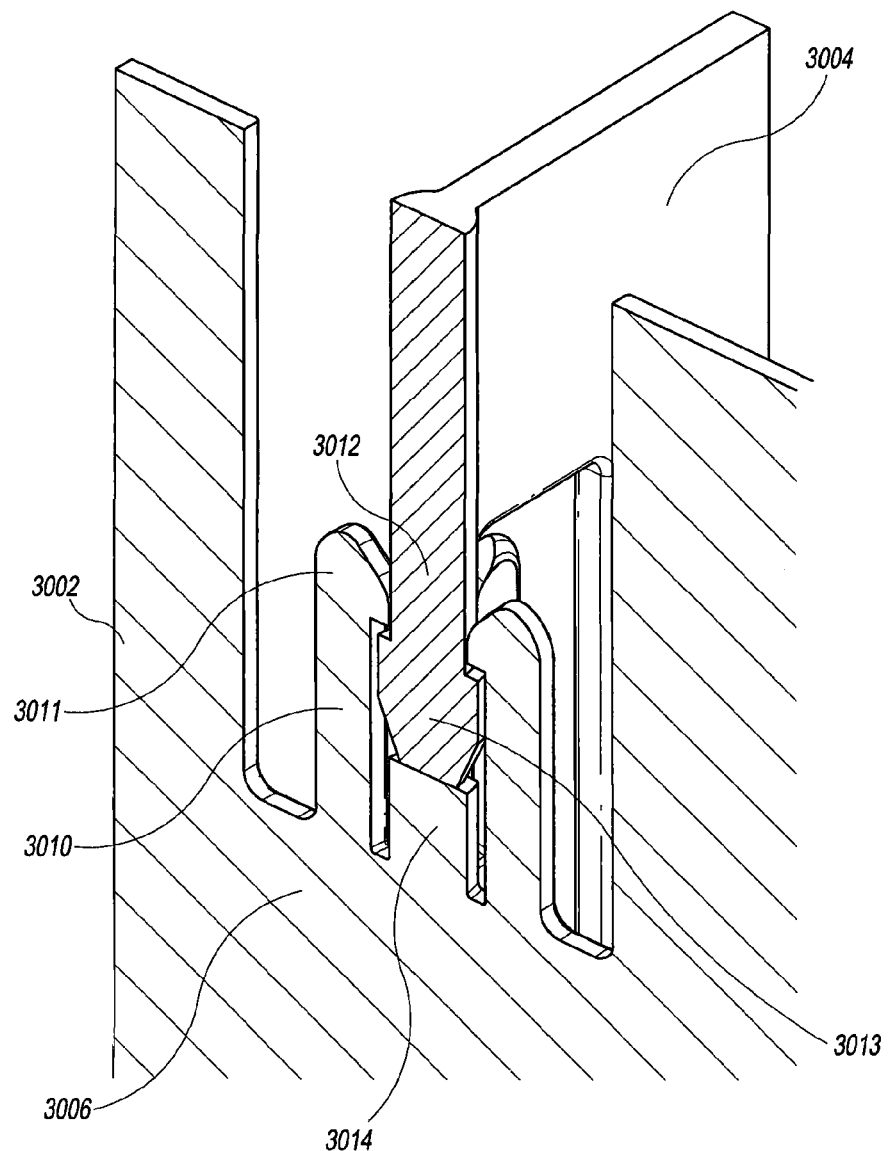
Figure 32D:
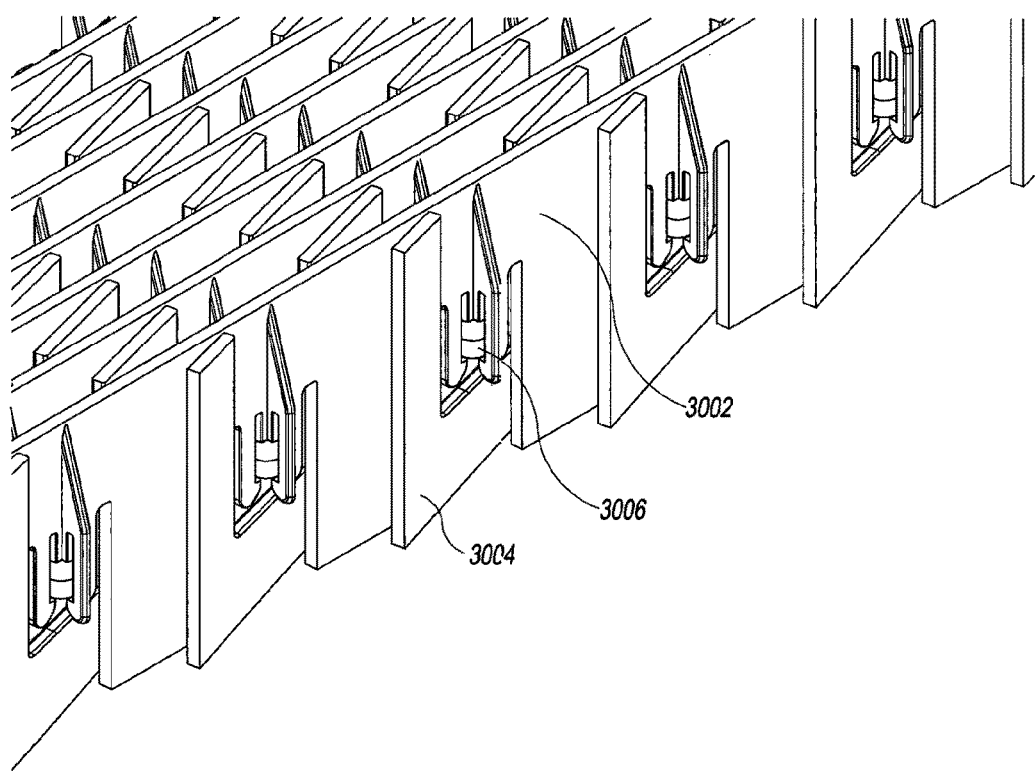

It will be noted that due to the addition of additional clasps 3010 in comparison to the embodiment illustrated in FIGS. 31A-F, the embodiment illustrated here will have a compressed configuration that is slightly larger, as illustrated in FIG. 32D. This may be useful in some situations; for example, some wounds may require a more gradual closure of the wound margins, and the embodiment described here may be well adapted for this purpose. For example, in clinical situations involving compartment syndrome, especially in the abdomen, application of full wound closure may not be appropriate or desirable, as wound closure may cause complications such as excessive pressure on organs and underlying tissue structures and/or reduction of blood flow to distal anatomical structures. Additionally, in some cases a too rapid or complete wound closure may be too painful for a patient. Accordingly, limiting the amount of closure may therefore be beneficial in such types of wounds. Limiting the amount of closure may also be beneficial in cases of compartment syndrome in the lower limbs.

FIGS. 33A-E illustrate an embodiment of a stabilizing structure 3301 comprising an interlock mechanism 3006 arranged in a tubular conformation. In this embodiment, a cup-shaped member 3020 is preferably configured to receive the enlarged end 3013 of the projection 3012. The projection 3012 may extend vertically from the top strip 3002. The cup-shaped member 3020 is preferably cylindrical or tubular in shape, and may extend vertically from the bottom strip 3004, although it will be understood that the cup-shaped member 3020 and projection 3012 may be located on opposite strips.

Preferably, one or more slits 3021 are formed into the cup-shaped member 3020 so as to permit some "give" to permit the projection 3012 to be received into the cup-shaped member. A lip or hook 3022 may also aid in securing the enlarged end 3013 of the projection 3012. A stabilizing post 3014 may also be present to prevent the projection 3012 from extending too deeply into the cup-shaped member 3020.

Figure 33A:
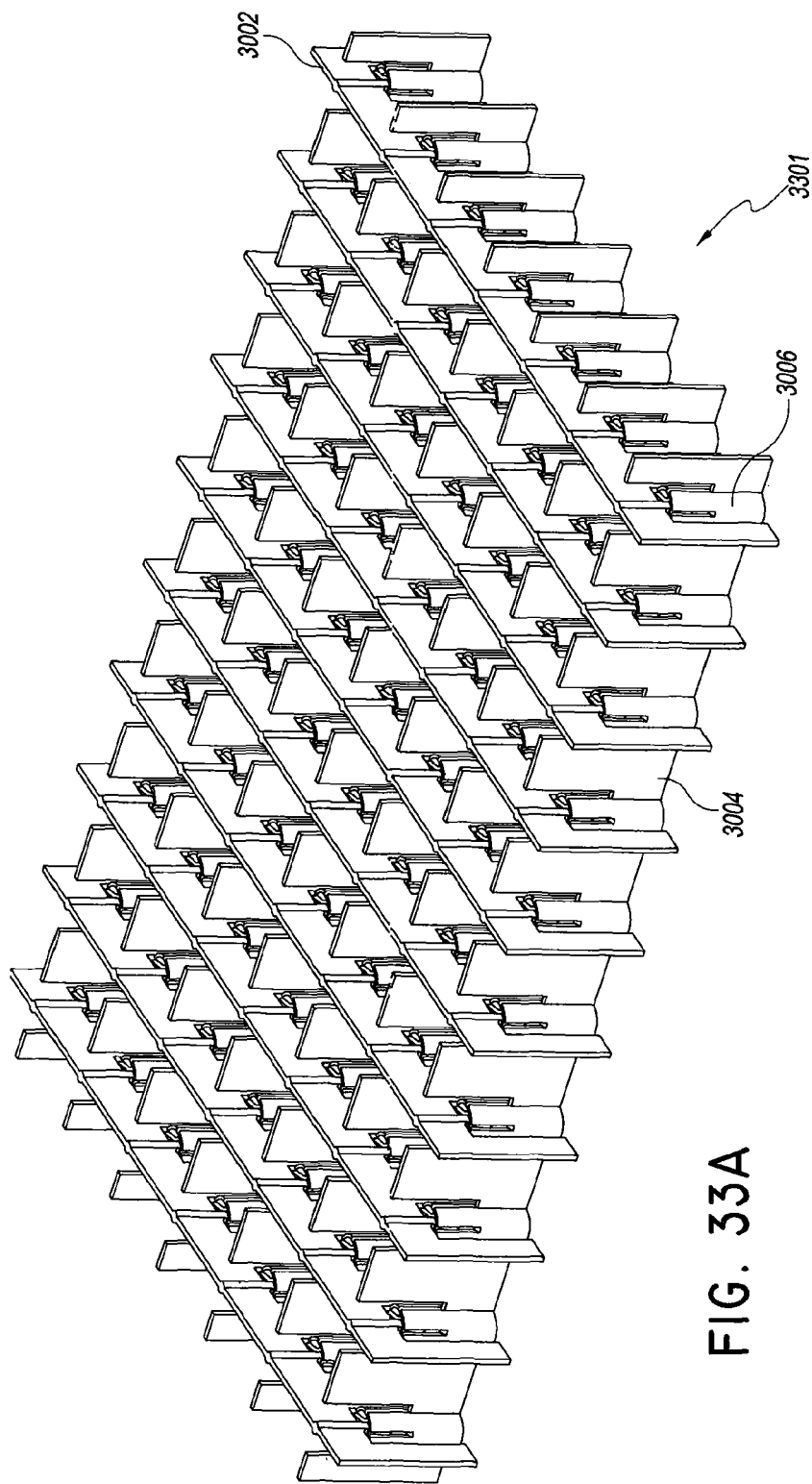
FIGS. 33A-E illustrate multiple views of an embodiment of a stabilizing structure.
Figure 33B:
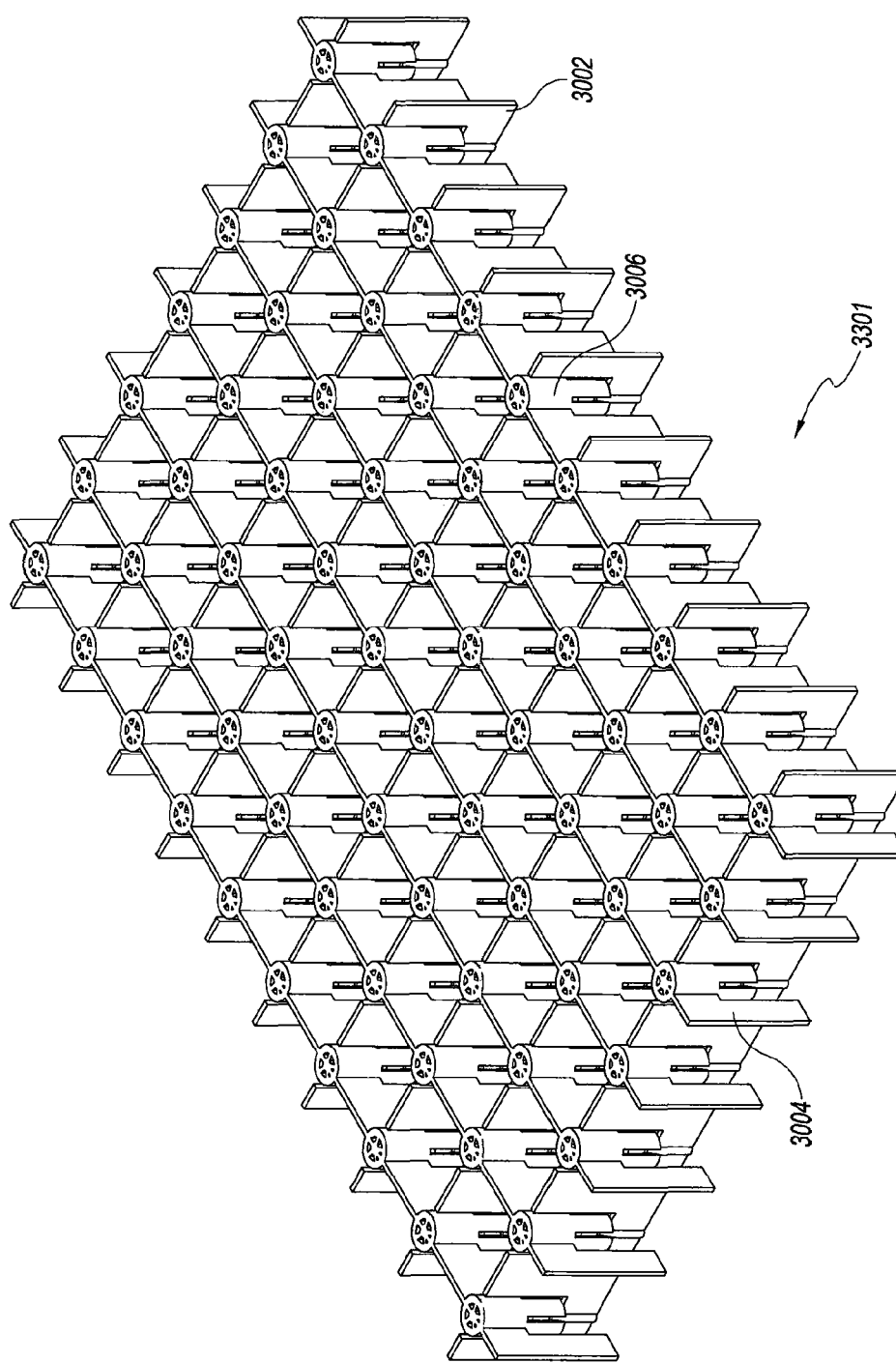
Figure 33C:
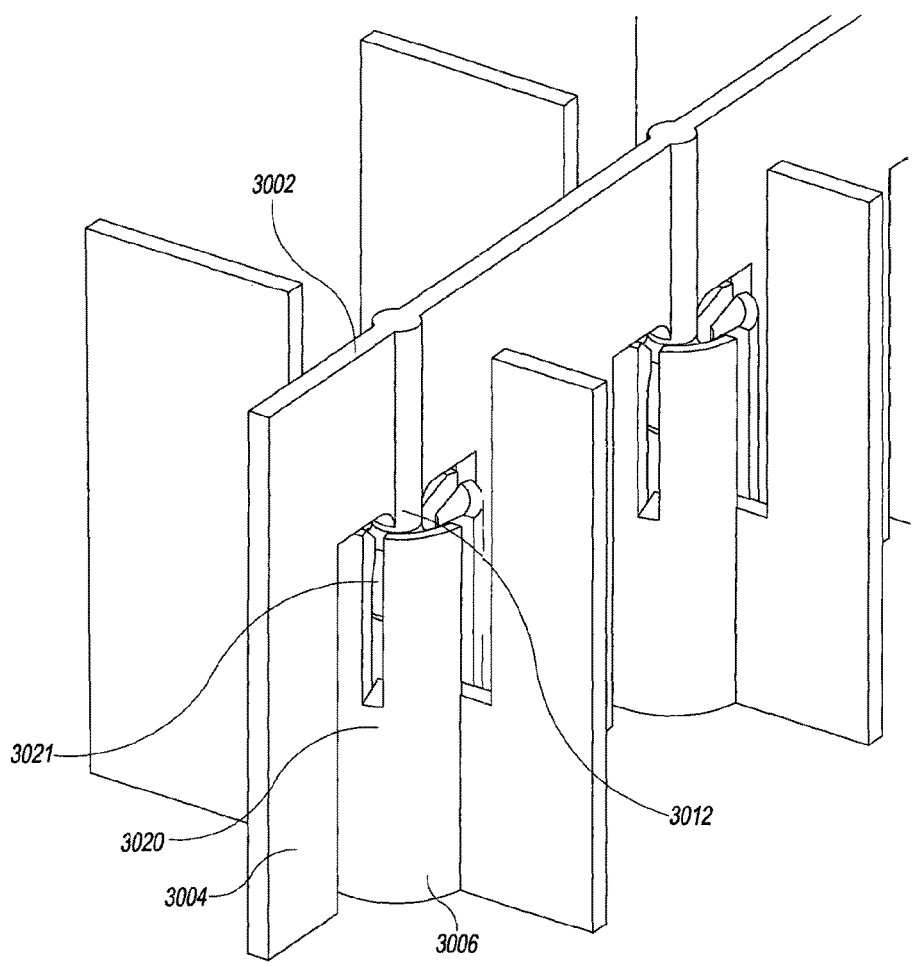
Figure 33D:
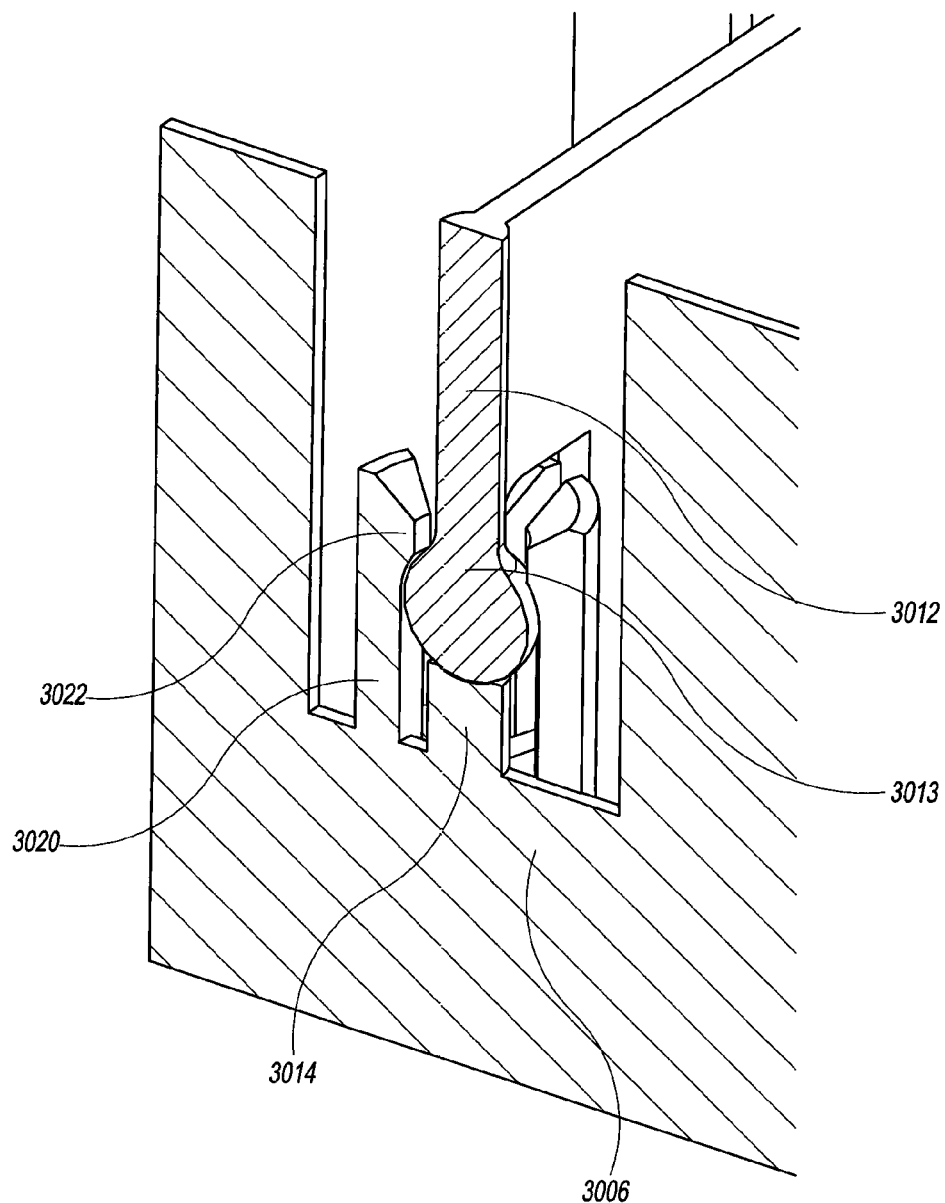
Figure 33E:
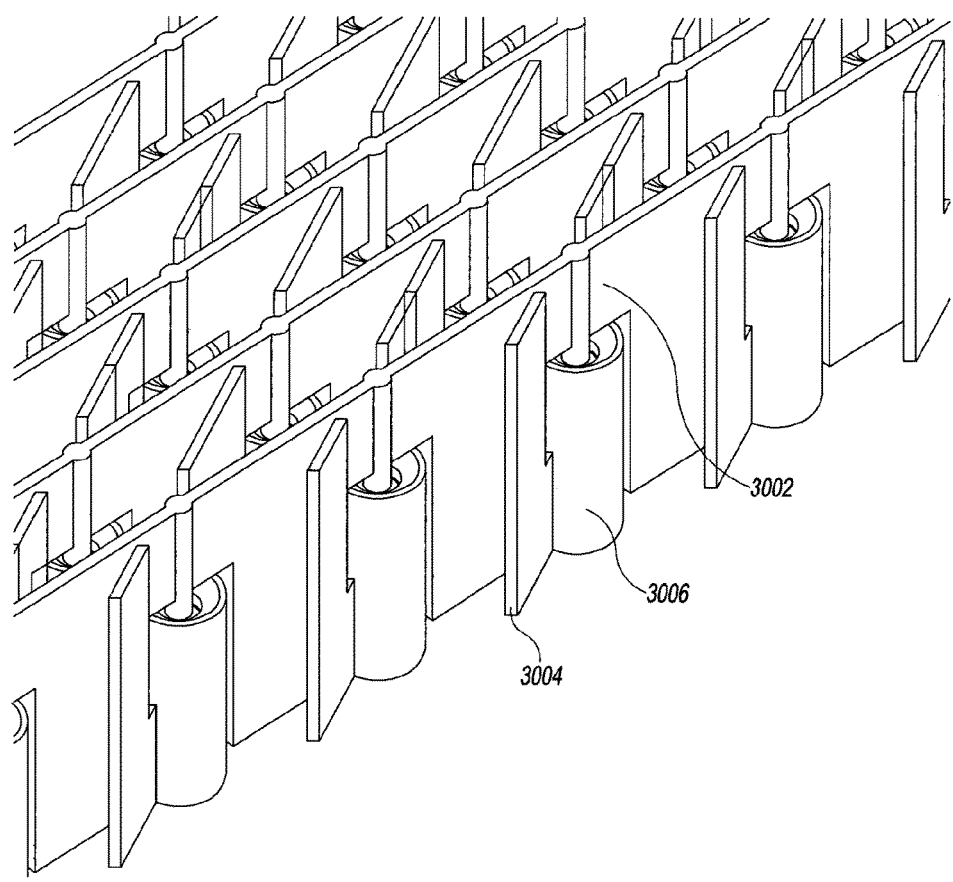

FIG. 33E illustrates a compressed view of an embodiment of the stabilizing structure 3301. Compared to FIG. 31F, this embodiment has a slightly larger compressed configuration.

Figure 34:
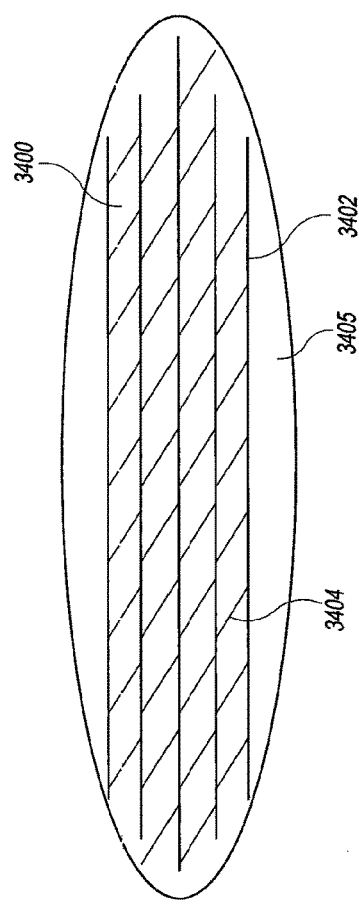
FIG. 34 schematically illustrates an embodiment of a stabilizing structure.

FIG. 34 schematically illustrates an embodiment of a stabilizing structure 3400 configured to be inserted into a wound. Here, the stabilizing structure 3400 is shown inserted into a wound 3405. Preferably, the stabilizing structure 3400 preferably comprises at least one, and more preferably at least two, long strips 3402 whose longitudinal length may be oriented along a longitudinal axis of the wound 3405, or along a direction along which closure is sought. Each of the one or more long strips 3402 are preferably substantially rigid and extend substantially along the entire length of the wound 3405. In a preferred embodiment, the long strip 3402 is continuous and does not have any breaks or hinges along its length. This is in contrast to certain other embodiments described above.

One or more struts 3404 are preferably attached at one or more points to the long strip 3402. Preferably, these struts 3404 are movably attached, for example via a hinge-like attachment or flexible joint, such that these may collapse in a direction perpendicular to a longitudinal length defined by the length of the one or more long strips 3402. In some embodiments, the struts 3404 may be angled at a non-perpendicular angle with respect to the long strip 3402 so as to collapse more readily. In embodiments comprising two or more long strips 3402, the struts 3404 may be hinged between two parallel long strips 3402.

It will be recognized that while these struts 3404 may be configured to collapse along a direction perpendicular to the longitudinal length of the one or more long strips 3402, the struts 3404 are preferably rigid in a vertical direction (i.e., in the direction extending upward from a plane defined by the wound 3405). As such, a combination of the struts 3404 and the long strips 3402 may thus form a stabilizing structure 3400 that is substantially rigid in a vertical direction while being collapsible in a horizontal direction perpendicular to the longitudinal axis of the long strips 3402 (i.e., in the plane of the wound 3405).

Figure 35B:
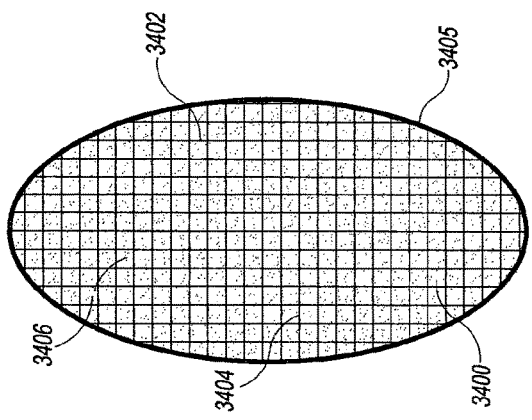
FIG. 35B illustrates a top view of an embodiment of an oval shaped stabilizing structure with foam.
Figure 35A:
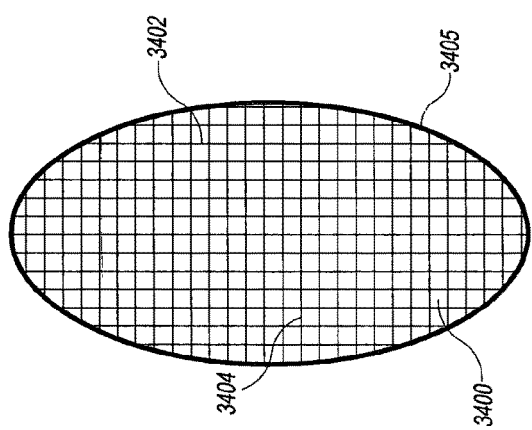
FIG. 35A illustrates a top view of an embodiment of an oval shaped stabilizing structure.

FIG. 35A illustrates a top view of an embodiment of stabilizing structure 3400 cut into an oval shape and inserted into a wound 3405. Preferably, the stabilizing structure 3400 comprises a plurality of elongate strips 3402 whose longitudinal length may be oriented along a longitudinal axis of the wound 3405, or along a direction along which closure is sought. Each of the plurality of elongate strips 3402 is preferably substantially rigid and extends substantially along the entire length of the wound 3405. A plurality of intervening members are positioned between adjacent elongate strips 3402. These intervening members may be struts 3404 as described with respect to FIG. 34, preferably attached at one or more points to the elongate strips 3402. The intervening members may also be portions of elongate strips such as described with respect to FIGS. 31A-33E above, extending perpendicular or at an angle to elongate strips 3402. The stabilizing structure of FIG. 30A may also comprise the embodiments described with respect to FIGS. 29A-30F.

FIG. 35B illustrates a top view of an embodiment of an oval shaped stabilizing structure 3400 inserted into a wound 3405. This embodiment may have the same configuration as described above with respect to FIG. 35A. Additionally, foam 3406 can be inserted between and around the stabilizing structure.

Stabilizing Structures and Wound Closure Devices of FIGS. 36A-39 and 41-43

As with the other stabilizing structures and wound closure devices described elsewhere in the specification, the stabilizing structures and wound closure devices of FIGS. 36A-39 and 41-43 may be incorporated into the wound packing and wound treatment apparatus embodiments described elsewhere in the specification, such as in relation to FIGS. 8A-10.

Figure 36A:
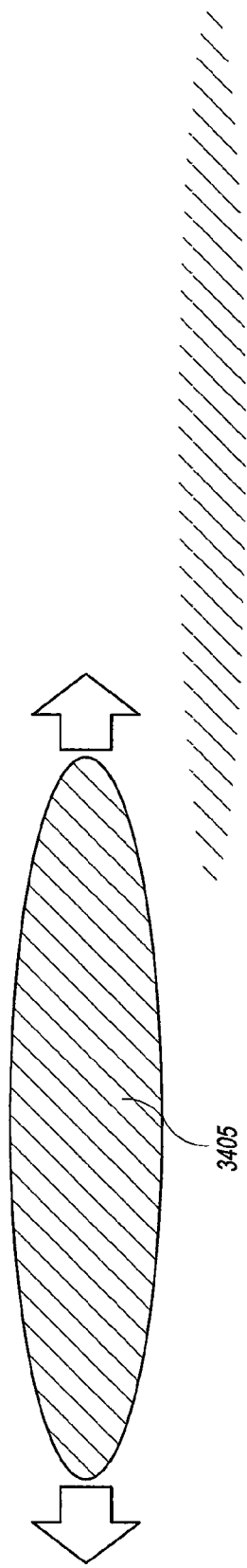
FIGS. 36A-B illustrate embodiments of methods for closing a wound.

FIG. 36A illustrates an embodiment of a method for the closure of a wound using any of the stabilizing structures described in this section or elsewhere in this specification before or as hereafter described, through the application of tension along an axis of wound 3405. In this example, when the wound is viewed from above, tension is applied along the longitundinal axis of the wound, generally represented by arrows 3407. Tension along the longitundinal axis prevents contraction of the wound along the longitudinal axis, however the tension along the longitudinal axis can cause the lateral edges of the wound to be drawn together, promoting wound closure. In some embodiments, additional inward tension can be applied to the lateral edges of the wound, thereby providing additional wound closing force.

Figure 36B:
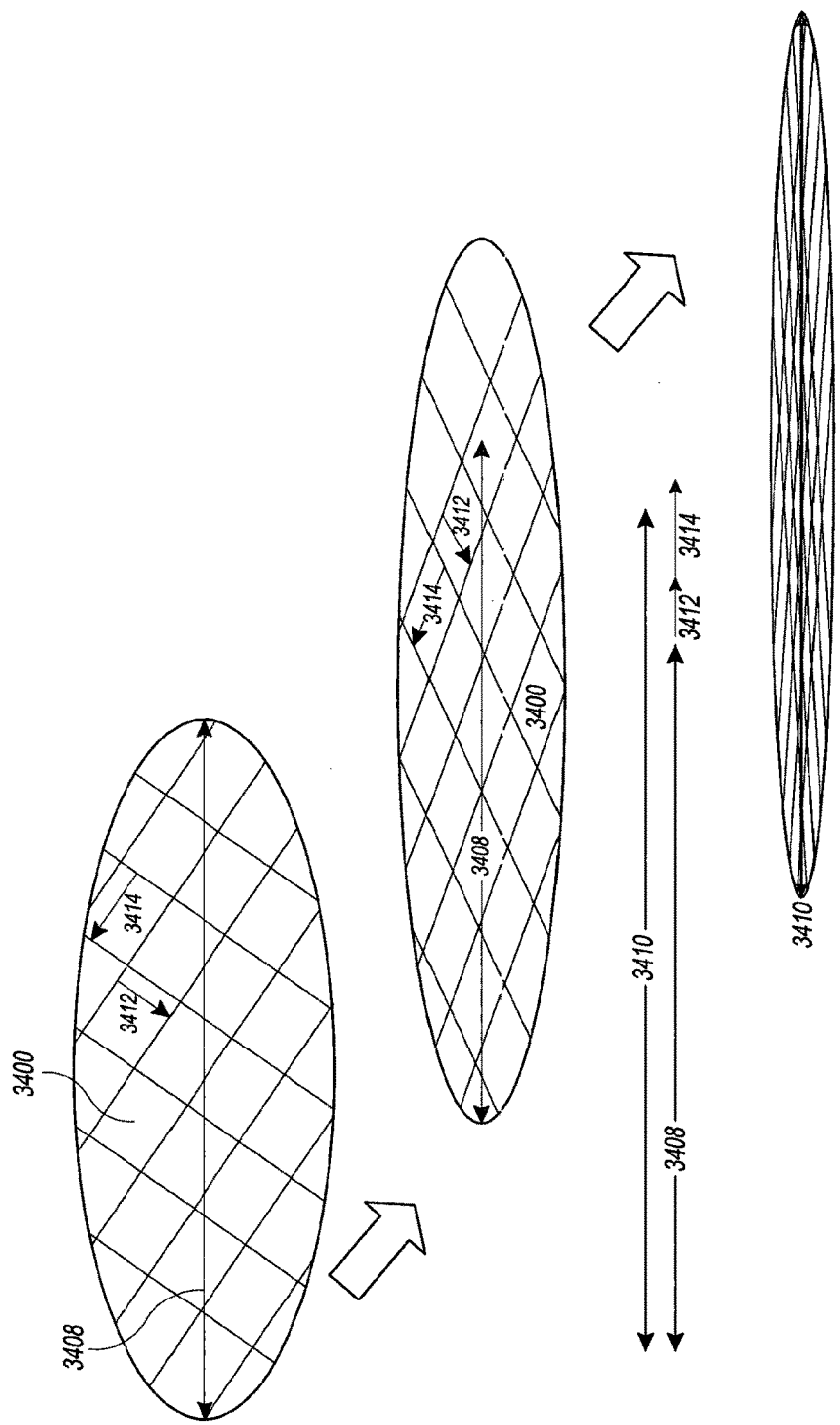

FIG. 36B illustrates an embodiment of a method for the closure of a wound through the use of a stabilizing structure 3400 that collapses and lengthens when a wound is treated under negative pressure. As illustrated, the stabilizing structure 3400 may be cut to an appropriate size to approximate the shape of the wound (e.g., in an oval shape), and the stabilizing structure is placed in the wound 3405. In some embodiments as described above, the stabilizing structure may have a plurality of diamond-shaped cells, and the cells are arranged in the wound in an orientation that causes the cells to be flattened as the lateral edges of the wound come closer together, while becoming longer along the longitudinal axis of the wound. It will be recognized that while this structure is configured to collapse under negative pressure horizontally within the wound in a direction perpendicular to the longitudinal axis of the wound, the structure is substantially rigid in the vertical direction. Line 3408 represents the length of the structure prior to lengthening under negative pressure, while line 3410 represents the final length of the structure after collapsing and lengthening under negative pressure. Lines 3412 and 3414 represent the lengths of particular sections within the stabilizing structure. In certain embodiments, when a wound is treated with application of negative pressure, the structure will collapse inward on one axis, thereby lengthening the structure by some additional amount in another axis that can be the sum of the lengths of lines 3412 and 3414. In some embodiments, the structure can lengthen by amounts other than the sum of lines 3410 and 3412.

In some embodiments, the collapse can occur slowly, thereby applying increasing longitudinal tension over a long period of time. In certain embodiments, the collapse and lengthening of the structure can occur immediately upon application of negative pressure. In further embodiments, the collapse can occur at any rate.

Figure 37A:
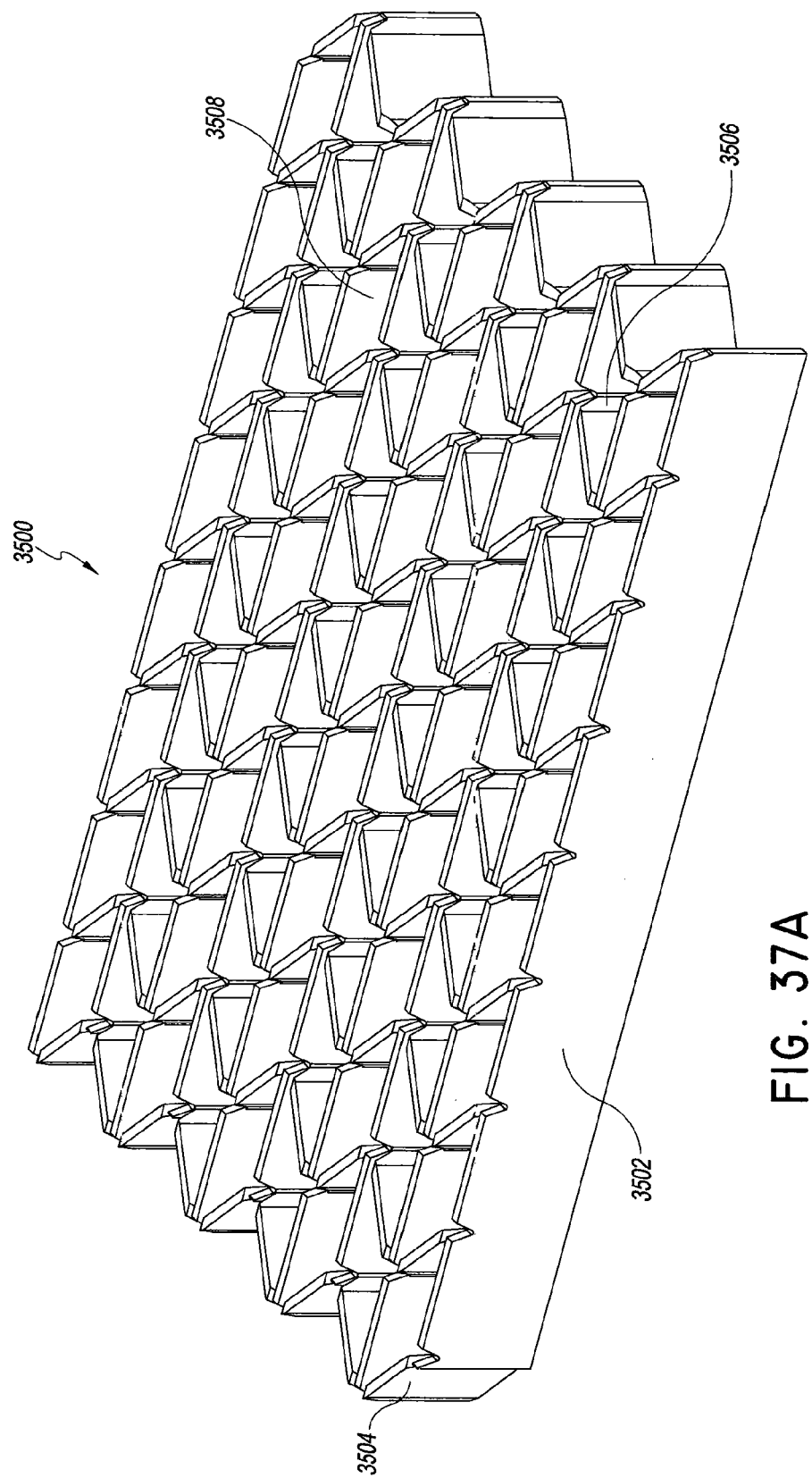
FIGS. 37A-C illustrate multiple views of an embodiment of a stabilizing structure.
Figure 37B:
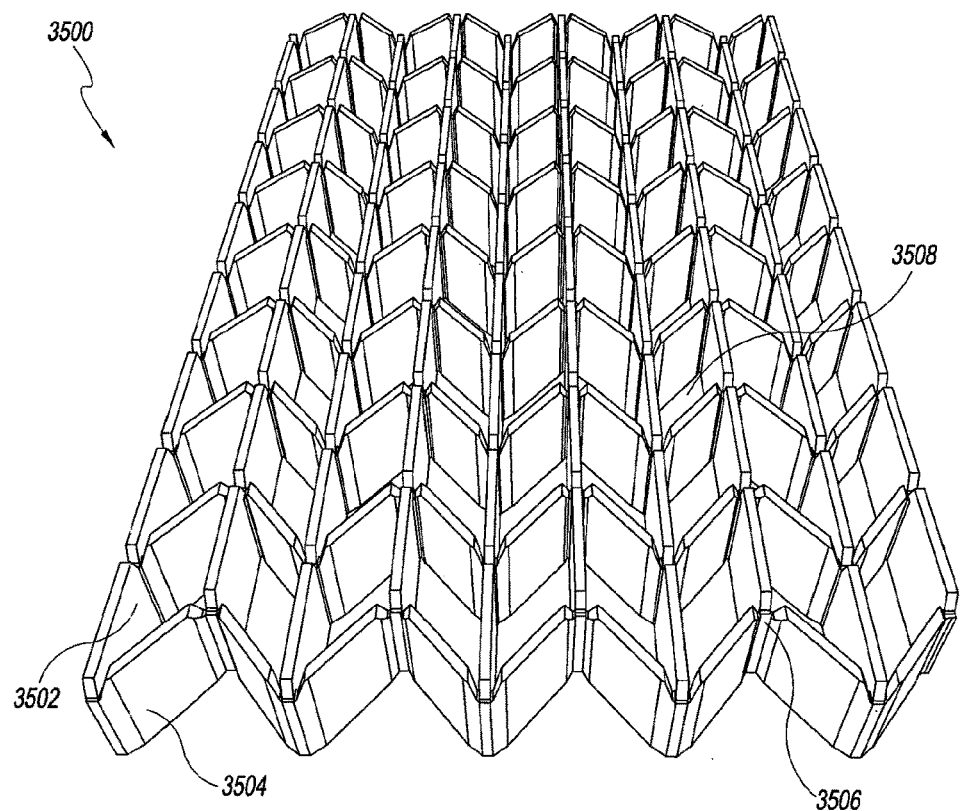
Figure 37C:
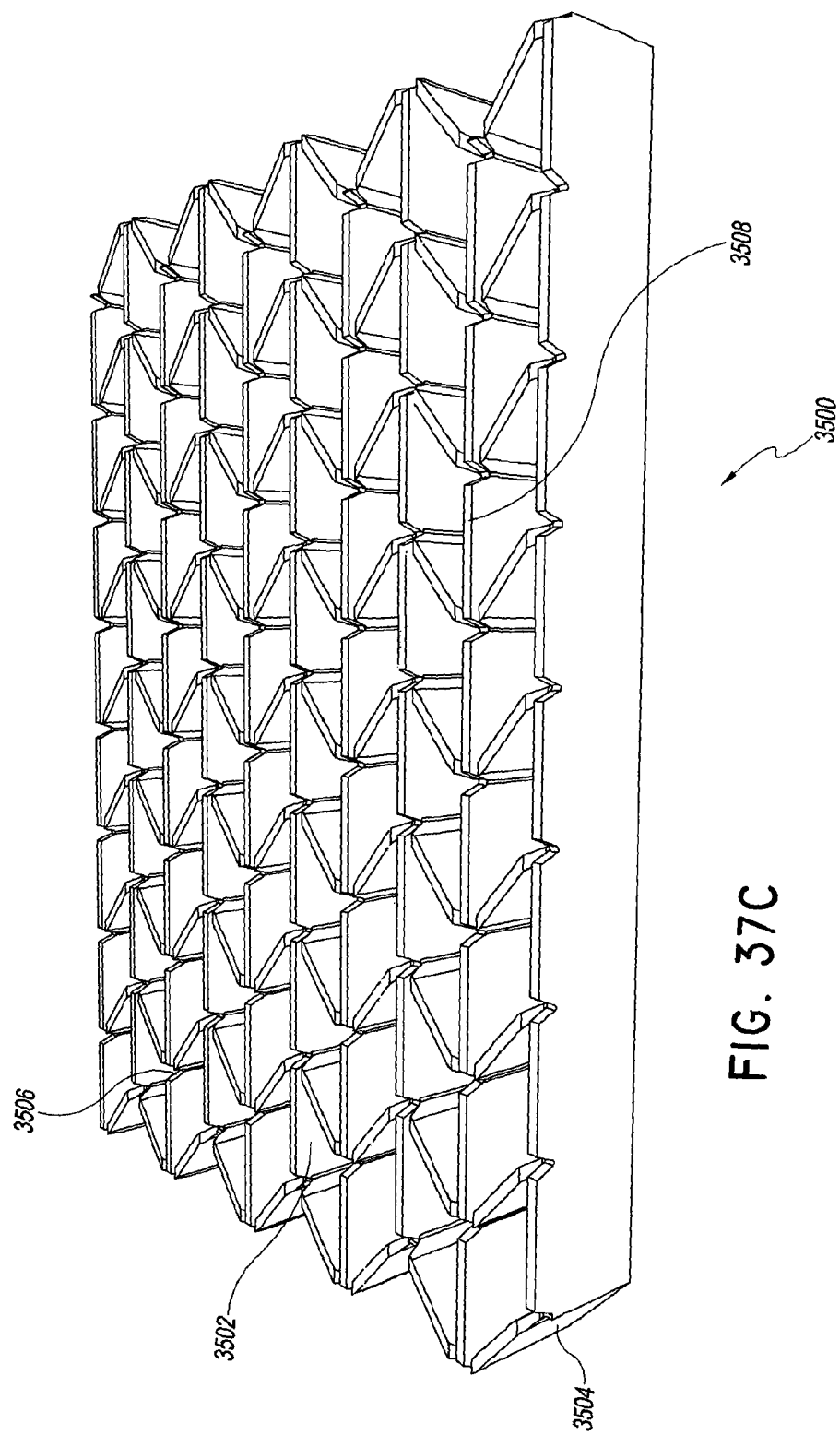

FIGS. 37A-C illustrate another embodiment of a stabilizing structure 3500. The stabilizing structure 3500 comprises a plurality of elongate strips 3502 arranged in parallel, and whose longitudinal length can be aligned with the longitudinal axis of a wound when placed in a wound. The stabilizing structure further comprises a plurality of intervening members 3504 connected to the elongate strips 3502 by a plurality of joints 3506. As illustrated, the plurality of intervening members 3504 between adjacent elongate strips 3502 define a row of cells 3508 between each pair of adjacent elongate strips.

In some embodiments, the elongate strips 3502 are rigid. In certain embodiments, the elongate strips 3502 are semi-rigid. In particular embodiments, the elongate strips 3502 are flexible. In some embodiments, the elongate strips 3502 are compressible. As illustrated in FIGS. 37A-37C, one embodiment comprises a plurality of strips that are rigid in a vertical dimension but also are flexible and capable of bending along their length.

In some embodiments, the intervening members 3504 are rigid. In certain embodiments the intervening members 3504 are semi-rigid. In particular embodiments, the intervening members are flexible. In some embodiments, the intervening members 3504 are compressible. As illustrated in FIG. 37A-37C, one embodiment comprises intervening members in the form of panels equally spaced apart between adjacent strips, to define a plurality of similar-shaped (e.g., diamond-shaped) cells. In other embodiments, the intervening members need not be equally spaced. The intervening members may be attached to the strips by joints 3506 in the form of a hinge (e.g., a living hinge or a more flexible piece of material between the strips and the intervening members).

In some embodiments, the plurality of intervening members 3504 are configured to pivot relative to the elongate strips 3502 and to collapse so as to allow the elongate strips to collapse relative to one another and come closer together. In some embodiments, the joints 3506 are configured to pivot and collapse in only one direction. In certain embodiments, the joints 3506 are configured to pivot and collapse in both directions, comprising a full 180 degrees of rotation relative to the elongate strips 3502. In certain embodiments, when the joints pivot, they pivot completely so as to rest the intervening members 3504 against the elongate strips 3502. In some embodiments, the joints do not pivot completely and the intervening members do not come to rest against the elongate strips 3502.

Preferentially, in certain embodiments, by controlling the direction in which the pivoting occurs, the collapsed length of the stabilizing structure 3500 can be controlled. In particular embodiments, because of the rigidity of the elongate strips, the cells 3508 in a row between adjacent elongate strips are configured to collapse together as the adjacent elongate strips 3502 collapse relative to one another. In some embodiments, one or more rows of cells 3508 between adjacent strips 3502 are configured to collapse in a first direction, and one or more rows of cells between adjacent strips 3502 are configured to collapse in a second direction opposite the first direction. As illustrated in FIGS. 37A-37C, the orientation of cells in adjacent rows alternates so that cells of a first row collapse in a first direction, and cells of a next row collapse in an opposite second direction. Joints 3506 may be configured so that joints 3506 in adjacent rows collapse in different directions.

By configuring the joints 3506 and/or cells of the stabilizing structure to pivot and collapse in preferred directions, the length of the collapsed structure can be modified. The embodiment shown in FIGS. 37A-37C will have a shorter collapsed length than a structure where all the rows of cells 3508 are configured to collapse in the same direction. Thus, the collapsed length of the structure can be controlled depending on the orientation of the cells and the direction in which the intervening members collapse between adjacent rows. In some embodiments as described above with respect to FIGS. 36A-36B, the stabilizing structure preferably lengthens after collapse under negative pressure. In other embodiments, it may be preferred that the stabilizing structure not lengthen after collapse under negative pressure.

Figure 38A:
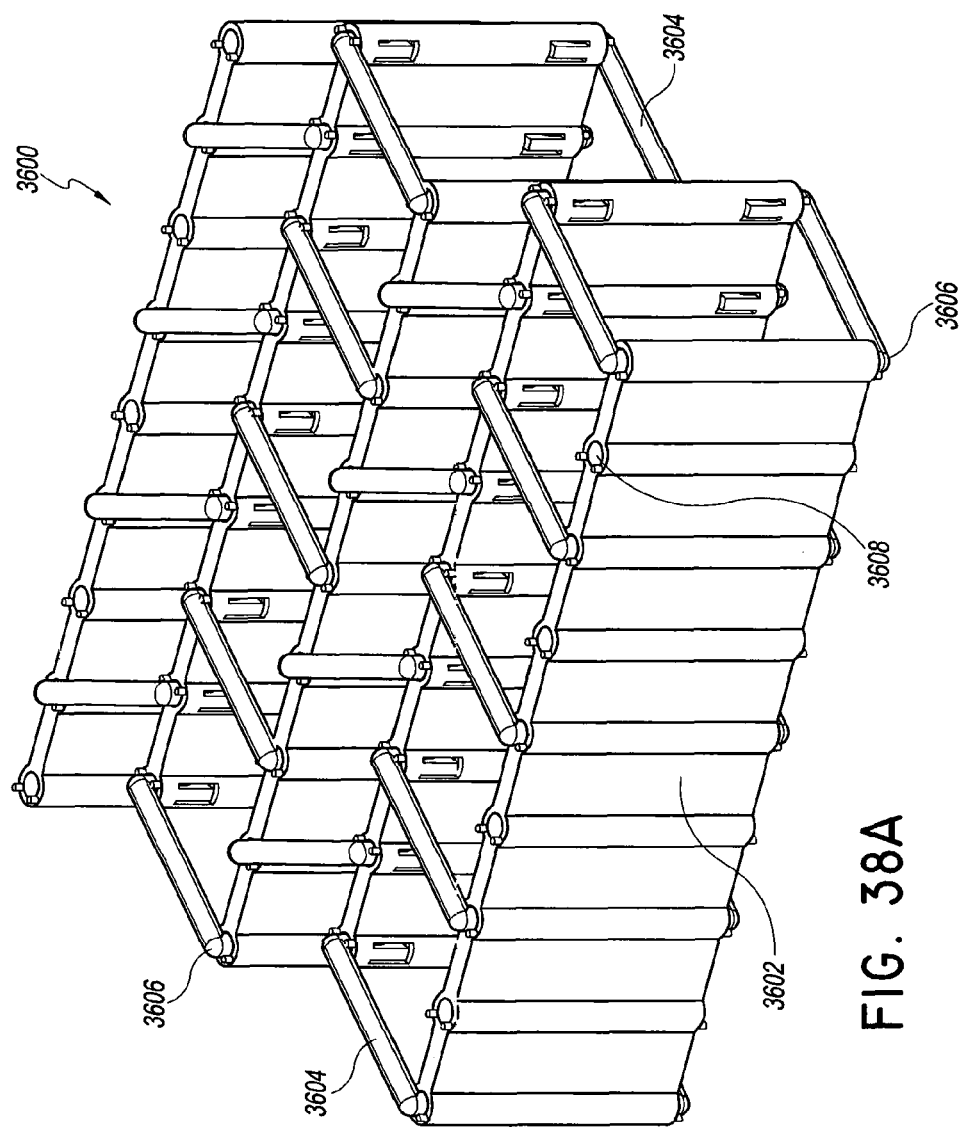
Figure 38B:
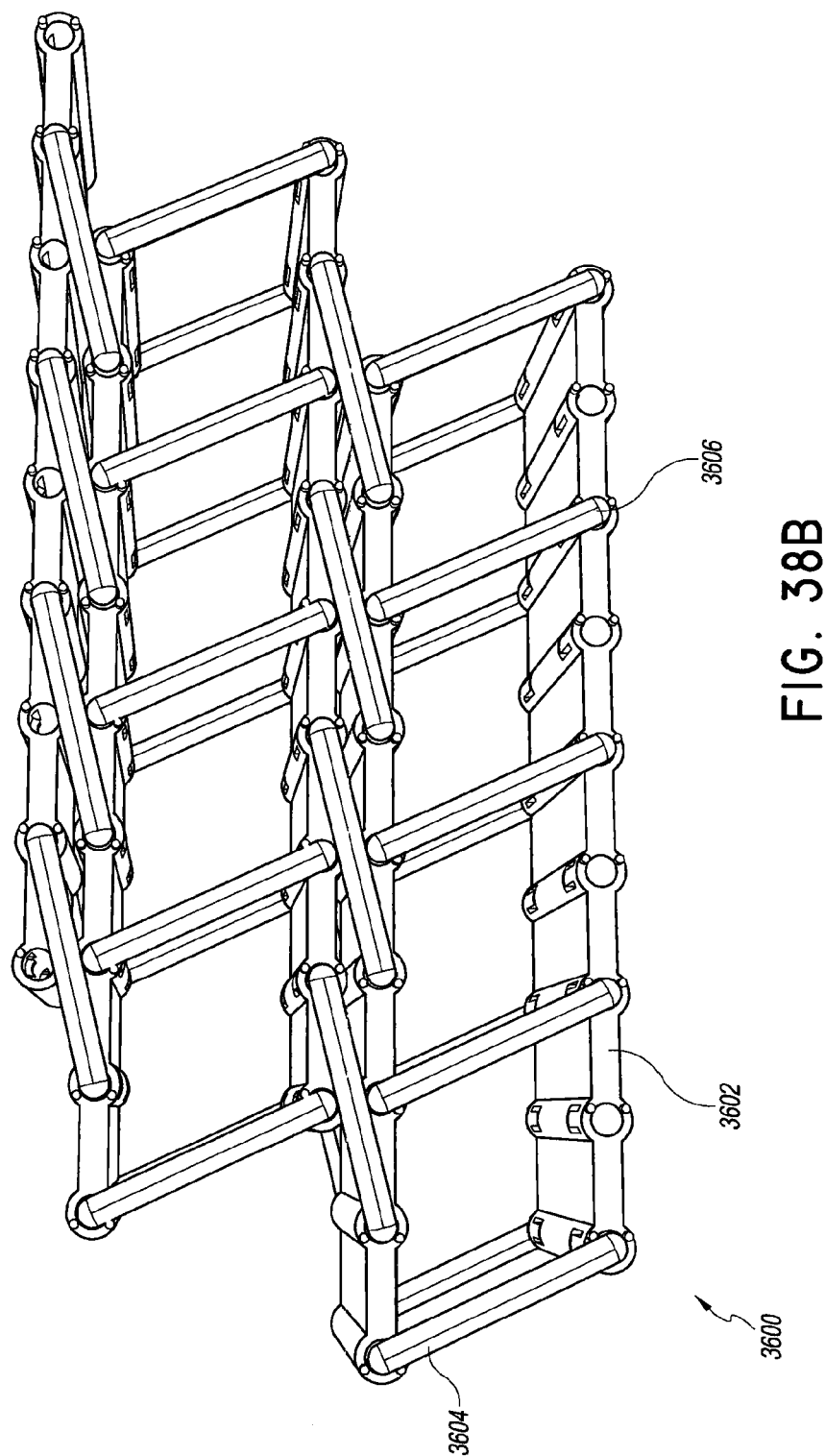
Figure 38C:
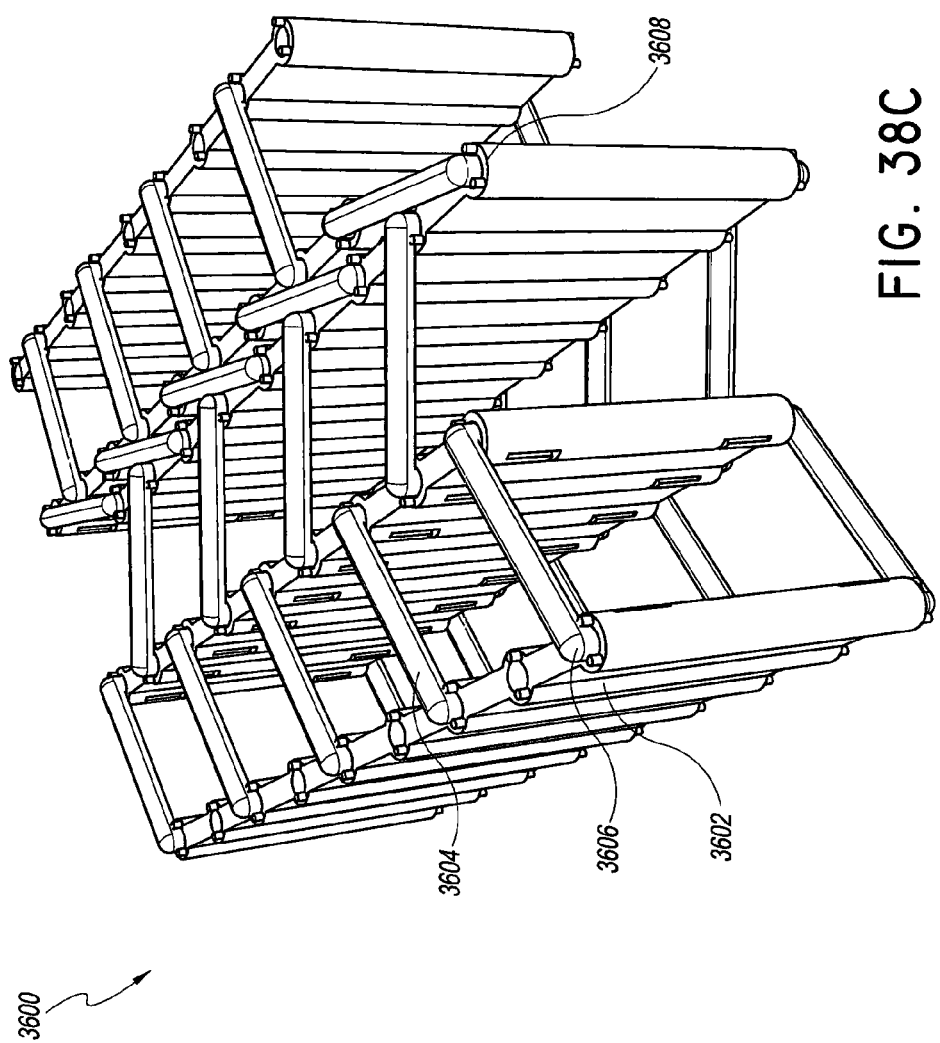
Figure 38D:
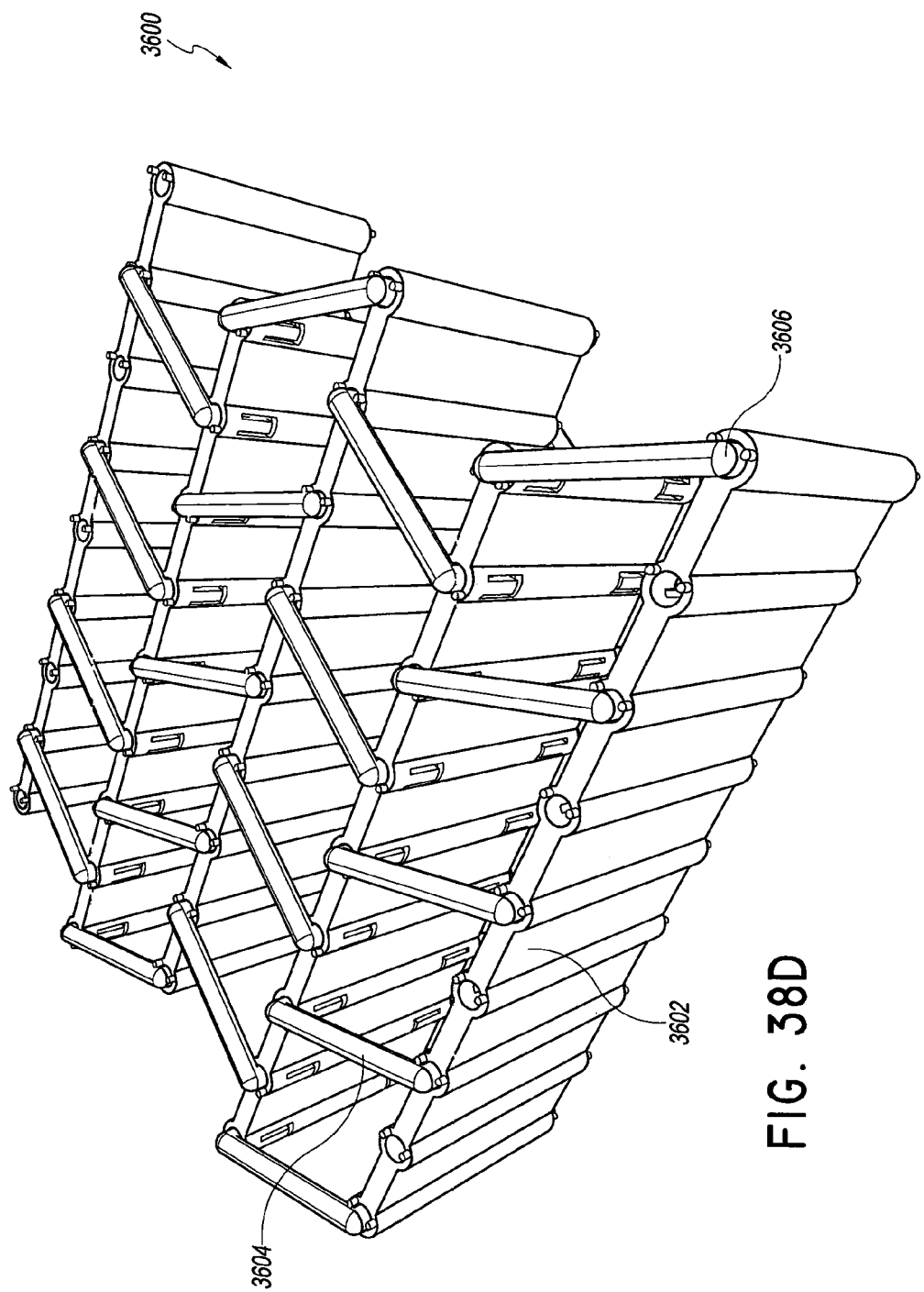

In FIGS. 38A-38C, the intervening members 3504 in adjacent rows are generally aligned so that the intervening members connect to the elongate strips at approximately the same location on opposite sides of the strip and share the same joint 3506 location. In other embodiments, the intervening members 3504 between a first elongate strip 3502 and a second elongate strip 3502 are offset relative to intervening members 3504 between the second 3502 and a third adjacent strip 3502. In these embodiments, the intervening members 3504 are staggered such that they do not share the same joint 3506 location.

As shown in FIGS. 38A-38C, the enclosed cell 3508 formed by two intervening members and two sections of the elongate strips is a quadrilateral. In some preferred embodiments, the enclosed shape can be a square, rectangle, diamond, oblong, oval, and/or parallelepiped. In some embodiments, the enclosed shape is a rhomboid. In certain embodiments the enclosed shape is a trapezoid.

In certain preferred embodiments, the joint 3506 may be configured to limit the range of motion of the intervening member 3504, and may be used to prevent the intervening members 3504 from becoming fully perpendicular to the adjacent strips. Thus, the joint may be configured to pre-set the intervening members 3504 in a partially collapsed position. For example, a lip or other portion of material at the joint may be used to limit the angular motion of the intervening members. The lip or other portion of material may also prevent the joint from collapsing completely flat. In some embodiments, the joint may be configured to prevent the intervening members from rotating in 180 degrees along the plane formed by the strips.

In some embodiments, when the stabilizing structure 3500 is placed in a wound, the elongate strips 3502 are positioned generally parallel to the lateral edges of the wound. Preferably, the stabilizing structure is configured in the wound such that the elongate strips are positioned parallel to the longitudinal axis of the wound, as described with respect to FIGS. 36A-36B above. The strips may also bend along their length and bow outwardly to fit within the wound. The stabilizing structure may be cut to an appropriate size to fit the structure in the wound. In other embodiments, the elongate strips 3502 are positioned perpendicular to the edge of the wound, or may not be oriented along any edge of the wound.

In the embodiments of FIGS. 37A-37C, as well as in other embodiments of stabilizing structures described in this section or elsewhere in this specification, the strips can be constructed from a material selected from the group consisting of silicone, polyurethane rigid plastics, semi-rigid plastics, flexible plastic materials, composite materials, biocompatible materials and foam. In some embodiments, the intervening members can be constructed from a material selected from the group consisting of silicone, polyurethane, rigid plastics, semi-rigid plastics, flexible plastic materials, composite materials, biocompatible materials and foam. In some embodiments, the stabilizing structure is surrounded by absorbent materials. In certain embodiments the stabilizing structure is surrounded by non-absorbent materials. In some embodiments the material surrounding the stabilizing structure is foam. In particular embodiments, the spaces between the intervening members 3504 and the elongate strips 3502 are filled with foam.

FIGS. 38A-G illustrate an embodiment of a stabilizing structure 3600 that is similar to the ones described above in relation to FIGS. 37A-C and FIG. 36B. As illustrated in FIG. 38A, in some embodiments, the stabilizing structure 3600 comprises a plurality of elongate strips 3602 connected by a plurality of intervening members 3604 at a plurality of joints 3606. As illustrated in FIGS. 38A-G, the plurality of intervening members comprise a plurality of bars 3604 connecting adjacent elongate strips and connected to the elongate strips at upper and lower joint locations. The plurality of joints in one embodiment comprise a plurality of pins 3606 connected to the bars and received in upper and lower vertical openings in the strips 3602. Other types of joints are also contemplated, including ball joints. The bars are preferably equally spaced within a row between adjacent elongate strips, and may be offset or staggered in an adjacent row, such that in an adjacent row, the bars connect to the elongate strip at a location between the bars of the first row. In other embodiments, the intervening member can comprise a wire or other elongate structure configured to extend between adjacent elongate strips.

Preferably, as illustrated in the top view of FIG. 38B and the front view of FIG. 38C, in certain embodiments the pins cause the bars to protrude above the vertical top and the vertical bottom of the elongate strips 3602. In other embodiments, the bars 3604 may be connected to the elongate strips so that they are located flush with the vertical top and vertical bottom of the elongate strips 3602. In further other embodiments, the bars 3604 may be connected so that they are located below the vertical top of the elongate strips 3602 and above the vertical bottom of the elongate strip.

As illustrated in FIGS. 38A and 38C, the joints 3606 can preferably comprise a plurality of stops 3608 configured to limit the rotation of the bars relative to the strips. The stops may protrude vertically from the strips to limit the movement of the bars. For example, these stops may be used to prevent the bars from becoming fully perpendicular with respect to the adjacent strips, and may be used to provide a preferential direction of collapse to adjacent rows. As shown in FIG. 38A, a first row may have bars angled in a first direction, and a second row may have bars angled in a second direction. In some embodiments, there are two stops per bar on a given strip, to restrict motion in two directions. In other embodiments, there is one stop or three or more stops per bar on a given strip.

Figure 38E:
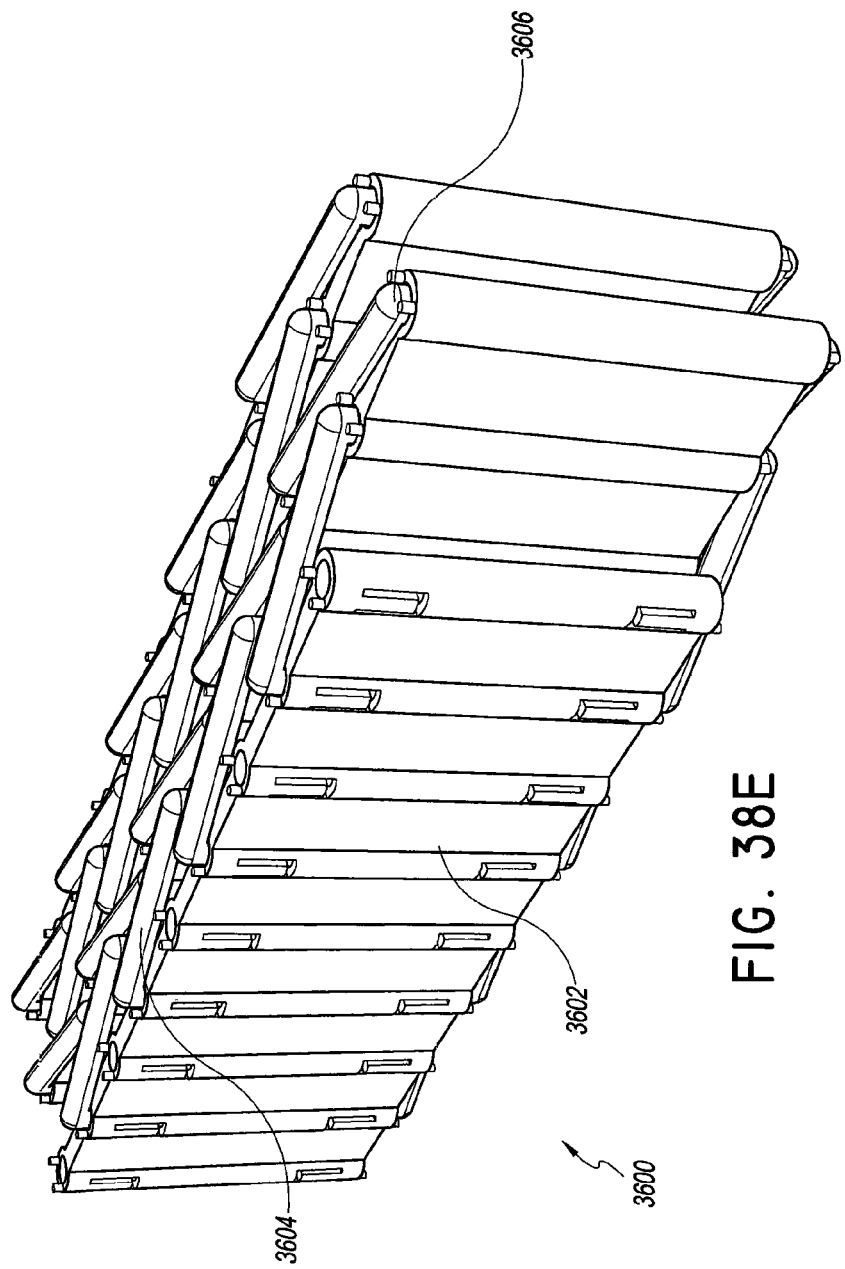
Figure 38G:
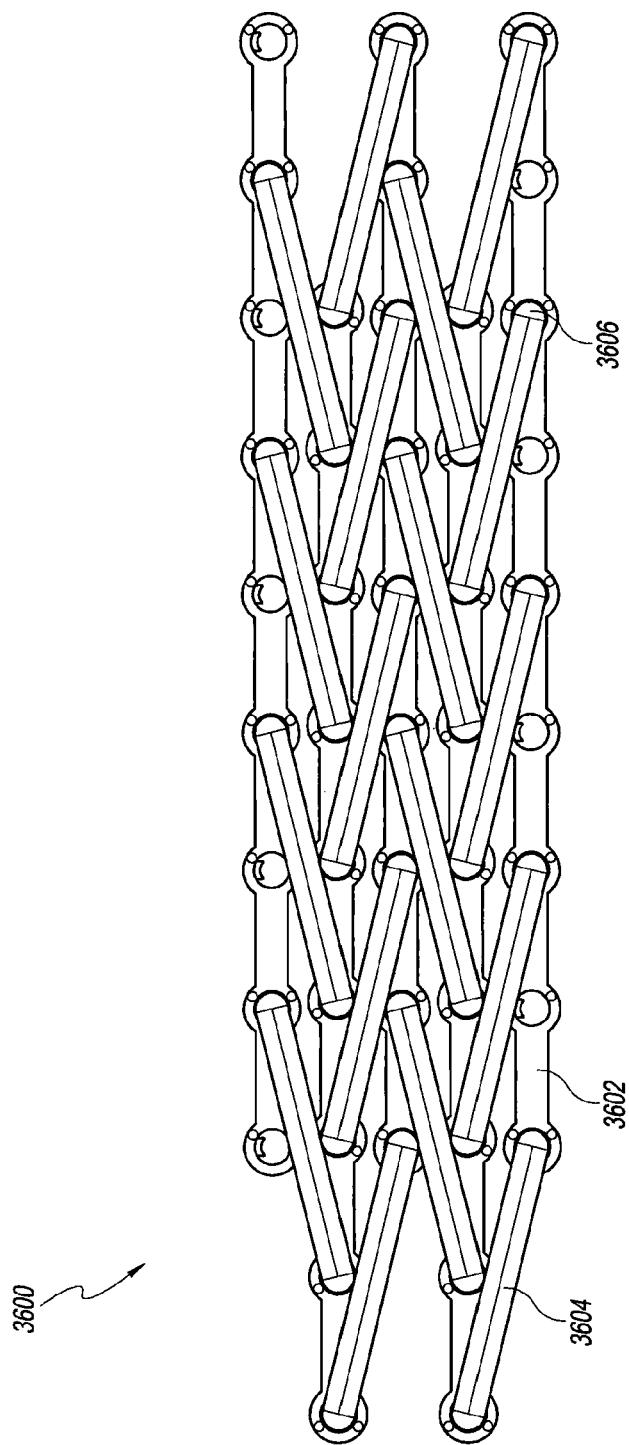

FIGS. 38E-G illustrate the stabilizing structure 3600 in a collapsed configuration. Similar to the structures of FIGS. 37A-C and FIG. 36B, the structure 3600 may be positioned in a wound in an orientation configured to collapse in a direction perpendicular to the longitudinal axis of the wound. As described above, the stabilizing structure may be surrounded by or filled with absorbent material such as foam. In one embodiment, because the vertical space between the upper and lower bars of the structure 3600 are open (as best shown in FIG. 38C), elongate blocks of foam or other compressible material may be placed in between adjacent strips to provide a desired compressibility as the structure collapses.

Figure 39:
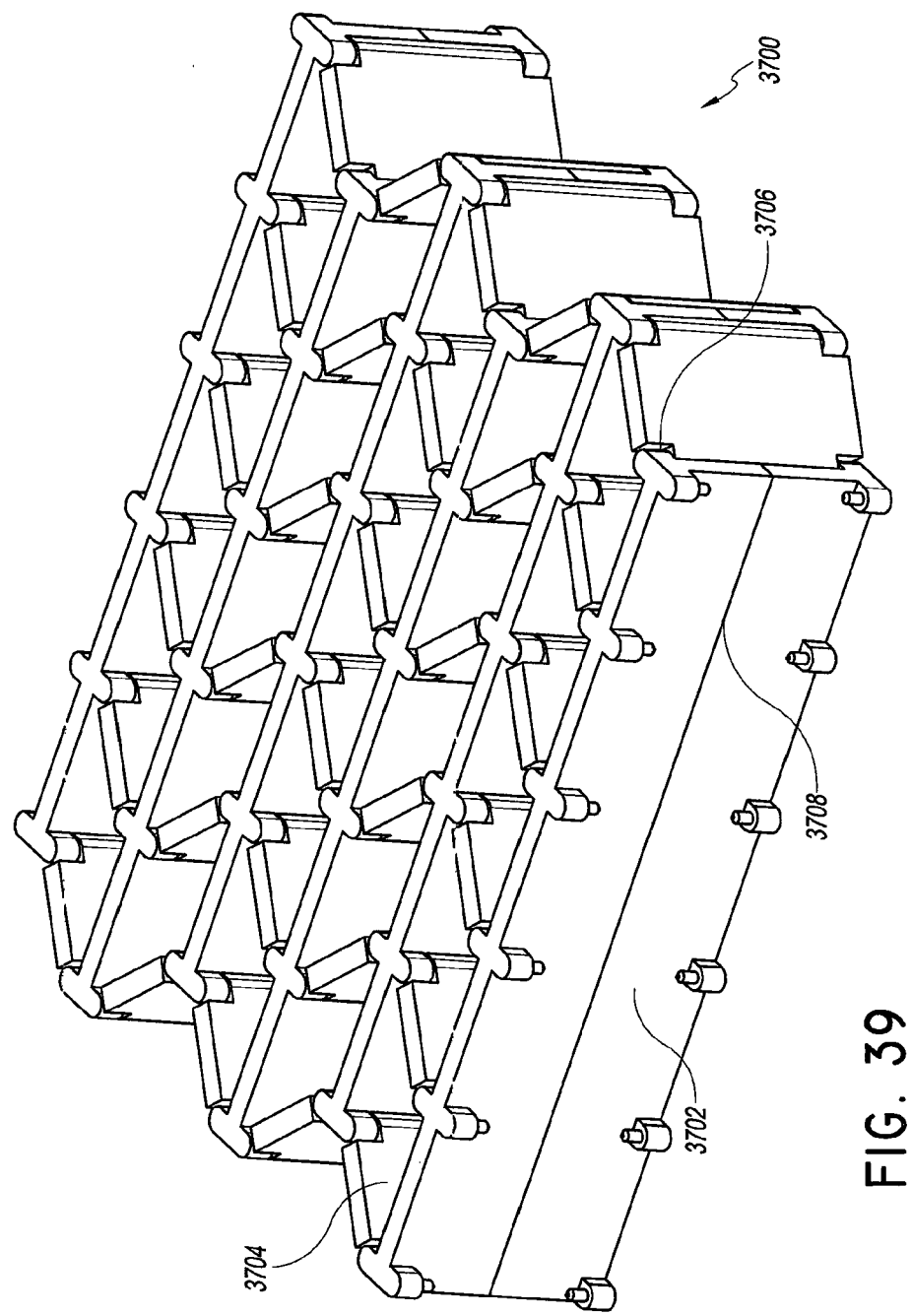
FIG. 39 illustrates one embodiment of a hinged stabilizing structure for closing a wound.

FIG. 39 illustrates an embodiment of a stabilizing structure 3700 that is similar to the structures described above in relation to FIG. 36B, FIGS. 37A-C and FIGS. 38A-G. In certain embodiments, the stabilizing structure 3700 can collapse in any manner described above. The elongate strip 3702 as illustrated is formed in two halves, and can be separated along line 3708. The intervening members 3704 can be in the form of panels as described above. The joints 3706 on the upper half of an elongate strip may comprise pins located on opposite sides of the strip extending downward from the top of the upper half of the strip. The joints 3706 on the lower half of an elongate strip may comprise pins located on opposite sides of the strip extending upward from the bottom of the lower half of the strip. These pins may engage vertical openings located at the four corners of the intervening member 3704. As the upper and lower halves are brought together, the pins may engage the openings in the panels. The upper and lower halves may be secured by any number of mechanisms, such as with adhesive and mechanical connections.

In the FIG. 39 embodiment, with the ability to separate the two halves of 3702 along line 3708, intervening members 3704 may be easily removed or replaced. In some embodiments, only some of the intervening members 3704 are removed. In certain embodiments, alternating intervening members 3704 are removed. In certain preferred embodiments, intervening members are removed in a preferential manner so as to allow the stabilizing structure 3700 to collapse in a controlled manner most appropriate for a particular wound. For example, the joints 3706 may have variable levels of resistance to rotation, thus allowing for control over the collapse of the structure by adding or removing the intervening members 3704. Additionally, stops such as those described in relation to FIG. 38A, could be incorporated into the structure or any other structure described in this section or elsewhere in this specification to further control collapse. In some embodiments, the intervening members are replaced or removed to maximize the collapsed length of the structure 3700. In certain embodiments, intervening members are replaced or removed to minimize the collapsed length of structure 3700. In some embodiments, intervening members are replaced or removed to attain a desired length for the collapsed structure.

Figure 41:
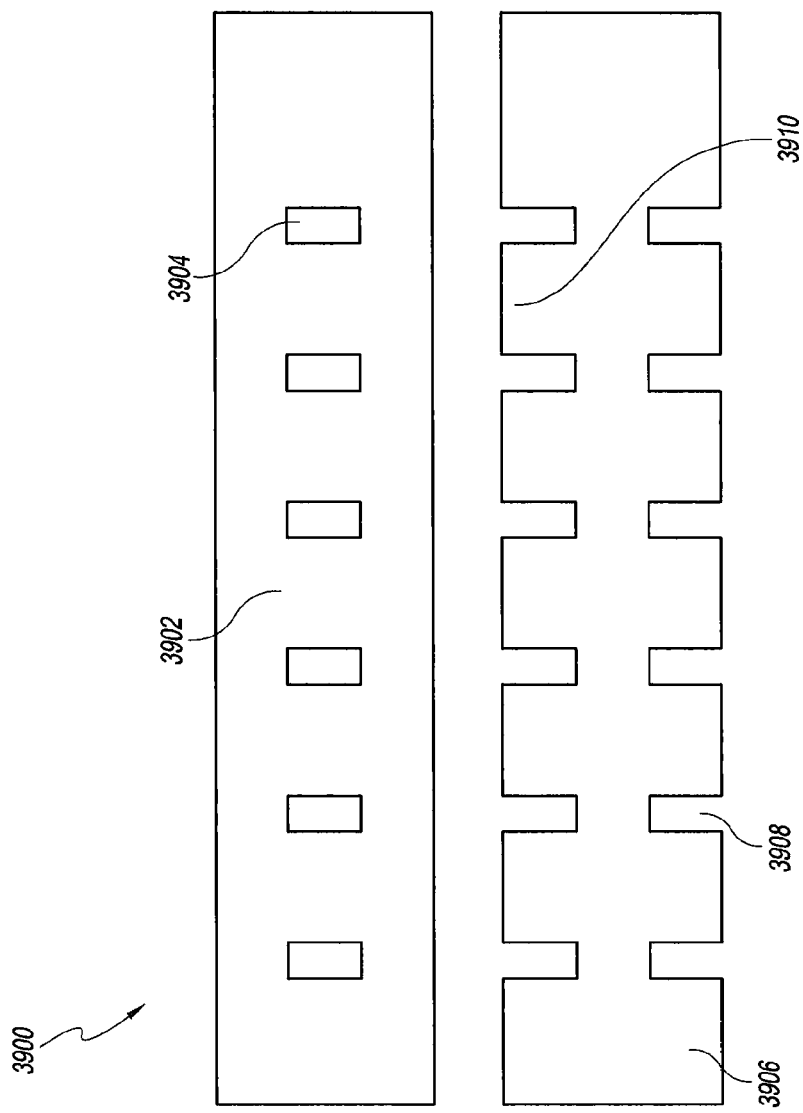
FIG. 41 illustrates one embodiment of a stabilizing structure for a wound.

FIG. 41 illustrates another embodiment of elongate strips 3900 that may be used to form a stabilizing structure, similar to that described in FIGS. 16A-D. The first strip 3902 illustrated in the upper portion of FIG. 41 may be an elongate strip having a plurality of spaced apart openings 3904 extending along a central axis of the strip. The second strip 3906 illustrated in the lower portion of FIG. 41 may have a plurality of spaced apart notches 3908 extending from the upper and lower edges of the second strip and separate by a middle portion. A plurality of the first strips 3902 and a plurality of the second strips 3906 can be assembled into a stabilizing structure similar to what is shown in FIGS. 16A, 16C and 16D, wherein the plurality of first strips 3902 are arranged in parallel to each other, and the plurality of second strips 3906 are arranged in parallel to each other. The plurality of first 3902 and second strips 3906 engage one another by the middle portions 3910 of the second strips positioned through the openings 3904 in the first strips, to place the plurality of first strips at an angle to the plurality of second strips. This structure is configured to collapse in a horizontal plane while remaining rigid in the vertical plane.

Figure 42:
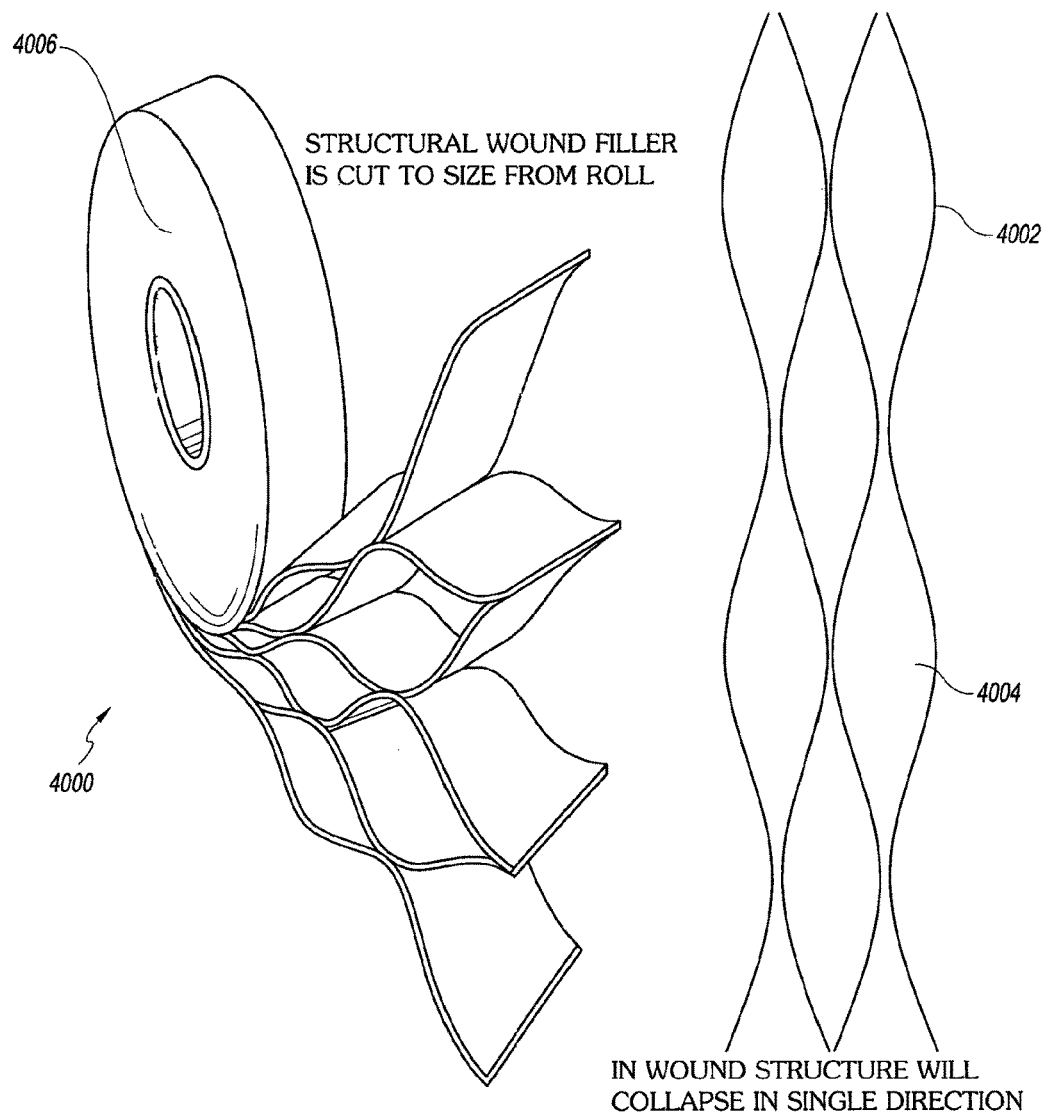
FIG. 42 illustrates an embodiment of a stabilizing structure for a wound cut from a roll.

FIG. 42 illustrates an embodiment of a stabilizing structure 4000 similar to the embodiment of FIG. 21 described above. A plurality of longitudinal strips 4002 can be provided each in the form of a wavy strip that, when joined face-to-face, form one or more circular or ovoid cells 4004. The entire structure can be collapsed into a substantially flat configuration, and can be contained within a roll 4006. To use the stabilizing structure, a portion of the structure can be unrolled and cut at a desired length. Preferably, as the stabilizing structure is unrolled it expands to its natural, deployed configuration. It will be appreciated that other embodiments of the stabilizing structure, and not just embodiments using the wavy strips of FIG. 16, may be assembled into a rolled configuration.

Figure 43:
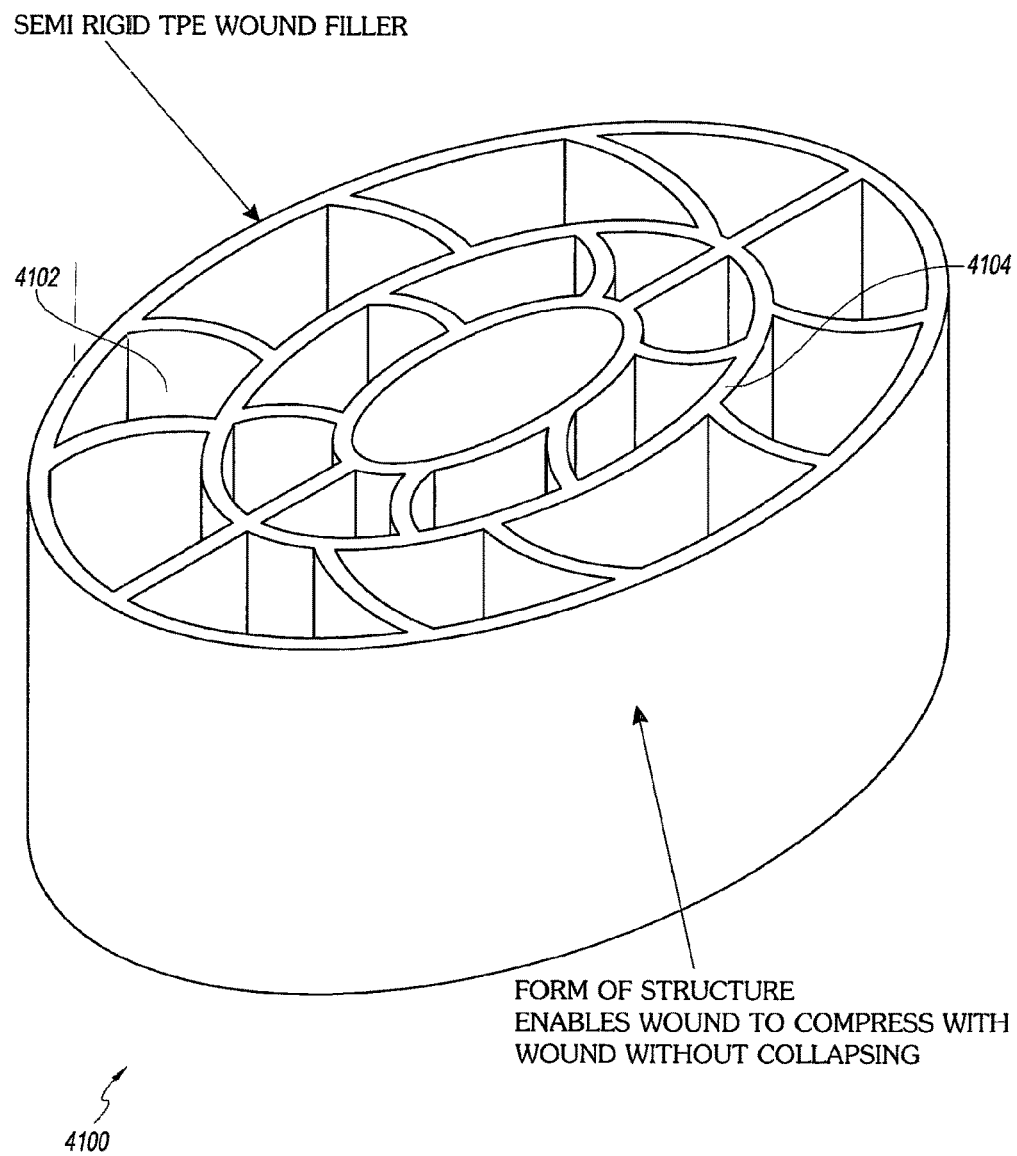
FIG. 43 illustrates an embodiment of a stabilizing structure having an oval shape.

FIG. 43 illustrates another embodiment of a stabilizing structure. In this embodiment, the stabilizing structure 4100 has an elongate, preferably oval shape, wherein cells 4102 within the oval shape have a plurality of cells arranged in a plurality of concentric rings 4104. In the embodiment illustrated, a central oval cell is surrounded by two oval-shaped rings. Other embodiments can include more than two oval-shaped rings.

Stabilizing Structures and Wound Closure Devices of FIGS. 44A-52

As with the other stabilizing structures and wound closure devices described elsewhere in the specification, the stabilizing structures and wound closure devices of FIGS. 44A-52 may be incorporated into the wound packing and wound treatment apparatus embodiments described elsewhere in the specification, such as in relation to FIGS. 8A-10.

FIGS. 44A-F illustrate embodiments of a stabilizing structure 4200 that are similar to the embodiments described above in relation to FIGS. 37A-40. The stabilizing structure may comprise a plurality of elongate strips 4202 arranged in parallel, whose longitudinal length can be aligned with the longitudinal axis when placed in a wound. The stabilizing structure can further comprise a plurality of intervening members 4204 connected to the elongate strips 4202 via joints 4206. In certain embodiments, the stabilizing structure 4200 can collapse in any manner described in this section or elsewhere in this specification with or without the application of negative pressure. For example, the stabilizing structure may collapse significantly more in one plane than in another plane. In some embodiments, the stabilizing structure can be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam.

The stabilizing structure 4200 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can placed into a wound for a period of time and then removed or replaced with another stabilizing structure. For example, a stabilizing structure could be inserted into a wound for a period of time, promoting closure of the wound by drawing the edges closer together. After a period of time has passed, the stabilizing structure can be replaced by a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue.

In some embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate.

In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Figure 44A:
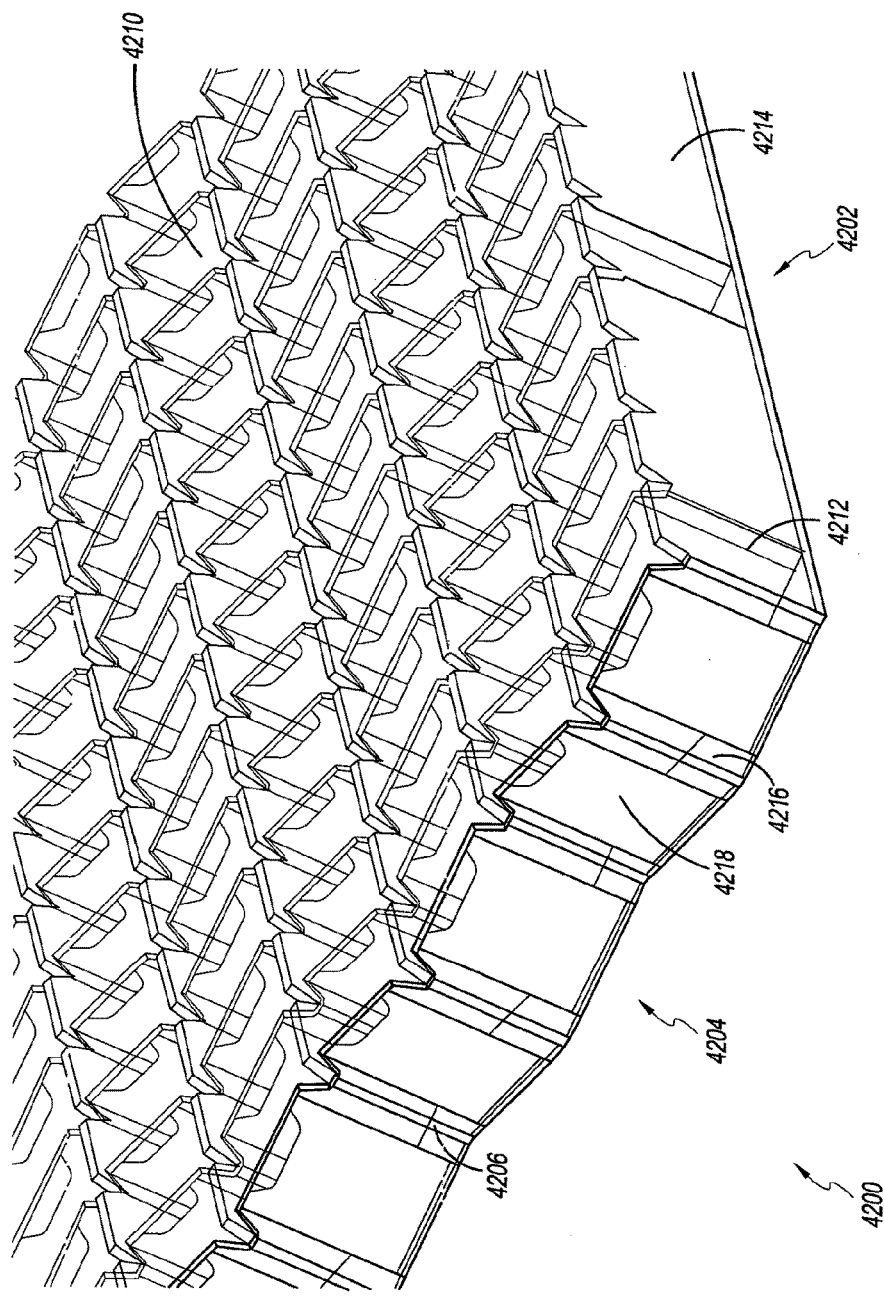
FIGS. 44A-F illustrate multiple views of an embodiment of a stabilizing structure.
Figure 44B:
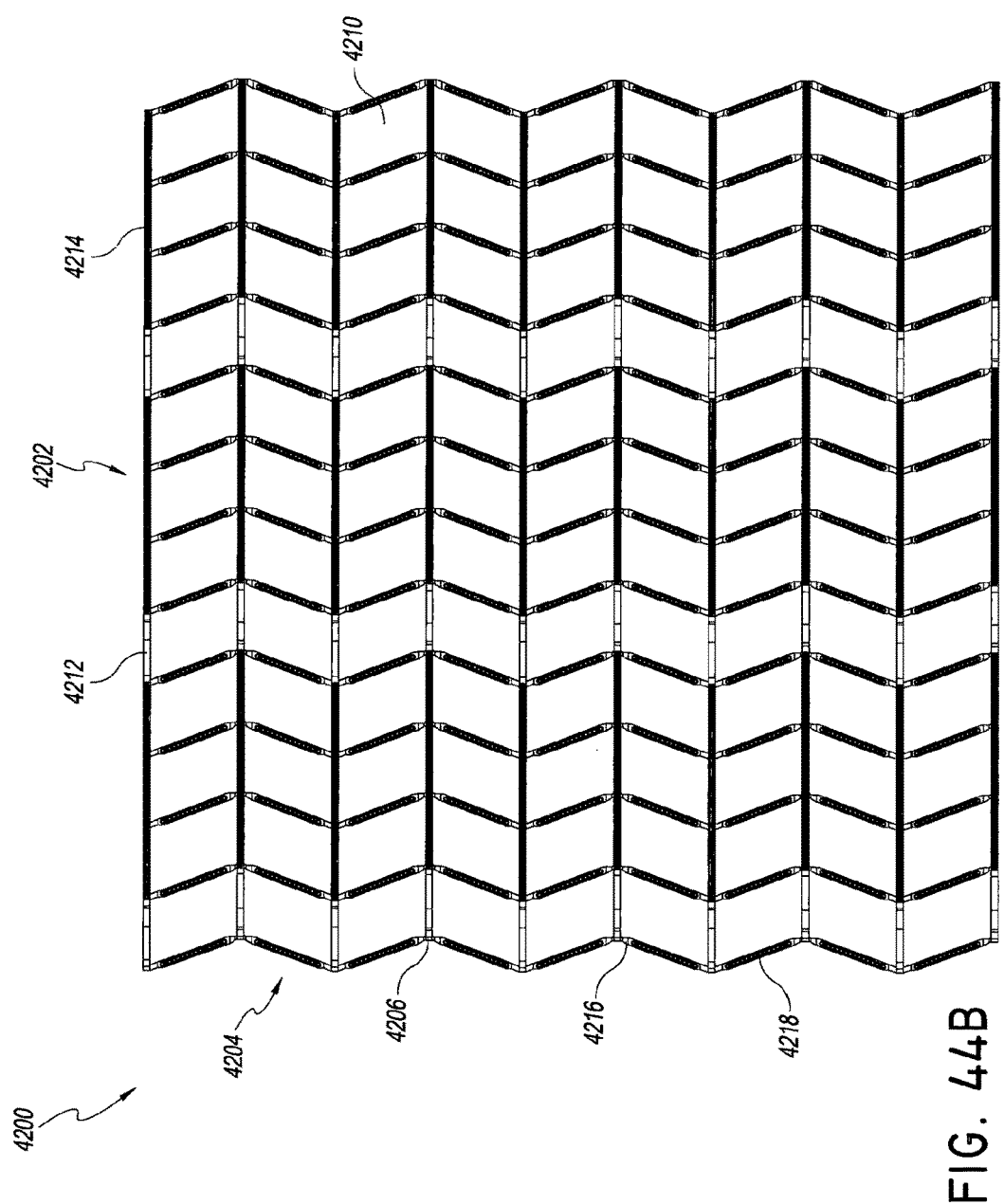

As illustrated in the perspective view of FIG. 44A and the top view of FIG. 44B, the intersection of the intervening members 4204 and the elongate strips 4202 may define a plurality of cells 4210. In certain embodiments, the cells 4210 may be of any of the shapes and sizes described in this section or elsewhere in this specification, such as those described in relation to FIGS. 37A-37C. For instance, a cell may be in the shape of a square, a diamond, an oblong, an oval, and/or a parallelepiped.

The joints 4206 are configured to allow the intervening members 4204 to collapse, similar to the joints described in FIGS. 37A-C and FIG. 39. The joints 4206 can be configured to allow the intervening members to collapse in any manner as described in this section or elsewhere in this specification in relation to other embodiments, such as those described in relation to FIGS. 37A-C. For example, the joints 4206 may be configured to allow or preferentially cause a first row of intervening members 4204 to collapse in one direction, while allowing or preferentially causing an adjacent row to collapse in another direction.

The elongate strips 4202 may comprise alternating flexing segments 4212 and supporting segments 4214. In a preferred embodiment, the flexing segments 4212 can be constructed from a flexible or semi-flexible material such as silicone and/or polyurethane. However, any flexible or semi-flexible material may be suitable. The flexing segments 4212 can flex in any direction, allowing the stabilizing structure to collapse more readily in any direction, but particularly in the horizontal plane. In a preferred embodiment, the supporting segments 4214 can be constructed from a rigid or semi-rigid material such as polyvinyl chloride (PVC). However, any rigid or semi-rigid material may be suitable. In the embodiment illustrated, the elongate strips 4202 comprise elongate strips of a first material such as silicone and/or polyurethane, with a plurality of elongate inserts of a second, more rigid material 4214 embedded into the first material. Thus, the flexing segments 4212 are the areas in the elongate strips 4202 where the more rigid inserts are not located.

As illustrated in FIGS. 44A-D, the supporting segments 4214 may be larger than the flexing segments 4212. In one embodiment, the supporting segments 4214 can be approximately three times as large as the flexing segments 4212 (such as by spanning three cells 4210). In other embodiments, the supporting segments 4214 may be the same size as the flexing segments 4212. In further embodiments, the flexing segments 4212 can be larger than the supporting segments 4214. Alternatively, the lengths and widths of the individual segments of the elongate strips 4202 can be variable. For example, the height of the supporting segments 4214 can be reduced, such that they do not extend from approximately the top to approximately the bottom of the stabilizing structure 4200. In some embodiments a smaller supporting segment could encompass approximately half the height of the elongate strip 4202. In certain embodiments, the supporting segment 4214 could be located in the upper or in the lower portion of the elongate strip. Such embodiments may be accomplished by utilizing an insert of a second material that has a smaller height than the height of the first material forming the elongate strip 4202.

In some embodiments, the supporting segment does not alternate with the flexing segment 4212 and instead, the elongate strips 4202 are comprised entirely of supporting segments 4214 (e.g., a silicone strip or other material with an embedded more rigid insert extending the entire length thereof, or simply a more rigid material by itself). Alternatively, the entirety of the elongate strip 4202 can be comprised only of flexing segments 4212 (e.g., a strip made only of silicone or other more flexible material).

The elongate strips 4202 may be manufactured from a female mold that may further encompass the entire stabilizing structure 4200. The supporting segments 4214 can be inserted into the female mold, followed by an injection of a flexible polymer such as silicone and/or polyurethane to encase the supporting segments 4214 within the flexible polymer frame. The supporting segments 4214 can be inserted into the mold in any desired manner or quantity, allowing for many potential variations of the stabilizing device.

In further embodiments, the supporting segments 4214 are insertable and/or removable from the elongate strips 4202, and may be inserted and/or removed to alter the collapsibility of the stabilizing structure 4200. Supporting segments 4214 can be inserted and/or removed from the stabilizing structure 4200 after it has been placed in a wound to variably control the collapse of the stabilizing structure 4200. In such embodiments, the elongate strips 4202 may form pockets that are open from one side (e.g., from the top) to allow insertion and removal of the supporting segments 4214.

Figure 44D:
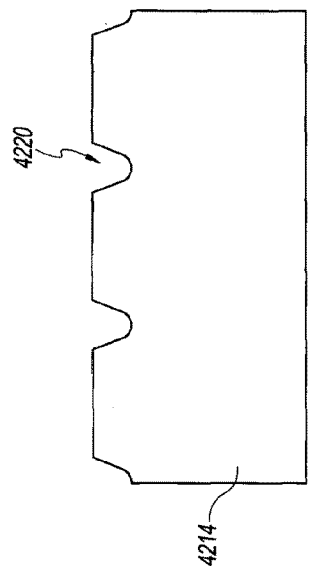
Figure 44F:
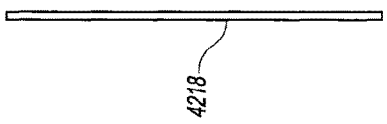
Figure 44C:
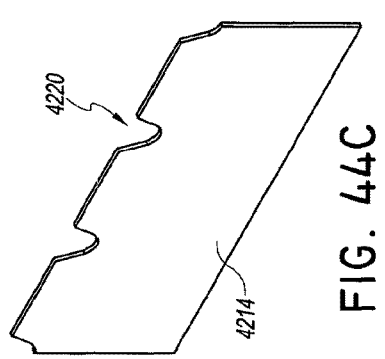

FIGS. 44C-D illustrate in greater detail an embodiment of an individual supporting segment 4214. The supporting member 4214 may be a flat, plate-like structure having a rectangular shape, with a length greater than its height, and two parallel surfaces. The supporting segment can comprise at least one notch 4220, preferably located on the upper edge of the supporting segment. In other embodiments, the notch or notches can be located on the bottom or the sides of the supporting segment. In further embodiments, the top notch could have a corresponding bottom notch. In certain embodiments, the notch could be configured so as to allow tearing of the supporting segment in a transecting line across the supporting segment. The notch or notches 4220 may advantageously provide flexibility to the structure. The notches 4220 may allow the stabilizing structure to flex more easily in the horizontal plane or in the vertical plane. The notches 4220 may further allow the stabilizing structure to twist in multiple planes. The notches 4220 may also improve fluid flow within the stabilizing structure 4200. In some embodiments, the supporting segment does not contain a notch and the uppermost edge is flat. The notch 4220 can be located at other locations on the supporting segment, for example the bottom edge or the sides. The shape of the notch can be a rounded triangle as in FIGS. 44C-D or any other similar shape.

Figure 44E:
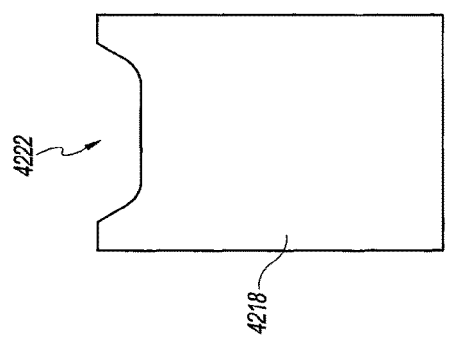
Figure 45A:
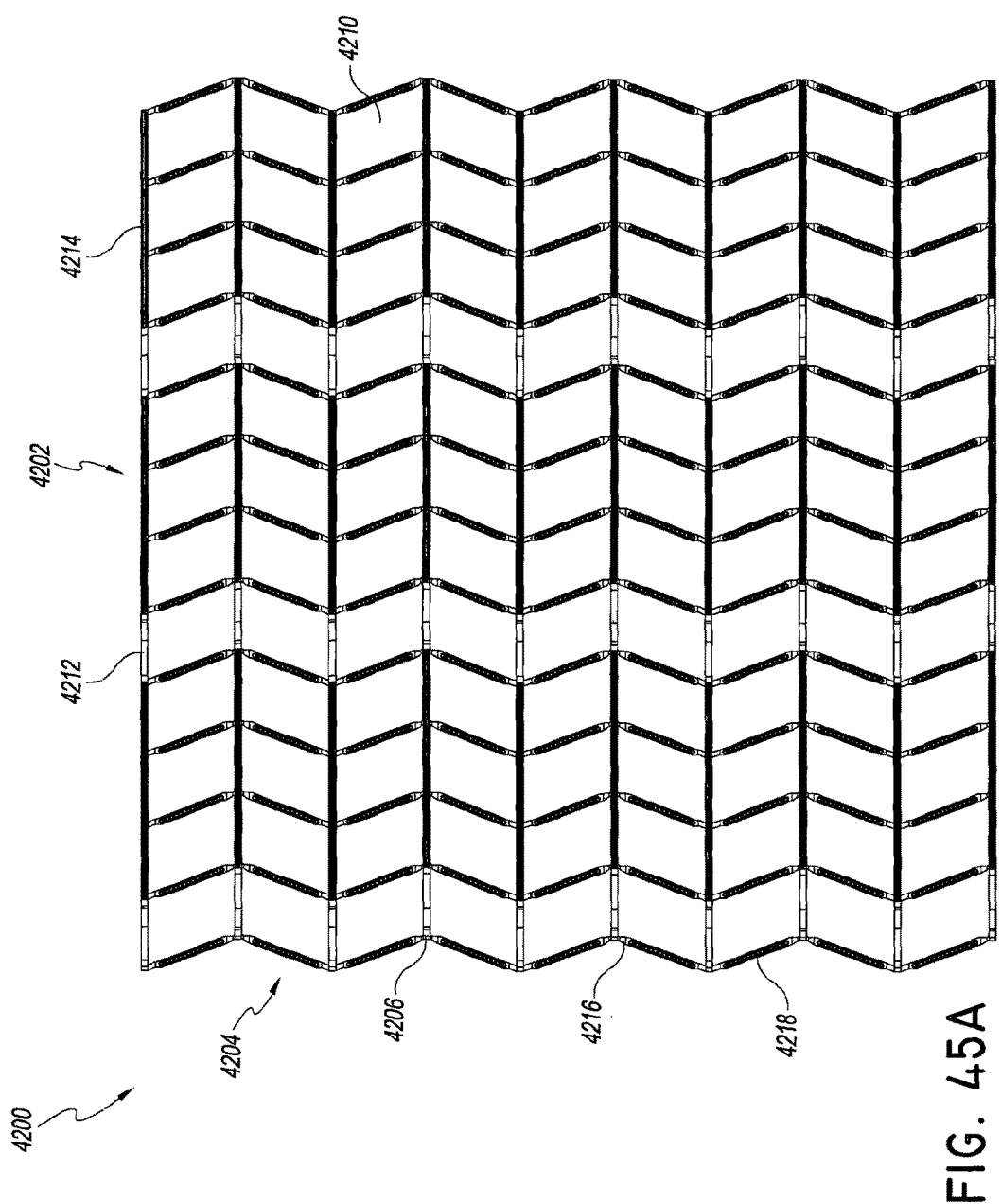
FIGS. 45A-D illustrate multiple views of an embodiment of a stabilizing structure comprising openings for fluid passage.
Figure 45B:
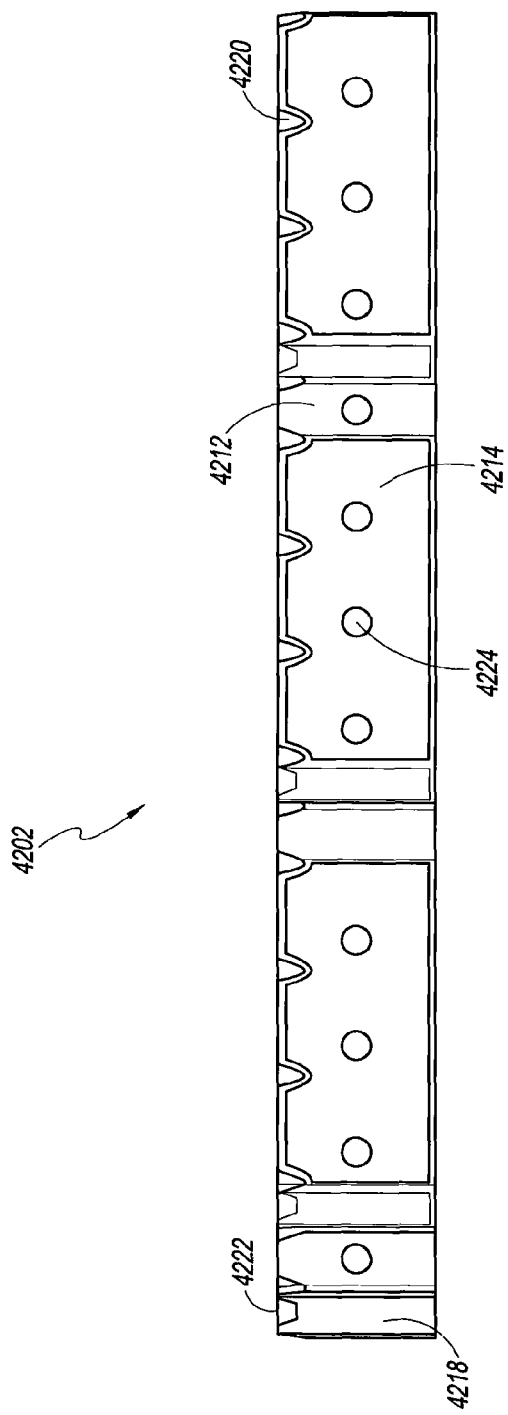
Figure 45D:
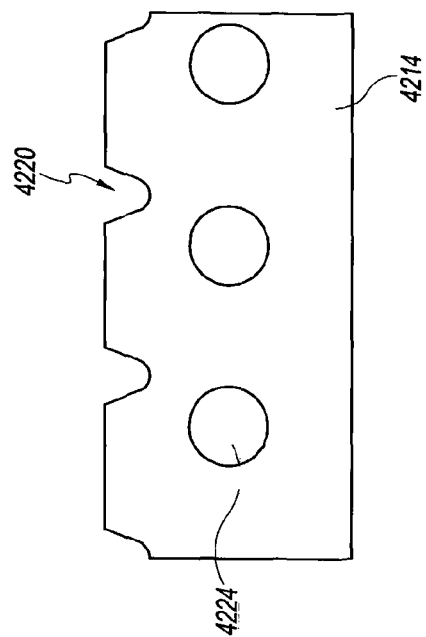
Figure 45C:
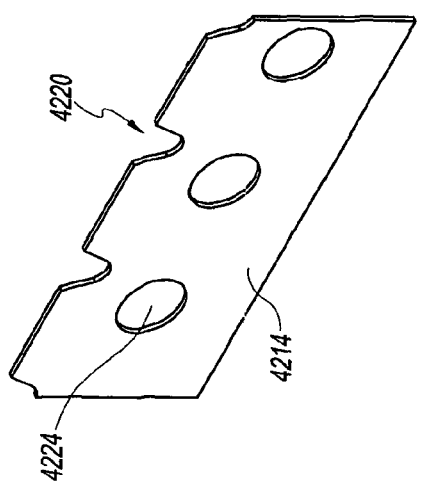

The intervening members 4204 in some embodiments may comprise a first material 4216 with an embedded insert 4218 made of a more rigid material. One embodiment of the embedded insert is illustrated in FIGS. 44E-F. In certain embodiments, the insert 4218 is placed within a female mold and a flexible polymer such as silicone and/or polyurethane is injected around the insert to entomb the insert 4218 within a flexible polymer frame. The inserts 4218 can be inserted into the mold in any desired manner or quantity, allowing for many potential variations of the stabilizing device. In other embodiments, the first material 4216 may be in the form of a sleeve configured to receive the insert 4218. Further, the sleeve 4216 may be configured to allow for the removal of an insert 4218, such as by providing an opening in the top of the sleeve. In a preferred embodiment, the first material 4216 is constructed from a flexible or semi-flexible material such as silicone and/or polyurethane. However, any flexible or semi-flexible material may be suitable. In a preferred embodiment, the insert 4218 is constructed from a rigid or semi-rigid material such as polyvinyl chloride. However, any rigid or semi-rigid material may be suitable.

FIG. 44E illustrates a front view of insert 4218, while FIG. 44F illustrates a side view of insert 4218. The insert in one embodiment may be a flat, plate-like structure having a rectangular shape, with a height greater than its width, and two parallel surfaces. The insert can comprise an indent 4222. The indent is preferably located at the upper portion of the insert, however, the indent 4222 can be positioned on either side of the insert, or on the bottom. The indent 4222 can be configured such that it aids in allowing fluid to flow through the stabilizing structure by providing a flow path. The indent 4222 can improve flexibility of the stabilizing structure 4200 and be configured to allow for a more efficient collapse of the stabilizing structure 4200.

In some embodiments, the stabilizing structure 4200 of FIGS. 44A-B can be configured to include perforations or detachable sections that allow portions of the device to separate from the remainder of the device. For example, perforations may be incorporated into the joints 4206 between various cells contained within the stabilizing structure 4200, allowing for the removal of individual rows or cells to alter the shape of the stabilizing structure 4200. In some embodiments, as described above in relation to FIGS. 44C-D, the sections may be detached along perforations or lines in the elongate strips corresponding to the notches 4220.

In some embodiments, the inserts 4218 may be entombed within first material 4216 in a variable number of intervening members 4204 to control the shape and collapse of the stabilizing structure 4200. In other embodiments, the inserts 4218 may be inserted directly into sleeves comprised of first material 4216 within the intervening members 4204 to control the shape and collapse of the stabilizing structure 4200.

For example, the inserts 4218 can be present in at least about 5% of the intervening members, at least about 10% of the intervening members, at least about 15% of the intervening members, at least about 20% of the intervening members, at least about 25% of the intervening members, at least about 30% of the intervening members, at least about 35% of the intervening members, at least about 40% of the intervening members, at least about 45% of the intervening members, at least about 50% of the intervening members, at least about 55% of the intervening members, at least about 60% of the intervening members, at least about 65% of the intervening members, at least about 70% of the intervening members, at least about 75% of the intervening members, at least about 80% of the intervening members, at least about 85% of the intervening members, at least about 90% of the intervening members, at least about 95% of the intervening members, or about 100% of the intervening members.

In certain embodiments, a variable number of supporting segments 4214 may be entombed within elongate strips 4202 to control the collapsibility of the stabilizing structure 4200. In other embodiments, a variable number of supporting segments may be inserted into a pocket contained within the elongate strips 4202 to control the collapsibility of the stabilizing structure. For example, the supporting segments 4214 can be present in at least about 5% of the total length of the elongate strips, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the total length of the elongate strips.

In certain embodiments, the inserts 4218 or supporting segments 4214 may be inserted and/or removed over time to variably control the collapse of the stabilizing structure 4200. For example, although initially all the available sleeves 4216 of the stabilizing structure may contain an insert, after the initial placement of the stabilizing structure in a wound, additional inserts 4218 may be removed over time, thus causing the stabilizing structure 4200 to collapse even further. Inserts can also be added to the stabilizing structure after it is inserted into a wound, thereby decreasing the collapsibility of the stabilizing structure 4200. Thus, the addition and/or removal of the inserts 4216 or supporting segments 4214 allows for variable control of the collapse of the stabilizing structure 4200. In similar fashion, supporting segments 4214 can be inserted and removed from the elongated strips over time to provide variable control over the collapse of the stabilizing structure 4200.

In certain embodiments of the stabilizing structures described in this section or elsewhere in this specification, such as in stabilizing structure 4200 as described in FIG. 44A, the flexibility of various sections of the stabilizing structure is enhanced by thinning of that section. For example, in certain embodiments, rather than using a flexible material for a flexing segment 4212 of elongate strip 4202, instead the flexing segment 4212 can be constructed of a similar material to that used to construct supporting segment 4214. In this embodiment, since supporting segment 4212 is thicker than flexing segment 4212 it will not flex to the degree of flexion that may be experienced by flexing segment 4212. In certain embodiments, the entire stabilizing structure 4200 may be constructed from a single rigid or semi-rigid material, but made to have different rigid and flexible portions by thinning certain areas of the stabilizing structure 4200. In further embodiments, the joints 4206 may be thinned to allow for greater flexibility as compared to the surrounding sections. In certain embodiments, thinning of a section of the stabilizing structure 4200, may allow the thinner portion to be more readily detached from the structure.

As described above in relation to FIGS. 19A-24B and applicable to all stabilizing structures or wound closure devices described in this section or elsewhere in the specification, a soft polymer could be molded over the entire stabilizing structure 4200 to soften the feel of the device, thereby protecting the surrounding organs and/or other tissues. In other embodiments, the soft polymer could be molded only over the bottom portion of the stabilizing device 4200, while in some embodiments the softer polymer can be molded over the top and/or the sides of the device. In some embodiments, the soft polymer could be molded over particular edges of the stabilizing structure 4200, such as those on the bottom, sides, and/or top. In certain embodiments, the soft polymer could be molded over any side or combination of sides of the stabilizing structure 4200. The soft polymer may act like a softened rim surrounding the hard edges of the stabilizing structure 4200.

FIGS. 45A-D illustrate multiple views of another embodiment of the stabilizing structure 4200, similar to the stabilizing structures depicted in FIGS. 37A-C and 44A-F. As in the stabilizing structure embodiment depicted in FIGS. 44A-F, the stabilizing structure 4200 comprises elongate strips 4202 and intervening members 4204. The elongate strips 4202 may comprise openings 4224 configured to allow the passage of fluid through the elongate strips 4202. To construct the openings, holes or other shapes may be punched directly through the elongate strips 4202. In the embodiment illustrated and as further shown in FIGS. 45C and 45D, the elongate strips 4202 further comprise more rigid inserts 4214 as described above. In such embodiments, the openings 4224 may be punched through the rigid inserts 4214 in locations of the strip where the inserts are located, as well as through flexing segments 4212 where the inserts are not located. The openings can be configured to evenly distribute fluid throughout the stabilizing device and/or direct fluid flow along a particular passage or direction. In other embodiments, the intervening members comprise openings, similar to the openings described in relation to the elongate strips.

Figure 46A:
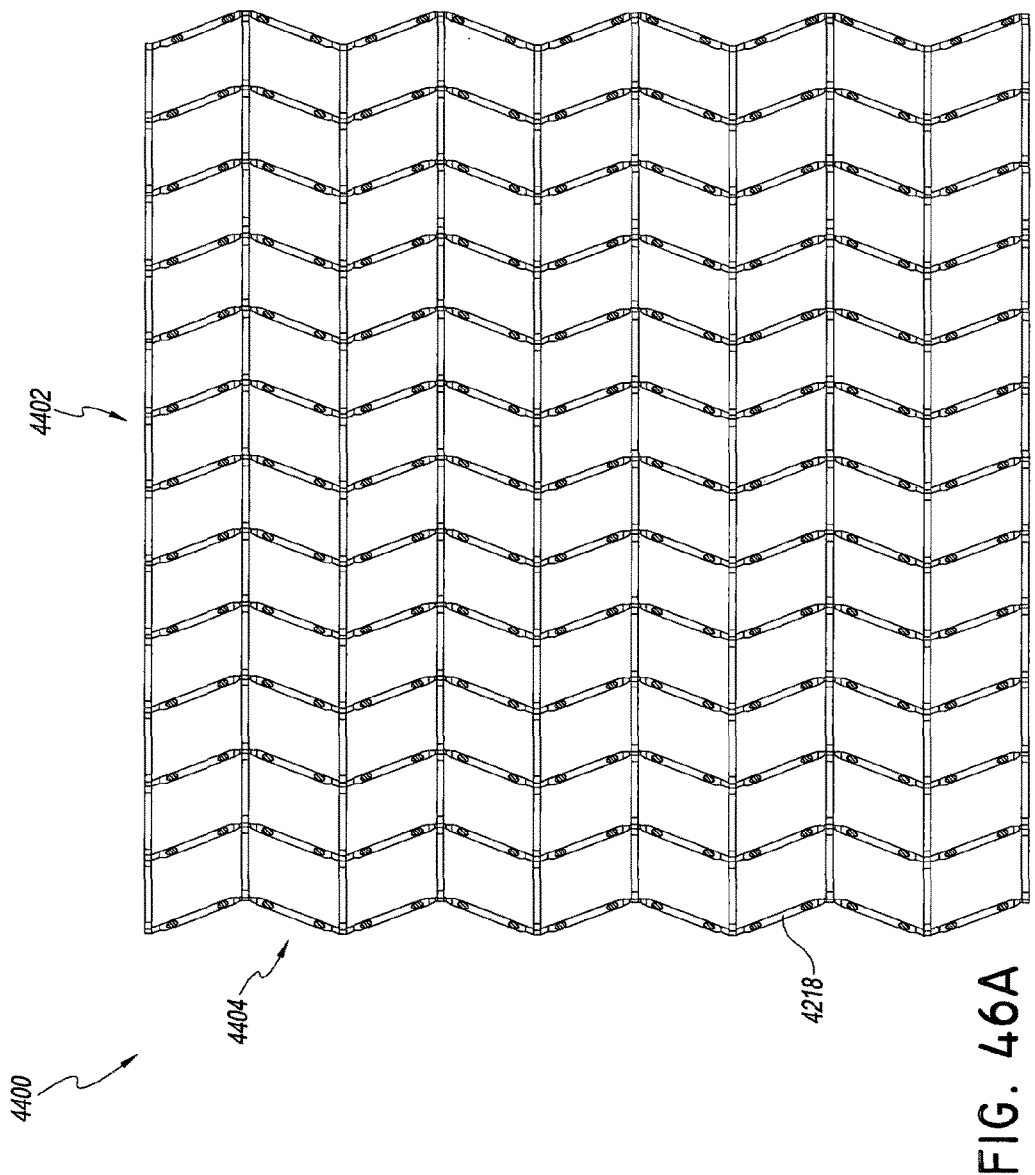

FIGS. 46A-B illustrate embodiments of a stabilizing structure 4400, with functional and structural elements similar to the embodiments of the stabilizing structure depicted in FIGS. 44A-F. Similar to the other stabilizing structures described previously, the stabilizing structure 4400 comprises elongate strips 4402 and intervening members 4404. The elongate strip 4402 may be a single unitary strip with no differing flexing segments or support segments. In certain embodiments, the elongate strip 4402 can be comprised entirely of rigid or semi-rigid materials such as polyvinyl chloride. In other embodiments, the elongate strip 4402 may be comprised entirely of flexible or semi-flexible material such as silicone and/or polyurethane. Similar to the embodiments described in FIGS. 44A-F, stabilizing structure 4400 may collapse in any manner described in this section or elsewhere in this specification within any timescale described in this section or elsewhere in this specification.

FIG. 46C depicts an embodiment wherein the elongate strips 4402 comprise openings 4416 to allow the passage of fluid, similar to the passage of fluid described in FIGS. 45A-D.

Figure 47A:
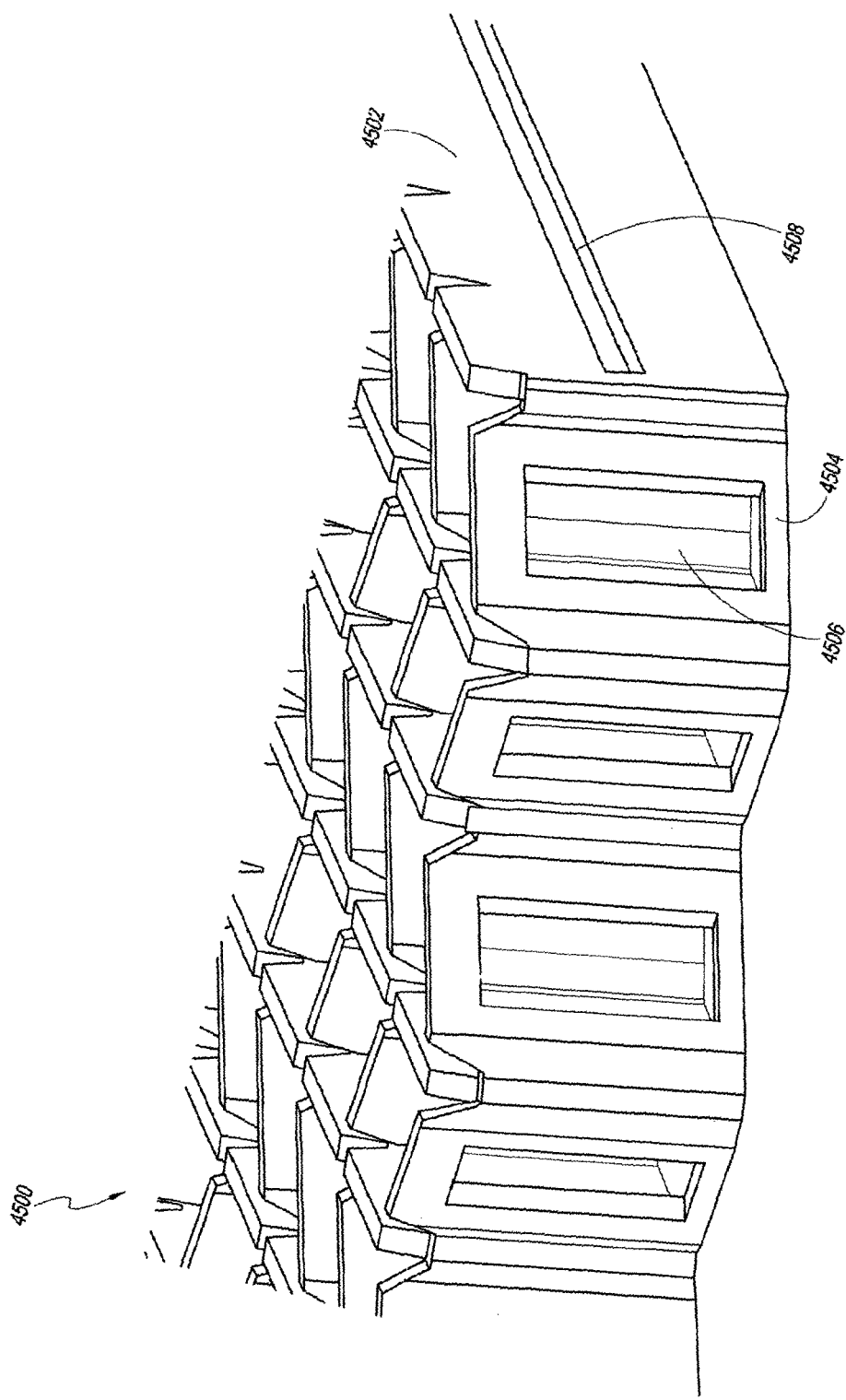
FIGS. 47A-B illustrate multiple embodiments of a stabilizing structure comprising windows.
Figure 47B:
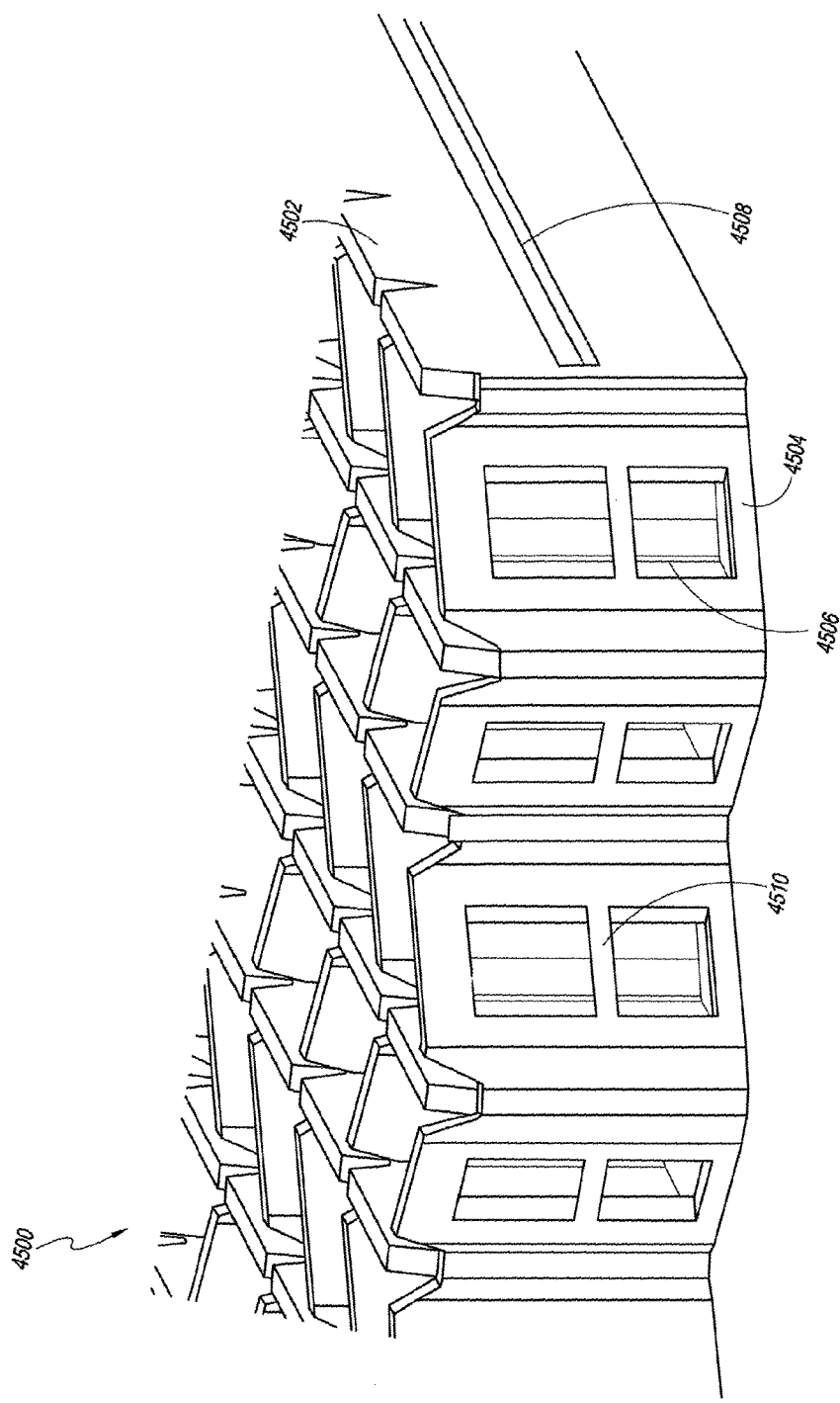
Figure 48A:
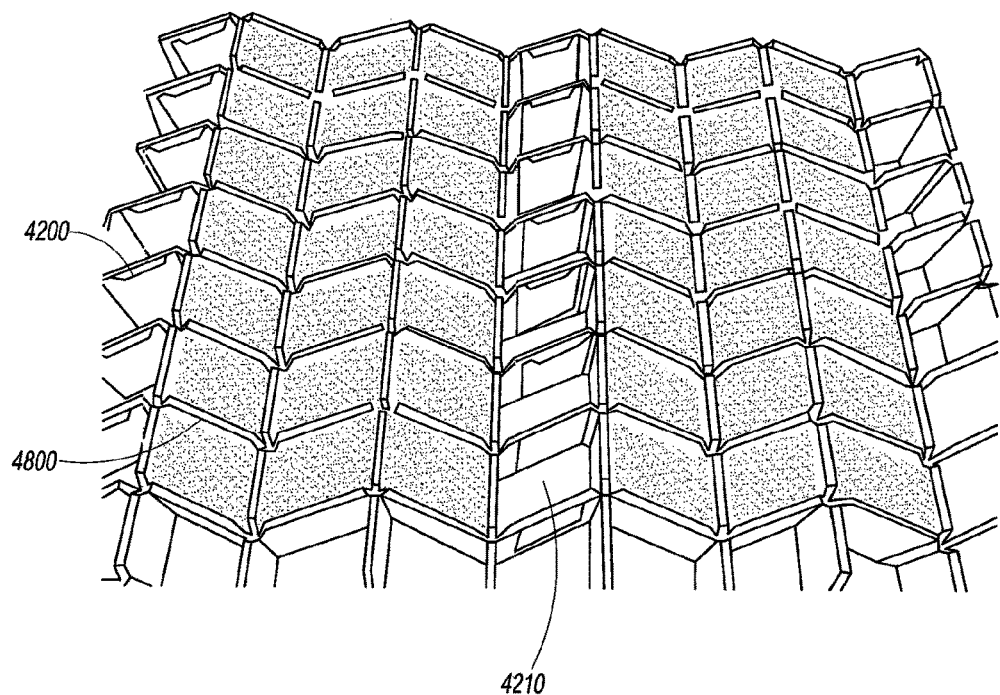
FIGS. 48A-C are photographs of various embodiments of a stabilizing structure comprising foam inserts.
Figure 48B:
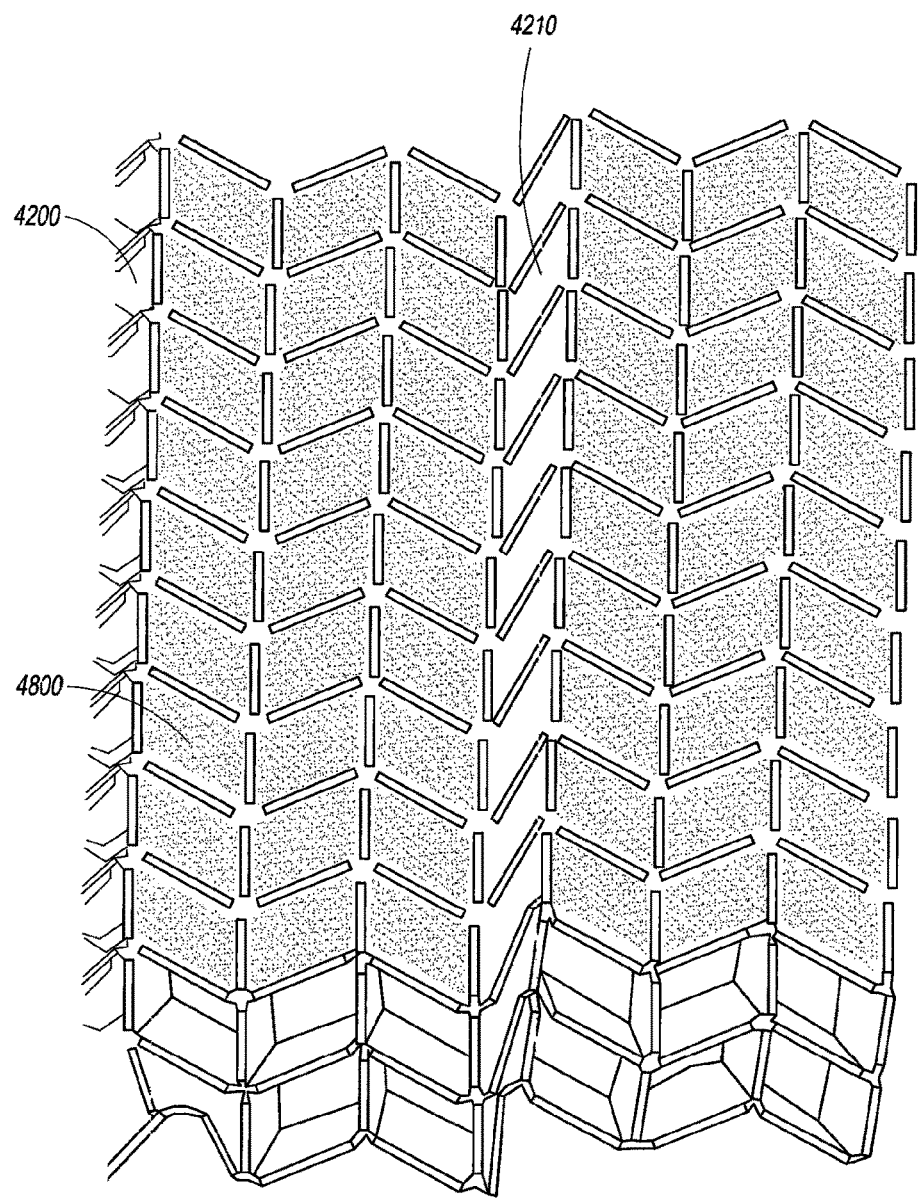
Figure 48C:
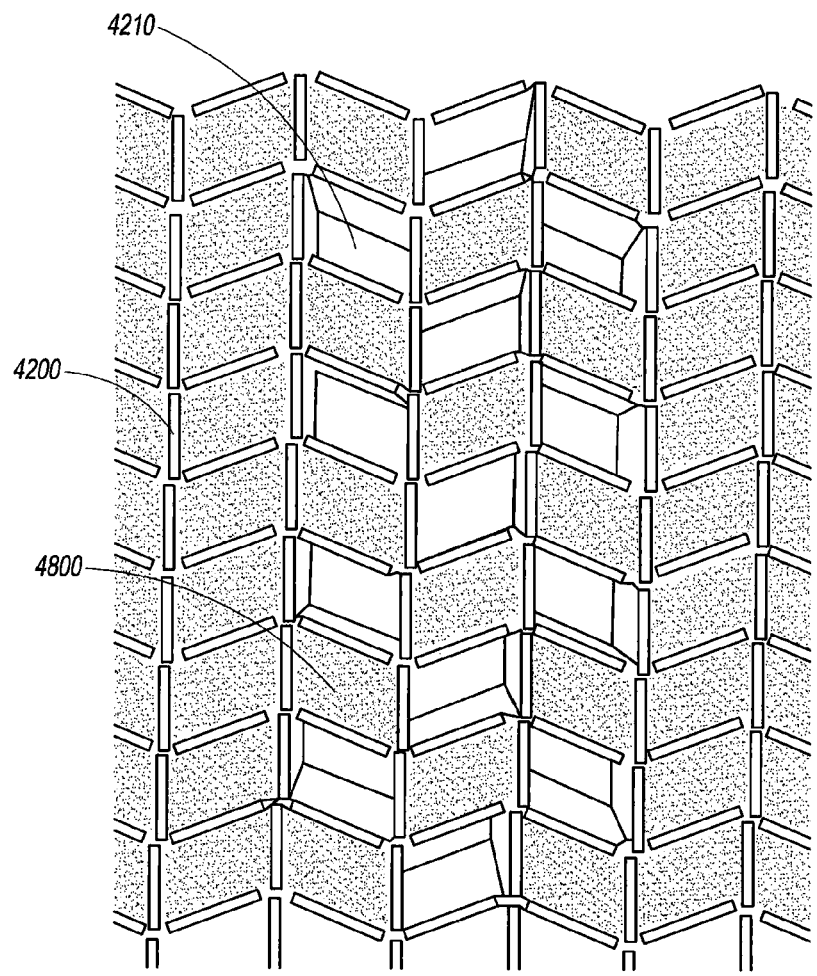

FIGS. 47A-B illustrate embodiments of stabilizing structure 4500 that are similar to the stabilizing structures described above in relation to FIGS. 37A-40. Stabilizing structure 4500 comprises elongate strips 4502 and intervening members 4504. Intervening members 4504 can further comprise windows 4506, configured to allow the passage of fluid. In some embodiments, all intervening members 4504 may comprise windows 4506, however in other embodiments only the horizontally outermost intervening members 4504 comprise windows 4506, while the inner intervening members are similar to other embodiments described in this section or elsewhere in this specification.

In certain embodiments, at least about 5% of the intervening members comprise windows, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the intervening members.

The elongate strip 4502 may further comprise a gap 4508, configured to allow the passage of fluid. The gap may extend nearly the entire length of the elongate strips 4502 or extend only a portion of the length of the elongate strip 4502.

FIG. 47B illustrates an embodiment of a stabilizing structure 4500, where the windows 4506 further comprise bars 4510. In certain embodiments, at least about 5% of the windows comprise bars, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the windows.

Stabilizing Structures and Wound Closure Devices of FIGS. 49A-D

As with the other stabilizing structures and wound closure devices described elsewhere in the specification, the stabilizing structures and wound closure devices of FIGS. 49A-F may be incorporated into the wound packing and wound treatment apparatus embodiments described elsewhere in the specification, such as in relation to FIGS. 8A-10.

Figure 49A:
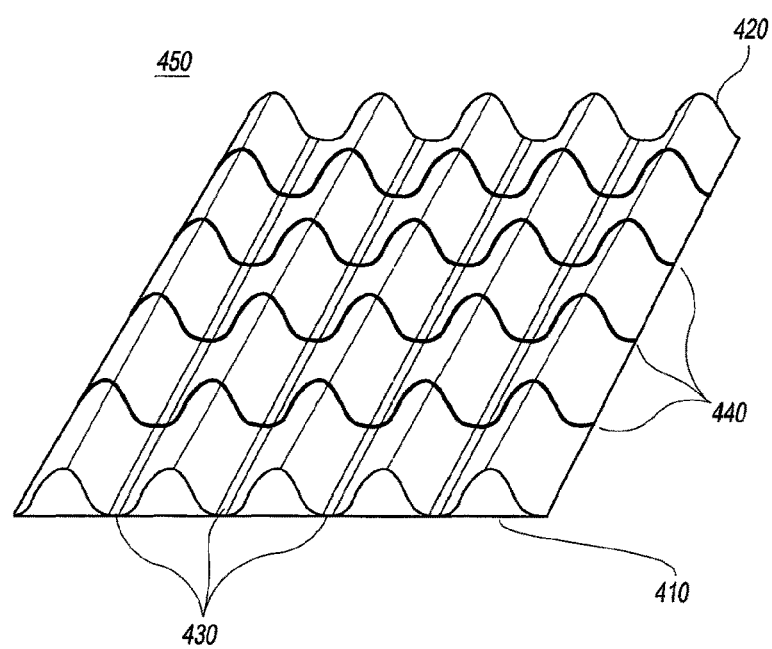
FIGS. 49A-F depict embodiments of various stabilizing structures.

FIG. 49A illustrates a stabilizing structure comprising a corrugated unit 450 comprising two sheets. A first sheet layer 410 is provided, and a second sheet-like layer 420 having an essentially sinusoidal cross section, for example, is coupled to the surface of the first sheet layer at locations 430. The coupling can be achieved by use of an adhesive or heat sealing. A two part silicone adhesive has been found suitable to provide coupling between sheet 410 and sheet 420. A bead of silicone material 440 may be optionally added to adjust the resiliency of the corrugated unit 450. A suitable sheet material is polyester or polyester fibers. Although sheet layer 420 is illustrated as having a sinusoidal cross-section, it is also contemplated that other cross-sections, such as pleated, may be used.

Figure 49B:
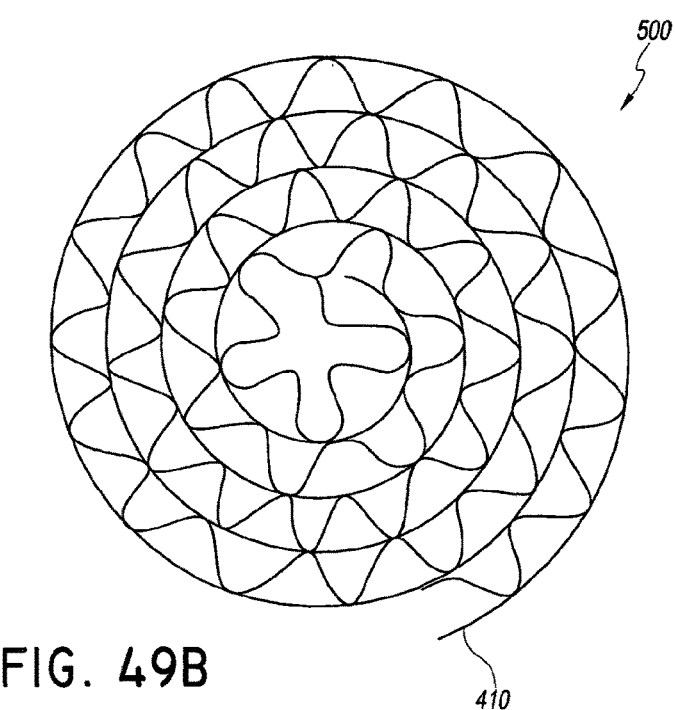
Figure 49C:
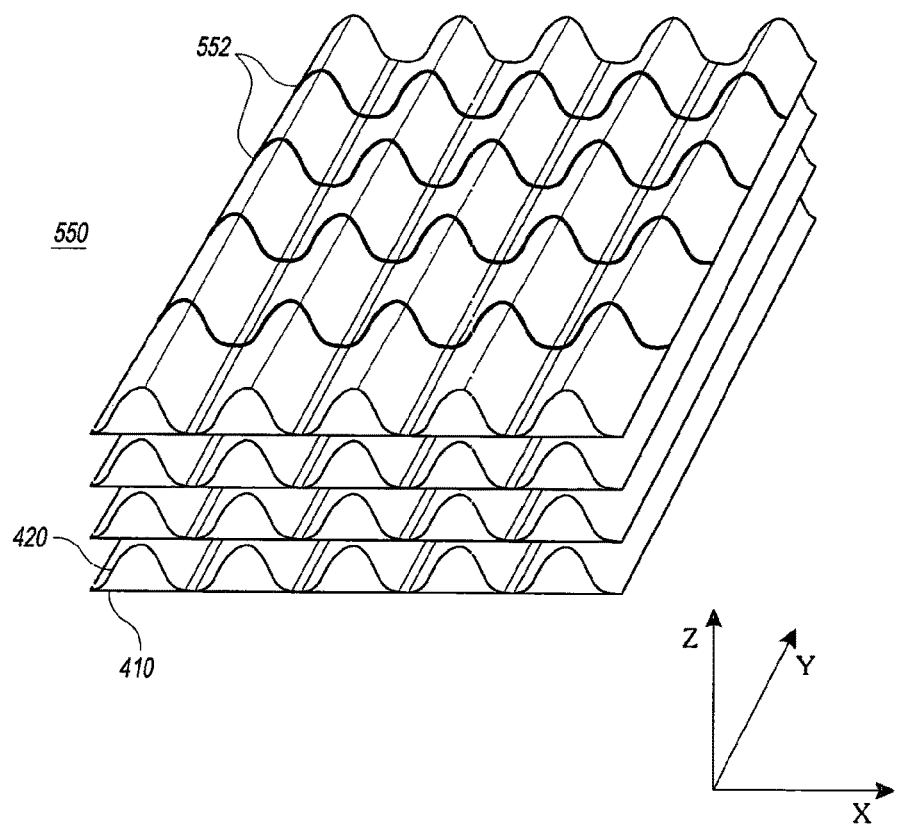
Figure 49D:
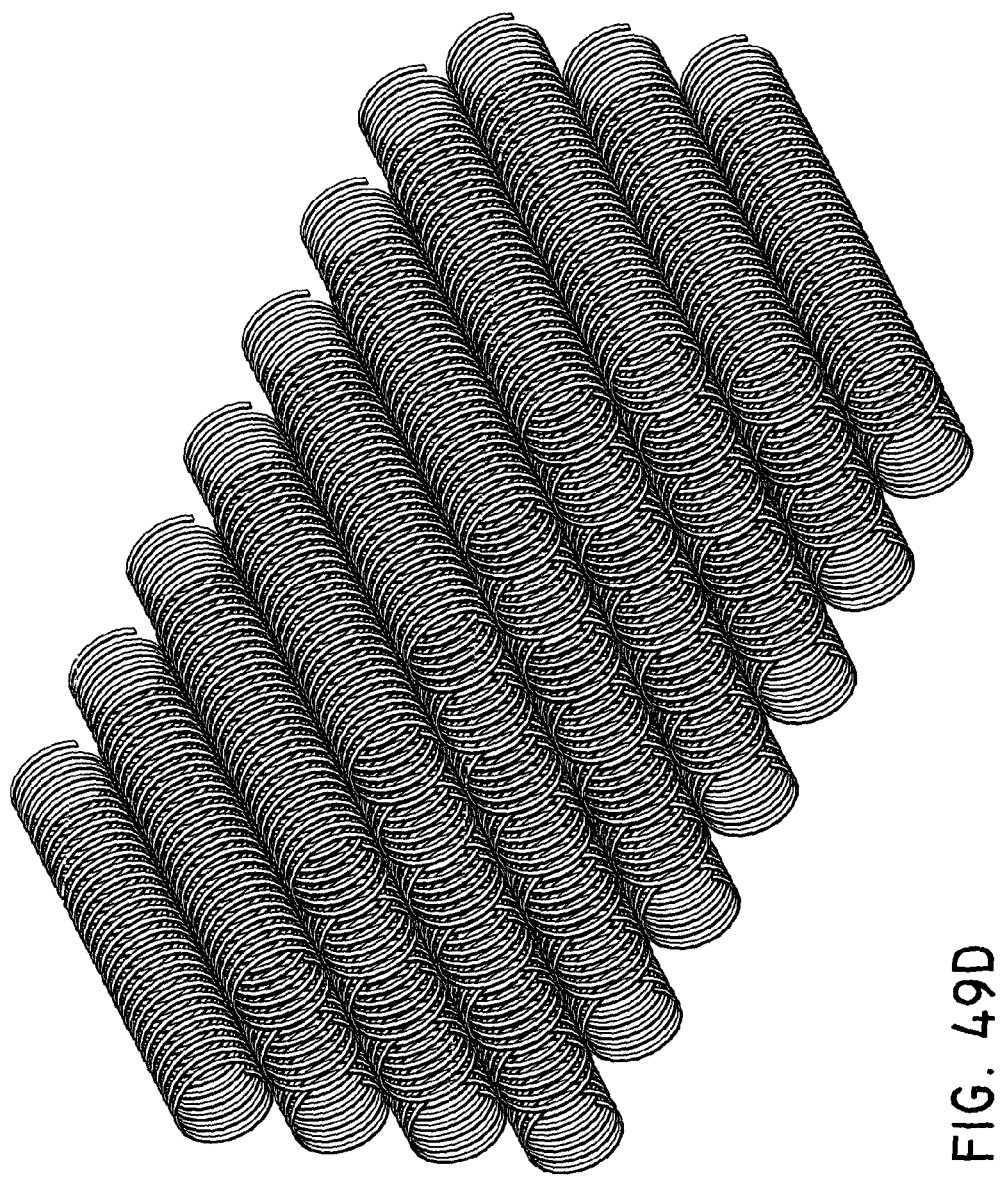

Corrugated unit 450 can be used as a stabilizing structure without further modification. It can also be used to form more complex three-dimensional structures. Spiral wound packing 500 illustrated in FIGS. 49B and 49C is formed by rolling corrugated unit 450 to expose a portion of the first flat sheet 410 along the circumference. More elaborate structures can also be formed from a plurality of corrugated units. For example, individual corrugated units may be coupled to each other by adhesive or heat sealing means to form multi-corrugated stabilizing structures 550, as shown in FIG. 49D. One or more beads of silicone material 552 can serve dual purposes of coupling the corrugated units 450, and improving the resiliency of the structure. It should be noted that, while FIG. 49D illustrates this embodiment with the peaks of each adjacent corrugation unit in alignment, a staggered configuration is also contemplated. Multi-corrugated stabilizing structures 550 can also be sliced along a cross section at a suitable thickness to produce cut corrugated wound packing. Alternatively, stabilizing structures 550 can be sliced at a bias to produce biased-cut corrugated wound packing.

Spiral stabilizing structures 500, cut corrugated stabilizing structures, and biased-cut corrugated stabilizing structures have the benefit of being highly compressible and highly resilient. Preferably, these stabilizing structures are sufficiently compressible to reduce to less than 50% of their original volume when subjected to the approximately 2 psi (pounds per square inch) compression force commonly encountered with the application of suction. More preferably, the stabilizing structure is sufficiently compressible to reduce to less than 25% of its original volume. Most preferably, the stabilizing structure is sufficiently compressible to reduce to less than 10% of its original volume.

Figure 49E:
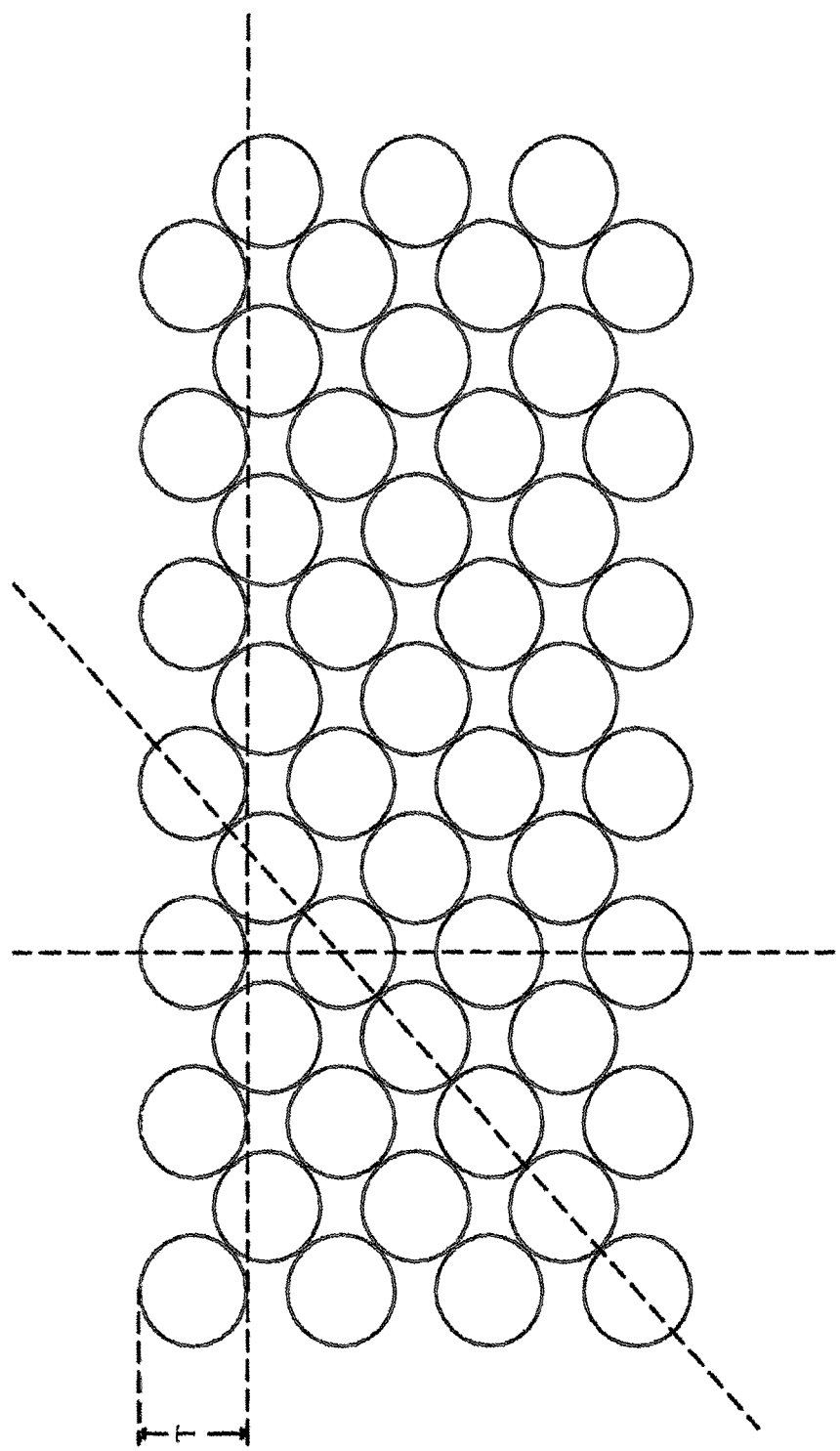
Figure 49F:
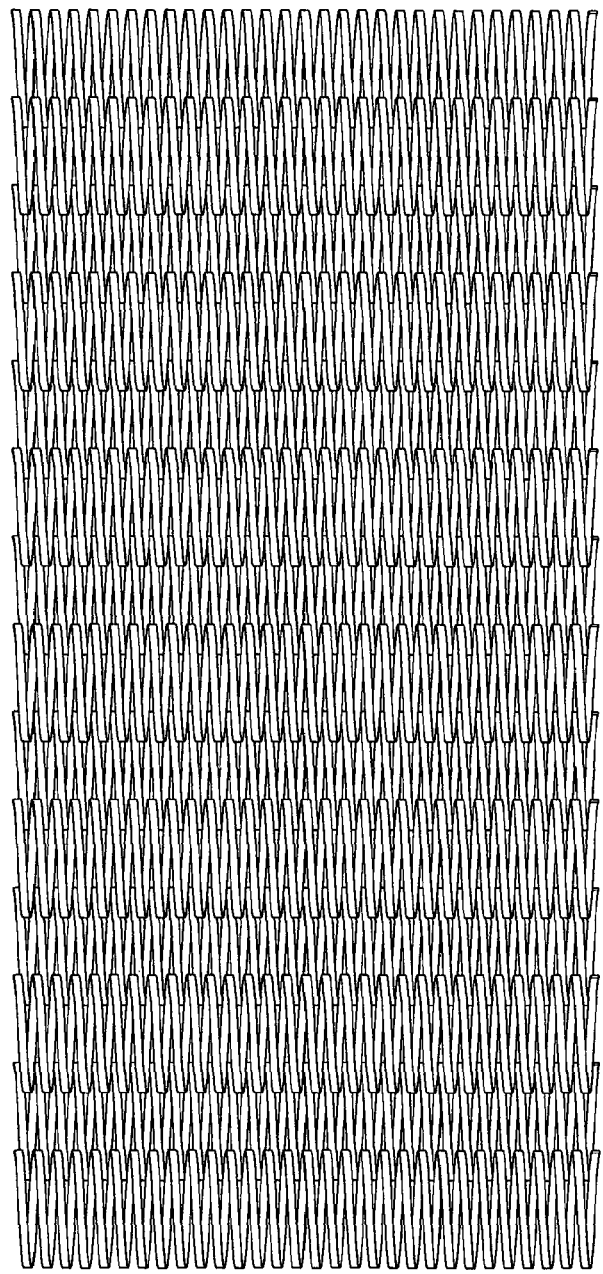

FIGS. 49D-49F illustrate another embodiment of a stabilizing structure. As shown in FIG. 49D, the stabilizing structure 1000 has a generally spiral shape exhibiting open areas 1020 along the longitudinal axis of the fiber spiral and open areas 1040 between adjacent segments of a particular spiral. Stabilizing structure 1000 is generally constructed from polymer fibers 1060, such as spandex.

To form the stabilizing structure 1000, fibers 1060 are wrapped around mandrels, such as a steel tube (not shown). The steel tubes with the spandex wrap are stacked in rows and a polyurethane film (not shown) is placed between each row. Desirably, the polyurethane film is about 0.003 inch thick. The stack of tubes is then clamped together and heated to about 320 degrees F. The polyurethane film melts and adheres to the spandex fibers, thus coupling the adjacent spirals to one another. After cooling, the steel tubes are removed. The stabilizing structure 1000, as illustrated in FIGS. 49D-49F, remains.

Figure 50:
FIG. 50 is a photograph of an embodiment having fingers that extend from the surface of a porous wound packing material.

Porous Material Surface of FIG. 50

FIG. 50 is a photograph of an embodiment of fingers 4602 present on a porous material surface 4600. The fingers 4602 may comprise any porous material described herein this section or elsewhere in the specification, such as foam. The fingers 4602 may extend from any surface of the wound packing materials described herein this section or elsewhere in the specification, particularly as depicted in FIGS. 1-10.

In certain embodiments, the fingers may extend from the frangible recess created in a wound packing material such as those depicted in FIGS. 8A-10. In some embodiments, the fingers may extend from at least about 10% of the exterior of the wound packing material, at least about 20%, at least about 30%, at least about 50%, at least about 75%, or about 100% of the exterior of the wound packing material. In embodiments, the fingers are interlocked into various frangible layers of the wound packing material such that when a portion of frangible material is removed, additional fingers are exposed.

The fingers 4602 can extend from the foam layer into a stabilizing structure or closure device, such as those described elsewhere in the specification. For example, the fingers 4602 may extend into and around the gaps or cells depicted in the stabilizing structures of FIGS. 44A-48C. The fingers 4602 may also extend around the outside of the perimeter of the stabilizing structure. In some embodiments, the fingers 4602 from porous material layer 4600 may extend through the interior or around the outside of a stabilizing structure to meet the fingers 4602 from a second porous material layer 4600.

In particular embodiments, the porous material layer 4600 may be located above or below the stabilizing structure or wound closure device. In some embodiments, the porous material layer 4600 is located both above and below the stabilizing structure or wound closure device. The porous material layer 4600 can surround the perimeter of the stabilizing structure or wound closure device or completely surround the entirety of the stabilizing structure or wound closure device. The porous material layer 4600 can be constructed from absorbent materials, materials configured to distribute fluid, or both.

Further Description of Secondary Wound Fillers

As described elsewhere in the specification, in some embodiments a wound treatment apparatus comprises: a body of a porous material, the body comprising frangible regions defining a plurality of portions, the frangible regions allowing the portions to be selectively removed from the body so as to form a recess in the body, the recess being bound by a bottom surface and a wall portion; and a secondary wound filler for positioning within the recess in the body.

In certain embodiments, the secondary wound filler may be configured to collapse significantly more within a horizontal plane than with a vertical plane. For example, the secondary wound filler may comprise:

a plurality of cells provided side-by-side in a plane, each cell defined by one or more walls, each cell having a top end and a bottom end with an opening extending through the top and bottom ends in the direction perpendicular to the plane;

wherein the secondary wound filler is configured to collapse significantly more within the plane than along the direction perpendicular to the plane.

In certain embodiments, the secondary wound filler is constructed from a material selected from the group consisting of silicone, rigid plastics, soft polymers, and foam. The cells may all be identical or they have different shapes. The walls of the cells may extend in a vertical direction. The plane may extend in a horizontal direction. In certain embodiments, the walls extend in a vertical direction and/or adjoin to adjacent cells. In some embodiments, the shape of each cell may be square, diamond, oblong, oval, or parallelepiped. Each cell may include a notch or a hole. At least one wall of each cell may be configured to fold against another wall of the cell. In embodiments, foam may surround or be within each cell, or it may surround the entire secondary wound filler. In some embodiments, each cell may be connected to an adjacent cell by a joint, wherein the joints are more flexible than the walls. In some embodiments, the cells are more collapsible in a first direction along the plane than in a second direction at an angle to the first direction along the same plane. The second direction may be perpendicular to the first direction.

In certain embodiments, the secondary wound filler may comprise a plurality of first strips extending in a first direction, and a plurality of intersecting strips extending in a second direction perpendicular to the first direction, wherein the structure is collapsible in the first and second directions. The walls may further comprise an insert disposed therein. The insert may be more rigid than one or more walls. The insert may be insertable into a preformed pocket within the one or more walls. In some embodiments, the walls may be molded around an individual insert.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound treatment apparatus comprising:
   a unitary body consisting of a single porous material, the body comprising frangible regions defining a plurality of portions, the frangible regions allowing the portions to be selectively removed from the body so as to form a recess in the body, the recess being bound by a bottom surface and a wall portion; and
   a secondary wound filler for positioning within the recess in the body, the secondary wound filler configured to be more compressible in a horizontal plane than in a vertical dimension when subjected to negative pressure.

2. The wound treatment apparatus of claim 1, wherein the portions can be removed manually.

3. The wound treatment apparatus of claim 1, wherein the frangible regions are defined by pre-cuts formed in the body.

4. The wound treatment apparatus of claim 3, wherein the pre-cuts are parallel.

5. The wound treatment apparatus of claim 3, wherein the pre-cuts are formed via laser ablation.

6. The wound treatment apparatus of claim 3, wherein the pre-cuts are formed via waterjet ablation.

7. The wound treatment apparatus of claim 3, wherein the pre-cuts are formed via die-cutting.

8. The wound treatment apparatus of claim 1, wherein the frangible regions are defined by a first set of parallel pre-cuts formed in the body.

9. The wound treatment apparatus of claim 8, wherein the frangible regions are further defined by a second set of parallel pre-cuts formed in the body.

10. The wound treatment apparatus of claim 9, wherein the frangible regions are further defined by a third set of parallel pre-cuts formed in the body.

11. The wound treatment apparatus of claim 1, wherein the body of porous material is formed from a wound packing foam.

12. The wound treatment apparatus of claim 1, wherein the body of porous material comprises a bottom portion, the bottom portion comprising a non-frangible section of porous material.

13. The wound treatment apparatus of claim 12, wherein the bottom portion is 5-20 mm thick.

14. The wound treatment apparatus of claim 1, further comprising a wound cover configured to be positioned over the body and over the wound closure device and sealed to skin surrounding a wound.

15. The wound treatment apparatus of claim 1, further comprising a source of negative pressure.

16. The wound treatment apparatus of claim 1, wherein the body of porous material comprises a bowl shaped recess.

17. The wound treatment apparatus of claim 1, wherein the body of porous material has a cubic shape.

18. A method of treating a wound, comprising:
providing a unitary body consisting of a single porous material, wherein the body comprises frangible regions;
removing portions of the porous body such that the body is a desirable shape to fit within a wound;
removing portions of the body to create a recess configured to receive a secondary wound filler; and
placing the secondary wound filler within the recess, the secondary wound filler configured to be more compressible in a horizontal plane than in a vertical dimension when subjected to negative pressure.

19. The method of claim 18, further comprising positioning the body and the secondary wound filler within a wound, and covering the body and the secondary wound filler with a wound cover.

20. The method of claim 19, further comprising applying negative pressure to the wound through the wound cover, the secondary wound filler and the body.

* * * * *

UNITED STATES PATENT AND TRADEMARK OFFICE
CERTIFICATE OF CORRECTION

PATENT NO.      : 10,220,125 B2
APPLICATION NO. : 14/905266
DATED           : March 5, 2019
INVENTOR(S)     : Edward Yerbury Hartwell It is certified that error appears in the above-identified patent and that said Letters Patent is hereby corrected as shown below:

In the Specification

In Column 2, Line 35, change "sterniotomies," to --sternotomies,--.

In Column 11, Line 40, change "sterniotomies," to --sternotomies,--.

In Column 14, Line 5, change "body" to --body.--.

In Column 23, Line 16, change "16A-24B" to --16A-24B,--.

In Column 29, Line 9, change "FIG." to --FIGS.--.

In Column 32, Line 65, change "FIG." to --FIGS.--.

In Column 37, Line 54, change "longitundinal" to --longitudinal--.

In Column 37, Line 55, change "longitundinal" to --longitudinal--.

Signed and Sealed this
Ninth Day of July, 2019

Andrei Iancu
*Director of the United States Patent and Trademark Office*